US012715928B2

(12) United States Patent
Beilhack et al.

(10) Patent No.: US 12,715,928 B2
(45) Date of Patent: Aug. 25, 2026

(54) TUMOR NECROSIS FACTOR (TNF) RECEPTOR SUPERFAMILY (TNFRSF) RECEPTOR-ACTIVATING ANTIBODY FUSION PROTEINS WITH FCγR-INDEPENDENT AGONISTIC ACTIVITY (TNFRSF RECEPTOR-ACTIVATING ANTIBODY FUSION PROTEINS WITH FCγR-INDEPENDENT AGONISTIC ACTIVITY; TRAAFFIAA)

(71) Applicant: JULIUS-MAXIMILIANS-UNIVERSITÄT WÜRZBURG, Würzburg (DE)

(72) Inventors: Andreas Beilhack, Würzburg (DE); Juliane Medler, Fluda (DE); Johannes Nelke, Würzburg (DE); Harald Wajant, Kist (DE)

(73) Assignee: JULIUS-MAXIMILIANS-UNIVERSITÄT WÜRZBURG, Würzburg (DE)

( * ) Notice: Subject to any disclaimer, the term of this patent is extended or adjusted under 35 U.S.C. 154(b) by 0 days.

(21) Appl. No.: 16/958,487

(22) PCT Filed: Dec. 20, 2018

(86) PCT No.: PCT/EP2018/086207

§ 371 (c)(1),
(2) Date: Jun. 26, 2020

(87) PCT Pub. No.: WO2019/129644

PCT Pub. Date: Jul. 4, 2019

(65) Prior Publication Data

US 2021/0079106 A1 Mar. 18, 2021

(30) Foreign Application Priority Data

Dec. 28, 2017 (EP) .................................... 17210849
Aug. 21, 2018 (EP) .................................... 18189937

(51) Int. Cl.
*C07K 16/28* (2006.01)

(52) U.S. Cl.
CPC ...... *C07K 16/2878* (2013.01); *C07K 2317/55* (2013.01); *C07K 2317/565* (2013.01); *C07K 2319/74* (2013.01)

(58) Field of Classification Search
None
See application file for complete search history.

(56) References Cited

U.S. PATENT DOCUMENTS

2014/0065142 A1* 3/2014 Roschke ............ A61K 39/3955 435/375
2015/0010567 A1* 1/2015 Bourquin ................ A61P 35/02 435/69.6
2015/0175692 A1* 6/2015 Di Padova .............. A61P 17/06 530/387.3
2016/0045597 A1* 2/2016 Corse ...................... A61P 35/00 424/174.1
2016/0368985 A1* 12/2016 Hotzel ............. G01N 33/57492
2017/0198050 A1 7/2017 Eckelman et al.
2018/0118836 A1* 5/2018 Bernett .............. C12N 15/8613
2019/0135929 A1* 5/2019 Faustman .......... A61K 39/3955

FOREIGN PATENT DOCUMENTS

EP 2604693 A2 6/2013
EP 3606956 A1 2/2020
JP 2014534243 A 12/2014
JP 2016529215 A 9/2016
WO WO-03/080672 A1 10/2003
WO WO-2007/146163 A2 12/2007
WO WO-2008091954 A2 * 7/2008 ........... A61K 39/395
WO WO-2010/005519 A1 1/2010
WO 2013/072523 A1 5/2013
WO WO-2014/207064 A1 12/2014
WO WO-2016126781 A1 * 8/2016 ............. A61K 38/19
WO 2016/145085 A2 9/2016
WO 2017/011837 A2 1/2017
WO WO-2017040312 A1 3/2017
WO WO-2017097407 A1 * 6/2017 ....... A61K 39/39591
WO WO-2017162890 A1 * 9/2017 .............. A61P 35/00
WO WO-2017/184619 A2 10/2017
WO WO-2018/185045 A1 10/2018

OTHER PUBLICATIONS

H Wajant, Cell Death and Differentiation (2015) 22, 1727-1741. (Year: 2015).*
Malia et al, Proteins, 2016; 84:427-434. (Year: 2016).*
Barthelemy et al., Journal of Biological Chemistry, 2008, 283:3639-3654. (Year: 2008).*
Beiboer et al., Journal of Molecular Biology, 2000, 296:833-849. (Year: 2000).*
Choi et al., 2011, Molecular BioSystems, 2011, 7:3327-334. (Year: 2011).*
De Genst et al., Developmental and Comparative Immunology, 2006, 30:187-98. (Year: 2006).*
Griffiths et al., The EMBO Journal, 1993, 12:725-734. (Year: 1993).*
Klimka et al., British Journal of Cancer, 2000, 83:252-260. (Year: 2000).*
Ward et al, Nature, 1989, 341:544-546. (Year: 1989).*
Altschul et al., Basic local alignment search tool, J. Mol. Biol., 215:403-410 (1990).

(Continued)

*Primary Examiner* — Misook Yu
*Assistant Examiner* — Cheom-Gil Cheong
(74) *Attorney, Agent, or Firm* — MARSHALL, GERSTEIN & BORUN LLP

(57) ABSTRACT

The present invention relates to tumor necrosis factor (TNF) receptor superfamily (TNFRSF) receptor-activating antibody fusion proteins with FcyR-independent agonistic activity, and to compositions and methods related thereto.

9 Claims, 25 Drawing Sheets

Specification includes a Sequence Listing.

(56) References Cited

OTHER PUBLICATIONS

Altschul et al., Gapped BLAST and PSI-BLAST: a new generation of protein database search programs, Nucleic Acids Res., 25:3389-3402 (1997).
Ausubel et al., Current protocols in Mmolecular biology, Greene Publishing Associates and Wiley Interscience; New York (1992).
Berg et al., Enforced covalent trimerization increases the activity of the TNF ligand family members TRAIL and CD95L, Cell Death Differ., 14:2021-2034 (2007).
Chothia et al., Conformations of immunoglobulin hypervariable regions, Nature, 342:877-883 (1989).
Clackson et al., Making antibody fragments using phage display libraries, Nature, 352:624-628 (1991).
Fellermeier et al., Advancing targeted co-stimulation with antibody-fusion proteins by introducing TNF superfamily members in a single-chain format, Oncoimmunology, 5(11):e1238540 (2016).
Ghahroudi et al., Selection and identification of single domain antibody fragments from camel heavy-chain antibodies, FEBS Lett., 414:521-526 (1997).
Giudicelli et al., IMGT/V-QUEST, an integrated software program for immunoglobulin and T cell receptor V-J and V-D-J rearrangement analysis, Nucleic Acids Res., 32:W435-W440 (2004).
Holliger et al., “Diabodies”: small bivalent and bispecific antibody fragments, Proc. Natl. Acad. Sci. USA., 90:6444-6448 (1993).
Holt et al., Domain antibodies: proteins for therapy, Trends Biotechnol., 21:484-490 (2003).
International Application No. PCT/EP2018/086207, International Preliminary Report on Patentability, mailed Jul. 9, 2020.
International Application No. PCT/EP2018/086207, International Search Report and Written Opinion, mailed Apr. 26, 2019.
Jones et al., Replacing the complementarity-determining regions in a human antibody with those from a mouse, Nature, 321:522-525 (1986).
Köhler et al., Continuous cultures of fused cells secreting antibody of predefined specificity, Nature, 256:495-497 (1975).
Kums et al., Quantitative analysis of cell surface antigen-antibody interaction using Gaussia princeps luciferase antibody fusion proteins, MAbs., 9:506-520 (2017).
Lang et al., Binding studies of TNF receptor superfamily (TNFRSF) receptors on intact cells, J. Biol. Chem., 291:5022-5037 (2016).
Marks et al., By-passing immunization. Human antibodies from V-gene libraries displayed on phage, J. Mol. Biol., 222:581-597 (1991).
Remington’S Pharmaceutical Sciences, Ed. AR Gennaro, 20th edition, Williams & Wilkins, PA, USA. (2000).
Riechmann et al., Reshaping human antibodies for therapy, Nature, 332:323-327 (1988).
Saerens et al., Single-domain antibodies as building blocks for novel therapeutics, Curr. Opin. Pharmacol., 8:600-608 (2008).
Sambrook et al., Molecular Cloning: A Laboratory Manual, 2nd Ed., Cold Spring Harbor Laboratory Press, Cold Spring Harbor, New York (1989).
Shivange et al., A single-agent dual-specificity targeting of FOLR1 and DR5 as an effective strategy for ovarian cancer, Cancer Cell, 34:331-345 (2018).
Siegel, Recombinant monoclonal antibody technology, Transfus. Clin. Biol., 9:15-22 (2002).
Trebing et al., A novel llama antibody targeting Fn14 exhibits anti-metastatic activity in vivo, MAbs., 6:297-308 (2014).
Wajant et al., Engineering death receptor ligands for cancer therapy, Cancer Lett., 332:163-174 (2013).
Wajant, Principles of antibody-mediated TNF receptor activation, Cell Death Differ., 22:1727-1741 (2015).
Weiss et al., Enhancement of TNF receptor p60-mediated cytotoxicity by TNF receptor p80: requirement of the TNF receptor-associated factor-2 binding site, J. Immunol., 158:2398-2404 (1997).
White et al., Conformation of the human immunoglobulin G2 hinge imparts superagonistic Properties to immunostimulatory anticancer antibodies, Cancer Cell, 27(1):138-148 (2015).
Wyzgol et al., Trimer stabilization, oligomerization, and antibody-mediated cell surface immobilization improve the activity of soluble trimers of CD27L, CD40L, 41BBL, and glucocorticoid-induced TNF receptor ligand, J. Immunol., 183:1851-1861 (2009).
Takkar et al., “Cross-competition or Epitope Binning Assays on the Octet HTX System,” Application Note 16, Life Sciences, 19 pages (2013).
Communication pursuant to Rule 114(2) EPC from European Application No. 18825694.5 dated Jan. 26, 2023.
Rudikoff et al., “Single amino acid substitution altering antigen-binding specificity,” Proc. Natl. Acad. Sci. USA, 79:1979-1983 (1982).
Tamura et al., “Structural Correlates of an Anticarcinoma Antibody: Identification of Specificity-Determining Residues (SDRs) and Development of a Minimally Immunogenic Antibody Variant by Retention of SDRs Only,” J. Immunol, 164(3):1432-1441 (2000).

* cited by examiner

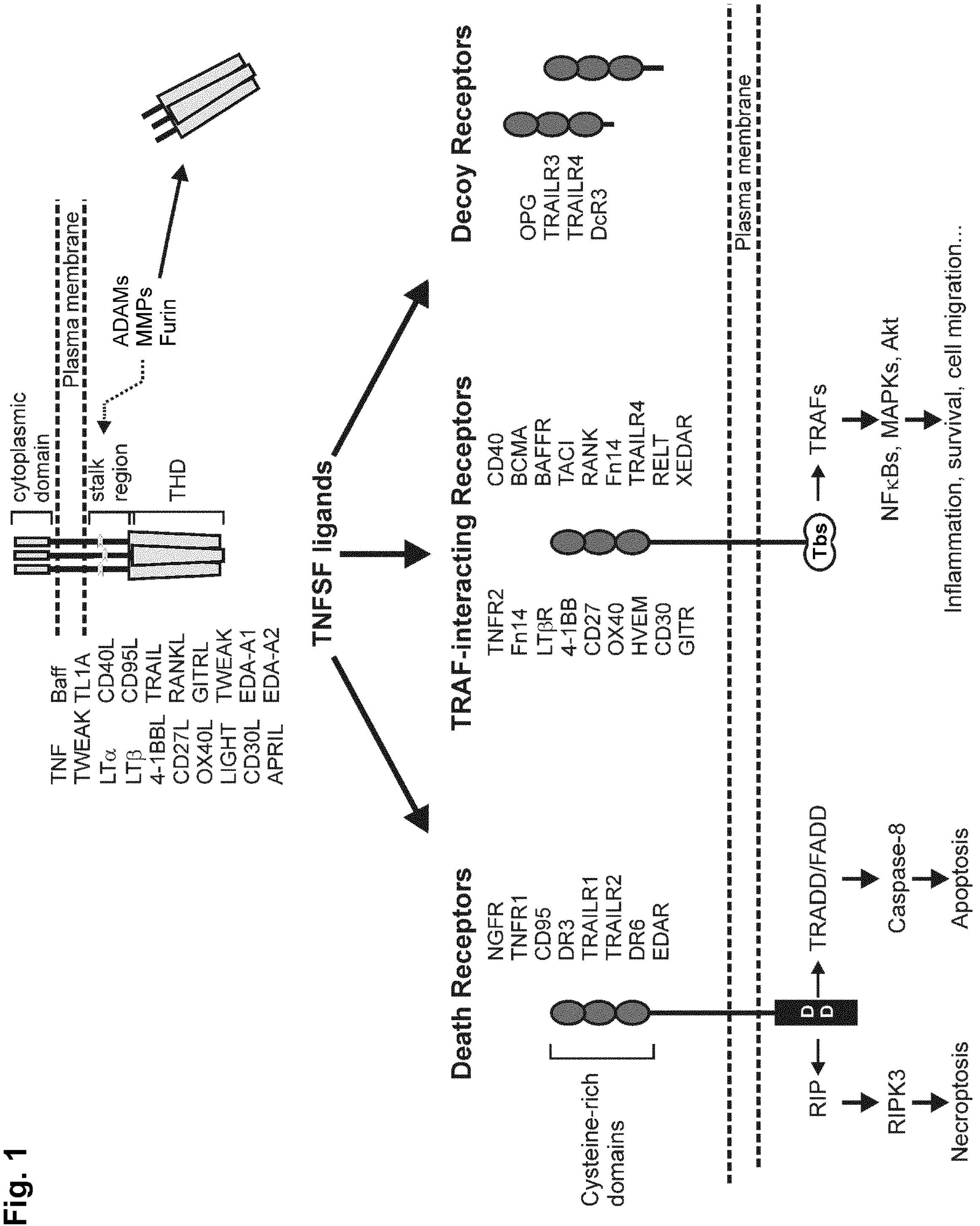
Fig. 1
TNF
TWEAK
LTα
LTβ
4-1BBL
CD27L
OX40L
LIGHT
CD30L
APRIL
Baff
TL1A
CD40L
CD95L
TRAIL
RANKL
GITRL
TWEAK
EDA-A1
EDA-A2
cytoplasmic domain
stalk region
THD
Plasma membrane
ADAMs
MMPs
Furin
TNFSF ligands
Death Receptors
NGFR
TNFR1
CD95
DR3
TRAILR1
TRAILR2
DR6
EDAR
TRAF-interacting Receptors
TNFR2
Fn14
LTβR
4-1BB
CD27
OX40
HVEM
CD30
GITR
CD40
BCMA
BAFFR
TACI
RANK
Fn14
TRAILR4
RELT
XEDAR
Decoy Receptors
OPG
TRAILR3
TRAILR4
DcR3
Cysteine-rich domains
Plasma membrane
D D
RIP
RIPK3
Necroptosis
TRADD/FADD
Caspase-8
Apoptosis
Tbs
TRAFs
NFκBs, MAPKs, Akt
Inflammation, survival, cell migration...

HT1080-41BB
IL8 (ng/ml)
mock
mFcγR2b
α-41BB: 4B4-1
HT1080-CD27
α-CD27: 57703
HT1080-CD40
α-CD40: HB14
HT1080-CD40
FcγR2b
α-CD95: E09
HT1080-Ox40
α-Ox40: BER-Act35
HeLa-TNFR2
α-TNFR2: utr1
HT1080-CD40
α-Fn14: ITEM-4
WiDr
α-TRAILR1: HS101
HT29
α-LTβR: 71315
HT29
α-TNFR1: 16803

IL8 (ng/ml)
0.8
0.6
0.4
0.2
0
anti-TNFR2
epitope location
own 1
mock
CD32A
CD32B
CRD1
own 2
CRD1
own 3
CRD2
own 4
CRD2
own 5
CRD3
ACRIS
CRD3
own 6
CRD4
own 7
CRD4

A

αCD40(G28.5)-IgG1(N297A)

scBAFF

C

HT1080-CD40

HEK293

L363

IL8 [ng/ml]

1.5
1.0
0.5
0

0 9.3 83.3 750

αCD40-IgG1(N297A)-CH-scBAFF (ng/ml)

B

Fig. 5
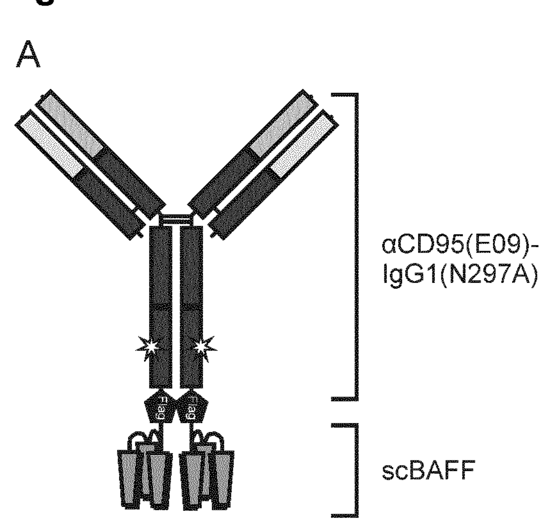
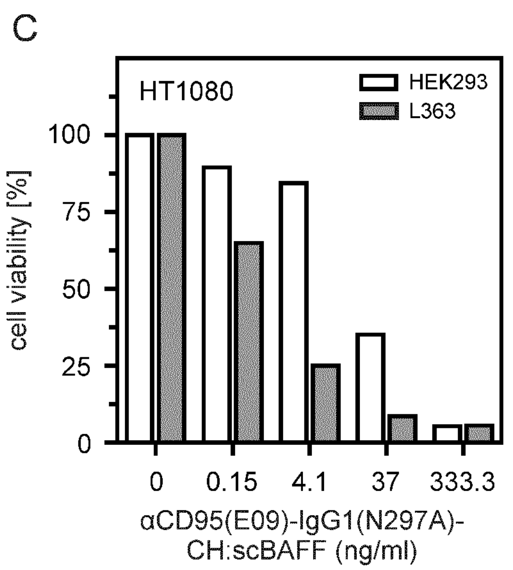
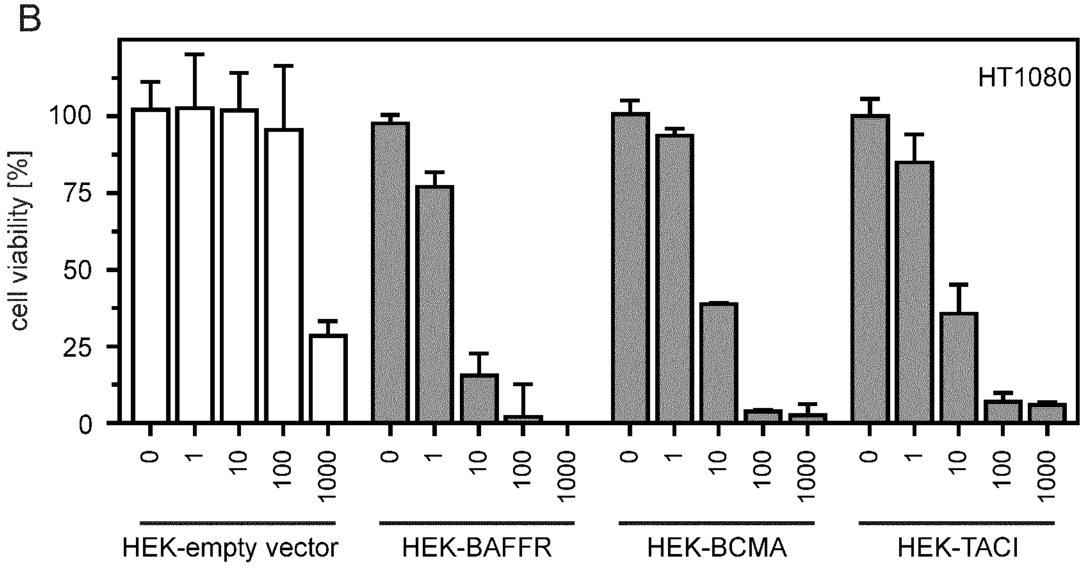

Fig. 9
A
αTNFR2(C4)-
IgG1(N297A)
scGITRL
or
sc(mu)41BBL
B
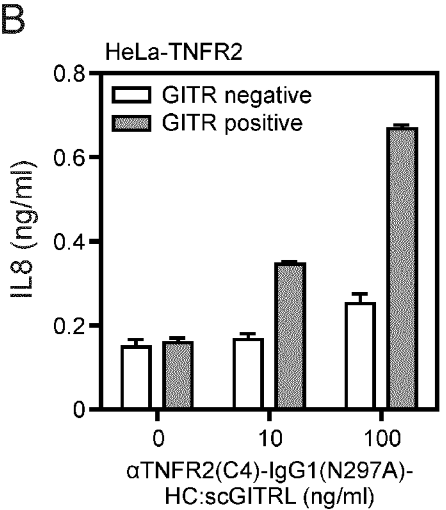
C
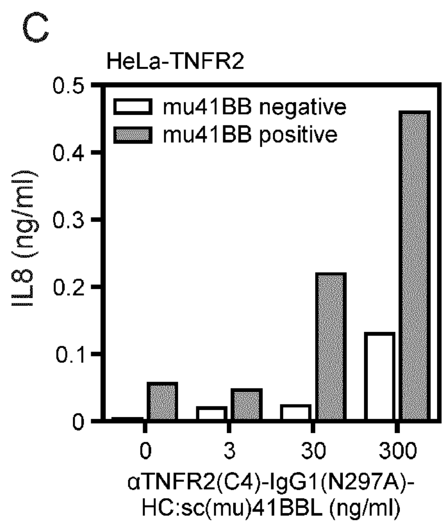
D
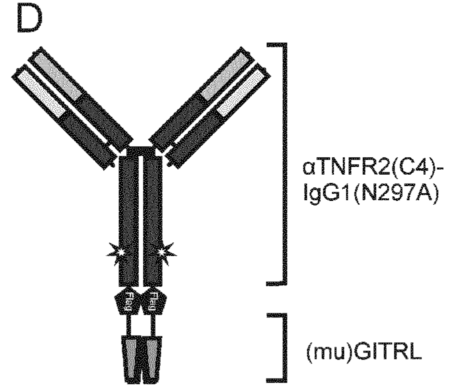
E
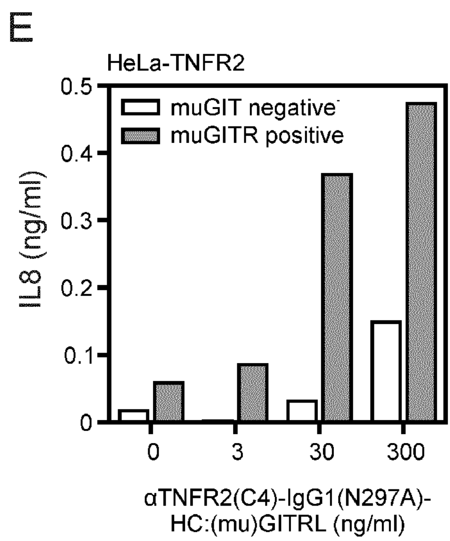

Fig. 10
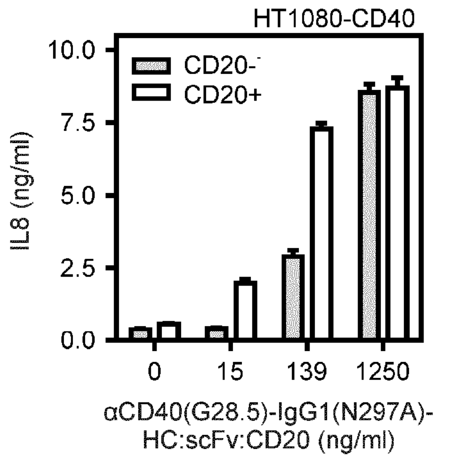
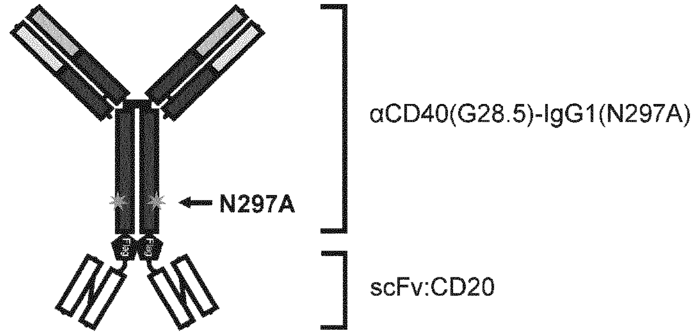

Fig. 11

Fig. 15
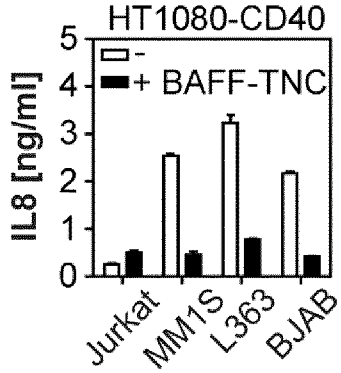
αCD40-IgG1(N297A)-HC:scBAFF (200 ng/ml)
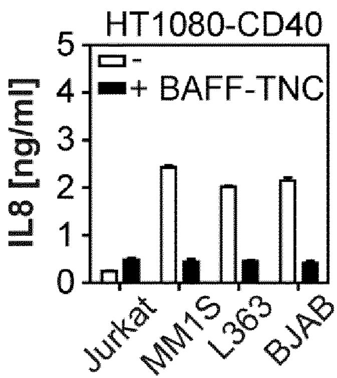
αCD40-FAB2-HC:scBAFF (200 ng/ml)
Fig. 16
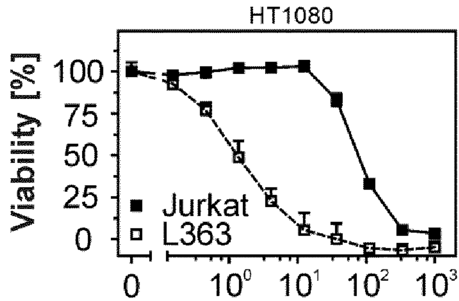
αCD95-IgG1(N297A)-HC:scBAFF (ng/ml)
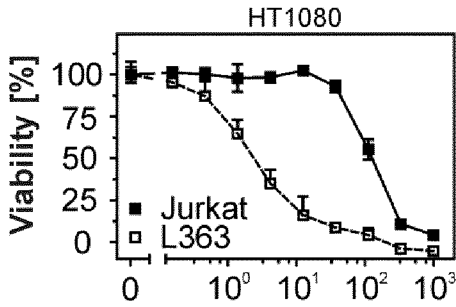
αCD95-FAB2-HC:scBAFF (ng/ml)
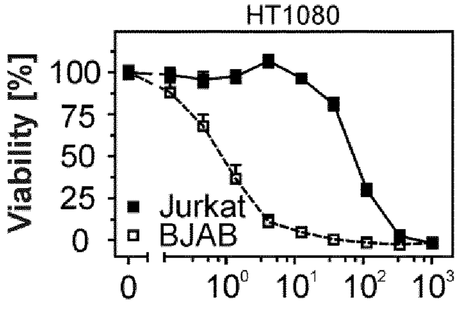
αCD95-IgG1(N297A)-HC:scBAFF (ng/ml)
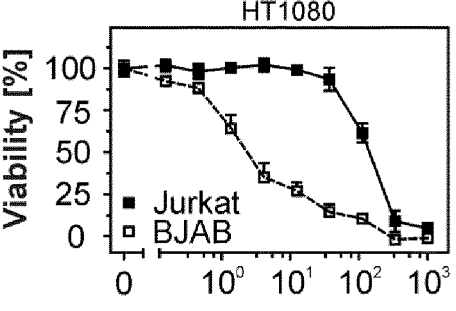
αCD95-FAB2-HC:scBAFF (ng/ml)

Fig. 17
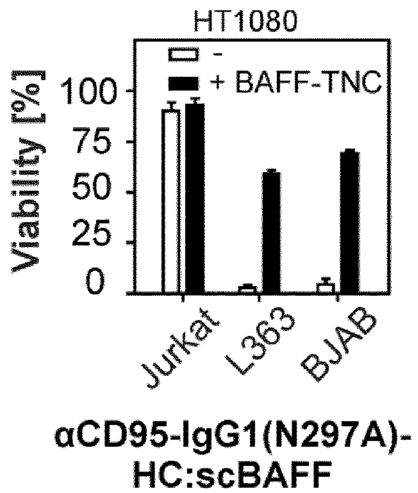
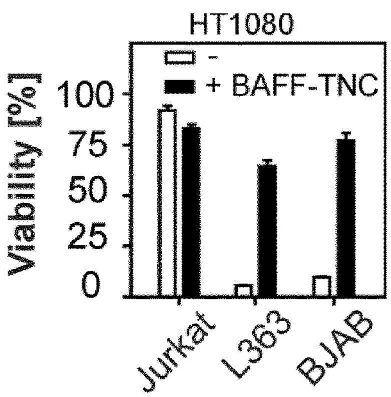
αCD95-FAB2-HC:scBAFF
Fig. 18
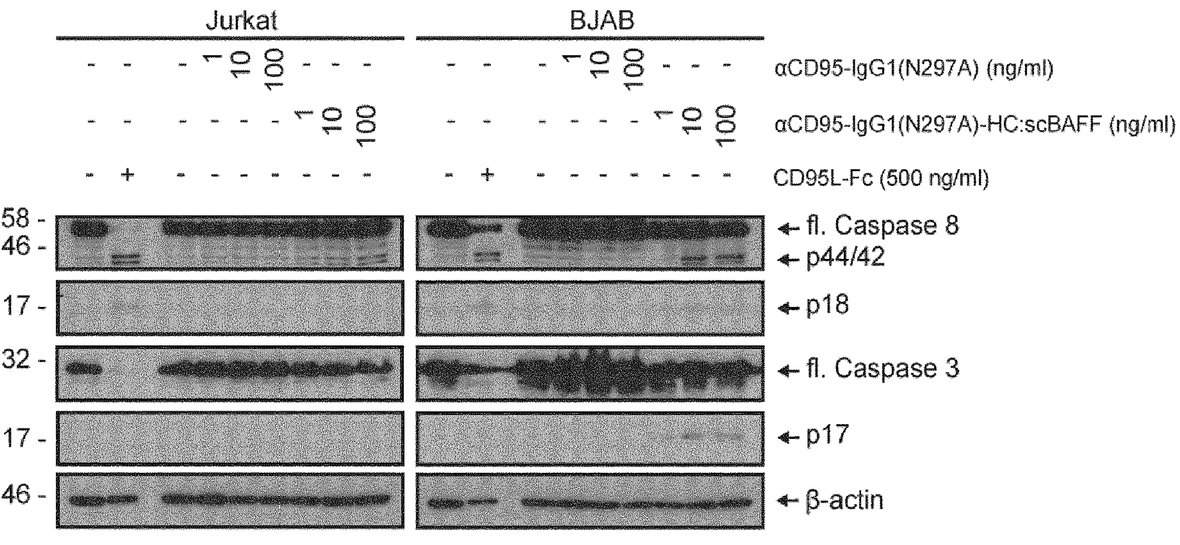
Jurkat: CD95⁺
BAFFR⁻/ TACI⁻/ BCMA⁻
BJAB: CD95⁺
BAFFR⁺/ TACI⁽⁺⁾/ BCMA⁻

Fig. 19

Fig. 20
A
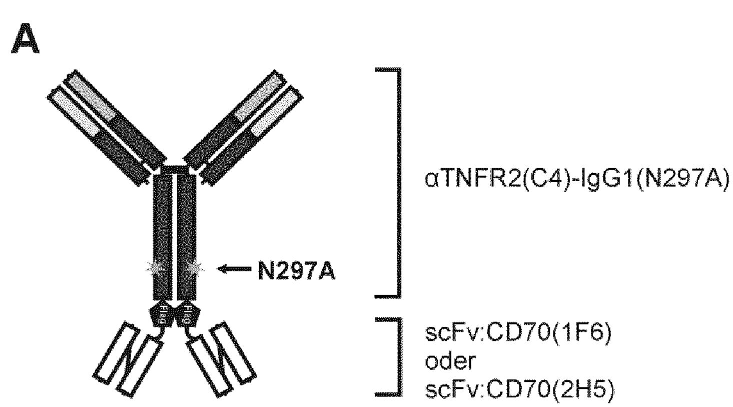
B
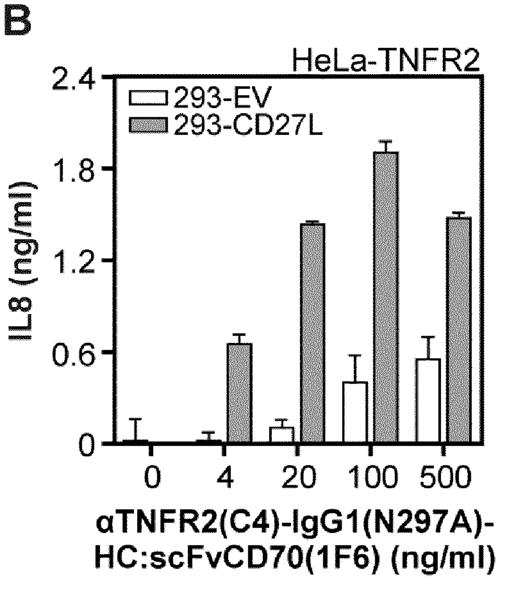
C
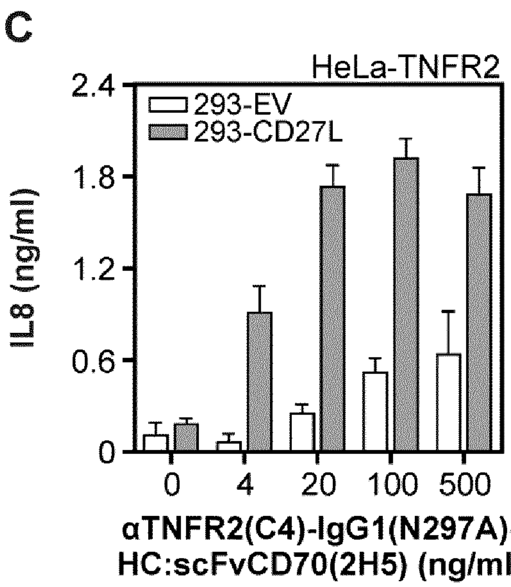

Fig. 21
A
IgG1(N297A)
with specificity for 4-1BB, CD40 or CD95
N297A
Flag
scFv:CD20
B
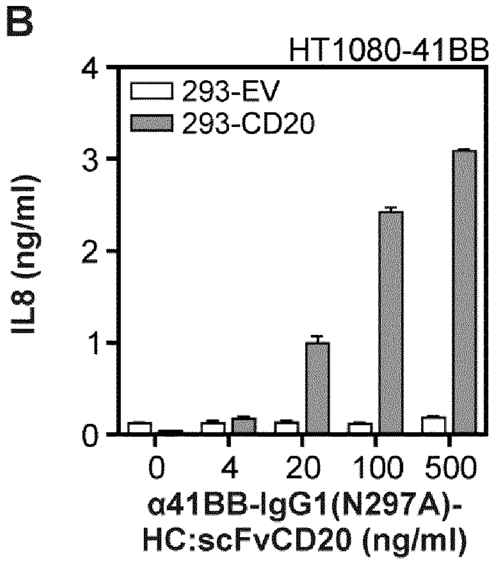
C
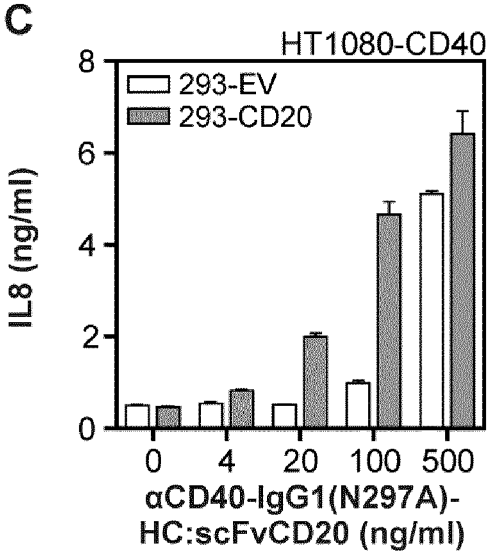
D
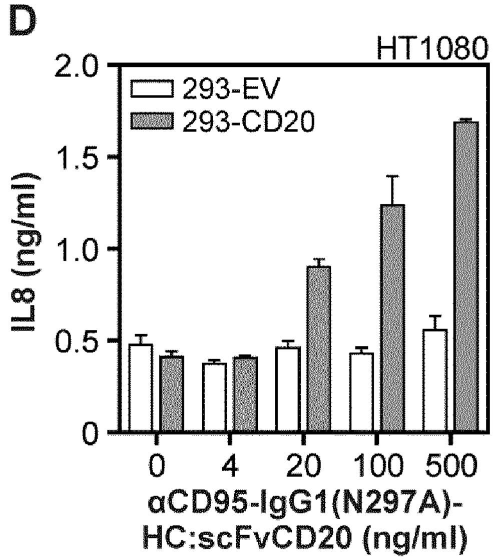

Fig. 22
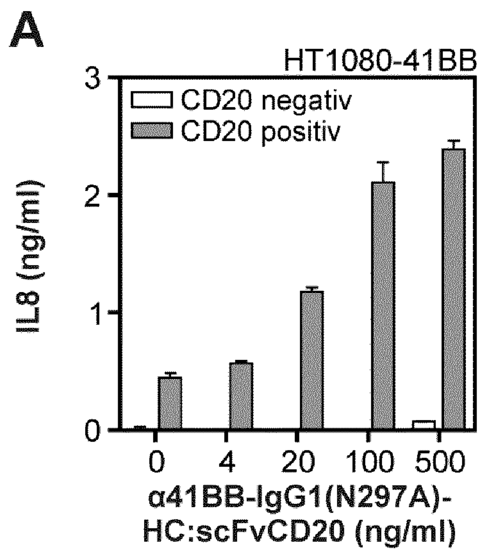
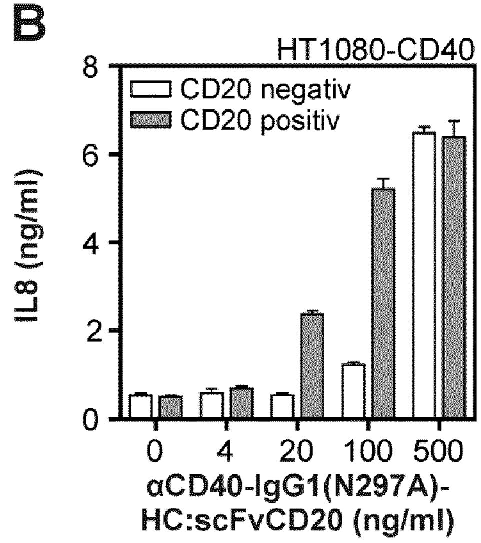
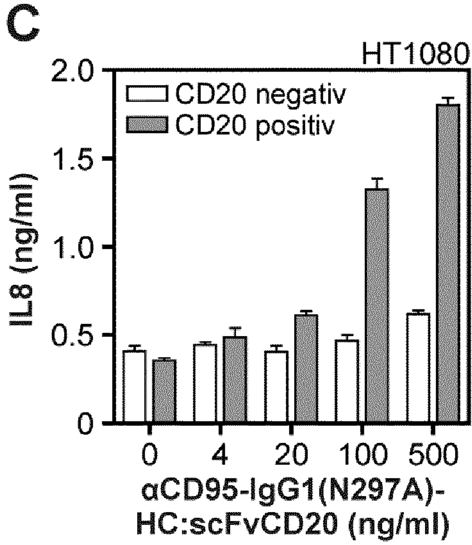

Fig. 24
A
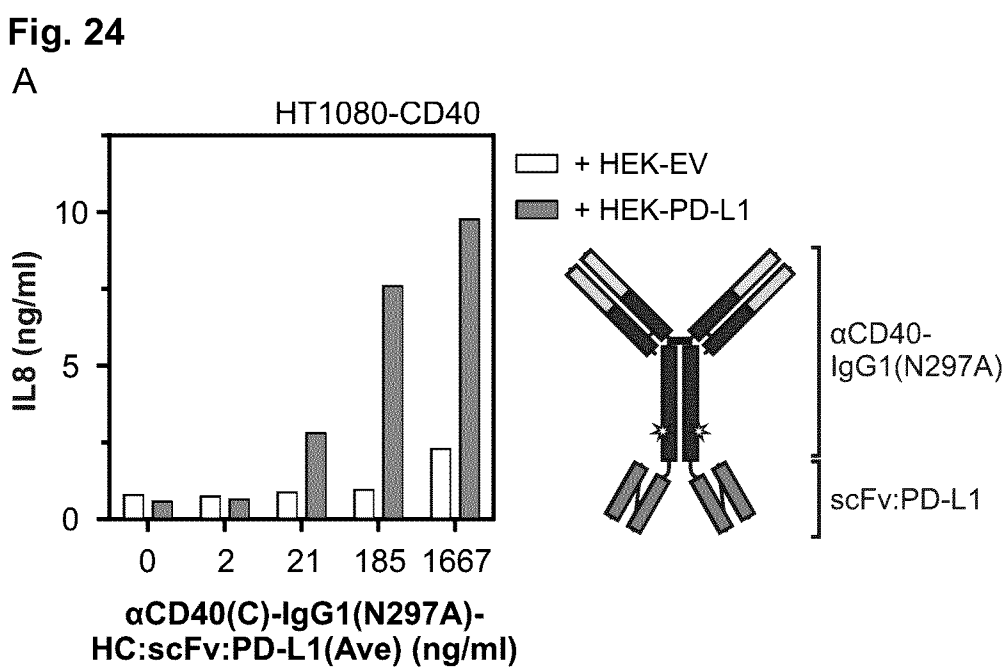
B
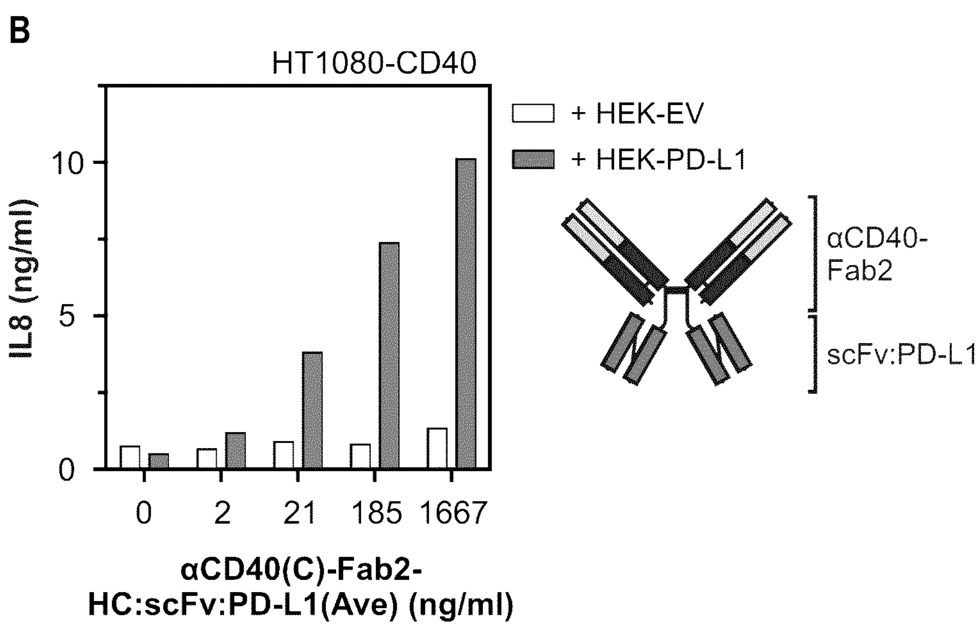

Fig. 25
A
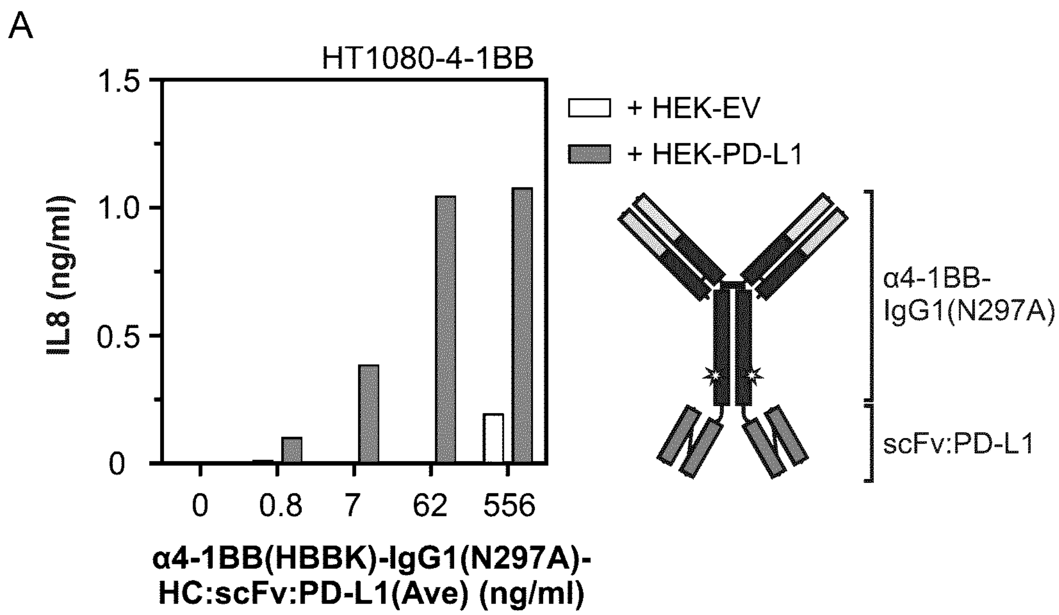
B
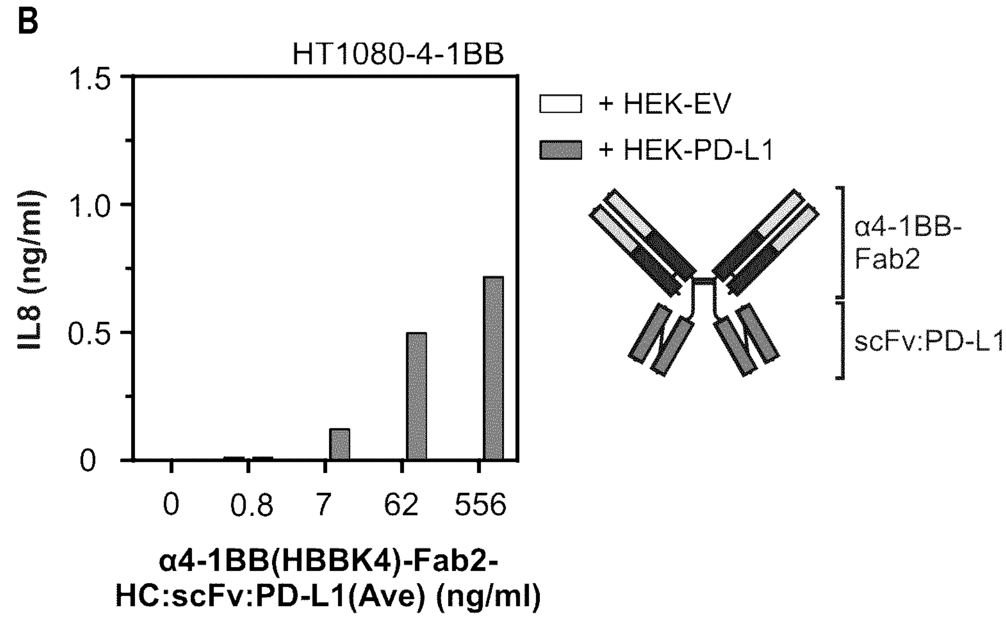

TUMOR NECROSIS FACTOR (TNF) RECEPTOR SUPERFAMILY (TNFRSF) RECEPTOR-ACTIVATING ANTIBODY FUSION PROTEINS WITH FCγR-INDEPENDENT AGONISTIC ACTIVITY (TNFRSF RECEPTOR-ACTIVATING ANTIBODY FUSION PROTEINS WITH FCγR-INDEPENDENT AGONISTIC ACTIVITY; TRAAFFIAA)

FIELD OF THE INVENTION

The present invention relates to tumor necrosis factor (TNF) receptor superfamily (TNFRSF) receptor-activating antibody fusion proteins with FcγR-independent agonistic activity (abbreviated TRAAFFIAA), and to compositions and methods related thereto.

BACKGROUND

Receptors of the Tumor Necrosis Factor (TNF) Receptor Superfamily and their Activation The majority of the receptors of the tumor necrosis factor (TNF) receptor superfamily (TNFRSF) are type 1 or type 3 transmembrane proteins which possess 1-6 structurally conserved cysteine-rich domains (CRDs) in their extracellular domain. Additionally, there are a few secreted or GPI-anchored receptor molecules, which are considered as being part of the TNFRSF due to the fact that they possess CRDs. Apart from the above, there are no other structural properties which are common to all receptors of the TNFRSF. According to structural and functional similarities, three sub-groups can be defined within the TNFRSF (FIG. 1):

1. The TNFRSF receptors of the death receptor sub-group which are defined by a structurally conserved protein-protein interaction domain in their intracellular domain, their "death domain" (DD), which gives rise to their name. Some but not all of these receptors are capable of inducing apoptosis or necroptosis but can also trigger other effects/signaling pathways. Examples are CD95 (also called Fas or Apo1), TRAILR1 (DR4) and TRAILR2 (DR5).
2. The TNFRSF receptors of the TRAF-interacting sub-group, which do not possess a DD but have short amino acid sequence motifs, by which they recruit adaptor proteins of the TNF receptor-associated factor (TRAF) family. With the aid of these TRAF proteins, the receptors of this TNFRSF sub-group can activate various signaling pathways. Examples are TNFR2, CD40, 4-1BB, OX40, CD27, Fn14 and BaffR.
3. The decoy TNFRSF receptors, which do not have an intracellular domain, and which are secreted and are anchored by a GPI moiety on the outer surface of the plasma membrane, respectively. These TNFRSF receptors do not signal themselves but control the activity of some receptors of the sub-groups 1 and 2.

Usually, the signal transduction-competent receptors of TNFRSF are naturally activated by interaction with ligands of the TNF superfamily (TNFSF). The allocation of ligands to the TNFSF is governed by the presence of a C-terminal conserved domain, the TNF homology domain (THD), Through their THD, the ligands of TNFSF form homotrimeric molecules and in a few cases also heterotrimeric molecules. Apart from LTalpha homotrimers, which are being secreted, all ligands of the TNF family are initially expressed as type II membrane proteins; thus, the THD has an extracellular localization. However, through proteolytic processing between the THD and the transmembrane domain of the TNFSF ligands, soluble trimeric ligand molecules can also be formed in these cases (FIG. 1). A single TNFRSF receptor molecule is recruited into the contact surface areas which are formed between adjacent protomers of the ligand trimer. A TNFSF ligand molecule therefore binds three receptors of the TNFRSF; this applies both to soluble and to membrane-bound TNFSF ligand molecules. As far as is known, the binding of membrane-bound TNFSF ligands always results in strong receptor activation. However, the extent of robust and efficient activation of intracellular signaling pathways after the binding of soluble TNFSF ligands depends on the specific TNFRSF receptor. Thus, TNFRSF receptors such as TNFR1, GITR, LTbR or DR3 are strongly activated by the binding of soluble ligand trimers, whereas TNFRSF receptors such as, for example, TNFR2, Fn14, TRAILR1, TRAILR2, CD95, OX40, CD27, 4-1BB and CD40 are not or only very poorly stimulated by soluble ligand trimers. In these cases, the soluble TNF ligands can then even act as competitive inhibitors of their membrane-bound form. The question of why the stimulation of the TNFRSF receptors of this second group by their membrane-bound ligands is much better than the stimulation by their soluble ligand molecules has not yet been resolved completely. However, it is currently thought that a trimeric ligand-receptor complex is not sufficient for the stimulation of most signaling pathways, and that at least two of these complexes must interact in a secondary manner in order to allow for an efficient initiation of signaling. In accordance with this, it was shown for some receptors of the TNFRSF that they possess an, albeit weak, ligand-independent autoaffinity. The membrane localization of the membrane-bound ligand trimers causes a spacial pre-orientation, a reduced diffusion compared to soluble ligands and a locally very high concentration of the interaction partners in the contact zone between the TNFRSF receptor- and the TNFSF ligand-expressing cell. Therefore, a spontaneous secondary aggregation of initially forming trimeric ligand-receptor complexes can probably occur in all cases of binding of membrane-bound ligands. In case of binding of soluble ligand trimers, however, the autoaffinity in case of the TNFRSF receptors of the second group is probably too weak to ensure this secondary aggregation. In accordance with this model, soluble fusion proteins and TNFSF ligand complexes, respectively, which comprise two or more trimeric ligand domains, can activate the TNFRSF receptors of the second group similarly well as membrane-bound ligands. Furthermore, it was also shown that the mere anchorage of trimeric soluble TNFSF ligands on cells or other surfaces is sufficient in order to also activate TNFRSF receptors of the second group (for review see Wajant et al., Cancer Lett. 2013 May 28; 332(2):163-74.).

A second possibility in order to activate receptors of the TNFRSF is the use of antibodies. This is of considerable importance given that various clinical concepts, especially in relation to the therapy of tumor diseases, aim at the activation of cell death-inducing or immune-stimulatory receptors of the TNFRSF. Thus, antibodies which inter alia target the TNFRSF receptors TRAILR2, CD40, Fn14, CD27, OX40 and 4-1BB are being tested or were tested in clinical studies. In this connection, the question of when and under which circumstances an anti-TNFRSF receptor-specific antibody acts in a receptor-stimulating fashion has long been neglected. It was typically assumed that this was primarily a question of the epitope that was concretely recognized by the antibody. Especially the past years have shown in this regard that, similar to soluble TNFSF ligands, mainly the valence and the way in which the molecule is presented determine whether receptor activation occurs, i.e. whether an antibody acts as an agonist. Thus, it was found for various bivalent IgG1 and IgG2 antibodies which recognize TNFRSF receptors, which are not adequately stimulated by soluble ligands, that they effectively act as agonists only if they are cross-linked by a second antibody or protein G in a secondary manner, or if these antibodies can simultaneously bind to cell-bound Fcγ receptors (FcγRs) (for review see Wajant 2015, Cell Death Differ. 2015 November; 22(11):1727-41, and FIGS. 2-3).

This can inter alia lead to the seemingly paradoxical situation that an antagonistic antibody which blocks ligand binding acts as a strong agonist upon binding to FcγRs, i.e. that not the recognized epitope but rather the form in which the antibody binds to its antigen is primarily responsible for the effect of the antibody (see FIG. 3D of Trebing et al., MAbs. 2014 January-February; 6(1):297-308, which is incorporated herein by reference in its entirety for all purposes). Further, the inventors have observed that IgG antibodies that recognize TNFRSF receptors which are already efficiently activated by soluble ligands generally act in an agonistic manner also without further cross-linking or FcγR binding (FIG. 2, see the panels containing the examples relating to αTNF1 and αLTßR).

The requirements for the agonistic activity of bivalent IgG antibodies that recognize TNFRSF receptors which are not stimulated by soluble TNF ligands and antibodies, respectively, complicate or even prevent their use in clinical approaches. Since the FcγR binding of such anti-TNFRSF receptor antibodies does not only result in the activation of the TNFRSF receptors but also stimulates Fcγ-receptors, unwanted effects can occur which complicate or even preclude a clinical use. The binding to activating FcγRs, may, for example, result in the removal/destruction of the TNFRSF receptor-expressing cell via ADCC, CDC or phagocytosis. In order to prevent this, IgG mutants can be used which interact with the inhibiting FcγR, CD32B, more strongly or preferably. However, the immune inhibitory activity of CD32B can be troublesome as well. More particularly, however, it is not guaranteed that a sufficient number of CD32B-expressing cells can always be found in the proximity of the target cells which express the targeted TNFRSF receptor. Although IgM antibodies and IgG3 antibodies, which are strongly prone to autoaggregation, can act in an agonistic manner in the absence of FcγR binding due to their high avidity—similar to soluble ligand trimers which have been oligomerized in a secondary manner—, the development of such antibodies is more laborious and less established than that of IgG1, IgG2 and IgG4 antibodies.

Therefore, there is a need for improved agents which target receptors of the TNFRSF. In particular, it would be desirable to obtain agents which effectively, and more reliably, target receptors of the TNFRSF, and which are less likely to have unwanted side effects than the existing TNFRSF-targeting agents.

DESCRIPTION OF THE INVENTION

The present invention solves the above problems and meets the above needs in the art.

Anti-TNFRSF receptor antibody fusion proteins according to the invention bind to cell-bound structures or to structures of the extracellular matrix in a manner that is independent of the antigen-binding domain of the antibody portion and of a possibly existing natural or mutated Fc domain. Surprisingly, the inventors have found for such fusion proteins that the anti-TNFRSF receptor antibody (or antigen-binding portion thereof) contained in these fusion proteins, after interaction with the targeted cellular structure or the extracellular matrix, acts as a strong agonist, i.e. in a TNFRSF receptor-stimulating manner, which is independent from FcγR binding (see, for instance, FIGS. 4-12 as a non-limiting example).

This is advantageous for several reasons: For example, a FcγR-independent stimulation is advantageous, because it is not limited to situations where FcγRs are expressed. Additionally, it is also advantageous, because side effects, which result from the stimulation of FcγRs, can be avoided. Such side effects include the removal/destruction of the TNFRSF receptor-expressing cell via ADCC, CDC or phagocytosis, and the immune inhibitory activity of the FcγR CD32B.

Thus, in one aspect, the present invention describes forms of antibody fusion proteins, which allow to efficiently stimulate receptors of the TNFRSF without binding to FcγRs. Upon suitable selection of the domain which is fused to the anti-TNFRSF receptor antibody, such tumor necrosis factor (TNF) receptor superfamily (TNFRSF)-receptor-activating antibody fusion proteins with FcγR-independent agonistic activity (TRAAFFIAAs) according to the invention can also be bifunctional and/or have prodrug-like properties. As referred to herein, "bifunctional" refers to the situation that the structure of the cell surface or extracellular matrix (e.g. the protein of the cell surface or extracellular matrix), when bound by the domain which is capable of binding to said structure in an FcγR-independent manner, is inhibited or stimulated. In such cases the TRAAFFIAA is bifunctional, because it not only activates TNFRSF receptor signalling but in addition modulates the activity of the targeted molecular structure. As referred to herein, prodrugs are activated by tumor-associated factors (e.g., enzymes, hypoxia). For example, a TRAAFFiAA targeting an tumor antigen acquires agonistic activity only in the tumor and thus acts like a prodrug.

From the work of the present inventors, is immediately evident that using an appropriately selected immobilization domain, which is used in a TRAAFFIAA, a local agonistic effect can be attained in vivo that is restricted to a target structure. It can thereby become possible to avoid systemic side effects that could be limiting to the therapy. TRAAFFIAAs therefore do not only advantageously stimulate TNFRSF receptors with antibodies in an FcγR-independent manner, but they also open up new fields of application, including clinical applications.

Thus, the present invention encompasses the following preferred embodiments:

1. A fusion protein, comprising:
   i) an anti-TNFRSF receptor antibody or an antigen-binding portion thereof, and
   ii) a domain which is capable of binding to a structure of the cell surface and/or to a structure of the extracellular matrix in an FcγR-independent manner.
2. The fusion protein according to item 1, wherein said structure is a structure of the cell surface of a TNFRSF receptor-expressing cell or a structure of the cell surface of a cell adjacent to a TNFRSF receptor-expressing cell.
3. The fusion protein according to item 1, wherein said structure is a structure of the extracellular matrix of a TNFRSF receptor-expressing cell or a structure of the extracellular matrix of a cell adjacent to a TNFRSF receptor-expressing cell.

4. The fusion protein according to item 2, wherein the structure is a cell surface protein or sugar, preferably a cell surface protein.
5. The fusion protein according to item 3, wherein the structure is an extracellular matrix protein or sugar, preferably an extracellular matrix protein.
6. The fusion protein according to any one of the preceding items, wherein the antibody or antigen-binding portion thereof according to i) is monoclonal.
7. The fusion protein according to any one of the preceding items, wherein the antibody or antigen-binding portion thereof according to i) is a full-length antibody, an Fab2 fragment, an Fab fragment or an antibody in which the VH and VL have been replaced by TNFRSF receptor-specific scFv fragments.
8. The fusion protein according to any one of the preceding items, wherein the antibody or antigen-binding portion thereof according to i) does not comprise an Fc domain.
9. The fusion protein according to any one of items 1-7, wherein the antibody or antigen-binding portion thereof according to i) is an antibody variant with reduced ability to bind to one or more FcγR types, preferably a full-length antibody comprising a N297A mutation.
10. The fusion protein according to any one of the preceding items, wherein the antibody or antigen-binding portion thereof according to i) is an IgG1, IgG2 or IgG4 antibody or antigen-binding portion thereof.
11. The fusion protein according to any one of the preceding items, wherein the antibody or antigen-binding portion thereof according to i) is a bivalent antibody or antigen-binding portion thereof.
12. The fusion protein according to any one of the preceding items, wherein the antibody or antigen-binding portion thereof according to I) is selected from the group consisting of an anti-TNFR2 antibody or antigen-binding portion thereof, an anti-CD40 antibody or antigen-binding portion thereof, an anti-CD95 antibody or antigen-binding portion thereof, an anti-Fn14 antibody or antigen-binding portion thereof, an anti-TRAILR2 antibody or antigen-binding portion thereof, an anti-TRAILR1 antibody or antigen-binding portion thereof, an anti-CD27 antibody or antigen-binding portion thereof, an anti-OX40 antibody or antigen-binding portion thereof, an anti-4-1BB antibody or antigen-binding portion thereof, an anti-BaffR antibody or antigen-binding portion thereof, an anti-TACT antibody or antigen-binding portion thereof, or an anti-BCMA antibody or antigen-binding portion thereof.
13. The fusion protein according to any one of the preceding items, wherein the antibody or antigen-binding portion thereof according to i) is selected from the group consisting of an anti-TNFR2 antibody or antigen-binding portion thereof, an anti-CD40 antibody or antigen-binding portion thereof, an anti-CD95 antibody or antigen-binding portion thereof, or an anti-Fn14 antibody or antigen-binding portion thereof.
14. The fusion protein according to any one of the preceding items, wherein the domain according to ii) comprises an scTNFSF ligand, and wherein said scTNFSF ligand is preferably a ligand of TNFR2, GITR, 4-1BB, BaffR, TACl, CD40, Fn14 or OX40,
15. The fusion protein according to any one of the preceding items, wherein the domain according to ii) comprises an antibody or an antigen-binding portion of an antibody, said antibody or antigen-binding portion being capable of binding to said structure of the cell surface and/or to said structure of the extracellular matrix.
16. The fusion protein according to item 15, wherein said antibody or antigen-binding portion capable of binding to said structure of the cell surface and/or to said structure of the extracellular matrix is a check point inhibitor antibody or antigen-binding portion thereof capable of binding to PD-L1, preferably Avelumab or a PD-L1-binding portion thereof.
17. The fusion protein according to item 15, wherein said antibody or antigen-binding portion capable of binding to said structure of the cell surface and/or to said structure of the extracellular matrix is an anti-CD27 antibody or antigen-binding portion thereof,
18. The fusion protein according to any one of items 15 to 17, wherein said antigen-binding portion capable of binding to said structure of the cell surface and/or to said structure of the extracellular matrix is an antigen-binding portion with reduced ability to bind to one or more FcγR types, preferably an Fab2 fragment, an scFv fragment or an Fab fragment, more preferably an scFv fragment or an Fab fragment.
19. The fusion protein according to any one of items 15 to 18, wherein said antigen-binding portion capable of binding to said structure of the cell surface and/or to said structure of the extracellular matrix is an Fab fragment,
20. The fusion protein according to any one of items 15 to 18, wherein said antigen-binding portion capable of binding to said structure of the cell surface and/or to said structure of the extracellular matrix is an scFv fragment.
21. The fusion protein according to any one of items 15 to 20, wherein said antigen-binding portion capable of binding to said structure of the cell surface and/or to said structure of the extracellular matrix or antigen-binding portion thereof is selected from the group consisting of an anti-CD20 antigen-binding portion, an anti-CD70 antigen-binding portion, an anti-CD19 antigen-binding portion, an anti-EGFR antigen-binding portion, an anti-Her2 antigen-binding portion, an anti-Fn14 antigen-binding portion, an anti-CD40L antigen-binding portion, or an anti-PD1L antigen-binding portion.
22. The fusion protein according to any one of the preceding items, wherein the domain according to ii) does not comprise an Fc domain.
23. The fusion protein according to any one of items 1-14, wherein the domain according to ii) does not comprise an antibody or antigen-binding fragment thereof.
24. The fusion protein according to any one of items 1-14 or 23, wherein said binding of the domain according to ii) to said structure of the cell surface and/or to said structure of the extracellular matrix is antigen-independent.
25. The fusion protein according to any one of items 1-16 and 18-24, wherein the domain according to ii) does not comprise anti-TNFRSF receptor antibody or antigen-binding portion thereof.
26. The fusion protein according to any one of the preceding items, wherein the domain according to ii) does comprise an interferon or an interleukin domain.
27. The fusion protein according to any one of the preceding items, wherein the domain according to ii) comprises, and preferably consists of, IL-2, IL-4, IL-10, IFNα, IFNβ or IFNγ, or comprises, and preferably consists of, a variant of IL-2, IL-4, IL-10, IFNα, IFNβ or IFNγ that is capable of binding to said structure of the cell surface and/or structure of the extracellular matrix in an FcγR-independent manner, and wherein said IL-2, IL-4, IL-10, IFNα, IFNβ or IFNγ is preferably human IL-2, human IL-4, human IL-10, human IFNα, human IRV or human IFNγ.

28. The fusion protein according to any one of the preceding items, wherein said fusion protein is capable of an increased stimulation of said TNFRSF receptor as compared to a protein comprising the anti-TNFRSF receptor antibody or an antigen-binding portion thereof according to i) but no domain according to ii).

29. A fusion protein of an anti-TNFRSF receptor antibody or an antigen-binding portion thereof, characterized in that it is capable of binding to a structure of the cell surface or to a structure of the extracellular matrix in an antigen- and FcγR-independent manner.

30. The fusion protein according to item 29, which is capable of an increased stimulation of the TNFRSF receptor upon binding to said structures.

31. The fusion protein according to item 29 or 30, said fusion protein being capable of binding to the TNFRSF receptors TNFR2, CD40, CD95, Fn14, TRAILR2, TRAILR1, CD27, OX40, 4-1BB, BaffR, TACl or BCMA.

32. The fusion protein according to any one of items 29 to 31, wherein said fusion protein is a fusion with an scFv domain capable of binding to said structure of the cell surface or to said structure of the extracellular matrix, or an scTNFSF ligand or other protein domain that is capable of binding to said structure of the cell surface or to said structure of the extracellular matrix.

33. The fusion protein according to any one of items 29 to 32, wherein said anti-TNFRSF receptor antibody or antigen-binding portion thereof is an $Fab_2$ or an Fab fragment.

34. The fusion protein according to any one of the preceding items, wherein said fusion protein is selected from a fusion protein comprising the amino acid sequences of SEQ ID NO: 19 and 23, a fusion protein comprising the amino acid sequences of SEQ ID NO: 21 and 23, a fusion protein comprising the amino acid sequences of SEQ ID NO: 22 and 23, a fusion protein comprising the amino acid sequences of SEQ ID NO: 24 and 31, a fusion protein comprising the amino acid sequences of SEQ ID NO: 25 and 31, a fusion protein comprising the amino acid sequences of SEQ ID NO: 26 and 31, a fusion protein comprising the amino acid sequences of SEQ 1D NO: 28 and 31, a fusion protein comprising the amino acid sequences of SEQ ID NO: 29 and 31, a fusion protein comprising the amino acid sequences of SEQ ID NO: 30 and 31, a fusion protein comprising the amino acid sequences of SEQ ID NO: 32 and 36, a fusion protein comprising the amino acid sequences of SEQ ID NO: 34 and 36, a fusion protein comprising the amino acid sequences of SEQ ID NO: 35 and 36, a fusion protein comprising the amino acid sequences of SEQ ID NO: 118 and 23, a fusion protein comprising the amino acid sequences of SEQ ID NO: 119 and 36, a fusion protein comprising the amino acid sequences of SEQ ID NO: 120 and 31, a fusion protein comprising the amino acid sequences of SEQ ID NO: 121 and 31, a fusion protein comprising the amino acid sequences of SEQ ID NO: 122 and 31, a fusion protein comprising the amino acid sequences of SEQ ID NO: 123 and 124, and a fusion protein comprising the amino acid sequences of SEQ ID NO: 125 and 36.

35. The fusion protein according to any one of items 1-33, wherein said anti-TNFRSF receptor antibody or antigen-binding portion thereof is an anti-CD40 antibody or antigen-binding portion thereof comprising a heavy chain comprising a CDR1 amino acid sequence according to SEQ ID NO: 37, a CDR2 amino acid sequence according to SEQ ID NO: 38, and the CDR3 amino acid sequence LDY, and comprising a light chain comprising a CDR1 amino acid sequence according to SEQ ID NO: 39, a CDR2 amino acid sequence according to SEQ ID NO: 40, and a CDR3 amino acid sequence according to SEQ ID NO: 41.

36. The fusion protein according to any one of items 1-33, wherein said anti-TNFRSF receptor antibody or antigen-binding portion thereof is an anti-CD95 antibody or antigen-binding portion thereof comprising a heavy chain comprising a CDR1 amino acid sequence according to SEQ ID NO: 42, a CDR2 amino acid sequence according to SEQ ID NO: 43, and a CDR3 amino acid sequence according to SEQ ID NO: 44, and comprising a light chain comprising a CDR1 amino acid sequence according to SEQ ID NO: 45, a CDR2 amino acid sequence according to SEQ ID NO: 46, and a CDR3 amino acid sequence according to SEQ ID NO: 47.

37. The fusion protein according to any one of items 1-33, wherein said anti-TNFRSF receptor antibody or antigen-binding portion thereof is an anti-DR5 antibody or antigen-binding portion thereof comprising a heavy chain comprising a CDR1 amino acid sequence according to SEQ ID NO: 48, a CDR2 amino acid sequence according to SEQ ID NO: 49, and a CDR3 amino acid sequence according to SEQ ID NO: 50, and comprising a light chain comprising a CDR1 amino acid sequence according to SEQ ID NO: 51, a CDR2 amino acid sequence according to SEQ ID NO: 52, and a CDR3 amino acid sequence according to SEQ ID NO: 53.

38. The fusion protein according to any one of items 1-33, wherein said anti-TNFRSF receptor antibody or antigen-binding portion thereof is an anti-Fn14 antibody or antigen-binding portion thereof comprising a heavy chain comprising a CDR1 amino acid sequence according to SEQ ID NO: 54, a CDR2 amino acid sequence according to SEQ ID NO: 55, and a CDR3 amino acid sequence according to SEQ ID NO: 56, and comprising a light chain comprising a CDR1 amino acid sequence according to SEQ ID NO: 57, a CDR2 amino acid sequence according to SEQ ID NO: 58, and a CDR3 amino acid sequence according to SEQ ID NO: 59.

39. The fusion protein according to any one of items 1-33, wherein said anti-TNFRSF receptor antibody or antigen-binding portion thereof is an anti-Fn14 antibody or antigen-binding portion thereof comprising a heavy chain comprising a CDR1 amino acid sequence according to SEQ ID NO: 84, a CDR2 amino acid sequence according to SEQ ID NO: 85, and a CDR3 amino acid sequence according to SEQ ID NO: 86, and comprising a light chain comprising a CDR1 amino acid sequence according to SEQ ID NO: 87, a CDR2 amino acid sequence according to SEQ ID NO: 88, and a CDR3 amino acid sequence according to SEQ ID NO: 89.

40. The fusion protein according to any one of items 1-33, wherein said anti-TNFRSF receptor antibody or antigen-binding portion thereof is an anti-TNFR2 antibody or antigen-binding portion thereof comprising a heavy chain comprising a CDR1 amino acid sequence according to SEQ ID NO: 60, a CDR2 amino acid sequence according to SEQ ID NO: 61, and a CDR3 amino acid sequence according to SEQ ID NO: 62, and comprising a light chain comprising a CDR1 amino acid sequence according to SEQ ID NO: 63, a CDR2 amino acid sequence according to SEQ ID NO: 64, and a CDR3 amino acid sequence according to SEQ ID NO: 65.

41. The fusion protein according to any one of items 1-33, wherein said anti-TNFRSF receptor antibody or antigen-binding portion thereof is an anti-4-1BB antibody or antigen-binding portion thereof comprising a heavy chain comprising a CDR1 amino acid sequence according to SEQ ID NO: 126, a CDR2 amino acid sequence according to SEQ ID NO: 127, and a CDR3 amino acid sequence according to SEQ ID NO: 128, and comprising a light chain comprising a CDR1 amino acid sequence according to SEQ ID NO: 129, a CDR2 amino acid sequence according to SEQ ID NO: 130, and a CDR3 amino acid sequence according to SEQ ID NO: 131.

42. The fusion protein according to any one of items 1-33, wherein said anti-TNFRSF receptor antibody or antigen-binding portion thereof is HBBK4 or a 4-1BB-binding portion thereof.

43. The fusion protein according to any one of items 1-33, wherein said anti-TNFRSF receptor antibody or antigen-binding portion thereof is an anti-4-1BB antibody or antigen-binding portion thereof comprising a heavy chain comprising a CDR1 amino acid sequence according to SEQ ID NO: 132, a CDR2 amino acid sequence according to SEQ ID NO: 133, and a CDR3 amino acid sequence according to SEQ ID NO: 134, and comprising a light chain comprising a CDR1 amino acid sequence according to SEQ ID NO: 135, a CDR2 amino acid sequence according to SEQ ID NO: 136, and a CDR3 amino acid sequence according to SEQ ID NO: 137.

44. The fusion protein according to any one of items 1-33, wherein said anti-TNFRSF receptor antibody or antigen-binding portion thereof is urelumab or a 4-1BB-binding portion thereof.

45. The fusion protein according to any one of items 1-33, wherein said anti-TNFRSF receptor antibody or antigen-binding portion thereof is an anti-4-1BB antibody or antigen-binding portion thereof comprising a heavy chain comprising a CDR1 amino acid sequence according to SEQ ID NO: 138, a CDR2 amino acid sequence according to SEQ ID NO: 139, and a CDR3 amino acid sequence according to SEQ ID NO: 140, and comprising a light chain comprising a CDR1 amino acid sequence according to SEQ ID NO: 141, a CDR2 amino acid sequence according to SEQ ID NO: 142, and a CDR3 amino acid sequence according to SEQ ID NO: 143.

46. The fusion protein according to any one of items 1-33, wherein said anti-TNFRSF receptor antibody or antigen-binding portion thereof is utomilumab or a 4-1BB-binding portion thereof.

47. The fusion protein according to any one of items 1-33, wherein said anti-TNFRSF receptor antibody or antigen-binding portion thereof is an antibody or antigen-binding portion thereof which is capable of cross-competing with the anti-TNFRSF receptor antibody according to item 35 for binding to CD40.

48. The fusion protein according to any one of items 1-33, wherein said anti-TNFRSF receptor antibody or antigen-binding portion thereof is an antibody or antigen-binding portion thereof which is capable of cross-competing with the anti-TNFRSF receptor antibody according to item 36 for binding to CD95.

49. The fusion protein according to any one of items 1-33, wherein said anti-TNFRSF receptor antibody or antigen-binding portion thereof is an antibody or antigen-binding portion thereof which is capable of cross-competing with the anti-TNFRSF receptor antibody according to item 37 for binding to DR5.

50. The fusion protein according to any one of items 1-33, wherein said anti-TNFRSF receptor antibody or antigen-binding portion thereof is an antibody or antigen-binding portion thereof which is capable of cross-competing with the anti-TNFRSF receptor antibody according to item 38 for binding to Fn14.

51. The fusion protein according to any one of items 1-33, wherein said anti-TNFRSF receptor antibody or antigen-binding portion thereof is an antibody or antigen-binding portion thereof which is capable of cross-competing with the anti-TNFRSF receptor antibody according to item 39 for binding to Fn14.

52. The fusion protein according to any one of items 1-33, wherein said anti-TNFRSF receptor antibody or antigen-binding portion thereof is an antibody or antigen-binding portion thereof which is capable of cross-competing with the anti-TNFRSF receptor antibody according to item 40 for binding to TNFR2.

53. The fusion protein according to any one of items 1-33, wherein said anti-TNFRSF receptor antibody or antigen-binding portion thereof is an antibody or antigen-binding portion thereof which is capable of cross-competing with the anti-TNFRSF receptor antibody according to item 41 for binding to 4-1BB.

54. The fusion protein according to any one of items 1-33, wherein said anti-TNFRSF receptor antibody or antigen-binding portion thereof is an antibody or antigen-binding portion thereof which is capable of cross-competing with the anti-TNFRSF receptor antibody according to item 42 for binding to 4-1BB.

55. The fusion protein according to any one of items 1-33, wherein said anti-TNFRSF receptor antibody or antigen-binding portion thereof is an antibody or antigen-binding portion thereof which is capable of cross-competing with the anti-TNFRSF receptor antibody according to item 43 for binding to 4-1BB.

56. The fusion protein according to any one of items 1-33, wherein said anti-TNFRSF receptor antibody or antigen-binding portion thereof is an antibody or antigen-binding portion thereof which is capable of cross-competing with the anti-TNFRSF receptor antibody according to item 44 for binding to 4-1BB.

57. The fusion protein according to any one of items 1-33, wherein said anti-TNFRSF receptor antibody or antigen-binding portion thereof is an antibody or antigen-binding portion thereof which is capable of cross-competing with the anti-TNFRSF receptor antibody according to item 45 for binding to 4-1BB.

58. The fusion protein according to any one of items 1-33, wherein said anti-TNFRSF receptor antibody or antigen-binding portion thereof is an antibody or antigen-binding portion thereof which is capable of cross-competing with the anti-TNFRSF receptor antibody according to item 46 for binding to 4-1BB.

59. The fusion protein according to any one of items 1-28 and 35-58, wherein the domain according to ii) comprises an antibody or antigen-binding portion thereof, said antibody or antigen-binding portion thereof being capable of binding to said structure of the cell surface and/or to said structure of the extracellular matrix, and wherein said antibody or antigen-binding portion thereof is an anti-CD20 antibody or antigen-binding portion thereof comprising a heavy chain comprising a CDR1 amino acid sequence according to SEQ ID NO: 66, a CDR2 amino acid sequence according to SEQ ID NO: 67, and a CDR3 amino acid sequence according to SEQ ID NO: 68, and comprising a light chain comprising a CDR1 amino acid sequence according to SEQ ID NO: 69, a CDR2 amino acid sequence according to SEQ ID NO: 70, and a CDR3 amino acid sequence according to SEQ ID NO: 71, 60. The fusion protein according to any one of items 1-28 and 35-58, wherein the domain according to ii) comprises an antibody or antigen-binding portion thereof, said antibody or antigen-binding portion thereof being capable of binding to said structure of the cell surface and/or to said structure of the extracellular matrix, and wherein said antibody or antigen-binding portion thereof is an anti-CD19 antibody or antigen-binding portion thereof comprising a heavy chain comprising a CDR1 amino acid sequence according to SEQ ID NO: 72, a CDR2 amino acid sequence according to SEQ ID NO: 73, and a CDR3 amino acid sequence according to SEQ ID NO: 74, and comprising a light chain comprising a CDR1 amino acid sequence according to SEQ ID NO: 75, a CDR2 amino acid sequence according to SEQ ID NO: 76, and a CDR3 amino acid sequence according to SEQ ID NO: 77.

61. The fusion protein according to any one of items 1-28 and 35-58, wherein the domain according to ii) comprises an antibody or antigen-binding portion thereof, said antibody or antigen-binding portion thereof being capable of binding to said structure of the cell surface and/or to said structure of the extracellular matrix, and wherein said antibody or antigen-binding portion thereof is an anti-CD70 antibody or antigen-binding portion thereof comprising a heavy chain comprising a CDR1 amino acid sequence according to SEQ ID NO: 78, a CDR2 amino acid sequence according to SEQ ID NO: 79, and a CDR3 amino acid sequence according to SEQ ID NO: 80, and comprising a light chain comprising a CDR1 amino acid sequence according to SEQ ID NO: 81, a CDR2 amino acid sequence according to SEQ 1D NO: 82, and a CDR3 amino acid sequence according to SEQ ID NO: 83.

62. The fusion protein according to any one of items 1-28 and 35-58, wherein the domain according to ii) comprises an antibody or antigen-binding portion thereof, said antibody or antigen-binding portion thereof being capable of binding to said structure of the cell surface and/or to said structure of the extracellular matrix, and wherein said antibody or antigen-binding portion thereof is an anti-CD70 antibody or antigen-binding portion thereof comprising a heavy chain comprising a CDR1 amino acid sequence according to SEQ ID NO: 90, a CDR2 amino acid sequence according to SEQ ID NO: 91, and a CDR3 amino acid sequence according to SEQ ID NO: 92, and comprising a light chain comprising a CDR1 amino acid sequence according to SEQ ID NO: 93, a CDR2 amino acid sequence according to SEQ ID NO: 94, and a CDR3 amino acid sequence according to SEQ ID NO: 95.

63. The fusion protein according to any one of items 1-28 and 35-58, wherein the domain according to ii) comprises an antibody or antigen-binding portion thereof, said antibody or antigen-binding portion thereof being capable of binding to said structure of the cell surface and/or to said structure of the extracellular matrix, and wherein said antibody or antigen-binding portion thereof is a) an anti-CD20 antibody or antigen-binding portion thereof which is capable of cross-competing with the anti-CD20 antibody according to item 59 for binding to CD20 or b) an anti-CD19 antibody or antigen-binding portion thereof which is capable of cross-competing with the anti-CD19 antibody according to item 60 for binding to CD19 or c) an anti-CD70 antibody or antigen-binding portion thereof which is capable of cross-competing with the anti-CD70 antibody according to item 61 for binding to CD70 or d) an anti-CD70 antibody or antigen-binding portion thereof which is capable of cross-competing with the anti-CD70 antibody according to item 62 for binding to CD70.

64, The fusion protein according to any one of items 1-28 and 35-63, wherein the domain according to ii) comprises an antigen-binding portion of an antibody, said antigen-binding portion being capable of binding to said structure of the cell surface and/or to said structure of the extracellular matrix, and wherein said antigen-binding portion capable of binding to said structure of the cell surface and/or to said structure of the extracellular matrix is an anti-CD20 scFv fragment comprising the amino acid sequence of SEQ ID NO: 96 or an anti-CD20 scFv fragment comprising an amino acid sequence at least 90% identical to the amino acid sequence of SEQ ID NO: 96.

65. The fusion protein according to any one of items 1-28 and 35-63, wherein the domain according to ii) comprises an antigen-binding portion of an antibody, said antigen-binding portion being capable of binding to said structure of the cell surface and/or to said structure of the extracellular matrix, and wherein said antigen-binding portion capable of binding to said structure of the cell surface and/or to said structure of the extracellular matrix is an anti-CD19 scFv fragment comprising the amino acid sequence of SEQ ID NO: 98 or an anti-CD19 scFv fragment comprising an amino acid sequence at least 90% identical to the amino acid sequence of SEQ ID NO: 98.

66. The fusion protein according to any one of items 1-28 and 35-63, wherein the domain according to ii) comprises an antigen-binding portion of an antibody, said antigen-binding portion being capable of binding to said structure of the cell surface and/or to said structure of the extracellular matrix, and wherein said antigen-binding portion capable of binding to said structure of the cell surface and/or to said structure of the extracellular matrix is an anti-CD70 scFv fragment comprising the amino acid sequence of SEQ ID NO: 144 or an anti-CD70 scFv fragment comprising an amino acid sequence at least 90% identical to the amino acid sequence of SEQ ID NO: 144.

67. The fusion protein according to any one of items 1-28 and 35-63, wherein the domain according to ii) comprises an antigen-binding portion of an antibody, said antigen-binding portion being capable of binding to said structure of the cell surface and/or to said structure of the extracellular matrix, and wherein said antigen-binding portion capable of binding to said structure of the cell surface and/or to said structure of the extracellular matrix is an anti-CD70 scFv fragment comprising the amino acid sequence of SEQ ID NO: 145 or an anti-CD70 scFv fragment comprising an amino acid sequence at least 90% identical to the amino acid sequence of SEQ ID NO: 145.

68. The fusion protein according to any one of items 1-28 and 35-58, wherein the domain according to ii) comprises an scTNFSF ligand, and wherein said scTNFSF ligand is a ligand of TNFR2, said ligand being an scTNF80 having the amino acid sequence of SEQ ID NO: 102 or an amino acid sequence at least 90% identical thereto.
69. The fusion protein according to any one of items 1-28 and 35-58, wherein the domain according to ii) comprises an scTNFSF ligand, and wherein said scTNFSF ligand is an scBaff having the amino acid sequence of SEQ ID NO: 103 or an amino acid sequence at least 90% identical thereto.
70. The fusion protein according to any one of items 1-28 and 35-58, wherein the domain according to ii) comprises an scTNFSF ligand, and wherein said scTNFSF ligand is an scGITRL having the amino acid sequence of SEQ ID NO: 104 or an amino acid sequence at least 90% identical thereto.
71. The fusion protein according to any one of items 1-28 and 35-58, wherein the domain according to ii) comprises an scTNFSF ligand, and wherein said scTNFSF ligand is an sc41BBL having the amino acid sequence of SEQ ID NO: 105 or an amino acid sequence at least 90% identical thereto.
72. The fusion protein according to any one of items 1-28 and 35-58, wherein the domain according to ii) comprises a TNFSF ligand, and wherein said TNFSF ligand is a GITRL having the amino acid sequence of SEQ ID NO: 106 or an amino acid sequence at least 90% identical thereto.
73. The fusion protein according to any one of the preceding items, wherein said structure of the cell surface or structure of the extracellular matrix is a structure of the cell surface or structure of the extracellular matrix of an immune cell.
74. The fusion protein according to any one of the preceding items, wherein said structure of the cell surface or structure of the extracellular matrix is a structure of the cell surface or structure of the extracellular matrix of a fibroblast.
75. The fusion protein according to any one of the preceding items, wherein said structure of the cell surface or structure of the extracellular matrix is a structure of the cell surface or structure of the extracellular matrix of a tumor cell.
76. A composition comprising a fusion protein according to any one of the preceding items, for use in medicine.
77. A nucleic acid, or a set of nucleic acids, encoding the fusion protein according to any one of items 1-75.
78. A method for producing a fusion protein according to any one of items 1-75, the method comprising expressing the nucleic acid or set of nucleic acids according to item 77 in at least one type of host cells, and harvesting the fusion protein.

BRIEF DESCRIPTION OF THE DRAWINGS

FIG. 1: The ligands and receptors of the TNFSF and TNFRSF.

Material & Methods: Hek293 cells (ATCC) which do not (or only moderately) express the indicated TNFRSF receptors and FcγRs were transiently transfected with pCMV-SPORT6 (Source Bicoscience) expression plasmids encoding murine FcγR2B or empty vector. Transfection of Hek293 cells with the FcγR expression plasmid or empty vector was performed using polyethylenimine (PEI) as described in Kums et al., MAbs. 2017 April; 9(3):506-520. Next day, Hek293 transfectants were harvested and aliquots of 20.000 cells were added to the wells of a 96-well plate in which the previous day cells have been seeded (10000-20000 cells/well) that respond to activation of the TNFRSF receptor of interest with IL8 production. The co-cultures were then stimulated overnight in triplicates with the indicated anti-TNFRSF receptor antibodies (3 μg/ml) and finally co-culture supernatants were evaluated by ELISA (BD Biosciences) for their IL8 content.

Figure 3:
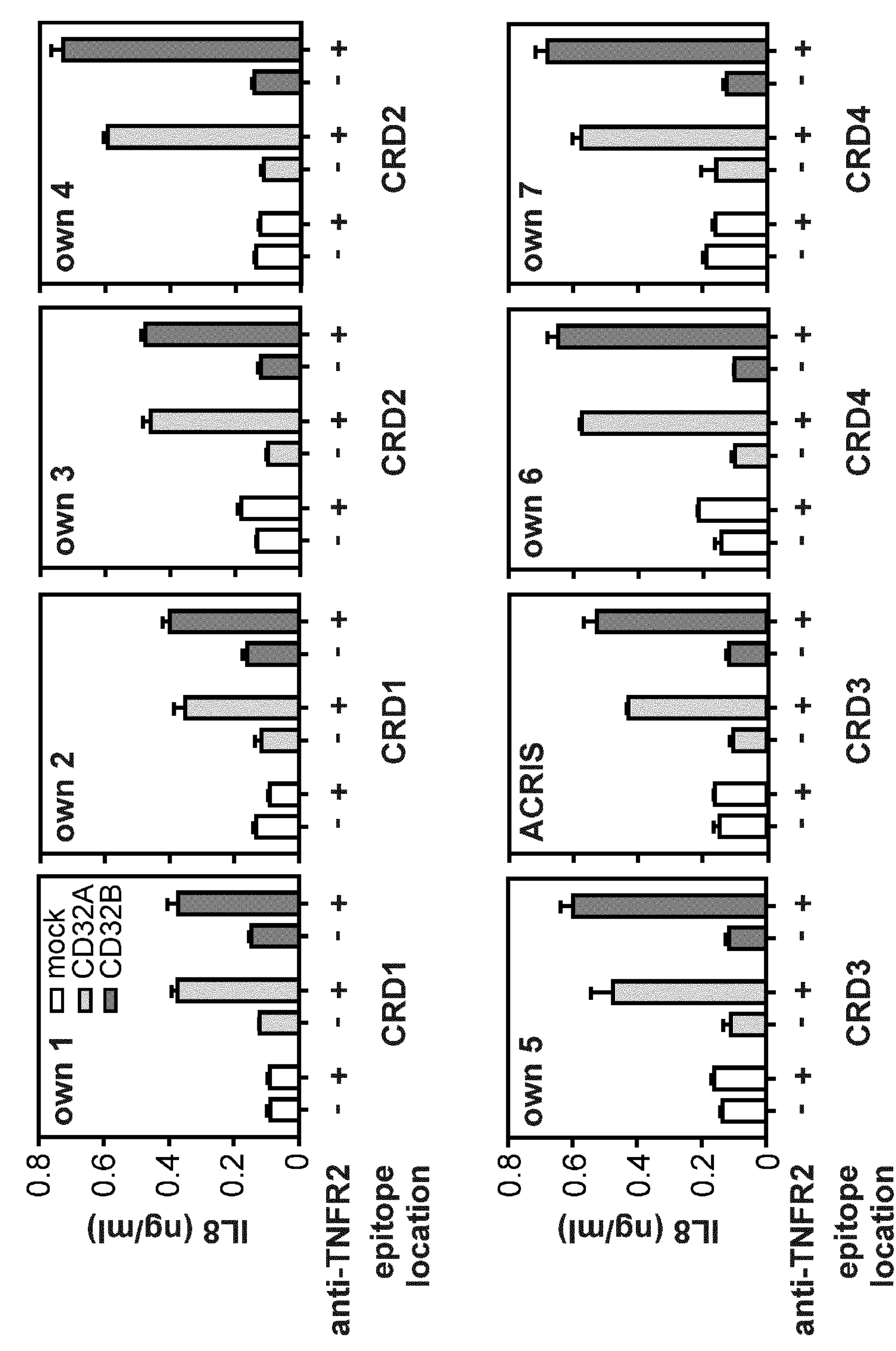

FIG. 3: FcγR-dependent stimulation of the TNFRSF receptor TNFR2 by receptor-specific IgGs. Hek293 cells transfected either with expression plasmids of the indicated FcγRs or with an empty vector were co-cultured with cells in which the stimulation of TNFR2 induces the production of IL8. After incubation with the indicated TNFR2-specific IgGs overnight, the production of IL8 was captured using ELISA.

Material & Methods: Hek293 cells (ATCC) which do not express TNFR2 or FcγRs were transiently transfected with pCMV-SPORT6 (Source Bicoscience) expression plasmids encoding the human activating FcγR CD32A (FcγR2IIA), the human inhibitory FcγR CD32B (FcγRIIB) or empty vector. Transfection of Hek293 cells with the FcγR expression plasmids or empty vector was performed using polyethylenimine (PEI) as described in Kums et al., MAbs. 2017 April; 9(3):506-520. Next day, Hek293 transfectants were harvested and aliquots of 20.000 cells were added to the wells of a 96-well plate in which the previous day HT1080 cells with stable expression of TNFR2 have been seeded at a density of 20000 cells/well. The cocultures were then stimulated overnight in triplicates with the indicated anti-human TNFR2 antibodies (1 μg/ml) which have been generated and produced in-house. The cysteine rich domain (CRD) subdomain of TNFR2 recognized by the antibodies is indicated (CRD1-CRD4). TNFR2 activation in the cells used result in enhanced IL8 production. Thus, to determine TNFR2 activity the IL8 content of the co-culture supernatants were finally evaluated by ELISA (BD Biosciences).

Figure 4:
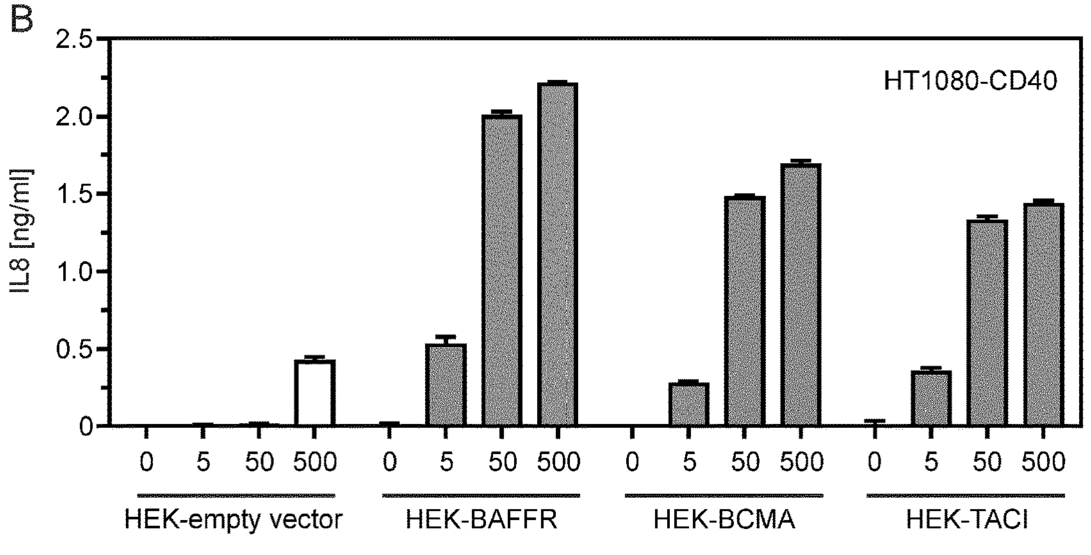

FIG. 4: An scBaff fusion protein of the anti-CD40 IgG1 G28.5 exhibits an increased CD40-stimulating activity after binding to BaffR, TACl or BCMA. (A) Structure of the fusion protein. (B). Hek293 cells were transfected with an empty vector and with expression plasmids encoding BaffR BCMA and TAU, respectively. On the next day, the transfectants were co-cultured with HT1080-CD40 cells, which do not express BaffR, BCMA and TACl but which strongly produce IL8 after CD40 stimulation. Cocultures were stimulated in triplicates with the indicated concentrations of anti-CD40(G28.5)-HC:scBaff. On the next day, the amount of human IL8 was determined in the supernatants of the different co-cultures. (C) Hek293 cells (BaffR, BCMA and TACl negative) and L363 cells expressing BaffR and TACl were co-cultured with HT1080-CD40 cells and the co-cultures were then stimulated with the indicated concentrations of anti-CD40(G28.5)-HC:scBaff. On the next day, the amount of human IL8 was again determined in the supernatants of the co-cultures. Please note, the three protomers of Baff in scBaff comprises only the extracellular TNF homology domain of the full length Baff molecule.

Material & Methods: Hek293 cells which do not express CD40, BaffR, TACl or BCMA were transiently transfected with expression plasmid encoding BaffR, TAD and BCMA or empty vector (=negative control) as described in Kums et al., MAbs. 2017 April; 9(3):506-520 for Hek293 cells and FcgR expression vectors. Transfectants were harvested and aliquots of 30.000 cells were added to the wells of a 96-well plate in which the previous day HT1080-CD40 cells (HT1080 cells stably transfected with CD40) have been seeded at a density of 20000 cells/well. Alternatively HT1080-CD40 cells were co-cultivated with 50.000 cells/well of the myeloma cell line L363 which expresses endogenously BaffR and TAU The HT1080-CD40 cells produce high amounts in response to CD40 activation, Co-cultures were stimulated overnight in triplicates with the TRAAF-FIAA anti-CD40(G28.5)-IgG1(N297)-scBaff and finally IL8 production was determined by ELISA.

FIG. 5: A scBaff fusion protein of the anti-CD95 IgG1 E09 exhibits an increased CD95-stimulating activity after binding to BaffR, TACl or BCMA. (A) Structure of the fusion protein. (B). Hek293 cells were transfected with an empty vector or with expression plasmids encoding Baff, BCMA and TACl. On the next day, the transfectants were co-cultured with HT1080 cells, which do not express BaffR, BCMA and TACl and which undergo apoptosis after CD95 stimulation. Co-cultures were treated with the indicated concentrations of anti-CD95(E09)-HC:scBaff and the next day viability of the adherently growing HT1080 cells were evaluated by crystal violet staining. (C) Hek293 cells (BaffR, BCMA and TACl negative) and L363 cells expressing BaffR and TACl were co-cultured with HT1080 cells. The co-cultures were again stimulated with anti-CD95 (E09)-HC:scBaff overnight and HT1080 viability was finally evaluated by crystal violet staining. Please note, the three protomers of Baff in scBaff comprises only the extracellular TNF homology domain of the full length Baff molecule.

Material & Methods: Hek293 cells which do not express BaffR, TACl or BCMA and neglectable amounts of CD95 were transiently transfected with expression plasmid encoding BaffR, TACl and BCMA or empty vector (=negative control) as described in Kums et al., MAbs. 2017 April; 9(3):506-520 for Hek293 cells and FcgR expression vectors. Transfectants were harvested and aliquots of 30.000 cells were added to the wells of a 96-well plate in which the previous day HT1080 cells have been seeded at a density of 20000 cells/well. Alternatively HT1080 cells were co-cultivated with 50.000 cells/well of the myeloma cell line L363 which expresses endogenously BaffR and TACl. HT1080 cells are sensitive for CD95-induced cell death in the absence of sensitizing agents. Co-cultures were stimulated overnight in triplicates with the TRAAFFIAA anti-CD95 (E09)-IgG1(N297)-scBaff and finally cell death induction was determined by crystal violet staining of the adherently growing HT1080 cells.

Figure 6:
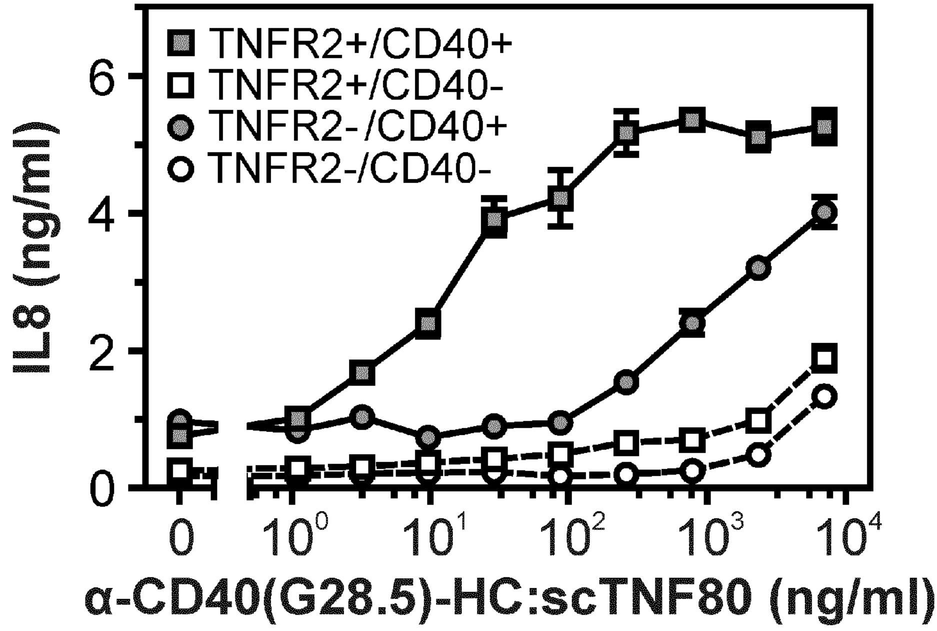

FIG. 6: A TNFR2-binding anti-CD40-IgG1 fusion protein has an increased CD40-stimulating activity after TNFR2 binding. HeLa cells, which neither express TNFR2 nor CD40, and HeLa-TNFR2 transfectants, which produce only moderate levels of IL8 after stimulation of the TNFR2, were co-cultured with HT1080 cells, which neither express TNFR2 nor CD40, and with HT1080-CD40 transfectants, which produce very high levels of IL8 after CD40 stimulation, and they were stimulated with the indicated concentrations of the TNFR2-targeting anti-CD40 fusion protein anti-CD40(G28.5)-HC:scTNF80. On the next day, the amount of IL8 was determined in the supernatants of the different co-cultures. Please note, the three protomers of TNF80 in scTNF80 comprises only the extracellular TNF homology domain of the full length murine TNF molecule including the TNFR2-specificity conferring mutations. As before assays were performed in technical triplicates in 96-well format.

Figure 7:
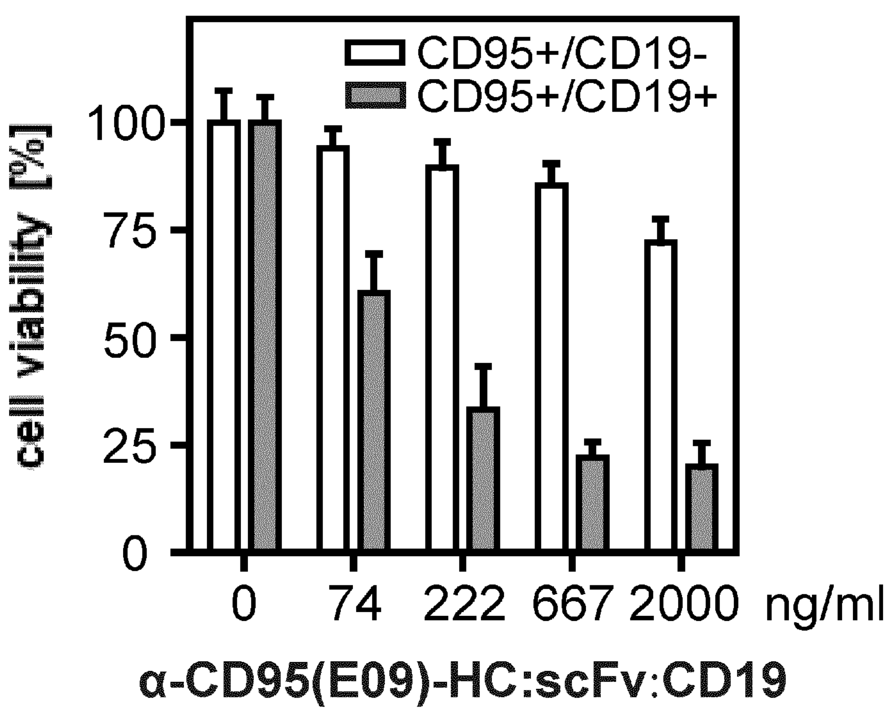

FIG. 7: A CD19-binding anti-CD95-IgG1-fusion protein shows an increased induction of cell death in HT1080 cells in co-culture with CD19-expressing cells. The CD95-sensitive cell line HT1080 which does not express CD19 was co-cultured with Jurkat (CD19-negative) cells and BJAB (CD19-positive) cells and incubated with the CD19-binding anti-CD95 fusion protein anti-CD95(E09)-HC:scFv:CD19 at the indicated concentrations. On the next day, the viability of the adherently growing HT1080 cells was determined by crystal violet staining.

Material & Methods; Assays were performed in technical triplicates in 96-well plates. HT1080 cells were seeded with 20000 cells per well. Jurkat and BJAB cells (30000 per well) were added the next together with the indicated concentration of anti-CD95(E09)-HC:scFv:CD19. Cell death induction was determined by crystal violet staining of the adherently growing HT1080 cells. Viability was normalized by help of untreated HT1080 cells (=100% viability) and HT1080 cells treated with a highly toxic mixture containing CHX, Velcade, and Fc-CD95L (=0 viability).

Figure 8:
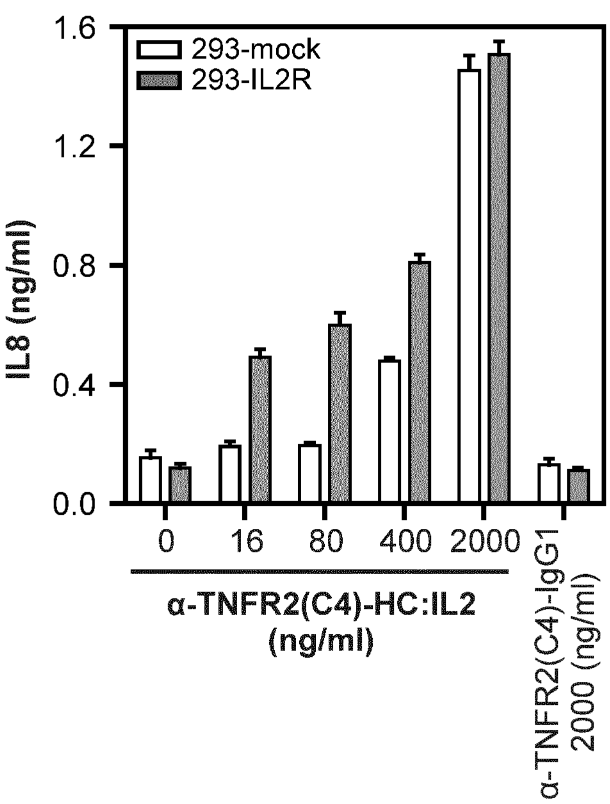

FIG. 8: An IL2 fusion protein of the TNFR2-specific antibody C4 increasingly stimulates TNFR2 in an IL2R-dependent manner. Hek293 cells, which neither express TNFR2 nor IL2R, were transfected with a mix of expression plasmids, which encode the subunits of IL2R, or with an empty vector. The Hek293 transfectants were then co-cultured with TNFR2-expressing HeLa transfectants and stimulated with the indicated concentrations of anti-TNFR2 (C4)-HC:IL2. On the next day, the production of IL8, which can be induced via TNFR2, was captured using ELISA.

Material & Methods: Hek293 cells were transiently transfected with a mixture of expression plasmids encoding the subunits of the IL-2 receptor or with empty vector as negative control as described in Kums et al., MAbs. 2017 April; 9(3):506-520 for Hek293 cells and FcgR expression vectors. Transfectants were harvested and aliquots of 20.000 cells were added to the wells of a 96-well plate in which the previous day HeLa-TNFR2 cells have been seeded at a density of 20000 cells/well. The HeLa-TNFR2 cells produce IL8 in response to TNFR2 activation. Co-cultures were stimulated overnight in triplicates with the TRAAFFIAA anti-TNFR2(C4)-HC:IL2 and finally 1L8 production was determined by ELISA.

FIG. 9: GITR- and 41BB-anchoring fusion proteins of the TNFR2-specific antibody C4 show enhanced TNFR2 activation upon GITR and 41BB binding. (A) Domain architecture of the human GITR and murine 4-1BB anchoring TNFR2-stimulating TRAAFFIAAs used. (B,C) Cells, which neither express GITR or 41BB, were transfected with empty vector or expression plasmids encoding human GITR (B) or murine 41BB (C). Transfectants were then co-cultured with HeLa-TNFR2 cells which produce IL8 in response to TNFR2 activation. Co-cultures were stimulated with the indicated concentrations of anti-TNFR2(C4)-HC:scGITRL (B) and anti-TNFR2(C4)-HC:sc(mu)4-1BBL (C). On the next day, the production of IL8 was determined using an IL8-specific ELISA. (D) Domain architecture of the murine GITR anchoring TNFR2-stimulating TRAAFFIAA used. (E) Cells transfected with empty vector or an murine GITR expression plasmid were co-cultivated with HeLa-TNFR2 cells. After stimulation with anti-TNFR2(C4)-HC:(mu) GITRL the production of IL8 was monitored the next day by ELISA. Please note, murine GITRL, in contrast to human GITRL and all other human and murine ligands of the TNFSF, is a dimeric molecule and interact with two instead of three receptor molecules. Thus, a single murine GITRL protomer is fused to the C-terminus of the heavy chain to allow the constitution of a single (mu)GITRL dimer acting as the anchoring domain of the corresponding antibody-(mu) GITRL. In contrast, the use of scTNFSF ligands (e.g. scGITRL, sc(mu)41BBL, scTNF80) as anchoring domains fused to the heavy chain results in two anchoring domains per antibody fusion protein. Please note, the three protomers of GITRL and (mu)41BBL in scGITRL and sc(mu)41BBL comprise only the extracellular TNF homology domain of the full length ligand molecules. Likewise (mu)GITRL only refers to the THD of murine fill length murine GITRL.

Material & Methods: Hek293 cells which do not express GITR, 41BB or TNFR2 were transiently transfected with expression plasmids encoding human or murine GITR or murine 41BB or empty vector (=negative control) as described in Kums et al., MAbs. 2017 April; 9(3):506-520 for Hek293 cells and FcgR expression vectors. Transfectants were harvested and aliquots of 20000 cells were added to the wells of a 96-well pleLa-TNFR2 have been seeded at a density of 20000 cells/well. The HeLa-TNFR2 cells produce 1L8 in response to TNFR2 activation. Co-cultures were stimulated overnight in triplicates with the indicated TRAAFFIAAs and finally IL8 production was determined by ELISA.

FIG. 10: A scFv fusion protein of the CD40-specific antibody G28.5 that anchor to the cell surface antigen CD20 increasingly stimulate CD40 in a CD20)-dependent manner. CD20-negative Jurkat and CD20-positive BJAB cells were co-cultured with CD40-responsive HT1080-CD40 cells and stimulated with the indicated concentrations of anti-CD40 (G28.5)-HC:scFv:CD20. On the next day, the production of IL8, which can be induced via CD40, was captured using ELISA. A variant of the IgG1 molecule with the N297A mutation which dampens the ADCC activity of the Fc domain in vivo were used, Material & Methods: Assays were performed in technical triplicates in 96-well plates. HT1080-CD40 cells were seeded with 20000 cells per well. Jurkat (CD20-) and BJAB cells (CD20+) (30000 per well) were added the next day together with the indicated concentrations of anti-CD40-HC:scFv:CD20. The IL8 content of the co-culture supernatants were finally evaluated by ELISA (BD Biosciences).

Figure 11:
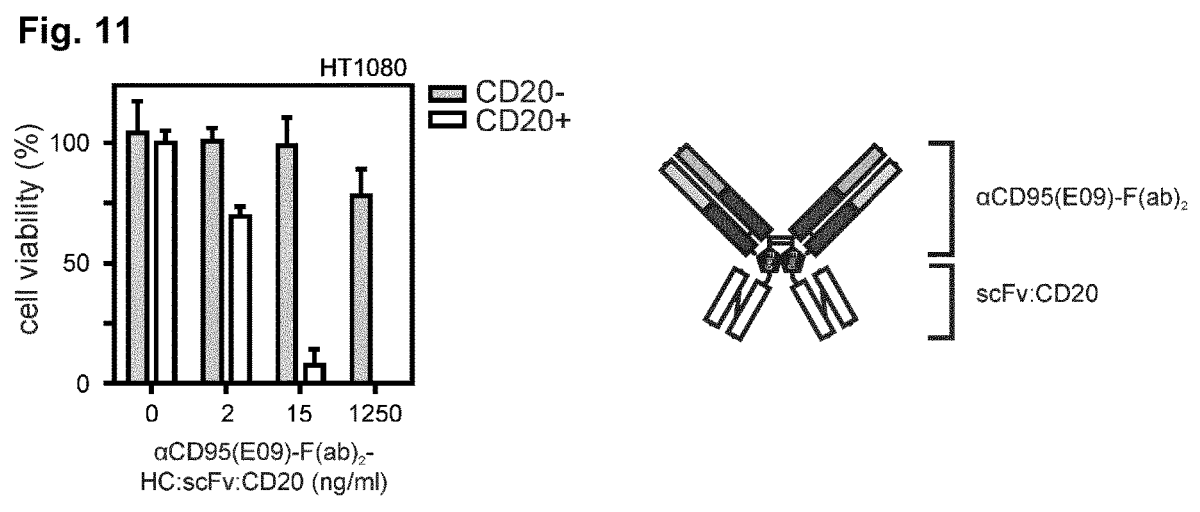

FIG. 11: A scFv:CD20 fusion protein of the anti-CD95-IgG1 $Fab_2$ fragment of the antibody E09 show an increased induction of cell death in HT1080 cells in co-culture with CD20-expressing cells. The CD95-sensitive cell line HT1080 was co-cultured with Jurkat (CD20-negative) cells and with BJAB-cells (CD20-positive). Co-cultures were treated with the CD20-binding anti-CD95 fusion protein anti-CD95-Fab2-HC:scFv:CD20 at the indicated concentrations. On the next day, the viability of the adherently growing HT1080 cells was determined by crystal violet staining.

Material & Methods: Assays were performed in technical triplicates in 96-well plates. HT1080 cells were seeded with 20000 cells per well. Jurkat and BJAB cells (30000 per well) were added the next together with the indicated TRAAFFIAA. HT1080 viability was normalized by help of untreated HT1080 cells (=100% viability) and HT1080 cells treated with a highly toxic mixture containing CHX, Velcade, and Fc-CD95L (=0 viability).

Figure 12:
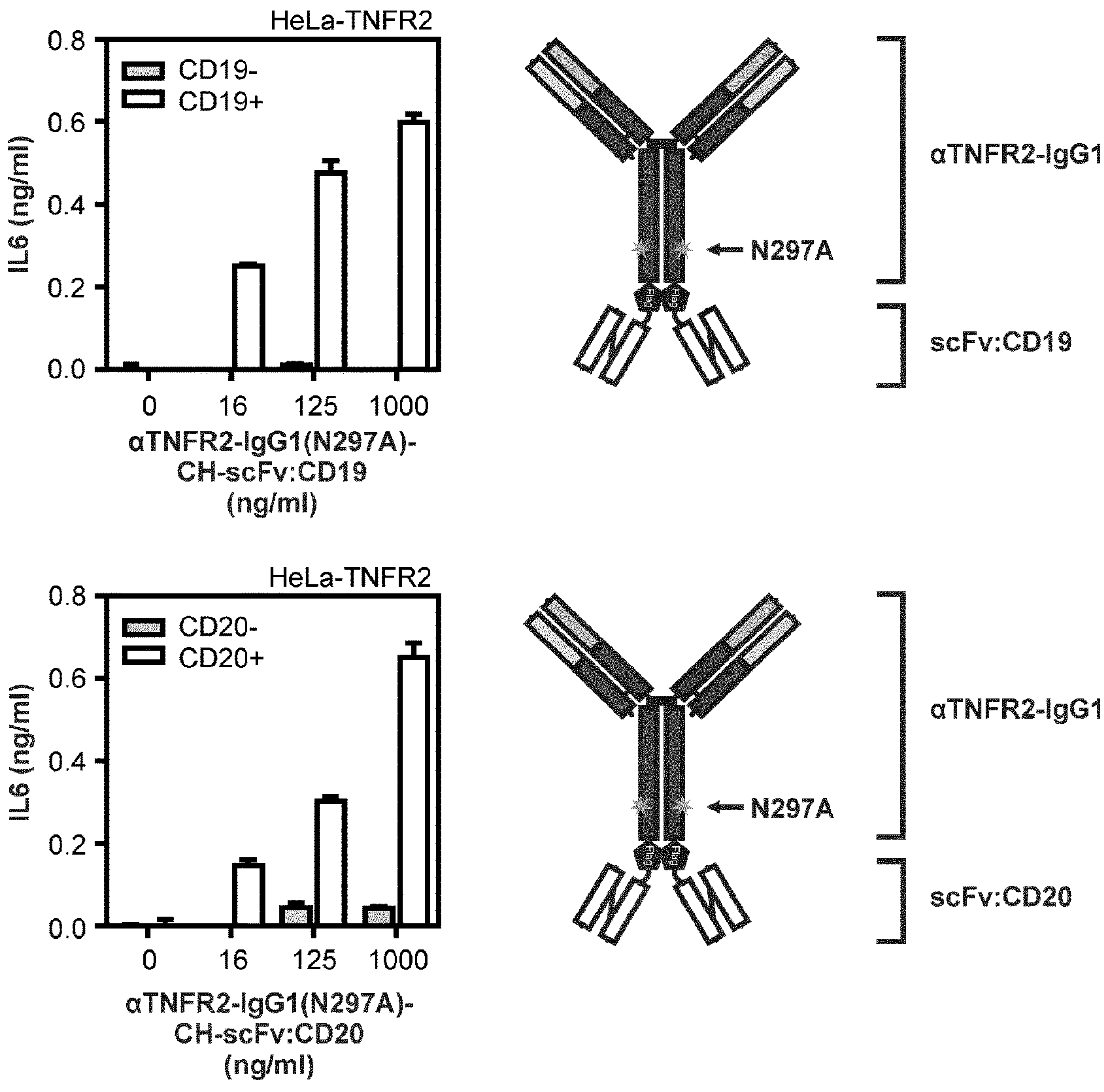

FIG. 12: Cell surface antigen-targeting scFv fusion proteins of the TNFR2-specific antibody C4 increasingly stimulate TNFR2 in an antigen-dependent manner. CD19- and CD20-negative Jurkat cells as well as CD19- and CD20-positive Rai cells were co-cultured with TNFR2-expressing HeLa transfectants and were stimulated with the indicated concentrations of anti-TNFR2-IgG1(N297A)-HC:scFv: CD19 (upper part) or the anti-TNFR2-IgG1(N297A)-HC: scFv:CD20 (lower part), respectively. On the next day, the production of IL8, which can be induced via TNFR2, was then captured using ELISA. Variants of the IgG1 variant N297A were used which cannot trigger ADCC. The parental TNFR2-specific mAb C4 which was used here was generated in house.

Material & Methods: Assays were performed in technical triplicates in 96-well plates. Upper part: HeLa-TNFR2 cells were seeded with 20000 cells per well, Jurkat (CD19-/CD20-) and RAJI cells (CD19-/CD20-) (30000 per well) were added the next day together with the indicated concentrations of anti-TNFR2-IgG1(N297A)-HC:scFv:CD19 (upper part) or the anti-TNFR2-IgG1(N297A)-HC:scFv: CD20 (lower part). The IL8 content produced by TNFR2 activation were finally evaluated by ELISA (BD Biosciences) analysis of the co-culture supernatant.

Figure 13:
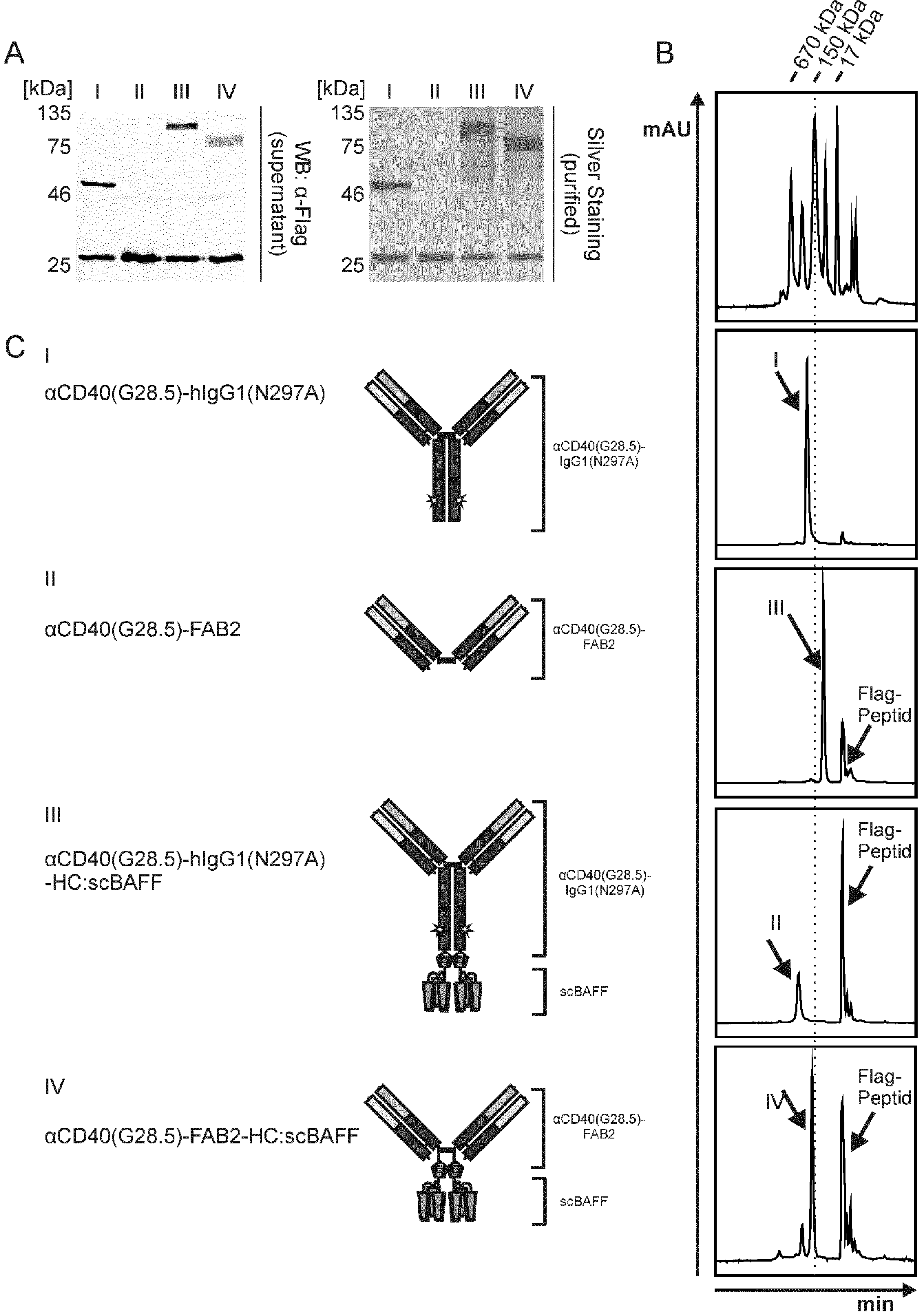

FIG. 13. Biochemical characterization of scBaff fusion proteins of the anti-CD40 G28.5. (A) Purified anti-CD40 (G28.5)-IgG1(N297) (I), anti-CD40(G28.5)-IgG1(N297)-HC:scBaff (II), anti-CD40(G28.5)-FAB2 (III) and anti-CD40(G28.5)-FAB2-HC:scBaff (IV) were separated by SDS-PAGE. Proteins were then either visualized by Western blotting with the mAb M2 which recognizes the Flag epitope present in the heavy and light chains of the various antibody fusion proteins (left panel) or by silver staining (right panel). Please note, the two chains of construct II are quite similar in size and therefore not resolved by SDS-PAGE. (B) Gel filtration analysis of a marker protein mixture and proteins I to IV. (C) Scheme of proteins I to IV Materials & Methods: Antibody fusion proteins were produced and purified as described in Kums et al., 2016. SDS-PAGE, silver staining and western blotting were performed as described in Lang et al., 2016. Kums J, Nelke J, Rüth B, Schäfer V, Siegmund D, Wajant H. Quantitative analysis of cell surface antigen-antibody interaction using *Gaussia princeps* luciferase antibody fusion proteins. MAbs. 2017 April; 9(3):506-520.

Lang I, Füllsack S, Wyzgol A, Fick A, Trebing J, Arana J A, Schäfer V, Weisenberger D, Wajant H. Binding Studies of TNF Receptor Superfamily (TNFRSF) Receptors on Intact Cells. J Biol Chem. 2016 Mar. 4; 291(10):5022-37.

Figure 14:
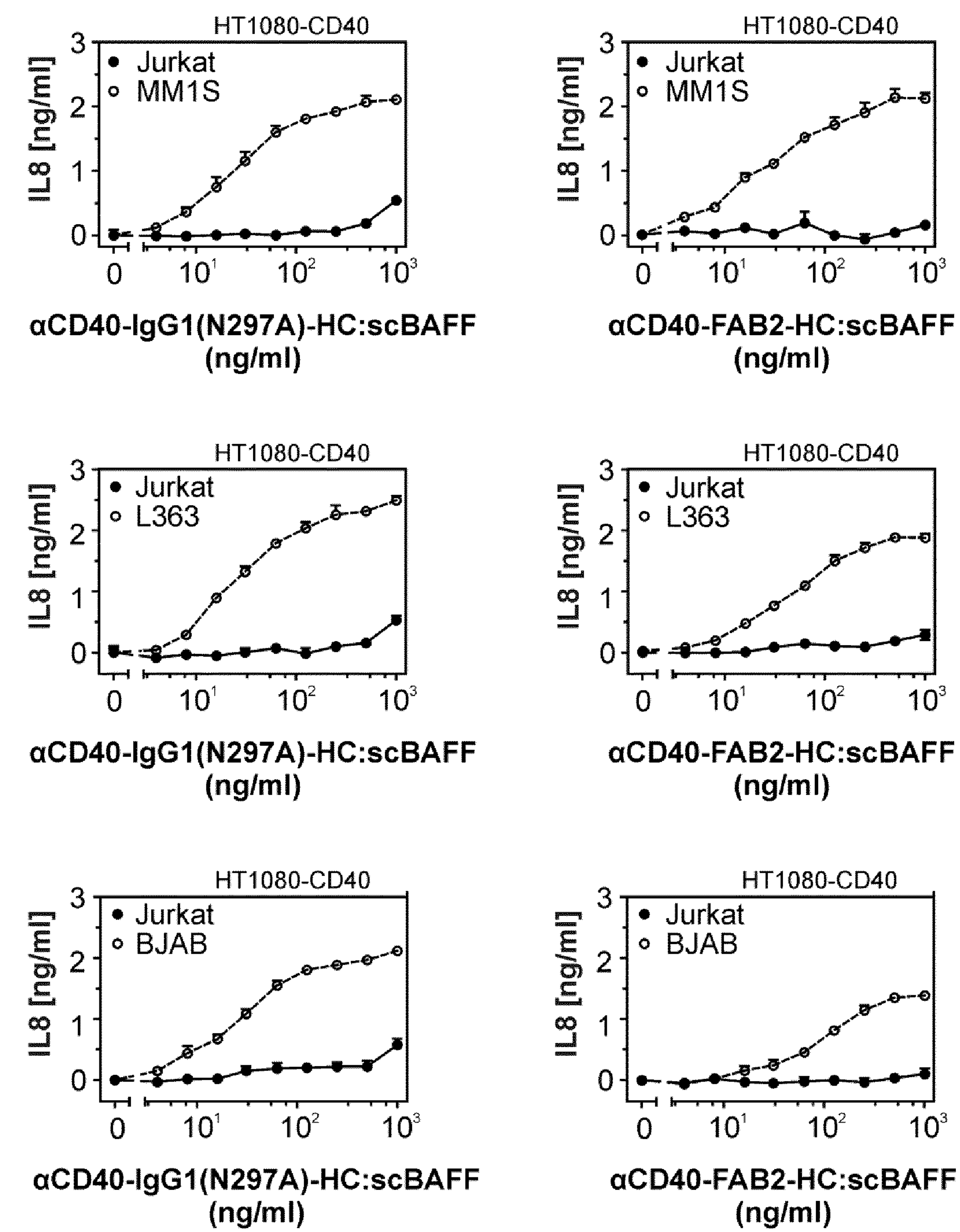

FIG. 14: scBaff fusion proteins of the IgG1(N297A) and FAB2 variant of the anti-CD40 G28.5 exhibit an increased CD40-stimulating activity after binding to lymphoma/myeloma cells with endogenous expression of BaffR and TACl.

MM1S (expressing BCMA and moderately TACl), L363 (expressing BCMA and moderately TACl) and BJAB (expressing BaffR) cells or as a control Jurkat cells which lack expression of all Baff binding receptors were co-cultured with HT1080-CD40 cells, which do not express BaffR, BCMA and TACl but which strongly produce IL8 after CD40 stimulation, Co-cultures were stimulated in triplicates with the indicated concentrations of anti-CD40(G28.5)-IgG1(N297A)-HC:scBaff or anti-CD40(G28.5)-FAB2-HC:scBaff. On the next day, the amount of human 1L8 was determined in the supernatants of the different co-cultures.

Material & Methods: HT1080-CD40 cells were cultivated overnight in 96-well plates (20.000 cells per well). Next day, 20.000 MM1S, L363, BJAB or Jurkat cells were added per well and the resulting co-cultures were stimulated for an additional night in triplicates with the indicated concentrations of anti-CD40(G28.5)-IgG1(N297A)-HC:scBaff and anti-CD40(G28.5)-FAB2-HC:scBaff. Cell supernatants were then analyzed for IL8 production by ELISA. Please note, MM1S, L363, BJAB and Jurkat cells produce no IL8 or neglectable amounts of IL8 compared to HT1080-CD40 cells.

FIG. 15: Competition with soluble Baff (TNC-Baff) inhibits IL8 production by anti-CD40(G28.5)-IgG1(N297A)-HC:scBaff and anti-CD40(G28.5)-FAB2-HC:scBaff. HT1080-CD40 cells were co-cultured with MM1S (expressing BCMA and moderately TACl), L363 (expressing BCMA and moderately TACl) and BJAB (expressing BaffR) cells or as a control Jurkat cells, Please note, HT1080-CD40 and Jurkat cells do not express Baff-interacting receptors (BaffR, TACl, BCMA). Cocultures were stimulated in triplicates with 200 ng/ml of anti-CD40(G28.5)-IgG1(N297A)-HC:scBaff or anti-CD40(G28.5)-FAB2-HC:scBaff in the presence and absence of an excess of soluble TNC-Baff (5 μg/ml). The next day, the amount of human 1L8 was determined in the supernatants of the various co-cultures.

Material & Methods: HT1080-CD40 cells were cultivated overnight in 96-well plates (20.000 cells per well). Next day, 20.000 MM15, L363, BJAB or Jurkat cells were added per well and the resulting co-cultures were stimulated for an additional night in triplicates with 200 ng/ml of CD40(G28.5)-IgG1(N297A)-HC:scBaff and anti-CD40(G28.5)-FAB2-HC:scBaff in the presence and absence of soluble TNC-Baff (5 μg/ml), a stabilized form of soluble Baff containing the trimerization domain of tenascin-C (Berg et al., 2007). Cell supernatants were then analyzed for 1L8 production by ELISA. Please note, MM1S, L363, BJAB and Jurkat cells produce no IL8 or neglectable amounts of IL8 compared to HT10890-CD40 cells. Berg D, Lehne M, Müller N, Siegmund D, Münkel S, Sebald W, Pfizenmaier K, Wajant H. Enforced covalent trimerization increases the activity of the TNF ligand family members TRAIL and CD95L. Cell Death Differ. 2007 December; 14(12):2021-34. Epub 2007 Aug. 17

FIG. 16: scBaff fusion proteins of the anti-CD95 IgG1 E09 or its FAB2 fragment induce cell death in adherent HT1080 cells after binding to lymphoma/myeloma suspension cells with endogenous expression of BaffR and TACl. Adherently growing HT1080 cells were co-cultured with MM1S (expressing BCMA and moderately TAD), L363 (expressing BCMA and moderately TACl) and BJAB (expressing BaffR) suspension cells or as a control Jurkat cells. Please note, HT1080 and Jurkat cells do not express Baff-interacting receptors (BaffR, TACl, BCMA). Co-cultures were stimulated in the presence of 1 μg/ml CHX in triplicates with the indicated concentrations of anti-CD95(E09)-IgG1(N297A)-HC:scBaff or anti-CD95(E09)-FAB2-HC:scBaff. The next day, cell viability was determined by crystal violet staining of remaining attached HT1080 cells.

Material & Methods: HT1080 cells have been seeded at a density of 20.000 cells/well. Next day, 20.000 MM1S, L363, BJAB or Jurkat suspension cells were added per well and the resulting co-cultures were stimulated overnight in triplicates with anti-CD95(E09)-IgG1(N297A)-HC:scBaff or anti-CD95(E09)-FAB2-HC:scBaff in the presence of 1 μg/ml. Finally, cell death induction was determined by crystal violet staining of the adherently growing HT1080 cells. Viability was normalized against untreated HT1080 cells (=100% viability) and HT1080 cells treated with a highly toxic mixture of 0.03% azid, 50 μg/ml CHX and 500 ng/ml Fc-CD95L (=0% viability).

FIG. 17: Competition with soluble Baff (TNC-Baff) inhibits anti-CD95(E09)-IgG1(N297A)-HC:scBaff and anti-CD95(E09)-FAB2.HC:scBaff induced HT1080 killing in cocultures of HT1080 cells and Baff interacting receptor expressing cells. HT1080 cells were co-cultured with MM1S (expressing BCMA and moderately TACl), L363 (expressing BCMA and moderately TACl) and BJAB (expressing BaffR) cells or as a control Jurkat cells. Please note, HT1080-CD40 and Jurkat cells do not express Baff-interacting receptors (BaffR, TACl, BCMA). Co-cultures were stimulated in the presence of 1 μg/ml CHX in triplicates with 20 ng/ml of anti-anti-CD95(E09)-IgG1(N297A)-HC:scBaff or anti-CD95(E09)-FAB2-HC:scBaff in the presence and absence of an excess of soluble TNC-Baff (5 μg/ml). The next day, cell viability was determined by crystal violet staining of remaining attached HT1080 cells.

Material & Methods: HT1080 cells have been seeded at a density of 20.000 cells/well. Next day, w0.000 MM1S, L363, BJAB or Jurkat suspension cells were added per well and the resulting co-cultures were stimulated overnight in triplicates with 20 ng/ml of anti-CD95(E09)-IgG1(N297A)-HC:scBaff or anti-CD95(E09)-FAB2-HC:scBaff in the presence and absence of soluble TNC-Baff (5 μg/ml). Finally, cell death induction was determined by crystal violet staining of the adherently growing HT1080 cells. Viability was normalized against untreated HT1080 cells (=100% viability) and HT1080 cells treated with a highly toxic mixture of 0.03% azid, 50 μg/ml CHX and 500 ng/ml Fc-CD95L (=0% viability). TNC-Baff is a stabilized form of soluble Baff containing the trimerization domain of tenascin-C (Berg et al., 2007). Berg D, Lehne M, Müller N, Siegmund D, Münkel S, Sebald W, Pfizenmaier K, Wajant H. Enforced covalent trimerization increases the activity of the TNF ligand family members TRAIL and CD95L. Cell Death Differ. 2007 December; 14(12):2021-34.

FIG. 18: anti-CD95(E09)-IgG1(N297A)-HC:scBaff but not anti-CD95(E09)-IgG1(N297A) activates apoptotic caspases in BaffR expressing cells. BJAB cells (expressing BaffR), and as a negative control Jurkat cells which express none of the Baff receptors (BaffR, TACl, BCMA), were treated overnight with the indicated concentrations anti-CD95(E09)-IgG1(N297A)-HC:scBaff and anti-CD95(E09)-IgG1(N297A). Next day, total cell lysates were analyzed by western blotting with respect to generation of the p18 fragment of caspase-8 and of the p17 fragment of caspase-3 which are indicative for apoptotic activation of these caspases. As a positive control, Jurkat and BJAB cells were challenged with 500 ng/ml Fc-CD95L which induces apoptosis in both cell lines.

Figure 19:
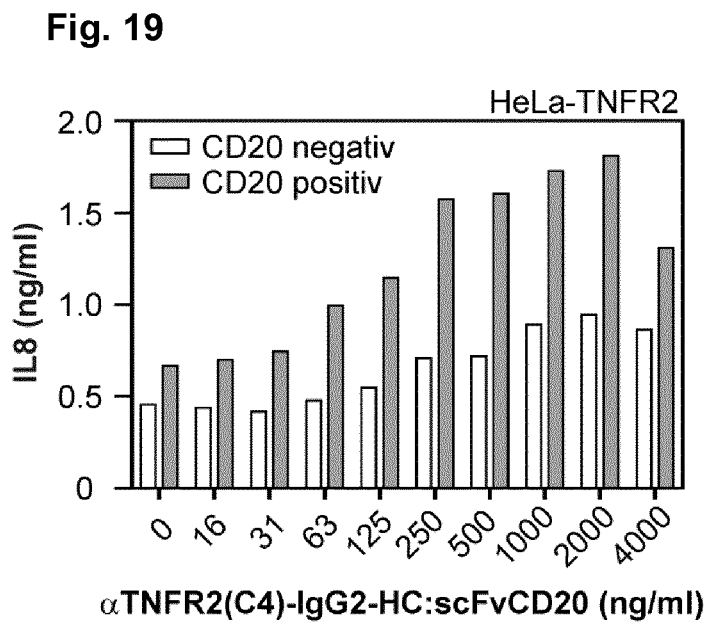

FIG. 19: A scFv fusion protein of the TNFR2-specific antibody C4 in the IgG2 isoform that anchor to the cell surface antigen CD20 increasingly stimulate TNFR2 in a CD20-dependent manner. CD20-negative Jurkat and CD20-positive BJAB cells were co-cultured with TNFR2-responsive HeLa-TNFR2 cells and stimulated with the indicated concentrations of anti-TNFR2(C4)-IgG2-HC:scFv:CD20. On the next day, the production of IL8, which can be induced via TNFR2, was measured using an ELISA.

Material & Methods: 20.000 HeLa-TNFR2 transfectants (Weiss et al., 1997) per well were seeded in 96-well plates. Next day, CD20-positive BJAB cells or as a negative control 20.000 Jurkat cells lacking endogenous CD20 expression were added. Co-cultures were then treated with the indicated concentrations of anti-INFR2(C4)-IgG2-HC:scFvCD20 and after an additional day, IL8 production was measured by ELISA.

Weiss T, Grell M, Hessabi B, Bourteele S, Müller G, Scheurich P, Wajant H. vEnhancement of TNF receptor p60-mediated cytotoxicity by TNF receptor p80: requirement of the TNF receptor-associated factor-2 binding site. J Immunol. 1997 Mar. 1; 158(5):2398-404.

FIG. 20: A scFv fusion protein of the TNFR2-specific antibody C4 in the IgG1 isoform that anchor to the cell surface antigen CD70 increasingly stimulate TNFR2 in an CD27L/CD70-dependent manner. (A) Structure of the fusion proteins. (B,C). Hek293 cells were transfected with an empty vector or with a CD27L (alternative name CD70) encoding expression plasmid. On the next day, the transfectants were co-cultured with HeLa-TNFR2 transfectants which produce IL8 upon TNFR2 expression. Co-cultures were treated with the indicated concentrations of anti-TNFR2(C4)-IgG1(N297A)-HC:scFv:CD70(1F6) (B) or anti-TNFR2(C4)-IgG1(N297A)-HC:scFv:CD70(2H5) (C), Finally, IL8 production was evaluated by ELISA.

Material & Methods: Hek293 cells which do not express TNFR2 or CD27L (CD70) were transiently transfected with an expression plasmid encoding CD27L (=negative control) as described in Kums et al., MAbs, 2017 April; 9(3):506-520 for Hek293 cells and FcgR expression vectors. Transfectants were harvested and aliquots of 20.000 cells were added to the wells of a 96-well plate in which the previous day HeLa-TNFR2 cells have been seeded at a density of 20.000 cells/well. Co-cultures were stimulated overnight in triplicates with the TRAAFFIAAs anti-TNFR2(C4)-IgG1 (N297A)-HC:scFv:CD70(1F6) (B) and anti-INFR2(C4)-IgG1 (N297A)-HC:scFv:CD70(2H5) (C). 2H5 and 1F6 are two different human CD70-specific antibodies.

FIG. 21: scFv:CD20 fusion protein of IgG1(N297) variants of the 4.1BB-specific antibody HBBK4, the CD40-specific antibody G28.5 and the CD95-specific antibody E09 induce IL8 production in HT1080.41BB, HT1080-CD40 and HT1080 (endogenous CD95 expression) cells in co-culture with CD20-expressing cells. (A) Scheme of fusion proteins (B-D) The indicated HT1080 variants were co-cultured with Hek293 cells transfected with empty vector or an CD20 expression plasmid. Co-cultures were then treated with the CD20-binding IgG1(N297A) fusion proteins anti-41BB(HBBK4)-IgG1(N297A)-HC:scFv:CD20 (B), anti-CD40(B28.5)-IgG1(N297A)-HC:scFv:CD20 (C) and anti-CD95(E09)-IgG1(N297A)-HC:scFv:CD20 (D) at the indicated concentrations. Next day, 1L8 production was measured by ELISA. In the case of the anti-CD95 variant the caspase inhibitor ZVAD was added to prevent apoptosis.

Material & Methods: HT1080-41BB transfectants (Wyzgol et al., 2009), HT1080-CD40 transfectants (Wyzgol et al., 2009) and HT1080 cells (endogenous CD95 expression) were seeded at a density of 20.000 cells/well. Next day, 20.000 Hek293 cells were added that have been transfected the previous day with empty vector (EV) or a CD27L (=CD70) expression plasmids. The resulting co-cultures were stimulated overnight in triplicates with the indicated concentrations of anti-41BB(HBBK4)-IgG1(N297A)-HC: scFvCD20 (B), anti-CD40(G28.5)-IgG1(N297A)-HC: scFvCD20 (C) and anti-CD95(E09)-IgG1(N297A)-HC: scFvCD20 (D). The latter was added in the presence of 20 μg/ml ZVAD to prevent apoptosis induction. IL8 was evaluated by ELISA.

Wyzgol A, Müller N, Fick A, Munkel S, Grigoleit G U, Pfizenmaier K, Wajant H. Trimer stabilization, oligomerization, and antibody-mediated cell surface immobilization improve the activity of soluble trimers of CD27L, CD40L, 41BBL, and glucocorticoid-induced TNF receptor ligand. J Immunol, 2009 Aug. 1; 183(3):1851-61.

FIG. 22: scFv:CD20 fusion protein of IgG1(N297) variants of the 4-1BB-specific antibody HBBK4, the CD40-specific antibody G28.5 and the CD95-specific antibody E09 elicit enhanced IL8 production by HT1080.41BB, HT1080-CD40 and HT1080 (endogenous CD95 expression) cells in co-culture with CD20-positive BJAB cells. (A-C) The indicated HT1080 variants were co-cultured with CD20-positive BJAB cells or as a negative control with Jurkat cells lacking endogenous CD20 expression. Co-cultures were then treated with the CD20-binding IgG1(N297A) fusion proteins anti-41BB(HBBK4)-IgG1(N297A)-HC:scFv:CD20 (A), anti-CD40(G28.5)-IgG1(N297A)-HC:scFv:CD20 (B) and anti-CD95(E09)-IgG1(N297A)-HC:scFv:CD20 (C) at the indicated concentrations. Next day, 1L8 production was measured by ELISA. In the case of the anti-CD95 variant the caspase inhibitor ZVAD was added to prevent apoptosis.

Material & Methods: HT1080-41BB transfectants (Wyzgol et al., 2009), HT1080-CD40 transfectants (Wyzgol et al., 2009) and HT1080 cells (endogenous CD95 expression) were seeded at a density of 20.000 cells/well. Next day, either 20.000 BJAB cells (CD20 positive) or 20.000 Jurkat cells (CD20 negative) were added. The resulting co-cultures were stimulated overnight in triplicates with the indicated concentrations of anti-41BB(HBBK4)-IgG1(N297A)-HC: scFvCD20 (A), anti-CD40(G28.5)-IgG1(N297A)-HC: scFvCD20 (B) and anti-CD95(E09)-IgG1(N297A)-HC: scFvCD20 (C). The latter was added in the presence of 20 μg/ml ZVAD to prevent apoptosis induction. IL8 was evaluated by ELISA.

Wyzgol A, Müller N, Fick A, Munkel S, Grigoleit G U, Pfizenmaier K, Wajant H. Trimer stabilization, oligomerization, and antibody-mediated cell surface immobilization improve the activity of soluble trimers of CD27L, CD40L, 41BBL, and glucocorticoid-induced TNF receptor ligand. J Immunol, 2009 Aug. 1; 183(3):1851-61.

Figure 23:
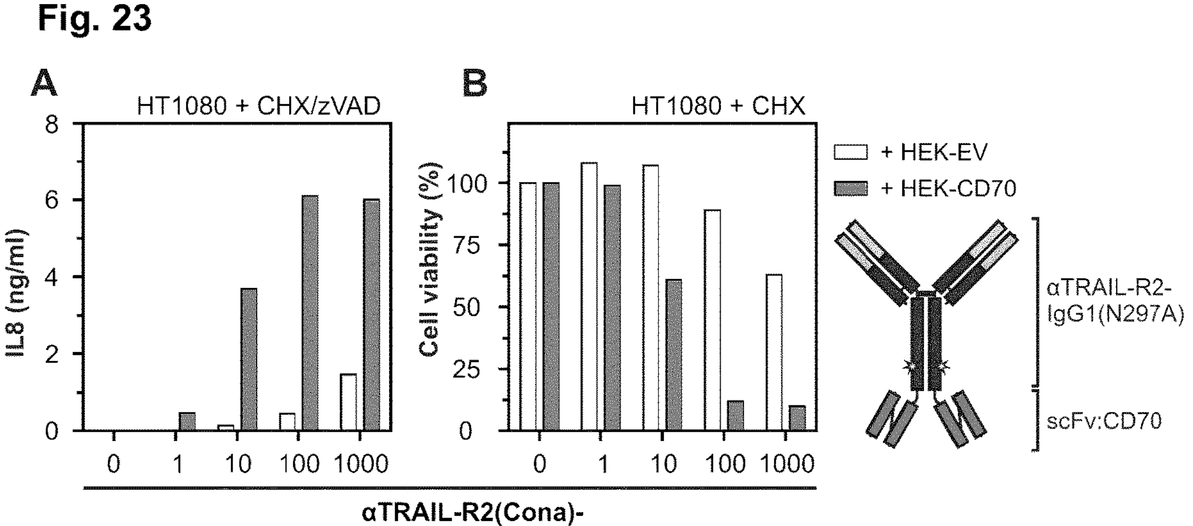

FIG. 23: A fusion protein of the TRAILR2-specific antibody Conatumumab (Cons) in the IgG1(N297A) isoform with the CD70-specific scFv 9G2 increasingly stimulate proinflammatory (A) and cytotoxic (B) TRAILR2 signaling in a CD70-dependent manner. Hek293 cells transiently transfected with a CD70-encoding expression plasmid or empty vector transfected Hek293 cells were co-cultured with TRAILR2-responsive HT1080 cells (no CD70 expression). To sensitize HT1080 cells for TRAILR2 signaling co-cultures were treated with 2.5 μg/ml CHX (B) or with CHX plus 20 μM of the caspase inhibitor ZVAD (A). CHX suppresses expression of the TRAILR2 signaling inhibitory FLIP proteins which have a high turnover. ZVAD prevents apoptosis and allows so evaluation of the gene inductive properties of TRAILR2. Co-cultures were then further treated with the indicated concentrations of anti-TRAILR2 (Cona)-IgG1(N297A)-HC:scFv:CD70(9G2) and after an additional day, IL8 production was measured by ELISA (A) or viability by crystal violet staining (B).

FIG. 24: Fusion proteins of the CD40-specific antibody C in the IgG1(N297A) or Fab2 format with a scFv derived of the check point inhibitor Avelumab (Ave) targeting PD-L1 activate CD40 in a PD-1L-restricted manner. Hek293 cells transiently transfected with a PD-1L-encoding expression plasmid or empty vector transfected Hek293 cells were co-cultured with CD40-responsive HT1080-CD40 cells, Co-cultures were then treated with the indicated concentrations of anti-CD40(C)-IgG1(N297A)-HC:scFv:PD-L1 (A) or anti-CD40(C)-Fab2-HC:scFv:PD-L1 (B). Next day, IL8 production, as a read out for CD40 activation, was measured by ELISA.

FIG. 25: Fusion proteins of the 41BB-specific antibody HBBK in the IgG1(N297A) or Fab2 format with a scFv derived of the check point inhibitor Avelumab (Ave) activate 41BB in a PD-1L-restricted manner. Hek293 cells transiently transfected with a PD-1L-encoding expression plasmid or empty vector transfected Hek293 cells were co-cultured with 41BB-responsive HT1080-41BB cells. Co-cultures were then treated with the indicated concentrations of anti-41BB(HBBK)-IgG1(N297A)-HC:scFv:PD-L1 (A) or anti-41BB(HBBK)-Fab2-HC:scFv:PD-L1 (B). Next day, IL8 production, as a read out for 41BB activation, was measured by ELISA.

Figure 26:
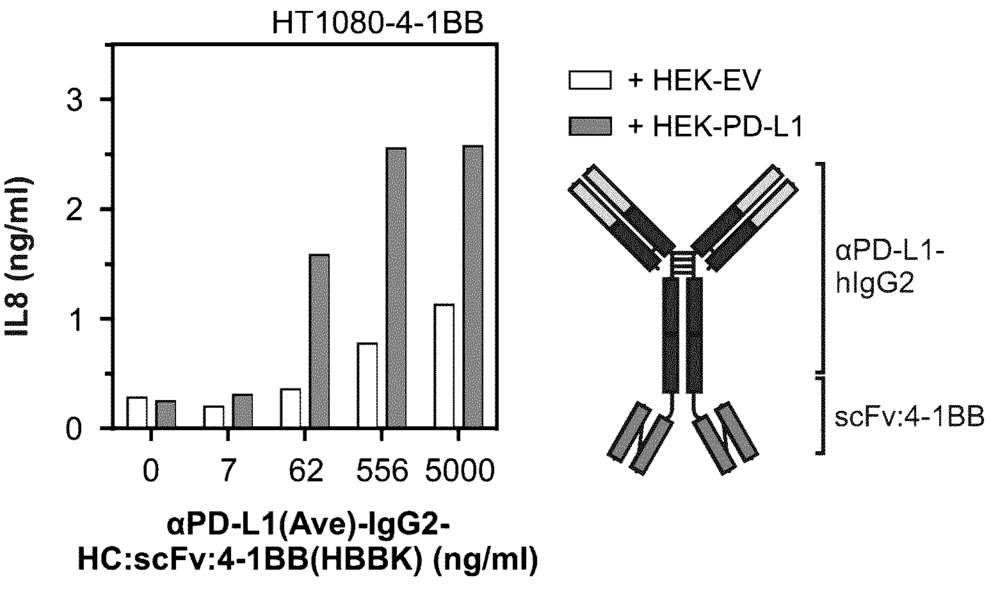

FIG. 26: A Fusion protein of the PD-1L-specific antibody Avelumab (Ave) in the IgG2 format with a scFv specific for 41BB shows enhanced 41BB activation in a PD-1L-restricted manner. Hek293 cells transiently transfected with a PD-1L-encoding expression plasmid or empty vector transfected Hek293 cells were co-cultured with 41BB-responsive HT1080-41BB cells. Co-cultures were then treated with the indicated concentrations of anti-PD-L1(Ave)-IgG2-1-1C: scFv:41BB(HBBK). Next day, IL8 production, as a read out for 41BB activation, was measured by ELISA. This example illustrates that scFvs derived of antibodies against receptors of the TNFRSF acquire anchoring-dependent agonistic activity after fusion to antibodies recognizing a cell surface exposed antigen. Thus, the TRAAFFIAA principle works with anti-TNFRSF receptor antibodies as TNFRSF receptor stimulating effector domain and scFvs as anchoring domain but also in the mirrored format with an antibody as anchoring domain and TNFRSF receptor-specific scFvs as effector domains.

Figure 27:
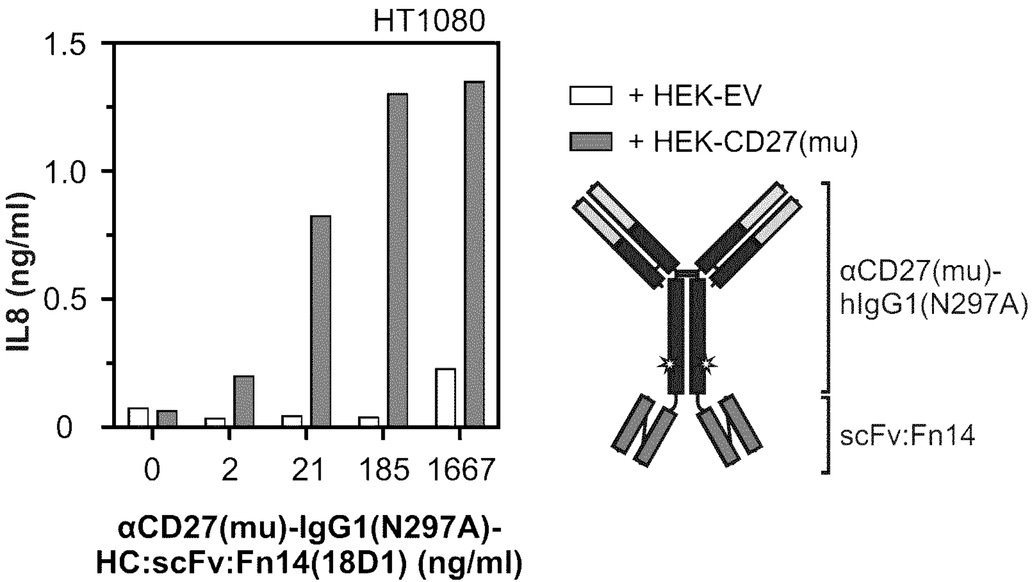

FIG. 27: A Fusion protein of a murine CD27-specific antibody in the IgG(N297A) format with the Fn14-specific scFv 18D1 shows enhanced Fn14 activation in a murine CD27-restricted manner. Hek293 cells (poorly Fn14 responsive) transiently transfected with a murine CD27-encoding expression plasmid or empty vector transfected Hek293 cells were co-cultured with highly Fn14-responsive HT1080 cells, Co-cultures were then treated with the indicated concentrations of anti-muCD27-IgG1(N297A)-HC:scFv14 (18D1). Next day, IL8 production, as a read out for Fn14 activation, was measured by ELISA. This example illustrates again that scFvs derived of antibodies against receptors of the TNFRSF acquire anchoring-dependent agonistic activity after fusion to antibodies recognizing a cell surface exposed antigen, Thus, the TRAAFFIAA principle works with anti-TNFRSF receptor antibodies as TNFRSF receptor stimulating effector domain and scFvs as anchoring domain but also in the mirrored format with an antibody as anchoring domain and TNFRSF receptor-specific scFvs as effector domains.

DETAILED DESCRIPTION OF THE INVENTION

Definitions and General Techniques

Unless otherwise defined below, the terms used in the present invention shall be understood in accordance with their common meaning known to the person skilled in the art.

All publications, patents and patent applications cited herein are hereby incorporated by reference in their entirety for all purposes.

A "scTNFSF" as used herein refers to a functional (meant is receptor binding) TNFSF ligand in a single-chain format. Typically, an scTNFSF comprises three units of the receptor binding domain of a TNFSF protomer, wherein said units are connected by polypeptide linkers and form an intramolecular trimer.

The term "antibody" as used herein refers to any functional antibody that is capable of specific binding to the antigen of interest, as generally outlined in chapter 7 of Paul, W. E. (Ed.): Fundamental Immunology 2nd Ed. Raven Press, Ltd., New York 1989, which is incorporated herein by reference. Without particular limitation, the term "antibody" encompasses antibodies from any appropriate source species, including chicken and mammalian such as mouse, goat, non-human primate and human. Preferably, the antibody is a humanized antibody. The antibody is preferably a monoclonal antibody which can be prepared by methods well-known in the art. The term "antibody" encompasses an IgG-1, -2, -3, or -4, IgE, IgA, IgM, or IgD isotype antibody. The term "antibody" encompasses monomeric antibodies (such as IgD, IgE, IgG) or oligomeric antibodies (such as IgA or IgM). The term "antibody" also encompasses—without particular limitations—isolated antibodies and modified antibodies such as genetically engineered antibodies, e.g. chimeric or humanized antibodies.

The nomenclature of the domains of antibodies follows the terms as known in the art. Each monomer of an antibody comprises two heavy chains and two light chains, as generally known in the art. Of these, each heavy and light chain comprises a variable domain (termed $V_H$ for the heavy chain and $V_L$ for the light chain) which is important for antigen binding. These heavy and light chain variable domains comprise (in an N-terminal to C-terminal order) the regions FR1, CDR1, FR2, CDR2, FR3, CDR3, and FR4 (FR, framework region; CDR, complementarity determining region which is also known as hypervariable region). The identification and assignment of the above-mentioned antibody regions within the antibody sequence is generally in accordance with Kabat et al. (Sequences of proteins of immunological interest, U.S. Dept. of Health and Human Services, Public Health Service, National Institutes of Health, Bethesda, Md. 1983), or Chothia et al. (Conformations of immunoglobulin hypervariable regions. Nature. 1989 Dec. 21-28; 342(6252):877-83,), or may be performed by using the IMGT/V-QUEST software described in Giudicelli et al. (IMGT/V-QUEST, an integrated software program for immunoglobulin and T cell receptor V-J and V-D-J rearrangement analysis. Nucleic Acids Res. 2004 Jul. 1; 32(Web Server issue):W435-40.), which is incorporated herein by reference. Preferably, the antibody regions indicated above are identified and assigned by using the IMGT/V-QUEST software.

A "monoclonal antibody" is an antibody from an essentially homogenous population of antibodies, wherein the antibodies are substantially identical in sequence (i.e. identical except for minor fraction of antibodies containing naturally occurring sequence modifications such as amino acid modifications at their N- and C-termini). Unlike polyclonal antibodies which contain a mixture of different antibodies directed to either a single epitope or to numerous different epitopes, monoclonal antibodies are directed to the same epitope and are therefore highly specific. The term "monoclonal antibody" includes (but is not limited to) antibodies which are obtained from a monoclonal cell population derived from a single cell clone, as for instance the antibodies generated by the hybridoma method described in Köhler and Milstein (Nature, 1975 Aug. 7; 256(5517):495-7) or Harlow and Lane ("Antibodies: A Laboratory Manual" Cold Spring Harbor Laboratory Press, Cold Spring Harbor, N.Y. 1988). A monoclonal antibody may also be obtained from other suitable methods, including phage display techniques such as those described in Clackson et al. (Nature. 1991 Aug. 15; 352(6336):624-8) or Marks et al. (J Mol Biol. 1991 Dec. 5; 222(3):581-97). A monoclonal antibody may be an antibody that has been optimized for antigen-binding properties such as decreased Kd values, optimized association and dissociation kinetics by methods known in the art. For instance, Kd values may be optimized by display methods including phage display, resulting in affinity-matured monoclonal antibodies. The term "monoclonal antibody" is not limited to antibody sequences from particular species of origin or from one single species of origin. Thus, the meaning of the term "monoclonal antibody" encompasses chimeric monoclonal antibodies such as humanized monoclonal antibodies and human antibodies.

"Humanized antibodies" are antibodies which contain human sequences and a minor portion of non-human sequences which confer binding specificity to an antigen of interest. Typically, humanized antibodies are generated by replacing hypervariable region sequences from a human acceptor antibody by hypervariable region sequences from a non-human donor antibody (e.g. a mouse, rabbit, rat donor antibody) that binds to an antigen of interest. In some cases, framework region sequences of the acceptor antibody may also be replaced by the corresponding sequences of the donor antibody. In addition to the sequences derived from the donor and acceptor antibodies, a "humanized antibody" may either contain other (additional or substitute) residues or sequences or not. Such other residues or sequences may serve to further improve antibody properties such as binding properties (e.g. to decrease Kd values) and/or immunogenic properties (e.g. to decrease antigenicity in humans). Non-limiting examples for methods to generate humanized antibodies are known in the art, e.g. from Riechmann et al. (Nature. 1988 Mar. 24; 332(6162):323-7) or Jones et al, (Nature. 1986 May 29-June 4; 321(6069):522-5).

The term "human antibody" relates to an antibody containing human variable and constant domain sequences. This definition encompasses antibodies having human sequences bearing single amino acid substitutions or modifications which may serve to further improve antibody properties such as binding properties (e.g. to decrease Kd values) and/or immunogenic properties (e.g. to decrease antigenicity in humans). The term "human antibody" excludes humanized antibodies where a portion of non-human sequences confers binding specificity to an antigen of interest.

An "antigen-binding portion" of an antibody as used herein refers to a portion of an antibody that retains the capability of the antibody to specifically bind to the antigen. This capability can, for instance, be determined by determining the capability of the antigen-binding portion to compete with the antibody for specific binding to the antigen by methods known in the art. The antigen-binding portion may contain one or more fragments of the antibody. Without particular limitation, the antigen-binding portion can be produced by any suitable method known in the art, including recombinant DNA methods and preparation by chemical or enzymatic fragmentation of antibodies. Antigen-binding portions may be Fab fragments, F(ab') fragments, $Fab_2$ fragments, single chain antibodies (scFv), single-domain antibodies, diabodies or any other portion(s) of the antibody that retain the capability of the antibody to specifically bind to the antigen. It will be understood that in accordance with the meaning of the term "$Fab_2$" as known in the art, the term "$Fab_2$" is synonymous with the terms "Fab2", "$Fab_2$", and "FAB2". Thus, for the purposes of the present application, the term "$Fab_2$" is used interchangeably with the terms "Fab2", "Fab2", and "FAB2". An "antigen-binding portion capable of binding to said structure of the cell surface and/or to said structure of the extracellular matrix" in accordance with the invention is not particularly limited. For example, it can be an antigen-binding portion capable of binding to a tumor antigen. The "antigen-binding portion capable of binding to said structure of the cell surface and/or to said structure of the extracellular matrix" is preferably selected from the group consisting of an anti-CD20 antigen-binding portion, an anti-CD70 antigen-binding portion, an anti-CD19 antigen-binding portion, an anti-EGFR antigen-binding portion, an anti-Her2 antigen-binding portion, an anti-Fn14 antigen-binding portion, an anti-CD40L antigen-binding portion, and an anti-PD1L antigen-binding portion. Alternatively, the "antigen-binding portion capable of binding to said structure of the cell surface and/or to said structure of the extracellular matrix" in accordance with the invention can be an anti-FAP antigen-binding portion, an anti-BCMA antigen-binding portion or an anti-Flt3 antigen-binding portion.

An "antibody" (e.g. a monoclonal antibody) or an "antigen-binding portion" may have been derivatized or be linked to a different molecule. For example, molecules that may be linked to the antibody are other proteins (e.g. other antibodies), a molecular label (e.g. a fluorescent, luminescent, colored or radioactive molecule), a pharmaceutical agent. The antibody or antigen-binding portion may be linked directly (e.g. in form of a fusion between two proteins), or via a linker molecule (e.g. any suitable type of chemical linker known in the art).

In connection with the invention including the fusion proteins of the invention, the meaning of an "anti-TNFRSF receptor antibody or antigen-binding portion thereof" is not particularly limited as long as it is an antibody or antigen-binding portion thereof against at least one TNFRSF receptor. In a preferred embodiment in accordance with all other embodiments of the invention, the anti-TNFRSF receptor antibody or antigen-binding portion thereof can be an anti-TNFRSF receptor antibody or antigen-binding portion thereof against a single type of TNFRSF receptor. In another preferred embodiment in accordance with all other embodiments of the invention, the anti-TNFRSF receptor antibody or antigen-binding portion thereof can be a bivalent anti-TNFRSF receptor antibody or antigen-binding portion thereof which is directed against two different types of TNFRSF receptors.

As used herein, the terms "binding" or "bind" refer to specific binding to the antigen of interest. Preferably, the Kd value is less than 100 nM, more preferably less than 50 nM, still more preferably less than 10 nM, still more preferably less than 5 nM and most preferably less than 2 nM.

The term "epitope" as used herein refers to a small portion of an antigen that forms the binding site for an antibody.

In the context of the present invention, for the purposes of characterizing the binding properties of antibodies or antibody fusion proteins, any binding or competitive binding of antibodies or the fusion proteins (e.g. TRAAFFIAAs) of the invention to the antigen of interest or to FcγRs or to the structures of the cell surface or of the extracellular matrix are preferably measured by using luciferase-tagged (e.g. *Gaussia princeps* luciferase (GpL)) variants of the antibody or the fusion proteins by cellular binding studies (for example as described in Kums et al., MAbs, 2017 April; 9(3):506-520) or by surface plasmon resonance measurements as reference standard assays.

The terms "$K_D$" or "$K_D$ value" relate to the equilibrium dissociation constant as known in the art. In the context of the present invention, these terms relate to the equilibrium dissociation constant of an antibody or a fusion protein (e.g. TRAAFFIAA) of the invention with respect to a particular antigen of interest or a FcγR of interest or with respect to the structure of the cell surface or the extracellular matrix. The equilibrium dissociation constant is a measure of the propensity of a complex (e.g. an antigen-antibody complex) to reversibly dissociate into its components (e.g. the antigen and the antibody). For the antibodies or fusion proteins according to the invention, $K_D$ values are preferably determined by cellular competitive binding studies with GpL-tagged variants of the antibody or of the fusion protein (e.g. the TRAAFFIAA) and the non-modified antibody or fusion protein (e.g. TRAAFFIAA) of interest or by using surface plasmon resonance measurements.

As used herein in connection with antibodies or antigen-binding portions thereof in accordance with the invention, terms such as "capable of cross-competing with an antibody" for binding to a particular protein such as a TNFRSF receptor generally mean that the antibody or antigen-binding portion thereof is capable of cross-competing when using an assay known in the art such as an Enzyme-linked Immunosorbent Assay (ELISA). As is known in the art, it will be understood that the term "capable of cross-competing with an antibody" refers to a cross-competition for specific binding to said particular protein. As skilled person will be able to determine appropriate conditions for the detection of a cross-competition for such specific binding.

An "isolated antibody" or "isolated TRAAFFIA" or "isolated fusion protein" as used herein has been identified and separated from the majority of components (by weight) of its source environment, e.g. from the components of a hybridoma cell culture or a different cell culture that was used for its production (e.g. producer cells such as CHO or HEK293 cells that recombinantly express the antibody or fusion protein such as TRAAFFIA). The separation is performed such that it sufficiently removes components that may otherwise interfere with the suitability of the antibody or fusion protein such as TRAAFFIA for the desired applications (e.g. with a therapeutic use of the antibody or fusion protein such as TRAAFFIA according to the invention). Methods for preparing isolated antibodies or antibody fusion proteins are known in the art and include Protein A chromatography, anion exchange chromatography, cation exchange chromatography, virus retentive filtration and ultrafiltration. Preferably, the isolated antibody or fusion protein such as TRAAFFIA preparation is at least 70% pure (w/w), more preferably at least 80% pure (w/w), still more preferably at least 90% pure (w/w), still more preferably at least 95% pure (w/w), and most preferably at least 99% pure (w/w), as measured by using the Lowry protein assay.

A "diabody" as used herein is a small bivalent antigen-binding antibody portion which comprises a heavy chain variable domain linked to a light chain variable domain on the same polypeptide chain linked by a peptide linker that is too short to allow pairing between the two domains on the same chain. This results in pairing with the complementary domains of another chain and in the assembly of a dimeric molecule with two antigen binding sites. Diabodies may be bivalent and monospecific (such as diabodies with two antigen binding sites for the antigen), or may be bivalent and bispecific (e.g. diabodies with two antigen binding sites, one being a binding site for an antigen, and the other one being a binding site for a different antigen). A detailed description of diabodies can be found in Holliger P et al. (""Diabodies": small bivalent and bispecific antibody fragments." Proc Natl Acad Sci USA. 1993 Jul. 15; 90(14):6444-8.).

A "single-domain antibody" (which is also referred to as "Nanobody™") as used herein is an antibody fragment consisting of a single monomeric variable antibody domain. Structures of and methods for producing single-domain antibodies are known from the art, e.g. from Holt L J et al. ("Domain antibodies: proteins for therapy." Trends Biotechnol, 2003 November; 21(11):484-90.), Saerens D et al. ("Single-domain antibodies as building blocks for novel therapeutics." Curr Opin Pharmacol. 2008 October; 8(5): 600-8. Epub 2008 Aug. 22.), and Arbabi Ghahroudi M et al. ("Selection and identification of single domain antibody fragments from camel heavy-chain antibodies." FEBS Lett. 1997 Sep. 15; 414(3):521-6.).

A "fusion protein" as referred to herein in connection with the invention is not limited to particular types of fusion proteins as long as the parts of the fusion protein are fused by covalent bonds. For example, the parts of the fusion protein can be fused by expression in one or more single polypeptide chain(s), by one or more disulfide linkages, by chemical conjugation (preferably by chemical conjugation using click chemistry) and/or by any other covalent linkage which is known in the art as a suitable link for proteins. Preferably, the parts of the fusion protein are fused by expression in one or more single polypeptide chain(s) and/or by one or more disulfide linkages. Thus, in the fusion proteins of the invention, the anti-TNFRSF receptor antibody or antigen-binding portion thereof and the domain which is capable of binding to a structure of the cell surface and/or to a structure of the extracellular matrix in an FcγR-independent manner can be fused by expression in one or more single polypeptide chain(s), by one or more disulfide linkages, by chemical conjugation (preferably by chemical conjugation using click chemistry) and/or by any other covalent linkage which is known in the art as a suitable link for proteins. Preferably, the anti-TNFRSF receptor antibody or antigen-binding portion thereof and the domain which is capable of binding to a structure of the cell surface and/or to a structure of the extracellular matrix in an FcγR-independent manner are fused by expression in one or more single polypeptide chain(s) and/or by one or more disulfide linkages. In all embodiments of the invention wherein the domain which is capable of binding to a structure of the cell surface and/or to a structure of the extracellular matrix in an FcγR-independent manner comprises an antigen-binding portion of an antibody, said antigen-binding portion being capable of binding to said structure of the cell surface and/or to said structure of the extracellular matrix, wherein said antigen-binding portion capable of binding to said structure of the cell surface and/or to said structure of the extracellular matrix is an antigen-binding portion with reduced ability to bind to one or more FcγR types, said antigen-binding portion being an Fab2 fragment; or a full-length antibody being capable of binding to said structure of the cell surface and/or to said structure of the extracellular matrix;

it is very preferred that the anti-TNFRSF receptor antibody or antigen-binding portion thereof and said domain are fused by chemical conjugation, preferably by chemical conjugation using click chemistry Generally, in connection with all fusion proteins of the invention, it will be understood that the parts of the fusion proteins (e.g. the anti-TNFRSF receptor antibody or antigen-binding portion thereof and the domain which is capable of binding to a structure of the cell surface and/or to a structure of the extracellular matrix in an FcγR-independent manner) can be fused using linker sequences. In that case, the fusion protein of the invention will comprise such linker sequences. Suitable linker sequences are known in the art and comprise, for example, peptide linkers, without being limited thereto. For example, in those fusion proteins of the invention where the anti-TNFRSF receptor antibody or antigen-binding portion thereof and the domain which is capable of binding to a structure of the cell surface and/or to a structure of the extracellular matrix in an FcγR-independent manner is fused by expression in one or more single polypeptide chain(s), said one or more single polypeptide chain(s) may comprise one or more peptide linker sequences between the anti-TNFRSF receptor antibody or antigen-binding portion thereof and the domain which is capable of binding to a structure of the cell surface and/or to a structure of the extracellular matrix in an FcγR-independent manner.

In connection with the invention, the term "a domain which is capable of binding to a structure of the cell surface and/or to a structure of the extracellular matrix in an FcγR-independent manner" means that the domain is capable of binding to a structure of the cell surface and/or to a structure of the extracellular matrix that is different from an FcγR. Unless indicated otherwise, this does not exclude the possibility that the domain can also comprise an additional part (e.g. an Fc domain) which is capable of binding to an FcγR.

In accordance with the present invention, each occurrence of the term "comprising" may optionally be substituted with the term "consisting of", Methods and Techniques Generally, unless otherwise defined herein, the methods used in the present invention (e.g. cloning methods or methods relating to antibodies) are performed in accordance with procedures known in the art, e.g. the procedures described in Sambrook et al. ("Molecular Cloning: A Laboratory Manual.", 2nd Ed., Cold Spring Harbor Laboratory Press, Cold Spring Harbor, N.Y. 1989), Ausubel et al. ("Current Protocols in Molecular Biology." Greene Publishing Associates and Wiley Interscience; New York 1992), and Harlow and Lane ("Antibodies: A Laboratory Manual" Cold Spring Harbor Laboratory Press, Cold Spring Harbor, N.Y. 1988), all of which are incorporated herein by reference.

Binding of fusion proteins and their domains to their respective target proteins can be assessed by methods known in the art. The binding is preferably assessed by surface plasmon resonance measurements.

Sequence Alignments of sequences according to the invention are performed by using the BLAST algorithm (see Altschul et al, (1990) "Basic local alignment search tool." Journal of Molecular Biology 215. p. 403-410.; Altschul et al.: (1997) Gapped BLAST and PSI-BLAST: a new generation of protein database search programs. Nucleic Acids Res. 25:3389-3402, all of which are incorporated herein by reference). Preferably, the following parameters are used: Max target sequences 10; Word size 3; BLOSUM 62 matrix; gap costs: existence 11, extension 1; conditional compositional score matrix adjustment. Thus, when used in connection with sequences, terms such as "identity" or "identical" refer to the identity value obtained by using the BLAST algorithm.

Antibody fusion proteins according to the invention can be produced by any method known in the art, including but not limited to the methods referred to in Siegel D L ("Recombinant monoclonal antibody technology." Transfus Clin Biol. 2002 January; 9(1):15-22,which is incorporated herein by reference).

Stimulation of TNFRSF receptors can be measured by any methods known in the art. For example, in case of the TNFRSF receptors TNFR2, CD40, CD95, Fn14, the stimulation can be measured by using a cell-based IL8 secretion assay, and subsequent detection of the secreted IL8, e.g. by ELISA. Non-limiting examples of cells which can be used for such cell-based IL8 secretion assays are HT1080 CD40 transfectants, which can be used for measuring CD40 stimulation, Widr cells, which can be used for measuring Fn14 stimulation, H1080-cells, which can be used for measuring CD95 stimulation, and TNFR2-expressing HeLa transfectants, which can be used for measuring TNFR2 stimulation. Non-limiting examples of such assays can be found in Examples 1-3 and in the corresponding figures. For TNFRSF receptors which have cytotoxic effects when stimulated such as CD95, cell permeable caspase inhibitors such as ZVAD are preferably added to the assay, in order to prevent the induction of cell death. The stimulation of the various TNFRSF receptors addressed by the fusion proteins of the invention (e.g. TRAAFFIAAS) can also be measured by any method that allow detection of the stimulation of the classical NFκB pathway (e.g. phosphorylation and degradation of IκBα, IKK activation, phosphorylation and nuclear translocation of p65, detection of target genes) or the alternative NFκB pathway (eg. p100 processing, NIK accumulation). Stimulation of CD95 and the TRAIL death receptors (DR4, DR5) by TRAAFFIAAs can also be evaluated my measuring cell death induction by various methods. CD40 stimulation by TRAAFFIAs can furthermore be evaluated by measuring maturation of dendritic cells.

Preparation of Compositions of the Invention

Compositions in accordance with the present invention are prepared in accordance with known standards for the preparation of pharmaceutical compositions.

For instance, the compositions are prepared in a way that they can be stored and administered appropriately, e.g. by adding pharmaceutically acceptable components such as carriers, excipients or stabilizers.

Such pharmaceutically acceptable components are not toxic in the amounts used when administering the pharmaceutical composition to a patient. The pharmaceutical acceptable components added to the pharmaceutical compositions may depend on the particular intended use of the pharmaceutical compositions and the route of administration.

In general, the pharmaceutically acceptable components used in connection with the present invention are used in accordance with knowledge available in the art, e.g. from Remington's Pharmaceutical Sciences, Ed. A R Gennaro, 20th edition, 2000, Williams & Wilkins, PA, USA.

Sequences

The amino acid sequences referred to in the present application are represented in an N-terminal to C-terminal order using the one-letter amino acid code. The nucleic acid sequences referred to in the present application are represented in a 5' to 3' order using the standard nucleic acid code. Asterisks indicate the end of the protein sequence. Underlined nucleic acid sequences represent restriction endonuclease sites.

The following non-limiting exemplary sequences were used in the experimental examples of the present application:

TABLE 1

| Protein | Combination of plasmids used (as indicated by their nucleic acid SEQ ID NOs) |
|---|---|
| Anti-CD40(G28.5)-HC:scTNF80 | 1 + 5 |
| Anti-CD40(G28.5)-IgG1 | 2 + 5 |
| Anti-CD40-IgG1(N297A)-HC:scFv:CD20 | 3 + 5 |
| Anti-CD40(G28.5)-IgG1(N297A)-HC:scBaff | 4 + 5 |
| Anti-TNFR2-(C4)-IgG1 | 9 + 13 |
| Anti-TNFR2(C4)-HC:1L2 | 6 + 13 |
| Anti-TNFR2-IgG1(N297A)-HC:scFv:CD19 | 7 + 13 |
| Anti-INFR2-IgG1(N297A)-HC:scFv:CD20 | 8 + 13 |
| Anti-TNFR2(C4)-IgG1(N297A-HC:scGITRL | 10 + 13 |
| Anti-TNFR2(C4)-IgG1(N297A)-HC:sc(mu)41BBL | 11 + 13 |
| Anti-TNFR2(C4)-IgG1(N297A)-HC:(mu)GITRL | 12 + 13 |
| Anti-CD95(E09)-HC:scFv:CD19 | 14 + 18 |
| Anti-CD95(E09)-IgG1 | 15 + 18 |
| Anti-CD95(E09)-F(ab)2-HC:scFv:CD20 | 16 + 18 |
| Anti-CD95(E09)-IgG1(N297A)-HC:scBaff | 17 + 18 |
| Anti-CD40(G28.5)-FAB2 | 108 + 5 |
| Anti-CD40(G28.5)-FAB2-HC:scBaff | 109 + 5 |
| Anti-CD95(E09)-FAB2-HC:scBaff | 110 + 18 |
| Anti-TNFR2(C4)-IgG2-HC:scFv:CD20 | 111 + 13 |
| Anti-TNFR2(C4)-IgG1(N297A)-HC:scFv:CD70(1F6) | 112 + 13 |
| Anti-TNFR2(C4)-IgG1(N297A)-HC:scFv:CD70(2H5) | 113 + 13 |
| Anti-41BB(HBBK4)-IgGl(N297A)-HC:scFv:CD20 | 114 + 115 |
| Anti-CD95(E09)-IgG1(N297A)-HC:scFv:CD20 | 116 + 18 |
| Anti-TRAILR2(Cona)-IgG1(N297A)-HC:scFv:CD70(9G2) | 146 + 147 |
| Anti-CD40(C)-IgG1(N297A)-HC:scFv:PD-L1 | 148 + 149 |
| Anti-CD40(C)-Fab2-HascFv:PD-L1 | 150 + 149 |
| anti-41BB(HBBK)-IgG1(N297A)-HC:scFv:PD-L1 | 151 + 115 |
| anti-41BB(HBBK)-Fab2-1-1C:scFv:PD-L1 | 152 + 115 |
| anti-PD-Li(Ave)-IgG2-HC:scFv:41BB(HBBK). | 153 + 154 |
| anti-muCD27-IgG1(N297A)-HC:scFv14(1801). | 155 + 156 |

| SEQ ID NO (of plasmid nucleic acid and resulting [protein] sequence) | Name of Plasmid |
|---|---|
| 1 [19] | anti-CD40-Flag-VH-heavy-full-scTNF80(mu)-pCR3 (N297A) |
| 2 [20] | anti-CD40-Flag-VH-heavy-full-pCR3 (hlgG1) |
| 3 [21] | anti-CD40-Flag-VH-heavy-full-scFv-anti-CD20-pCR3 (N297A) |
| 4 [22] | anti-CD40-Flag-VH-heavy-full-scBaff-pCR3 (N297A) |
| 5 [23] | anti-CD40-Flag-VL-light-fuIl-pCR3 |
| 6 [24] | C4-HC-full-IL2(mu)-pCR3 (hlgG1)(Flagless) |
| 7 [25] | C4-HC-heavy-full-scFv-anti-CD19-pCR3 (N297A)(Flagless) |
| 8 [26] | C4-HC-heavy-full-scFv-anti-CD20-pCR3 (N297A)(Flagless) |
| 9 [27] | C4-HC-heavy-full-pCR3 (hlgG1)(Flagless) |
| 10 [28] | C4-HC-heavy-full-scGITRL-pCR3 (N297A) |
| 11 [29] | C4-HC-heavy-full-sc(mu)41BBL-pCR3 (N297A) |
| 12 [30] | C4-HC-heavy-full-(mu)GITRL-pCR3 (N297A) |
| 13 [31] | C4-LC-light-full-pCR3 (Flagless) |
| 14 [32] | anti-CD95(E09)-Flag-VH-heavy-full-scFv-anti-CD19-pCR3 (hlgG1) |
| 15 [33] | anti-CD95(E09)-Flag-VH-heavy-full-pCR3 (hlgG1) |
| 16 [34] | anti-CD95(E09)-Flag-FAB2(1-114)-scFv-anti-CD20-pCR3 (hlgG1) |
| 17 [35] | anti-CD95(E09)-Flag-VH-heavy-full-scBaff-pCR3 (N297A) |
| 18 [36] | anti-CD95(E09)-Flag-VL-light-full-pCR3 |
| 108 [117] | anti-CD40(G28.5)-VH(1-114)-pCR3 |
| 109 [118] | anti-CD40(G28.5)-VH(1-114)-scBaff-pCR3 |
| 110 [119] | anti-CD95(E09)-VH(1-114)-scBaff-pCR3 |
| 111 [120] | anti-TNFR2(C4)-IgG2-VH-scFv:CD20-pCR3 |
| 112 [121] | anti-TNFR2(C4)-IgG1(N297A)-VH-scFv:CD70(1F6)-pCR3 |
| 113 [122] | anti-TNFR2(C4)-IgG1(N297A)-VH-scFv:CD70(2H5)-pCR3 |
| 114 [123] | anti-41BB(HBBK4)-IgG1(N297A)-VH-scFv:CD20-pCR3 |
| 115 [124] | anti-41BB(HBBK4)-Flag-VL-pCR3 |
| 116 [125] | anti-CD95(E09)-IgG1(N297A)-VH-scFv:CD20-pCR3 |

-continued

| SEQ ID NO (of plasmid nucleic acid and resulting [protein] sequence) | Name of Plasmid |
|---|---|
| 146 [157] | anti-TRAILR2(Cona)-IgG1(N297A)-VH-scFv:CD70(9G2) |
| 147 [158] | anti-TRAILR2(Cona)-VL |
| 148 [159] | anti-CD40(C)-IgG1(N297A)-VH-scFv:PD-L1(Ave) |
| 149 [160] | anti-CD40(C)-VL |
| 150 [161] | anti-CD40(C)-Fab2-scFv:PD-L1(Ave) |
| 151 [116] | anti-41BB(HBBK)-IgG1(N297A)-VH-scFvPD-L1(Ave) |
| 152 [163] | anti-41BB(HBBK)-Fab2-scFv:PD-L1(Ave) |
| 153 [164] | anti-PD-Li(Ave)-IgG2-VH-scFv:41BB(HBBK) |
| 154 [165] | anti-PD-L1(Ave)-VL |
| 155 [166] | anti-muCD27-IgG1(N297A)-VH-scFv:Fn14(18D1) |
| 156 [167] | anti-muCD27-VL |

SEQ ID NO: 1: anti-CD40-Flag-VH-heavy-full-scTNF80(mu)-pCR3 (N297A):
atgaacttcggcttcagcctgatcttcctggtgctggtgctgaagggcgtgcagtgcgaagtgaagctggtgccccggcaattggactacaaggacga cgacgacaaagaattggatatccagctccagcagtctggccctggactcgtcaaaccatctcagagcctgtctctcacctgttctgtcaccggatactcc atcaccaccaactacaactggaattggattcggcagtttcctgggaacaaactcgaatggatgggatacatccgatacgacggcactagtgaataca ccccatctctcaaaaatcgggtgtccattacccgggacacttctatgaaccagttctttctccgactcacctctgtgacacctgaggataccgccacatact actgtgctagactggactactgggggcagggaacactggtgaccgtgtcatctggatccagcagcgcctctacaaagggccccagcgtgttccctctg gcccctagcagcaagagcacatctggcggaacagccgccctgggctgcctcgtgaaggactactttcccgagcccgtgaccgtgtcctggaactctg gcgctctgacaagcggcgtgcacacctttccagccgtgctgcagagcagcggcctgtactctctgagcagcgtcgtgacagtgcccagcagctctctg ggcacccagacctacatctgcaacgtgaaccacaagcccagcaacaccaaggtggacaagaaggtggaacccaagagctgcgacaagaccc acacctgtcccccttgtcctgcccccgaactgctgggaggcccttccgtgttcctgttcccccaaagcccaaggacaccctgatgatcagccggaccc ccgaagtgacctgcgtggtggtggatgtgtcccacgaggaccctgaagtgaagtttaattggtacgtggacggcgtggaagtgcacaacgccaagac caagcctagagaggaacagtacgccagcacctaccgggtggtgtccgtgctgacagtgctgcaccaggactggctgaacggcaaagagtacaag tgcaaggtgtccaacaaggccctgcctgcccccatcgagaaaaccatcagcaaggccaagggccagccccgcgaaccccaggtgtacacactgc ccccaagcagggacgagctgaccaagaaccaggtgtccctgacctgtctcgtgaaaggcttctaccccagcgatatcgccgtggaatgggagagc aacggccagcccgagaacaactacaagaccaccccccctgtgctggacagcgacggctcattcttcctgtacagcaagctgaccgtggacaagtc ccggtggcagcagggcaacgtgttcagctgcagcgtgatgcacgaggccctgcacaaccactacacccagaagtccctgagcctgagccccggc aaggaattcgagttcacacgggacaaacctgtggctcatgtggtggccaatcatcaggtggaggaacagctggaatggctgagtcagagagcaaa cgccctgctggcaaatgggatggacctcaaagacaatcagctcgtggtgcctgccgatggactgtacctggtgtactctcaggtcctgtttaagggaca gggatgccccgattacgtgctgctcacccacactgtgtcacgcttcgccatctcataccaggagaaagtcaatctcctctccgccgtgaaatcaccatgt cctaaggatactcccgagggagccgaactgaaaccttggtacgaacccatctacctgggcggcgtgtttcagctggagaaaggcgatcagctctccg ccgaagtgaatctgcccaaatacctcaactttagggaatccggacaggtctactttggcgtgattgccctgggaggcggatctggaggaggctctggc gggggatctgggggcggatccgacaaacctgtggcacacgtcgtggcaaaccatcaggtcgaggaacagctcgagtggctgtcacagagggcca atgccctgctggcaaatggaatggatctgaaggataatcagctcgtcgtgcctgccgacggcctctacctcgtctactctcaggtcctctttaagggaca gggctgccccgactacgtcctgctcactcataccgtgagtcgcttcgctatttcataccaggaaaaagtcaacctgctgagtgctgtgaaatctccttgcc ctaaggataccccctgagggagccgaactcaaaccatggtacgagccaatctacctcggaggagtgtttcagctggaaaaaggggatcagctctccg ccgaagtcaacctccccaaatacctcaatttccgggaatccggacaggtgtactttggagtcattgccctgggaggcggctctggcgggggatctgga ggaggctccggaggaggcagtgacaaacccgtcgctcacgtggtggcaaatcatcaggtcgaggaacagctggaatggctgtctcagagagcaa acgctctcctcgccaatggaatggatctcaaggacaaccagctcgtcgtccctgccgatggactctacctggtctactctcaggtgctctttaagggaca -continued gggatgccccgattacgtcctgctcacacacaccgtgtctcgctttgctatttcataccaggagaaagtcaatctgctgtctgccgtcaaatctccttgtcca aaagacacacccgagggagccgaactcaaaccttggtacgagccaatctacctgggggggagtgtttcagctggagaaggggggatcagctctccgc cgaagtgaatctcccaaaatacctcaattttcgggaatccggacaggtctactttggagtgattgccctgtag SEQ ID NO: 19: Protein construct expressed from SEQ ID NO: 1:
MNFGFSLIFL VLVLKGVQCE VKLVPRQLDY KDDDDKELDI QLQQSGPGLV KPSQSLSLTC

SVTGYSITTN YNWNWIRQFP GNKLEWMGYI RYDGTSEYTP SLKNRVSITR DTSMNQFFLR

LTSVTPEDTA TYYCARLDYW GQGTLVTVSS GSSSASTKGP SVFPLAPSSK STSGGTAALG

CLVKDYFPEP VTVSWNSGAL TSGVHTFPAV LQSSGLYSLS SVVTVPSSSL GTQTYICNVN

HKPSNTKVDK KVEPKSCDKT HTCPPCPAPE LLGGPSVFLF PPKPKDTLMI SRTPEVTCVV

VDVSHEDPEV KFNWYVDGVE VHNAKTKPRE EQYASTYRVV SVLTVLHQDW LNGKEYKCKV

SNKALPAPIE KTISKAKGQP REPQVYTLPP SRDELTKNQV SLTCLVKGFY PSDIAVEWES

NGQPENNYKT TPPVLDSDGS FFLYSKLTVD KSRWQQGNVF SCSVMHEALH NHYTQKSLSL

SPGKEFEFTR DKPVAHVVAN HQVEEQLEWL SQRANALLAN GMDLKDNQLV VPADGLYLVY

SQVLFKGQGC PDYVLLTHTV SRFAISYQEK VNILSAVKSP CPKDTPEGAE LKPWYEPIYL

GGVFQLEKGD QLSAEVNLPK YLNFRESGQV YFGVIALGGG SGGGSGGGSG GGSDKPVAHV

VANHQVEEQL EWLSQRANAL LANGMDLKDN QLVVPADGLY LVYSQVLFKG QGCPDYVLLT

HTVSRFAISY QEKVNLLSAV KSPCPKDTPE GAELKPWYEP IYLGGVFQLE KGDQLSAEVN

LPKYLNFRES GQVYFGVIAL GGGSGGGSGG GSGGGSDKPV AHVVANHQVE EQLEWLSQRA

NALLANGMDL KDNQLVVPAD GLYLVYSQVL FKGQGCPDYV LLTHTVSRFA ISYQEKVNLL

SAVKSPCPKD TPEGAELKPW YEPIYLGGVF QLEKGDQLSA EVNLPKYLNF RESGQVYFGV

IAL*

SEQ ID NO: 2: anti-CD40-Flag-VH-heavy-full-pCR3 (hIgG1):
atgaacttcggcttcagcctgatcttcctggtgctggtgctgaagggcgtgcagtgcgaagtgaagctggtgccccggcaattggactacaaggacga cgacgacaaagaattggatatccagctccagcagtctggccctggactcgtcaaaccatctcagagcctgtctctcacctgttctgtcaccggatactcc atcaccaccaactacaactggaattggattcggcagtttcctgggaacaaactcgaatggatgggatacatccgatacgacggcactagtgaataca ccccatctctcaaaaatcgggtgtccattacccgggacacttctatgaaccagttctttctccgactcacctctgtgacacctgaggataccgccacatact actgtgctagactggactactgggggcagggaacactggtgaccgtgtcatctggatcctctagcgccagcacaaagggccccagcgtgttccctctg gcccctagcagcaagagcacatctggcggaacagccgccctgggctgcctcgtgaaggactactttcccgagcccgtgacagtgtcctggaactctg gcgccctgacaagcggcgtgcacacctttccagccgtgctgcagagcagcggcctgtactctctgagcagcgtcgtgactgtgcccagcagcagcct gggcacccagacctacatctgcaacgtgaaccacaagcccagcaacaccaaggtggacaagaaggtggaacccaagagctgcgacaagacc cacacctgtccccccttgtcctgcccctgaactgctgggcggaccttccgtgttcctgttccccccaaagcccaaggacaccctgatgatcagccggacc cccgaagtgacctgcgtggtggtggatgtgtcccacgaggaccctgaagtgaagtttaattggtacgtggacggcgtggaagtgcacaacgccaaga ccaagcccagagaggaacagtacaacagcacctaccgggtggtgtccgtgctgacagtgctgcaccaggactggctgaacggcaaagagtacaa gtgcaaggtgtccaacaaggccctgcctgcccccatcgagaaaaccatcagcaaggccaagggccagccccgcgaaccccaggtgtacacact gcctcccagcagggacgagctgaccaagaaccaggtgtccctgacctgtctcgtgaaaggcttctaccccctccgatatcgccgtggaatgggagagc aacggccagcccgagaacaactacaagaccacccccccctgtgctggacagcgacggctcattcttcctgtacagcaagctgaccgtggacaagtc ccggtggcagcagggcaacgtgttcagctgcagcgtgatgcacgaggccctgcacaaccactacacccagaagtccctgagcctgagccccggc aagtaa SEQ ID NO: 20: Protein construct expressed from SEQ ID NO: 2:
MNFGESLIFL VLVLKGVQCE VKLVPRQLDY KDDDDKELDI QLQQSGPGLV KPSQSLSLTC

SVTGYSITTN YNWNWIRQFP GNKLEWMGYI RYDGTSEYTP SLKNRVSITR DTSMNQFFLR

LTSVTPEDTA TYYCARLDYW GQGTLVTVSS GSSSASTKGP SVFPLAPSSK STSGGTAALG

-continued

CLVKDYFPEP VTVSWNSGAL TSGVHTFPAV LQSSGLYSLS SVVTVPSSSL GTQTYICNVN

HKPSNTKVDK KVEPKSCDKT HTCPPCPAPE LLGGPSVFLF PPKPKDTLMI SRTPEVTCVV

VDVSHEDPEV KFNWYVDGVE VHNAKTKPRE EQYNSTYRVV SVLTVLHQDW LNGKEYKCKV

SNKALPAPIE KTISKAKGQP REPQVYTLPP SRDELTKNQV SLTCLVKGFY PSDIAVEWES

NGQPENNYKT TPPVLDSDGS FFLYSKLTVD KSRWQQGNVF SCSVMHEALH NHYTQKSLSL

SPGK*

SEQ ID NO: 3: anti-CD40-Flag-VH-heavy-full-scFv-anti-CD20-pCR3 (N297A):
atgaacttcggcttcagcctgatcttcctggtgctggtgctgaagggcgtgcagtgcgaagtgaagctggtgccccggcaattggactacaaggacga cgacgacaaagaattggatatccagctccagcagtctggccctggactcgtcaaaccatctcagagcctgtctctcacctgttctgtcaccggatactcc atcaccaccaactacaactggaattggattcggcagtttcciggg aacaaactcgaatggatgggatacatccgatacgacggcactagtgaataca ccccatctctcaaaaatcgggtgtccattacccgggacacttctatgaaccagttctttctccgactcacctctgtgacacctgaggataccgccacatact actgtgctagactggactactgggggcagggaacactggtgaccgtgtcatctggatccagcagcgcctctacaaagggccccagcgtgttccctctg gcccctagcagcaagagcacatctggcggaacagccgccctgggctgcctcgtgaaggactactttcccgagcccgtgaccgtgtcctggaactctg gcgctctgacaagcggcgtgcacacctttccagccgtgctgcagagcagcggcctgtactctctgagcagcgtcgtgacagtgcccagcagctctctg ggcacccagacctacatctgcaacgtgaaccacaagcccagcaacaccaaggtggacaagaaggtggaacccaagagctgcgacaagaccc acacctgtcccccttgtcctgcccccgaactgctgggaggcccttccgtgttcctgttcccccaaagcccaaggacaccctgatgatcagccggaccc ccgaagtgacctgcgtggtggtggatgtgtcccacgaggaccctgaagtgaagtttaattggtacgtggacggcgtggaagtgcacaacgccaagac caagcctagagaggaacagtacgccagcacctaccgggtggtgtccgtgctgacagtgctgcaccaggactggctgaacggcaaagagtacaag tgcaaggtgtccaacaaggccctgcctgcccccatcgagaaaaccatcagcaaggccaagggccagccccgcgaaccccaggtgtacacactgc cccaagcagggacgagctgaccaagaaccaggtgtccctgacctgtctcgtgaaaggcttctaccccagcgatatcgccgtggaatgggagagc aacggccagcccgagaacaactacaagaccaccccccctgtgctggacagcgacggctcattcttcctgtacagcaagctgaccgtggacaagtc ccggtggcagcagggcaacgtgttcagctgcagcgtgatgcacgaggccctgcacaaccactacacccagaagtccctgagcctgagccccggc aaggaattccaggtacaactgcagcagcctggggctgagctggtgaagcctggggcctcagtgaagatgtcctgcaaggcttctggctacacatttac cagttacaatatgcactgggtaaaacagacacctggtcggggcctggaatggattggagctatttatcccggaAatggtgatacttcctacaatcagaa gttcaaaggcaaggccacattgactgcagacaaatcctccagcacagcctacatgcagctcagcagcctgacatctgaggactctgcggtctattact gtgcaagatcgacttactacggcggtgactggtacttcaatgtctggggcgcagggaccacggtcaccgtctcttcaggaggaggcggatccggcgg aggcggaagcggtggcggaggctctcaaattgttctctcccagtctccagcaatcctgtctgcatctccaggggagaaggtcacaatgacttgcaggg ccagctcaagtgtaagttacatccactggttccagcagaagCcaggatcctcccccaaaccctggatttatgccacatccaacctggcttctggagtcc ctgttcgcttcagtggcagtgggtctgggacttcttactctctcacaatcagcagagtggaggcgaagatgctgccacttattactgccagcagtggacta gtaacccacccacgttcggaGgggggaccaagctggaaatcaaacgttaa SEQ ID NO: 21: Protein construct expressed from SEQ ID NO: 3:
MNFGESLIFL VLVLKGVQCE VKLVPRQLDY KDDDDKELDI QLQQSGPGLV KPSQSLSLTC

SVTGYSITTN YNWNWIRQFP GNKLEWMGYI RYDGTSEYTP SLKNRVSITR DTSMNQFFLR

LTSVTPEDTA TYYCARLDYW GQGTLVTVSS GSSSASTKGP SVFPLAPSSK STSGGTAALG

CLVKDYFPEP VTVSWNSGAL TSGVHTFPAV LQSSGLYSLS SVVTVPSSSL GTQTYICNVN

HKPSNTKVDK KVEPKSCDKT HTCPPCPAPE LLGGPSVFLF PPKPKDTLMI SRTPEVTCVV

VDVSHEDPEV KENWYVDGVE VHNAKTKPRE EQYASTYRVV SVLTVLHQDW LNGKEYKCKV

SNKALPAPIE KTISKAKGQP REPQVYTLPP SRDELTKNQV SLTCLVKGFY PSDIAVEWES

NGQPENNYKT TPPVLDSDGS FFLYSKLTVD KSRWQQGNVF SCSVMHEALH NHYTQKSLSL

SPGKEFQVQL QQPGAELVKP GASVKMSCKA SGYTFTSYNM HWVKQTPGRG LEWIGAIYPG

NGDTSYNQKF KGKATLTADK SSSTAYMQLS SLTSEDSAVY YCARSTYYGG DWYFNVWGAG

TTVTVSSGGG GSGGGGSGGG GSQIVLSQSP AILSASPGEK VTMTCRASSS VSYIHWFQQK

-continued

PGSSPKPWIY ATSNLASGVP VRFSGSGSGT SYSLTISRVE AEDAATYYCQ QWTSNPPTFG

GGTKLEIKR*

SEQ ID NO: 4: anti-CD40-Flag-VH-heavy-fun-scBaff-pCR3 (N297A):
atgaacttcggcttcagcctgatcttcctggtgctggtgctgaagggcgtgcagtgcgaagtga agctggtgccccggcaattggactacaaggacgacgacgacaaagaattggatatccagctcca gcagtctggccctggactcgtcaaaccatctcagagcctgtctctcacctgttctgtcaccgga tactccatcaccaccaactacaactggaattggattcggcagtttcctgggaacaaactcgaat ggatgggatacatccgatacgacggcactagtgaatacaccccatctctcaaaaatcgggtgtc cattacccgggacacttctatgaaccagttctttctccgactcacctctgtgacacctgaggat accgccacatactactgtgctagactggactactgggggcagggaacactggtgaccgtgtcat ctggatccagcagcgcctctacaaagggccccagcgtgttccctctggcccctagcagcaagag cacatctggcggaacagccgccctgggctgcctcgtgaaggactactttcccgagcccgtgacc gtgtcctggaactctggcgctctgacaagcggcgtgcacacctttccagccgtgctgcagagca gcggcctgtactctctgagcagcgtcgtgacagtgcccagcagctctctgggcacccagaccta catctgcaacgtgaaccacaagcccagcaacaccaaggtggacaagaaggtggaacccaagagc tgcgacaagacccacacctgtccccccttgtcctgcccccgaactgctgggaggcccttccgtgt tcctgttcccccccaaagcccaaggacaccctgatgatcagccggacccccgaagtgacctgcgt ggtggtggatgtgtcccacgaggaccctgaagtgaagtttaattggtacgtggacggcgtggaa gtgcacaacgccaagaccaagcctagagaggaacagtacgccagcacctaccgggtggtgtccg tgctgacagtgctgcaccaggactggctgaacggcaaagagtacaagtgcaaggtgtccaacaa ggccctgcctgcccccatcgagaaaaccatcagcaaggccaagggccagccccgcgaaccccag gtgtacacactgcccccaagcagggacgagctgaccaagaaccaggtgtccctgacctgtctcg tgaaaggcttctaccccagcgatatcgccgtggaatgggagagcaacggccagcccgagaacaa ctacaagaccaccccccctgtgctggacagcgacggctcattcttcctgtacagcaagctgacc gtggacaagtcccggtggcagcagggcaacgtgttcagctgcagcgtgatgcacgaggccctgc acaaccactacacccagaagtccctgagcctgagccccggcaagctcgagggacccgaggaaac tgtgactcaggactgtctccagctcattgccgatagtgaaacccctaccatccagaaaggctct tacaccttcgtgccatggctgctgtcattcaaacggggatctgctctggaggagaaggaaaaca aaatcctggtcaaggaaaccggctacttcttcatctacggccaggtcctctacaccgacaaaac atacgctatggggcatctcattcagcggaaaaaagtccacgtgttcggcgacgaactctctctc gtgacactgttccggtgtattcagaacatgcccgagactctgcccaataatagctgctactctg ctggcattgccaaactggaggagggcgacgaactccagctggctattcctagggaaaatgccca gattagcctggacggggatgtgacatttttggcgccctgaaactgctgggaggcggagggagt ggcgggggaggctctggacctgaggaaactgcgacccaggattgtctccagctcattgccgata gtgagactcctaccattcagaagggatcttacacctttgtgccttggctgctgtctttcaaacg gggctctgctctggaggaaaaggagaacaaaattctggtcaaagagactggctacttcttcatc tacggccaggtgctgtacaccgacaaaacatacgccatgggccatctcattcagcggaaaaaag tccacgtgttcggcgacgaactctctctcgtgacactgttccggtgtatccagaacatgcccga gacactgcccaataatagctgctactctgccggcattgctaaactggaggagggggacgaactc cagctggctattcctagggaaaatgcccagatttctctcgatggggatgtgacattcttcgggg ccctcaaactgctgggaggcggcggatctggcggaggcgggagtcaattcgcagcaggtccaga -continued agaaacagtcactcaagactgcttgcaactgattgcagacagtgaaacaccaactatacaaaaa ggatcttacacatttgttccatggcttctcagctttaaaaggggaagtgccctagaagaaaaag agaataaaatattggtcaaagaaactggttactttttttatatatggtcaggttttatatactga taagacctacgccatgggacatctaattcagaggaagaaggtccatgtctttggggatgaattg agtctggtgactttgtttcgatgtattcaaaatatgcctgaaacactacccaataattcctgct attcagctggcattgcaaaactggaagaaggagatgaactccaacttgcaataccaagagaaaa tgcacaaatatcactggatggagatgtcacatttttttggtgcattgaaactgctgtga SEQ ID NO: 22: Protein construct expressed from SEQ ID NO: 4:
MNFGESLIFL VLVLKGVQCE VKLVPRQLDY KDDDDKELDI QLQQSGPGLV KPSQSLSLTC

SVTGYSITTN YNWNWIRQFP GNKLEWMGYI RYDGTSEYTP SLKNRVSITR DTSMNQFFLR

LTSVTPEDTA TYYCARLDYW GQGTLVTVSS GSSSASTKGP SVFPLAPSSK STSGGTAALG

CLVKDYFPEP VTVSWNSGAL TSGVHTFPAV LQSSGLYSLS SVVTVPSSSL GTQTYICNVN

HKPSNTKVDK KVEPKSCDKT HTCPPCPAPE LLGGPSVFLF PPKPKDTLMI SRTPEVTCVV

VDVSHEDPEV KFNWYVDGVE VHNAKTKPRE EQYASTYRVV SVLTVLHQDW LNGKEYKCKV

SNKALPAPIE KTISKAKGQP REPQVYTLPP SRDELTKNQV SLTCLVKGFY PSDIAVEWES

NGQPENNYKT TPPVLDSDGS FFLYSKLTVD KSRWQQGNVF SCSVMHEALH NHYTQKSLSL

SPGKLEGPEE TVTQDCLQLI ADSETPTIQK GSYTFVPWLL SFKRGSALEE KENKILVKET

GYFFIYGQVL YTDKTYAMGH LIQRKKVHVF GDELSLVTLF RCIQNMPETL PNNSCYSAGI

AKLEEGDELQ LATPRENAQI SLDGDVTFFG ALKLLGGGGS GGGGSGPEET VTQDCLQLTA

DSETPTIQKG SYTFVPWLLS FKRGSALEEK ENKILVKETG YFFIYGQVLY TDKTYAMGHL

IQRKKVHVFG DELSLVTLFR CIQNMPETLP NNSCYSAGIA KLEEGDELQL AIPRENAQIS

LDGDVTFFGA LKLLGGGGSG GGGSQFAAGP EETVTQDCLQ LIADSETPTI QKGSYTEVPW

LLSFKRGSAL EEKENKILVK ETGYFFIYGQ VLYTDKTYAM GHLIQRKKVH VFGDELSLVT

LERCTQNMPE TLPNNSCYSA GIAKLEEGDE LQLAIPRENA QISLDGDVTF FGALKLL*

SEQ ID NO: 5: anti-CD40-Flag-VL-light-full-pCR3:
atgaacttcggcttcagcctgatcttcctggtgctggtgctgaagggcgtgcagtgcgaagtga agctggtgccccggcaattggactacaaggacgacgacgacaaagaattggacatcgtgatgac tcagaacccactgtctctgcctgtgtctctgggggatgaggctagcatttcttgccgctcatct cagtcactggagaactccaatggcaacaccttcctgaattggtttttccagaaacccggccagt cacctcagctgctcatctaccgagtgagcaatcggtttagcggagtgcccgatcgattctctgg ctccggatctgggaccgactttaccctgaaaatctcacgagtggaggccgaggatctgggagtg tacttctgtctccaggtcacacatgtgccttacacatttggcggcggaacaactctcgaaatca aaggatccgaaatcaagcgtacggtggccgctcccagcgtgttcatcttcccacctagcgacga gcagctgaagtccggcacagcctctgtcgtgtgcctgctgaacaacttctacccccgcgaggcc aaggtgcagtggaaggtggacaatgccctgcagagcggcaacagccaggaaagcgtgaccgagc aggacagcaaggactccacctacagcctgagcagcaccctgaccctgagcaaggccgactacga gaagcacaaggtgtacgcctgcgaagtgacccaccagggcctgtctagccccgtgaccaagagc ttcaaccggggcgagtgctaa SEQ ID NO: 23: Protein construct expressed from SEQ ID NO: 5:
MNFGFSLIFL VLVLKGVQCE VKLVPRQLDY KDDDDKELDI VMTQNPLSLP VSLGDEASIS

CRSSQSLENS NGNTFLNWFF QKPGQSPQLL IYRVSNRFSG VPDRFSGSGS GTDFTLKISR

VEAEDLGVYF CLQVTHVPYT FGGGTTLEIK GSEIKRTVAA PSVFIFPPSD EQLKSGTASV

VCLLNNFYPR EAKVQWKVDN ALQSGNSQES VTEQDSKDST YSLSSTLTLS KADYEKHKVY

ACEVTHQGLS SPVTKSFNRG EC*

SEQ ID NO: 6: C4-HC-full-IL2(mu)-pCR3 (hIgG1) (Flagless):
atgaacttcggcttcagcctgatcttcctggtgctggtgctgaagggcgtgcagtgcgaagtga agctggtgccccggcaattgcaggttcagctgctgcagtctggacctgagctggtgaagcctgg ggcttcagtgaagttgtcctgcaaggcttctggttatagtttcacaagttacgatattaactgg gtgaagcagaggcctggacagggacttgagtgggttggatggatttatcctagagatggtgata ctaagtacaatgagaaattcaagggcaaggccatattgactgtagacacatcctccaacacagc gtacatgaacctccacagcctgacatctgaggactctgcggtctatttctgtgcaagactaact gggccctactggtacttcgatgtctggggcacagggaccacggtcaccgtctcctcaggatcct ctagcgccagcacaaagggccccagcgtgttccctctggcccctagcagcaagagcacatctgg cggaacagccgccctgggctgcctcgtgaaggactactttcccgagcccgtgacagtgtcctgg aactctggcgccctgacaagcggcgtgcacacctttccagccgtgctgcagagcagcggcctgt actctctgagcagcgtcgtgactgtgcccagcagcagcctgggcacccagacctacatctgcaa cgtgaaccacaagcccagcaacaccaaggtggacaagaaggtggaacccaagagctgcgacaag acccacacctgtccccccttgtcctgcccctgaactgctgggcggaccttccgtgttcctgttcc ccccaaagcccaaggacaccctgatgatcagccggacccccgaagtgacctgcgtggtggtgga tgtgtcccacgaggaccctgaagtgaagtttaattggtacgtggacggcgtggaagtgcacaac gccaagaccaagcccagagaggaacagtacaacagcacctaccgggtggtgtccgtgctgacag tgctgcaccaggactggctgaacggcaaagagtacaagtgcaaggtgcccaacaaggccctgcc tgcccccatcgagaaaaccatcagcaaggccaagggccagccccgcgaaccccaggtgtacaca ctgcctcccagcagggacgagctgaccaagaaccaggtgtccctgacctgtctcgtgaaaggct tctacccctccgatatcgccgtggaatgggagagcaacggccagcccgagaacaactacaagac cacccccccctgtgctggacagcgacggctcattcttcctgtacagcaagctgaccgtggacaag tcccggtggcagcagggcaacgtgttcagctgcagcgtgatgcacgaggccctgcacaaccact acacccagaagtccctgagcctgagccccggcaaggaattgcccggtaccgcccctaccagcag cagcacctctagctctacagccgaggctcaacaacaacaacaacagcaacagcagcagcagcag cacctggaacagctgctgatggacctgcaggaactgctgagccggatggaaaactaccggaacc tgaagctgccccggatgctgaccttcaagttctacctgcccaagcaggccaccgagctgaagga tctgcagtgcctggaagatga.gctgggcccccctgagacacgtgctggatctgacccagagcaag agctttcagctggaagatgccgagaacttcatcagcaacatcagagtgaccgtcgtgaagctga agggcagcgacaacaccttcgagtgccagttcgacgacgagagcgctaccgtggtggacttcct gcggagatggatcgccttctgccagagcatcatcagcaccagcccccagtaa SEQ ID NO: 24: Protein construct expressed from SEQ ID NO: 6
MNFGESLIFL VLVLKGVQCE VKLVPRQLQV QLLQSGPELV KPGASVKLSC KASGYSFTSY

DINWVKQRPG QGLEWVGWIY PRDGDTKYNE KFKGKAILTV DTSSNTAYMN LHSLTSEDSA

VYFCARLTGP YWYFDVWGTG TTVTVSSGSS SASTKGPSVF PLAPSSKSTS GGTAALGCLV

KDYFPEPVTV SWNSGALTSG VHTFPAVLQS SGLYSLSSVV TVPSSSLGTQ TYICNVNHKP

SNTKVDKKVE PKSCDKTHTC PPCPAPELLG GPSVFLFPPK PKDTLMISRT PEVTCVVVDV

SHEDPEVKFN WYVDGVEVHN AKTKPREEQY NSTYRVVSVL TVLHQDWLNG KEYKCKVSNK

ALPAPIEKTI SKAKGQPREP QVYTLPPSRD ELTKNQVSLT CLVKGFYPSD IAVEWESNGQ

-continued

PENNYKTTPP VLDSDGSFFL YSKLTVDKSR WQQGNVFSCS VMHEALHNHY TQKSLSLSPG

KELPGTAPTS SSTSSSTAEA QQQQQQQQQQ QQHLEQLLMD LQELLSRMEN YRNLKLPRML

TFKFYLPKQA TELKDLQCLE DELGPLRHVL DLTQSKSFQL EDAENFISNI RVTVVKLKGS

DNTFECQFDD ESATVVDFLR RWIAFCQSII STSPQ*

SEQ ID NO: 7: C4-HC-heavy-konst-full-scFv-anti-CD19-pCR3 (N297A) (Flagless):
atgaacttcggcttcagcctgatcttcctggtgctggtgctgaagggcgtgcagtgcgaagtga agctggtgccccggcaattgcaggttcagctgctgcagtctggacctgagctggtgaagcctgg ggcttcagtgaagttgtcctgcaaggcttctggttatagtttcacaagttacgatattaactgg gtgaagcagaggcctggacagggacttgagtgggttggatggatttatcctagagatggtgata ctaagtacaatgagaaattcaagggcaaggccatattgactgtagacacatcctccaacacagc gtacatgaacctccacagcctgacatctgaggactctgcggtctatttctgtgcaagactaact gggccctactggtacttcgatgtctggggcacagggaccacggtcaccgtctcctcaggatcca gcagcgcctctacaaagggccccagcgtgttccctctggcccctagcagcaagagcacatctgg cggaacagccgccctgggctgcctcgtgaaggactactttcccgagcccgtgaccgtgtcctgg aactctggcgctctgacaagcggcgtgcacacctttccagccgtgctgcagagcagcggcctgt actctctgagcagcgtcgtgacagtgcccagcagctctctgggcacccagacctacatctgcaa cgtgaaccacaagcccagcaacaccaaggtggacaagaaggtggaacccaagagctgcgacaag acccacacctgtccccccttgtcctgcccccgaactgctgggaggcccttccgtgttcctgttcc ccccaaagcccaaggacaccctgatgatcagccggacccccgaagtgacctgcgtggtggtgga tgtgtcccacgaggaccctgaagtgaagtttaattggtacgtggacggcgtggaagtgcacaac gccaagaccaagcctagagaggaacagtacgccagcacctaccgggtggtgtccgtgctgacag tgctgcaccaggactggctgaacggcaaagagtacaagtgcaaggcgtccaacaaggccctgcc tgcccccatcgagaaaaccatcagcaaggccaagggccagccccgcgaaccccaggtgtacaca ctgcccccaagcagggacgagctgaccaagaaccaggtgtccctgacctgtctcgtgaaaggct tctaccccagcgatatcgccgtggaatgggagagcaacggccagcccgagaacaactacaagac cacccccccctgtgctggacagcgacggctcattcttcctgtacagcaagctgaccgtggacaag tcccggtggcagcagggcaacgtgttcagctgcagcgtgatgcacgaggccctgcacaaccact acacccagaagtccctgagcctgagccccggcaaggaattcgacattcagatgacgcagtctcc atcctccatgtctgtatctctgggagacacagtcagcatcacttgccatgcaagtcagggcatt agcagtaatatagggtggttgcagcagaaaccagggaaatcatttaagggcctgatctatcatg gaaccaacttggaagatggagttccatcaaggttcagtggcagtggatctggagcagattattc tctcaccatcagcagcctggaatctgaagattttgcagactattactgtgtacagtatgctcag tttccgtacacgttcggaggggggaccaagctggagctgaaacgtggtggtggtggttctggtg gtggtggttctggcggcggcggctccagtggtggtggatcccaggttcagctgcagcaatctgg acctgagctggtgaagcctggggcctcagtgaagatttcctgcaaagcttctggctacgcattc agtagctcttggatggactgggtgaagcagaggcctggacagggtcttgagtggattggacgga tttatcctggagatggagatactaactacaatgggaagttcaagggcaaggccacactgactgc agacaaatcctccagcacagcctacatgcagctcagcagcctgacctctgtggactctgcggtc tatttctgtgcaaggtccattactacggtagtagggtggtacttcgatgtctggggcgcaggga ccacggtcaccgtttcctcctaa -continued SEQ ID NO: 25: Protein construct expressed from SEQ ID NO: 7:
MNFGESLIFL VLVLKGVQCE VKLVPRQLQV QLLQSGPELV KPGASVKLSC KASGYSFTSY

DINWVKQRPG QGLEWVGWIY PRDGDTKYNE KFKGKAILTV DTSSNTAYMN LHSLTSEDSA

VYFCARLTGP YWYFDVWGTG TIVTVSSGSS SASTKGPSVF PLAPSSKSTS GGTAALGCLV

KDYFPEPVTV SWNSGALTSG VHTFPAVLQS SGLYSLSSVV TVPSSSLGTQ TYICNVNHKP

SNIKVDKKVE PKSCDKTHTC PPCPAPELLG GPSVFLFPPK PKDTLMISRT PEVTCVVVDV

SHEDPEVKFN WYVDGVEVHN AKTKPREEQY ASTYRVVSVL TVLHQDWLNG KEYKCKVSNK

ALPAPIEKTI SKAKGQPREP QVYTLPPSRD ELTKNQVSLT CLVKGFYPSD IAVEWESNGQ

PENNYKTTPP VLDSDGSFFL YSKLTVDKSR WQQGNVESCS VMHEALHNHY TQKSLSLSPG

KEFDIQMTQS PSSMSVSLGD TVSITCHASQ GISSNIGWLQ QKPGKSFKGL IYHGTNLEDG

VPSRFSGSGS GADYSLTISS LESEDFADYY CVQYAQFPYT FGGGTKLELK RGGGGSGGGG

SGGGGSSGGG SQVQLQQSGP ELVKPGASVK ISCKASGYAF SSSWMDWVKQ RPGQGLEWIG

RIYPGDGDTN YNGKFKGKAT LTADKSSSTA YMQLSSLTSV DSAVYFCARS ITTVVGWYFD

VWGAGTTVTV SS*

SEQ ID NO: 8: C4-HC-heavy-konst-full-scFv-anti-CD20-pCR3 (N297A) (Flagless):
atgaacttcggcttcagcctgatcttcctggtgctggtgctgaagggcgtgcagtgcgaagtga agctggtgccccggcaattgcaggttcagctgctgcagtctggacctgagctggtgaagcctgg ggcttcagtgaagttgtcctgcaaggcttctggttatagtttcacaagttacgatattaactgg gtgaagcagaggcctggacagggacttgagtgggttggatggatttatcctagagatggtgata ctaagtacaatgagaaattcaagggcaaggccatattgactgtagacacatcctccaacacagc gtacatgaacctccacagcctgacatctgaggactctgcggtctatttctgtgcaagactaact gggccctactggtacttcgatgtctggggcacagggaccacggtcaccgtctcctcaggatcca gcagcgcctctacaaagggccccagcgtgttccctctggcccctagcagcaagagcacatctgg cggaacagccgccctgggctgcctcgtgaaggactactttcccgagcccgtgaccgtgtcctgg aactctggcgctctgacaagcggcgtgcacacctttccagccgtgctgcagagcagcggcctgt actctctgagcagcgtcgtgacagtgcccagcagctctctgggcacccagacctacatctgcaa cgtgaaccacaagcccagcaacaccaaggtggacaagaaggtggaacccaagagctgcgacaag acccacacctgtccccctgtcctgcccccgaactgctgggaggcccttccgtgttcctgttcc ccccaaagcccaaggacaccctgatgatcagccggacccccgaagtgacctgcgtggtggtgga tgtgtcccacgaggaccctgaagtgaagtttaattggtacgtggacggcgtggaagtgcacaac gccaagaccaagcctagagaggaacagtacgccagcacctaccgggtggtgtccgtgctgacag tgctgcaccaggactggctgaacggcaaagagtacaagtgcaaggtgtccaacaaggccctgcc tgcccccatcgagaaaaccatcagcaaggccaagggccagccccgcgaaccccaggtgtacaca ctgcccccaagcagggacgagctgaccaagaaccaggtgtccctgacctgtctcgtgaaaggct tctaccccagcgatatcgccgtggaatgggagagcaacggccagcccgagaacaactacaagac caccccccctgtgctggacagcgacggctcattcttcctgtacagcaagctgaccgtggacaag tcccggtggcagcagggcaacgtgttcagctgcagcgtgatgcacgaggccctgcacaaccact acacccagaagtccctgagcctgagccccggcaaggaattccaggtacaactgcagcagcctgg ggctgagctggtgaagcctggggcctcagtgaagatgtcctgcaaggcttctggctacacattt accagttacaatatgcactgggtaaaacagacacctggtcggggcctggaatggattggagcta tttatcccggaaatggtgatacttcctacaatcagaagttcaaaggcaaggccacattgactgc agacaaatcctccagcacagcctacatgcagctcagcagcctgacatctgaggactctgcggtc -continued tattactgtgcaagatcgacttactacggcggtgactggtacttcaatgtctggggcgcaggga ccacggtcaccgtctcttcaggaggaggcggatccggcggaggcggaagcggtggcggaggctc tcaaattgttctctcccagtctccagcaatcctgtctgcatctccaggggagaaggtcacaatg acttgcagggccagctcaagtgtaagttacatccactggttccagcagaagccaggaccctccc ccaaaccctggatttatgccacatccaacctggcttctggagtccctgttcgcttcagtggcag tgggtctgggacttcttactctctcacaatcagcagagtggaggctgaagatgctgccacttat tactgccagcagtggactagtaacccacccacgttcggaggggggaccaagctggaaatcaaac gttaa SEQ ID NO: 26: Protein construct expressed from SEQ ID NO: 8:
MNFGFSLIFL VLVLKGVQCE VKLVPRQLQV QLLQSGPELV KPGASVKLSC KASGYSFTSY

DINWVKQRPG QGLEWVGWIY PRDGDTKYNE KFKGKAILTV DTSSNTAYMN LHSLTSEDSA

VYFCARLTGP YWYFDVWGTG TTVTVSSGSS SASTKGPSVF PLAPSSKSTS GGTAALGCLV

KDYFPEPVTV SWNSGALTSG VHTFPAVLQS SGLYSLSSVV TVPSSSLGTQ TYICNVNHKP

SNTKVDKKVE PKSCDRTHTC PPCPAPELLG GPSVFLFPPK PKDTLMISRT PEVTCVVVDV

SHEDPEVKFN WYVDGVEVHN AKTKPREEQY ASTYRVVSVL TVLHQDWLNG KEYKCKVSNK

ALPAPIEKTI SKAKGQPREP QVYTLPPSRD ELTKNQVSLT CLVKGFYPSD IAVEWESNGQ

PENNYKTTPP VLDSDGSFFL YSKLTVDKSR WQQGNVESCS VMHEALHNHY TQKSLSLSPG

KEFQVQLQQP GAELVKPGAS VKMSCKASGY TFTSYNMHWV KQTPGRGLEW IGAIYPGNGD

TSYNQKFKGK ATLTADKSSS TAYMQLSSLT SEDSAVYYCA RSTYYGGDWY FNVWGAGTTV

TVSSGGGGSG GGGSGGGGSQ IVLSQSPAIL SASPGEKVTM TCRASSSVSY IHWFQQKPGP

SSKPWIYATS NLASGVPVRF SGSGSGTSYS LTISRVEAED AATYYCQQWT SNPPTFGGGT

KLEIKR*

SEQ ID NO: 9: C4-HC-heavy-full-pCR3 (IgG1) (Flagless):
atgaacttcggcttcagcctgatcttcctggtgctggtgctgaagggcgtgcagtgcgaagtga agctggtgccccggcaattgcaggttcagctgctgcagtctggacctgagctggtgaagcctgg ggcttcagtgaagttgtcctgcaaggcttctggttatagtttcacaagttacgatattaactgg gtgaagcagaggcctggacagggacttgagtgggttggatggatttatcctagagatggtgata ctaagtacaatgagaaattcaagggcaaggccatattgactgtagacacatcctccaacacagc gtacatgaacctccacagcctgacatctgaggactctgcggtctatttctgtgcaagactaact gggccctactggtacttcgatgtctggggcacagggaccacggtcaccgtctcctcaggatcct ctagcgccagcacaaagggccccagcgtgttccctctggcccctagcagcaagagcacatctgg cggaacagccgccctgggctgcctcgtgaaggactactttcccgagcccgtgacagtgtcctgg aactctggcgccctgacaagcggcgtgcacacctttccagccgtgctgcagagcagcggcctgt actctctgagcagcgtcgtgactgtgcccagcagcagcctgggcacccagacctacatctgcaa cgtgaaccacaagcccagcaacaccaaggtggacaagaaggtggaacccaagagctgcgacaag acccacacctgtccccccttgtcctgcccctgaactgctgggcggaccttccgtgttcctgttcc ccccaaagcccaaggacaccctgatgatcagccggacccccgaagtgacctgcgtggtggtgga tgtgtcccacgaggaccctgaagtgaagtttaattggtacgtggacggcgtggaagtgcacaac gccaagaccaagcccagagaggaacagtacaacagcacctaccgggtggtgtccgtgctgacag tgctgcaccaggactggctgaacggcaaagagtacaagtgcaaggtgtccaacaaggccctgcc tgcccccatcgagaaaaccatcagcaaggccaagggccagccccgcgaaccccaggtgtacaca ctgcctcccagcagggacgagctgaccaagaaccaggtgtccctgacctgtctcgtgaaaggct tctacccctccgatatcgccgtggaatgggagagcaacggccagcccgagaacaactacaagac cacccccccctgtgctggacagcgacggctcattcttcctgtacagcaagctgaccgtggacaag tcccggtggcagcagggcaacgtgttcagctgcagcgtgatgcacgaggccctgcacaaccact acacccagaagtccctgagcctgagccccggcaagtaa SEQ ID NO: 27: Protein construct expressed from SEQ ID NO: 9:
MNFGESLIFL VLVLKGVQCE VKLVPRQLQV QLLQSGPELV KPGASVKLSC KASGYSFTSY

DINWVKQRPG QGLEWVGWIY PRDGDTKYNE KFKGKAILTV DTSSNTAYMN LHSLTSEDSA

VYFCARLTGP YWYFDVWGTG TTVTVSSGSS SASTKGPSVF PLAPSSKSTS GGTAALGCLV

KDYFPEPVTV SWNSGALTSG VHTFPAVLQS SGLYSLSSVV TVPSSSLGTQ TYICNVNHKP

SNTKVDKKVE PKSCDKTHTC PPCPAPELLG GPSVFLFPPK PKDTLMISRT PEVTCVVVDV

SHEDPEVKFN WYVDGVEVHN AKTKPREEQY NSTYRVVSVL TVLHQDWLNG KEYKCKVSNK

ALPAPIEKTI SKAKGQPREP QVYTLPPSRD ELTKNQVSLT CLVKGFYPSD IAVEWESNGQ

PENNYKTTPP VLDSDGSFFL YSKLTVDKSR WQQGNVFSCS VMHEALHNHY TQKSLSLSPG

K*

SEQ ID NO: 10: C4-HC-heavy-full-scGITRL-pCR3 (N297A):
atgaacttcggcttcagcctgatcttcctggtgctggtgctgaagggcgtgcagtgcgaagtga agctggtgccccggcaattgcaggttcagctgctgcagtctggacctgagctggtgaagcctgg ggcttcagtgaagttgtcctgcaaggcttctggttatagtttcacaagttacgatattaactgg gtgaagcagaggcctggacagggacttgagtgggttggatggatttatcctagagatggtgata ctaagtacaatgagaaattcaagggcaaggccatattgactgtagacacatcctccaacacagc gtacatgaacctccacagcctgacatctgaggactctgcggtctatttctgtgcaagactaact gggccctactggtacttcgatgtctggggcacagggaccacggtcaccgtctcctcaggatcca gcagcgcctctacaaagggccccagcgtgttccctctggcccctagcagcaagagcacatctgg cggaacagccgccctgggctgcctcgtgaaggactactttcccgagcccgtgaccgtgtcctgg aactctggcgctctgacaagcggcgtgcacacctttccagccgtgctgcagagcagcggcctgt actctctgagcagcgtcgtgacagtgcccagcagctctctgggcacccagacctacatctgcaa cgtgaaccacaagcccagcaacaccaaggtggacaagaaggtggaacccaagagctgcgacaag acccacacctgtccccccttgtcctgcccccgaactgctgggaggcccttccgtgttcctgttcc ccccaaagcccaaggacaccctgatgatcagccggacccccgaagtgacctgcgtggtggtgga tgtgtcccacgaggaccctgaagtgaagtttaattggtacgtggacggcgtggaagtgcacaac gccaagaccaagcctagagaggaacagtacgccagcacctaccgggtggtgtccgtgctgacag tgctgcaccaggactggctgaacggcaaagagtacaagtgcaaggtgtccaacaaggccctgcc tgcccccatcgagaaaaccatcagcaaggccaagggccagccccgcgaaccccaggtgtacaca ctgcccccaagcagggacgagctgaccaagaaccaggtgtccctgacctgtctcgtgaaaggct tctaccccagcgatatcgccgtggaatgggagagcaacggccagcccgagaacaactacaagac cacccccccctgtgctggacagcgacggctcattcttcctgtacagcaagctgaccgtggacaag tcccggtggcagcagggcaacgtgttcagctgcagcgtgatgcacgaggccctgcacaaccact acacccagaagtccctgagcctgagccccggcaaggaattcggcggagggagcggacagctgga aactgccaaagaaccctgtatggccaaattcggaccactgcctagcaaatggcagatggctagt agcgaacctccatgtgtgaacaaagtgagcgattggaaactcgagatcctccagaatggactgt acctcatctacggacaggtcgccccaaatgccaattacaatgatgtggccccctttgaagtccg -continued gctctacaaaaacaaggatatgatccagaccctcaccaacaaatccaaaatccagaatgtgggc ggcacatacgaactccatgtcggcgataccatcgatctcattttcaactctgaacaccaggtgc tcaaaaacaacacctactggggaatcatcctgctggcaaaccctcagttcatctccggcggcgg ctctggcggcggatctggcggagggagtggcggaggctcacagctggagactgctaaagaaccc tgtatggcaaaattcgggcccctgccctcaaaatggcagatggcctcctctgaaccaccctgtg tgaacaaagtgagtgattggaaactggaaatcctccagaacggcctctacctcatctacggaca ggtggcacccaatgccaattacaacgacgtggcacccttcgaagtgagactgtacaaaaacaag gatatgatccagaccctcaccaacaaatcaaaaatccagaatgtcggagggacatacgaactcc atgtgggagacactatcgacctcattttcaattccgaacatcaggtcctgaaaaacaacactta ctggggcattattctgctcgccaatccacagtttattagtggaggcgggggatctgggggaggc tccggcggagggagtggaggcggatctcaattccaattagagactgctaaggagccctgtatgg ctaagtttggaccattaccctcaaaatggcaaatggcatcttctgaacctccttgcgtgaataa ggtgtctgactggaagctggagatacttcagaacggcttatatttaatttatggccaagtggct cccaatgcaaactacaatgatgtagctccttttgaggtgcggctgtataaaaacaaagacatga tacaaactctaacaaacaaatctaaaatccaaaatgtaggagggacttatgaattgcatgttgg ggacaccatagacttgatattcaactctgagcatcaggttctaaaaaataatacatactggggt atcattttactagcaaatccccaattcatctcctag SEQ ID NO: 28: Protein construct expressed from SEQ ID NO: 10:
MNFGFSLIFL VLVLKGVQCE VKLVPRQLQV QLLQSGPELV KPGASVKLSC KASGYSFTSY

DINWVKQRPG QGLEWVGWIY PRDGDTKYNE KFKGKAILTV DTSSNTAYMN LHSLTSEDSA

VYFCARLTGP YWYFDVWGTG TTVTVSSGSS SASTKGPSVF PLAPSSKSTS GGTAALGCLV

KDYFPEPVTV SWNSGALTSG VHTFPAVLQS SGLYSLSSVV TVPSSSLGTQ TYICNVNHKP

SNTKVDKKVE PKSCDKTHTC PPCPAPELLG GPSVFLFPPK PKDTLMISRT PEVTCVVVDV

SHEDPEVKFN WYVDGVEVHN AKTKPREEQY ASTYRVVSVL TVLHQDWLNG KEYKCKVSNK

ALPAPIEKTI SKAKGQPREP QVYTLPPSRD ELTKNQVSLT CLVKGFYPSD IAVEWESNGQ

PENNYKTTPP VLDSDGSFFL YSKLTVDKSR WQQGNVESCS VMHEALHNHY TQKSLSLSPG

KEFGGGSGQL ETAKEPCMAK FGPLPSKWQM ASSEPPCVNK VSDWKLEILQ NGLYLIYGQV

APNANYNDVA PFEVRLYKNK DMIQTLTNKS KIQNVGGTYE LHVGDTIDLI FNSEHQVLKN

NTYWGIILLA NPQFISGGGS GGGSGGGSGG GSQLETAKEP CMAKFGPLPS KWQMASSEPP

CVNKVSDWKL EILQNGLYLI YGQVAPNANY NDVAPFEVRL YKNKDMIQTL TNKSKIQNVG

GTYELHVGDT IDLIFNSEHQ VLKNNTYWGI ILLANPQFIS GGGGSGGGSG GGSGGGSQFQ

LETAKEPCMA KFGPLPSKWQ MASSEPPCVN KVSDWKLEIL QNGLYLIYGQ VAPNANYNDV

APFEVRLYKN KDMIQTLTNK SKIQNVGGTY ELHVGDTIDL IFNSEHQVLK NNTYWGIILL

ANPQFIS*

SEQ ID NO: 11: C4-HC-heavy-full-sc(mu)41BBL-pCR3 (N297A):
atgaacttcggcttcagcctgatcttcctggtgctggtgctgaagggcgtgcagtgcgaagtga agctggtgccccggcaattgcaggttcagctgctgcagtctggacctgagctggtgaagcctgg ggcttcagtgaagttgtcctgcaaggcttctggttatagtttcacaagttacgatattaactgg gtgaagcagaggcctggacagggacttgagtgggttggatggatttatcctagagatggtgata ctaagtacaatgagaaattcaagggcaaggccatattgactgtagacacatcctccaacacagc gtacatgaacctccacagcctgacatctgaggactctgcggtctatttctgtgcaagactaact -continued gggccctactggtacttcgatgtctggggcacagggaccacggtcaccgtctcctcaggatcca gcagcgcctctacaaagggccccagcgtgttccctctggcccctagcagcaagagcacatctgg cggaacagccgccctgggctgcctcgtgaaggactactttcccgagcccgtgaccgtgtcctgg aactctggcgctctgacaagcggcgcgcacacctttccagccgtgctgcagagcagcggcctgt actctctgagcagcgtcgtgacagtgcccagcagctctctgggcacccagacctacatctgcaa cgtgaaccacaagcccagcaacaccaaggtggacaagaaggtggaacccaagagctgcgacaag acccacacctgtccccccttgtcctgcccccgaactgctgggaggcccttccgtgttcctgttcc ccccaaagcccaaggacaccctgatgatcagccggacccccgaagtgacctgcgtggtggtgga tgtgtcccacgaggaccctgaagtgaagtttaattggtacgtggacggcgtggaagtgcacaac gccaagaccaagcctagagaggaacagtacgccagcacctaccgggtggtgtccgtgctgacag tgctgcaccaggactggctgaacggcaaagagtacaagtgcaaggtgtccaacaaggccctgcc tgcccccatcgagaaaaccatcagcaaggccaagggccagccccgcgaaccccaggtgtacaca ctgcccccaagcagggacgagctgaccaagaaccaggtgtccctgacctgtctcgtgaaaggct tctaccccagcgatatcgccgtggaatgggagagcaacggccagcccgagaacaactacaagac cacccccccctgtgctggacagcgacggctcattcttcctgtacagcaagctgaccgtggacaag tcccggtggcagcagggcaacgtgttcagctgcagcgtgatgcacgaggccctgcacaaccact acacccagaagtccctgagcctgagccccggcaaggaattcggcggtggaagtggtactgaacc gcgacccgctctcactataaccaccagccctaacttgggaacgcgggagaataacgcggatcaa gtaaccccagtttcccatatcgggtgtccaaataccactcaacaaggatcaccggtctttgcta agctcctggcgaaaaaccaagcgtccctctgtaatacaacccttaattggcactcccaagatgg ggcgggttcttcatacctctcacaggggctccgatacgaagaagacaaaaaggagctggtggtc gactcaccaggactttactatgtattcctggagttgaagctctctcctacattcaccaataccg gtcacaaagtacagggttgggtgagccttgtgctccaggcgaagccgcaggtggacgacttcga caaccttgcactcactgtagagctgttcccttgttccatggagaataaattggtggaccgctct tggagtcagctcctcctcctcaaggcgggtcatcgattgagcgttggccttcgggcatatcttc atggggcgcaagatgcataccgcgattgggaattgtcataccccaacacgacctcttttggcct gtttctggtcaaacccgacaatccgtgggaaggtgggggaagcggagggggttcaggaggagga tctgggggaggttcaactgaaccgaggcccgcgcttactatcacgacttccccaaatctgggga ctagggaaaacaatgccgatcaggtcactcctgttagtcacattggttgtcccaatacgaccca gcaaggctctccggtgtttgccaaactgttggccaaaaatcaggcgtcactttgtaatacaacg ctcaactggcatagtcaggatggggccggctcctcatacttgtctcaaggtcttaggtacgaag aagataagaaggagctggtggtagacagccccgggctctactatgtgttcctggagctcaaact gtcaccgacgttcactaacaccggtcataaggtacagggttgggtatccttggtgttgcaagca aaaccccaggtggacgatttcgataatcttgcgcttactgtagagctctttccatgttcaatgg aaaataaactggtcgataggagctggtcccaacttctccttcttaaagctggccatcgcctgag tgttggcctgagagcgtatcttcatggggcgcaggacgcttaccgggattgggaactgtcatac ccaaacaccaccagctttgggctcttccttgtaaagccagacaatccgtgggagggggaggcg ggagtgggggcgggtctggagggggcagtgggggggtagtacggagccgcgccccgccctgac catcacaacgtcacccaatcttgggactcgggagaataacgccgaccaggttacccctgtatcc catatcggttgtcctaatacgacacaacaaggcagtcctgtattcgctaaactcttggcaaaaa accaggccagtctttgtaatacgacgcttaattggcatagccaggacggtgcgggcagctccta -continued cctttcccaggggctcaggtatgaagaagataagaaagaactcgttgtagacagtcccggattg tattacgtttttttggaactcaagctctctccaaccttcaccaatacgggacataaggtccagg gctgggtgagcctcgtactccaggctaagccgcaagttgacgatttcgataatctcgctcttac agtggagttgtttccctgtagtatggagaataagctcgtcgaccggtcttggagccaacttctg ctgcttaaggctggtcaccggctcagtgtaggcctccgagcgtatttgcatggggcgcaggacg cctatcgagactgggagctttcctaccctaacacgaccagctttggactcttcttggtgaaacc tgacaatccgtgggaataa SEQ ID NO: 29: Protein construct expressed from SEQ ID NO: 11:
MNFGFSLIFL VLVLKGVQCE VKLVPRQLQV QLLQSGPELV KPGASVKLSC KASGYSFTSY

DINWVKQRPG QGLEWVGW1Y PRDGDTKYNE KFKGKAILTV DTSSNTAYMN LHSLTSEDSA

VYFCARLTGP YWYFDVWGTG TTVTVSSGSS SASTKGPSVF PLAPSSKSTS GGTAALGCLV

KDYFPEPVTV SWNSGALTSG VHTFPAVLQS SGLYSLSSVV TVPSSSLGTQ TYICNVNHKP

SNTKVDKKVE PKSCDKTHTC PPCPAPELLG GPSVFLFPPK PKDTLMISRT PEVTCVVVDV

SHEDPEVKFN WYVDGVEVHN AKTKPREEQY ASTYRVVSVL TVLHQDWLNG KEYKCKVSNK

ALPAPIEKTI SKAKGQPREP QVYTLPPSRD ELTKNQVSLT CLVKGFYPSD IAVEWESNGQ

PENNYKTTPP VLDSDGSFFL YSKLTVDKSR WQQGNVFSCS VMHEALHNHY TQKSLSLSPG

KEFGGGSGTE PRPALTITTS PNLGTRENNA DQVTPVSHIG CPNTTQQGSP VFAKLLAKNQ

ASLCNTTLNW HSQDGAGSSY LSQGLRYEED KKELVVDSPG LYYVFLELKL SPTFTNTGHK

VQGWVSLVLQ AKPQVDDFDN LALTVELFPC SMENKLVDRS WSQLLLLKAG HRLSVGLRAY

LHGAQDAYRD WELSYPNTTS FGLFLVKPDN PWEGGGSGGG SGGGSGGGST EPRPALTITT

SPNLGTRENN ADQVTPVSHI GCPNTTQQGS PVFAKLLAKN QASLCNTTLN WHSQDGAGSS

YLSQGLRYEE DKKELVVDSP GLYYVFLELK LSPTFTNTGH KVQGWVSLVL QAKPQVDDFD

NLALTVELFP CSMENKLVDR SWSQLLLLKA GHRLSVGLRA YLHGAQDAYR DWELSYPNTT

SFGLFLVKPD NPWEGGGGSG GGSGGGSGGG STEPRPALTI TTSPNLGTRE NNADQVTPVS

HIGCPNTTQQ GSPVFAKLLA KNQASLCNTT LNWHSQDGAG SSYLSQGLRY EEDKKELVVD

SPGLYYVFLE LKLSPTFTNT GHKVQGWVSL VLQAKPQVDD FDNLALTVEL FPCSMENKLV

DRSWSQLLLL KAGHRLSVGL RAYLHGAQDA YRDWELSYPN TTSFGLFLVK PDNPWE*

SEQ ID NO: 12: C4-HC-heavy-full-(mu)GITRL-pCR3 (N297A):
atgaacttcggcttcagcctgatcttcctggtgctggtgctgaagggcgtgcagtgcgaagtga agctggtgccccggcaattgcaggttcagctgctgcagtctggacctgagctggtgaagcctgg ggcttcagtgaagttgtcctgcaaggcttctggttatagtttcacaagttacgatattaactgg gtgaagcagaggcctggacagggacttgagtgggttggatggatttatcctagagatggtgata ctaagtacaatgagaaattcaagggcaaggccatattgactgtagacacatcctccaacacagc gtacatgaacctccacagcctgacatctgaggactctgcggtctatttctgtgcaagactaact gggccctactggtacttcgatgtctggggcacagggaccacggtcaccgtctcctcaggatcca gcagcgcctctacaaagggccccagcgtgttccctctggcccctagcagcaagagcacatctgg cggaacagccgccctgggctgcctcgtgaaggactactttcccgagcccgtgaccgtgtcctgg aactctggcgctctgacaagcggcgtgcacacctttccagccgtgctgcagagcagcggcctgt actctctgagcagcgtcgtgacagtgcccagcagctctctgggcacccagacctacatctgcaa cgtgaaccacaagcccagcaacaccaaggtggacaagaaggtggaacccaagagctgcgacaag acccacacctgtccccccttgtcctgcccccgaactgctgggaggcccttccgtgttcctgttcc -continued ccccaaagcccaaggacaccctgatgatcagccggacccccgaagtgacctgcgtggtggtgga tgtgtcccacgaggaccctgaagtgaagtttaattggtacgtggacggcgtggaagtgcacaac gccaagaccaagcctagagaggaacagtacgccagcacctaccgggtggtgtccgtgctgacag tgctgcaccaggactggctgaacggcaaagagtacaagtgcaaggtgtccaacaaggccctgcc tgcccccatcgagaaaaccatcagcaaggccaagggccagccccgcgaaccccaggtgtacaca ctgcccccaagcagggacgagctgaccaagaaccaggtgtccctgacctgtctcgtgaaaggct tctaccccagcgatatcgccgtggaatgggagagcaacggccagcccgagaacaactacaagac cacccccccctgtgctggacagcgacggctcattcttcctgtacagcaagctgaccgtggacaag tcccggtggcagcagggcaacgtgttcagctgcagcgtgatgcacgaggccctgcacaaccact acacccagaagtccctgagcctgagccccggcaaggaattcccaactgccatcgagtcctgcat ggttaagtttgaactatcatcctcaaaatggcacatgacatctcccaaacctcactgtgtgaat acgacatctgatgggaagctgaagatactgcagagtggcacatatttaatctacggccaagtga ttcctgtggataagaaatacataaaagacaatgccccctttcgtagtacagatatataaaaagaa tgatgtcctacaaactctaatgaatgattttcaaatcttgcctataggaggggtttatgaactg catgctggagataacatatatctgaagttcaactctaaagaccatattcagaaaactaacacat actgggggatcatcttaatgcctgatctaccattcatctcttag SEQ ID NO: 30: Protein construct expressed from SEQ ID NO: 12

MNFGESLIFL VLVLKGVQCE VKLVPRQLQV QLLQSGPELV KPGASVKLSC KASGYSFTSY

DINWVKQRPG QGLEWVGWIY PRDGDTKYNE KFKGKAILTV DTSSNTAYMN LHSLTSEDSA

VYFCARLTGP YWYFDVWGTG TTVTVSSGSS SASTKGPSVF PLAPSSKSTS GGTAALGCLV

KDYFPEPVTV SWNSGALTSG VHTFPAVLQS SGLYSLSSVV TVPSSSLGTQ TYICNVNHKP

SNTKVDKKVE PKSCDKTHTC PPCPAPELLG GPSVFLFPPK PKDTLMISRT PEVTCVVVDV

SHEDPEVKFN WYVDGVEVHN AKTKPREEQY ASTYRVVSVL TVLHQDWLNG KEYKCKVSNK

ALPAPIEKTI SKAKGQPREP QVYTLPPSRD ELTKNQVSLT CLVKGFYPSD IAVEWESNGQ

PENNYKTTPP VLDSDGSFFL YSKLTVDKSR WQQGNVFSCS VMHEALHNHY TQKSLSLSPG

KEFPTAIESC MVKFELSSSK WHMTSPKPHC VNTTSDGKLK ILQSGTYLIY GQVIPVDKKY

IKDNAPFVVQ IYKKNDVLQT LMNDFQILPI GGVYELHAGD NIYLKFNSKD HIQKTNTYWG

ITLMPDLPFT S*

SEQ ID NO: 13: C4-LC-light-full-pCR3 (Flagless):

atgaacttcggcttcagcctgatcttcctggtgctggtgctgaagggcgtgcagtgcgaagtga agctggtgccccggcaattggacattgtgatgacccagtctcacaaattcatgtccacatcagt aggagacagggtcagcatcacctgcaaggccagtcaggatgtggatactgctgtagcctggtat caacaaaaaccagggcaatctcctaaactactgatttactgggcatccacccggcacactggag tccctgatcgcttcacaggcagtggatctgggacagattatactctcaccatcagcagtgtgca ggctgaagacctggcgcgttattactgtcagcaatattatagtgttcctccgacgttcggtgga ggcaccaagctgggatccgaaatcaagcgtacggtggccgctcccagcgtgttcatcttcccac ctagcgacgagcagctgaagtccggcacagcctctgtcgtgtgcctgctgaacaacttctaccc ccgcgaggccaaggtgcagtggaaggtggacaatgccctgcagagcggcaacagccaggaaagc gtgaccgagcaggacagcaaggactccacctacagcctgagcagcaccctgaccctgagcaagg ccgactacgagaagcacaaggtgtacgcctgcgaagtgacccaccagggcctgtctagccccgt gaccaagagcttcaaccggggcgagtgctaa -continued SEQ ID NO: 31: Protein construct expressed from SEQ ID NO: 13:
MNFGFSLIFL VLVLKGVQCE VKLVPRQLDI VMTQSHKFMS TSVGDRVSIT CKASQDVDTA

VAWYQQKPGQ SPKLLIYWAS TRHTGVPDRF TGSGSGTDYT LTISSVQAED LARYYCQQYY

SVPPTFGGGT KLGSEIKRTV AAPSVFIFPP SDEQLKSGTA SVVCLLNNFY PREAKVQWKV

DNALQSGNSQ ESVTEQDSKD STYSLSSTLT LSKADYEKHK VYACEVTHQG LSSPVTKSFN

RGEC*

SEQ ID NO: 14: anti-CD95(E09)-Flag-VH-full-scFv-anti-CD19-pCR3 (IgG1):
atgaacttcggcttcagcctgatcttcctggtgctggtgctgaagggcgtgcagtgcgaagtga agctggtgccccggcaattggactacaaggacgacgacgacaaagaattccagctgcagctgca ggaatctggccctggcctcgtgaagcccagcgagacactgagcctgacctgtaccgtgtccggc gccagcatcagcgccaacagctactatggcgtgtgggtgcgccagagccctggcaagggactgg aatgggtgggatctatcgcctaccggggcaacagcaacagcggcagcacctactacaaccccag cctgaagtcccgggccaccgtgtctgtggacaccagcaagaaccaggtgtccctgcggctgacc tctgtgacagccgccgataccgccctgtactactgcgccagaaggcagctgctggacgacggca caggatatcagtgggccgccttcgatgtgtggggccagggaacaatggtcaccgtgtcctccag atcctctagcgccagcacaaagggccccagcgtgttccctctggcccctagcagcaagagcaca tctggcggaacagccgccctgggctgcctcgtgaaggactactttcccgagcccgtgacagtgt cctggaactctggcgccctgacaagcggcgtgcacacctttccagccgtgctgcagagcagcgg cctgtactctctgagcagcgtcgtgactgtgcccagcagcagcctgggcacccagacctacatc tgcaacgtgaaccacaagcccagcaacaccaaggtggacaagaaggtggaacccaagagctgcg acaagacccacacctgtcccccttgtcctgcccctgaactgctgggcggaccttccgcgttcct gttcccccccaaagcccaaggacaccctgatgatcagccggacccccgaagtgacctgcgtggtg gtggatgtgtcccacgaggaccctgaagtgaagtttaattggtacgtggacggcgtggaagtgc acaacgccaagaccaagcccagagaggaacagtacaacagcacctaccgggtggtgtccgtgct gacagtgctgcaccaggactggctgaacggcaaagagtacaagtgcaaggtgtccaacaaggcc ctgcctgcccccatcgagaaaaccatcagcaaggccaagggccagccccgcgaaccccaggtgt acacactgcctcccagcagggacgagctgaccaagaaccaggtgtccctgacctgtctcgtgaa aggcttctaccccctccgatatcgccgtggaatgggagagcaacggccagcccgagaacaactac aagaccacccccccctgtgctggacagcgacggctcattcttcctgtacagcaagctgaccgtgg acaagtcccggtggcagcagggcaacgtgttcagctgcagcgtgatgcacgaggccctgcacaa ccactacacccagaagtccctgagcctgagccccggcaagctcgaggacattcagatgacgcag tctccatcctccatgtctgtatctctgggagacacagtcagcatcacttgccatgcaagtcagg gcattagcagtaatatagggtggttgcagcagaaaccagggaaatcatttaagggcctgatcta tcatggaaccaacttggaagatggagttccatcaaggttcagtggcagtggatctggagcagat tattctctcaccatcagcagcctggaatctgaagattttgcagactattactgtgtacagtatg ctcagtttccgtacacgttcggaggggggaccaagctggagctgaaacgtggtggtggtggttc tggtggtggtggttctggcggcggcggctccagtggtggtggatcccaggttcagctgcagcaa tctggacctgagctggtgaagcctggggcctcagtgaagatttcctgcaaagcttctggctacg cattcagtagctcttggatggactgggtgaagcagaggcctggacagggtcttgagtggattgg -continued acggatttatcctggagatggagatactaactacaatgggaagttcaagggcaaggccacactg actgcagacaaatcctccagcacagcctacatgcagctcagcagcctgacctctgtggactctg cggtctatttctgtgcaaggtccattactacggtagtagggtggtacttcgatgtctggggcgc agggaccacggtcaccgtttcctcctaa SEQ ID NO: 32: Protein construct expressed from SEQ ID NO: 14:
MNFGFSLIFL VLVLKGVQCE VKLVPRQLDY KDDDDKEFQL QLQESGPGLV KPSETLSLTC

TVSGASISAN SYYGVWVRQS PGKGLEWVGS IAYRGNSNSG STYYNPSLKS RATVSVDTSK

NQVSLRLTSV TAADTALYYC ARRQLLDDGT GYQWAAFDVW GQGTMVTVSS RSSSASTKGP

SVFPLAPSSK STSGGTAALG CLVKDYFPEP VTVSWNSGAL TSGVHTFPAV LQSSGLYSLS

SVVTVPSSSL GTQTYICNVN HKPSNTKVDK KVEPKSCDKT HTCPPCPAPE LLGGPSVFLF

PPKPKDTLMI SRTPEVTCVV VDVSHEDPEV KFNWYVDGVE VHNAKTKPRE EQYNSTYRVV

SVLTVLHQDW LNGKEYKCKV SNKALPAPIE KTISKAKGQP REPQVYTLPP SRDELTKNQV

SLTCLVKGFY PSDIAVEWES NGQPENNYKT TPPVLDSDGS FFLYSKLTVD KSRWQQGNVF

SCSVMHEALH NHYTQKSLSL SPGKLEDIQM TQSPSSMSVS LGDTVSITCH ASQGISSNIG

WLQQKPGKSF KGLIYHGTNL EDGVPSRFSG SGSGADYSLT ISSLESEDFA DYYCVQYAQF

PYTFGGGTKL ELKRGGGGSG GGGSGGGGSS GGGSQVQLQQ SGPELVKPGA SVKISCKASG

YAFSSSWMDW VKQRPGQGLE WIGRIYPGDG DTNYNGKFKG KATLTADKSS STAYMQLSSL

TSVDSAVYFC ARSITTVVGW YFDVWGAGTT VTVSS*

SEQ ID NO: 15: anti-CD95-E09-Flag-VH-heavy-full-pCR3 (IgG1):
atgaacttcggcttcagcctgatcttcctggtgctggtgctgaagggcgtgcagtgcgaagtga agctggtgccccggcaattggactacaaggacgacgacgacaaagaattccagctgcagctgca ggaatctggccctggcctcgtgaagcccagcgagacactgagcctgacctgtaccgtgtccggc gccagcatcagcgccaacagctactatggcgtgtgggtgcgccagagccctggcaagggactgg aatgggtgggatctatcgcctaccggggcaacagcaacagcggcagcacctactacaaccccag cctgaagtcccgggccaccgtgtctgtggacaccagcaagaaccaggtgtccctgcggctgacc tctgtgacagccgccgataccgccctgtactactgcgccagaaggcagctgctggacgacggca caggatatcagtgggccgccttcgatgtgtggggccagggaacaatggtcaccgtgtcctccag atcctctagcgccagcacaaagggccccagcgtgttccatctggcccctagcagcaagagcaca tctggcggaacagccgccctgggctgcctcgtgaaggactactttcccgagcccgtgacagtgt cctggaactctggcgccctgacaagcggcgtgcacaccttcccagccgtgctgcagagcagcgg cctgtactctctgagcagcgtcgtgactgtgcccagcagcagcctgggcacccagacctacatc tgcaacgtgaaccacaagcccagcaacaccaaggtggacaagaaggtggaacccaagagctgcg acaagacccacacctgtccccccttgtcctgcccctgaactgctgggcggaccttccgtgttcct gttcccccccaaagcccaaggacaccctgatgatcagccggacccccgaagtgacctgcgtggtg gtggatgtgtcccacgaggaccctgaagtgaagtttaattggtacgtggacggcgtggaagtgc acaacgccaagaccaagcccagagaggaacagtacaacagcacctaccgggtggtgtccgtgct gacagtgctgcaccaggactggctgaacggcaaagagtacaagtgcaaggtgtccaacaaggcc ctgcctgcccccatcgagaaaaccatcagcaaggccaagggccagccccgcgaaccccaggtgc acacactgcctcccagcagggacgagctgaccaagaaccaggtgtccctgacctgtctcgtgaa -continued aggcttctacccctccgatatcgccgtggaatgggagagcaacggccagcccgagaacaactac aagaccaccccccctgtgctggacagcgacggctcattcttcctgtacagcaagctgaccgtgg acaagtcccggtggcagcagggcaacgtgttcagctgcagcgtgatgcacgaggccctgcacaa ccactacacccagaagtccctgagcctgagccccggcaagtaa SEQ ID NO: 33: Protein construct expressed from SEQ ID NO: 15:
MNFGFSLIFL VLVLKGVQCE VKLVPRQLDY KDDDDKEFQL QLQESGPGLV KPSETLSLTC

TVSGASISAN SYYGVWVRQS PGKGLEWVGS IAYRGNSNSG STYYNPSLKS RATVSVDTSK

NQVSLRLTSV TAADTALYYC ARRQLLDDGT GYQWAAFDVW GQGTMVTVSS RSSSASTKGP

SVFPLAPSSK STSGGTAALG CLVKDYFPEP VTVSWNSGAL TSGVHTFPAV LQSSGLYSLS

SVVTVPSSSL GTQTYICNVN HKPSNTKVDK KVEPKSCDKT HTCPPCPAPE LLGGPSVFLF

PPKPKDTLMI SRTPEVTCVV VDVSHEDPEV KFNWYVDGVE VHNAKTKPRE EQYNSTYRVV

SVLTVLHQDW LNGKEYKCKV SNKALPAPIE KTISKAKGQP REPQVYTLPP SRDELTKNQV

SLTCLVKGFY PSDIAVEWES NGQPENNYKT TPPVLDSDGS FFLYSKLTVD KSRWQQGNVF

SCSVMHEALH NHYTQKSLSL SPGK*

SEQ ID NO: 16: anti-CD95(E09)-Flag-VH-FAB2(1-114)-scFv-anti-CD20-PCR3 (IgG1):
atgaacttcggcttcagcctgatcttcctggtgctggtgctgaagggcgtgcagtgcgaagtga agctggtgccccggcaattggactacaaggacgacgacgacaaagaattgcagctgcagctgca ggaatctggccctggcctcgtgaagcccagcgagacactgagcctgacctgtaccgtgtccggc gccagcatcagcgccaacagctactatggcgtgtgggtgcgccagagccctggcaagggactgg aatgggtgggatctatcgcctaccggggcaacagcaacagcggcagcacctactacaaccccag cctgaagtcccgggccaccgtgtctgtggacaccagcaagaaccaggtgtccctgcggctgacc tctgtgacagccgccgataccgccctgtactactgcgccagaaggcagctgctggacgacggca caggatatcagtgggccgccttcgatgtgtggggccagggaacaatggtcaccgtgtcctccgg atcctctagcgccagcacaaagggccccagcgtgttccctctggcccctagcagcaagagcaca tctggcggaacagccgccctgggctgcctcgtgaaggactactttcccgagcccgtgacagtgt cctggaactctggcgccctgacaagcggcgtgcacacctttccagccgtgctgcagagcagcgg cctgtactctctgagcagcgtcgtgactgtgcccagcagcagcctgggcacccagacctacatc tgcaacgtgaaccacaagcccagcaacaccaaggtggacaagaaggtggaacccaagagctgcg acaagacccacacctgtccccccttgtcctgccctcgagcaggtacaactgcagcagcctggggc tgagctggtgaagcctggggcctcagtgaagatgtcctgcaaggcttctggctacacatttacc agttacaatatgcactgggtaaaacagacacctggtcggggcctggaatggatcggagctattt atcccggaaatggtgatacttcctacaatcagaagttcaaaggcaaggccacattgactgcaga caaatcctccagcacagcctacatgcagctcagcagcctgacatctgaggactctgcggtctat tactgtgcaagatcgacttactacggcggtgactggtacttcaatgtctggggcgcagggacca cggtcaccgtctcttcaggaggaggcggatccggcggaggcggaagcggtggcggaggctctca aattgttctctcccagtctccagcaatcctgtctgcatctccaggggagaaggtcacaatgact tgcagggccagctcaagtgtaagttacatccactggttccagcagaagccaggatcctccccca aaccctggatttatgccacatccaacctggcttctggagtccctgttcgcttcagtggcagtgg gtctgggacttcttactctctcacaatcagcagagtggaggctgaagatgctgccacttattac tgccagcagtggactagtaacccacccacgttcggagggggggaccaagctggaaatcaaacgtt aa SEQ ID NO: 34: Protein construct expressed from SEQ ID NO: 16:
MNFGESLIFL VLVLKGVQCE VKLVPRQLDY KDDDDKELQL QLQESGPGLV KPSETLSLTC

TVSGASISAN SYYGVWVRQS PGKGLEWVGS IAYRGNSNSG STYYNPSLKS RATVSVDTSK

NQVSLRLTSV TAADTALYYC ARRQLLDDGT GYQWAAFDVW GQGTMVTVSS GSSSASTKGP

SVFPLAPSSK STSGGTAALG CLVKDYFPEP VTVSWNSGAL TSGVHTFPAV LQSSGLYSLS

SVVTVPSSSL GTQTYICNVN HKPSNTKVDK KVEPKSCDKT HTCPPCPALE QVQLQQPGAE

LVKPGASVKM SCKASGYTFT SYNMHWVKQT PGRGLEWIGA IYPGNGDTSY NQKFKGKATL

TADKSSSTAY MQLSSLTSED SAVYYCARST YYGGDWYFNV WGAGTTVTVS SGGGGSGGGG

SGGGGSQIVL SQSPAILSAS PGEKVTMTCR ASSSVSYIHW FQQKPGSSPK PWIYATSNLA

SGVPVRFSGS GSGTSYSLTI SRVEAEDAAT YYCQQWTSNP PTFGGGTKLE IKR*

SEQ ID NO: 17: anti-CD95-E09-Flag-VH-heavy-full-scBaff-pCR3 (N297A):
atgaacttcggcttcagcctgatcttcctggtgctggtgctgaagggcgtgcagtgcgaagtga agctggtgccccggcaattggactacaaggacgacgacgacaaagaattgcagctgcagctgca ggaatctggccctggcctcgtgaagcccagcgagacactgagcctgacctgtaccgtgtccggc gccagcatcagcgccaacagctactatggcgtgtgggtgcgccagagccctggcaagggactgg aatgggtgggatctatcgcctaccggggcaacagcaacagcggcagcacctactacaaccccag cctgaagtcccgggccaccgtgtctgtggacaccagcaagaaccaggtgtccctgcggctgacc tctgtgacagccgccgataccgccctgtactactgcgccagaaggcagctgctggacgacggca caggatatcagtgggccgccttcgatgtgtggggccagggaacaatggtcaccgtgtcctccgg atccagcagcgcctctacaaagggccccagcgtgttccctctggcccctagcagcaagagcaca tctggcggaacagccgccctgggctgcctcgtgaaggactactttcccgagcccgtgaccgtgt cctggaactctggcgctctgacaagcggcgtgcacacctttccagccgtgctgcagagcagcgg cctgtactctctgagcagcgtcgtgacagtgcccagcagctctctgggcacccagacctacatc tgcaacgtgaaccacaagcccagcaacaccaaggtggacaagaaggtggaacccaagagctgcg acaagacccacacctgtccccctgtcctgcccccgaactgctgggaggcccttccgtgttcct gttcccccaaagcccaaggacaccctgatgatcagccggacccccgaagtgacctgcgtggtg gtggatgtgtcccacgaggaccctgaagtgaagtttaattggtacgtggacggcgtggaagtgc acaacgccaagaccaagcctagagaggaacagtacgccagcacctaccgggtggtgtccgtgct gacagtgctgcaccaggactggctgaacggcaaagagtacaagtgcaaggtgtccaacaaggcc ctgcctgcccccatcgagaaaaccatcagcaaggccaagggccagccccgcgaaccccaggtgt acacactgcccccaagcagggacgagctgaccaagaaccaggtgtccctgacctgtctcgtgaa aggcttctaccccagcgatatcgccgtggaatgggagagcaacggccagcccgagaacaactac aagaccacccccccctgtgctggacagcgacggctcattcttcctgtacagcaagctgaccgtgg acaagtcccggtggcagcagggcaacgtgttcagctgcagcgtgatgcacgaggccctgcacaa ccactacacccagaagtccctgagcctgagccccggcaagctcgagggacccgaggaaactgtg actcaggactgtctccagctcattgccgatagtgaaacccctaccatccagaaaggctcttaca ccttcgtgccatggctgctgtcattcaaacggggatctgctctggaggagaaggaaaacaaaat cctggtcaaggaaaccggctacttcttcatctacggccaggtcctctacaccgacaaaacatac gctatggggcatctcattcagcggaaaaaagtccacgtgttcggcgacgaactctctctcgtga -continued cactgttccggtgtattcagaacatgcccgagactctgcccaataatagctgctactctgctgg cattgccaaactggaggagggcgacgaactccagctggctattcctagggaaaatgcccagatt agcctggacggggatgtgacatttttggcgccctgaaactgctgggaggcggagggagtggcg ggggaggctctggacctgaggaaactgtgacccaggattgtctccagctcattgccgatagtga gactcctaccattcagaagggatcttacacctttgtgccttggctgctgtctttcaaacggggc tctgctctggaggaaaaggagaacaaaattctggtcaaagagactggctacttcttcatctacg gccaggtgctgtacaccgacaaaacatacgccatgggccatctcattcagcggaaaaaagtcca cgtgttcggcgacgaactctctctcgtgacactgttccggtgtatccagaacatgcccgagaca ctgcccaataatagctgctactctgccggcattgctaaactggaggaggggggacgaactccagc tggctattcctagggaaaatgcccagatttctctcgatggggatgtgacattcttcggggccct caaactgctgggaggcggcggatctggcggaggcgggagtcaattcgcagcaggtccagaagaa acagtcactcaagactgcttgcaactgattgcagacagtgaaacaccaactatacaaaaaggat cttacacatttgttccatggcttctcagctttaaaaggggaagtgccctagaagaaaaagagaa taaaatattggtcaaagaaactggttactttttatatatggtcaggttttatatactgataag acctacgccatgggacatctaattcagaggaagaaggtccatgtctttggggatgaattgagtc tggtgactttgtttcgatgtattcaaaatatgcctgaaacactacccaataattcctgctattc agctggcattgcaaaactggaagaaggagatgaactccaacttgcaataccaagagaaaatgca caaatatcactggatggagatgtcacatttttggtgcattgaaactgctgtga SEQ ID NO: 35: Protein construct expressed from SEQ ID NO: 17:
MNFGFSLIFL VLVLKGVQCE VKLVPRQLDY KDDDDKELQL QLQESGPGLV KPSETLSLTC

TVSGASISAN SYYGVWVRQS PGKGLEWVGS IAYRGNSNSG STYYNPSLKS RATVSVDTSK

NQVSLRLTSV TAADTALYYC ARRQLLDDGT GYQWAAFDVW GQGTMVTVSS GSSSASTKGP

SVFPLAPSSK STSGGTAALG CLVKDYFPEP VTVSWNSGAL TSGVHTFPAV LQSSGLYSLS

SVVTVPSSSL GTQTYICNVN HKPSNTKVDK KVEPKSCDKT HTCPPCPAPE LLGGPSVFLF

PPKPKDTLMI SRTPEVTCVV VDVSHEDPEV KFNWYVDGVE VHNAKTKPRE EQYASTYRVV

SVLTVLHQDW LNGKEYKCKV SNKALPAPIE KTISKAKGQP REPQVYTLPP SRDELTKNQV

SLTCLVKGFY PSDIAVEWES NGQPENNYKT TPPVLDSDGS FFLYSKLTVD KSRWQQGNVF

SCSVMHEALH NHYTQKSLSL SPGKLEGPEE TVTQDCLQLI ADSETPTIQK GSYTFVPWLL

SFKRGSALEE KENKILVKET GYFFIYGQVL YTDKTYAMGH LIQRKKVHVF GDELSLVTLF

RCIQNMPETL PNNSCYSAGI AKLEEGDELQ LAIPRENAQI SLDGDVTFFG ALKLLGGGGS

GGGGSGPEET VTQDCLQLIA DSETPTIQKG SYTFVPWLLS FKRGSALEEK ENKILVKETG

YFFIYGQVLY TDKTYAMGHL IQRKKVHVFG DELSLVTLFR CIQNMPETLP NNSCYSAGIA

KLEEGDELQL AIPRENAQIS LDGDVTFFGA LKLLGGGGSG GGGSQFAAGP EETVTQDCLQ

LIADSETPTI QKGSYTFVPW LLSFKRGSAL EEKENKILVK ETGYFFIYGQ VLYTDKTYAM

GHLIQRKKVH VFGDELSLVT LFRCIQNMPE TLPNNSCYSA GIAKLEEGDE LQLAIPRENA

QISLDGDVTF FGALKLL*

SEQ ID NO: 18: anti-CD95-E09-Flag-VL-light-full-pCR3:
atgaacttcggcttcagcctgatcttcctggtgctggtgctgaagggcgtgcagtgcgaagtgaagctggtgccccg gcaattggactacaaggacgacgacgacaaagaattgcagagcgtgctgacccagcctcctagcgtgtccgaagccc ctagacagaccgtgaccatcagctgctccggcaacagcttcaacatcggcagataccccgtgaactggtatcagcag ctgccaggcaaggcccctaaactgctgatctactataacaacctgcggttcagcggagtgtccgaccggttctctgg -continued cagcaagtctggcacatctgccagcctggccatccgggatctgctgtctgaggacgaggccgactactactgcagca cctgggacgacaccctgaagggctgggtgttcggcggaggcaccaaagtgacagtgctgggcggatccgaaatcaag cgtacggtggccgctcccagcgtgttcatcttcccacctagcgacgagcagctgaagtccggcacagcctctgtcgt gtgcctgctgaacaacttctacccccgcgaggccaaggtgcagtggaaggtggacaatgccctgcagagcggcaaca gccaggaaagcgtgaccgagcaggacagcaaggactccacctacagcctgagcagcaccctgaccctgagcaaggcc gactacgagaagcacaaggtgtacgcctgcgaagtgacccaccagggcctgtctagccccgtgaccaagagcttcaa ccggggcgagtgctaa SEQ ID NO: 36: Protein construct expressed from SEQ ID NO: 18:
MNFGESLIFL VLVLKGVQCE VKLVPRQLDY KDDDDKELQS VLTQPPSVSE APRQTVTISC

SGNSFNIGRY PVNWYQQLPG KAPKLLIYYN NLRFSGVSDR FSGSKSGTSA SLAIRDLLSE

DEADYYCSTW DDTLKGWVFG GGTKVTVLGG SEIKRTVAAP SVFIFPPSDE QLKSGTASVV

CLLNNFYPRE AKVQWKVDNA LQSGNSQESV TEQDSKDSTY SLSSTLTLSK ADYEKHKVYA

CEVTHQGLSS PVTKSFNRGE C*

TABLE 2

CDR sequences (according to Kabat). Note that heavy and light chain CDR sequences are indicated by "-H" and "-L", respectively.

| Antibody | CDR1-H | CDR2-H | CDR3-H | CDR1-L | CDR2-L | CDR3-L |
|---|---|---|---|---|---|---|
| aCD40 G28.5 | YSITTNYNWN (SEQ ID NO: 37) | YIRYDGTSEYTPSLKN (SEQ ID NO: 38) | LDY | SSQSLENSNGNTFLN (SEQ ID NO: 39) | RVSNRFS (SEQ ID NO: 40) | LQVTHVPYT (SEQ ID NO: 41) |
| aCD95 E09 | ASISANSYYGV (SEQ ID NO: 42) | SIAYRGNSNSGSTYYNPSLKS (SEQ ID NO: 43) | RQLLDDGTGYQWAAFDV (SEQ ID NO: 44) | SGNSFNIGRYPVN (SEQ ID NO: 45) | YNNLRFS (SEQ ID NO: 46) | STWDDTLKGWV (SEQ ID NO: 47) |
| aDR5 Conatu | GSISSGDYFWS (SEQ ID NO: 48) | HIHNSGTTYYNPSLKS (SEQ ID NO: 49) | DRGGDYYYGMDV (SEQ ID NO: 50) | RASQGISRSYLA (SEQ ID NO: 51) | GASSRAT (SEQ ID NO: 52) | QQFGSSPWT (SEQ ID NO: 53) |
| aFn14 P4A8 | YTFTDYGMH (SEQ ID NO: 54) | VISTYNGYTNYNQKFKG (SEQ ID NO: 55) | AYYGNLYYAMDY (SEQ ID NO: 56) | RASKSVSTSSYSYMH (SEQ ID NO: 57) | YASNLES (SEQ ID NO: 58) | QHSRELPFT (SEQ ID NO: 59) |
| aTNFR2 C4 | YSFTSYDIN (SEQ ID NO: 60) | WIYPRDGDTKYNEKFKG (SEQ ID NO: 61) | LTGPYWYFDV (SEQ ID NO: 62) | KASQDVDTAVA (SEQ ID NO: 63) | WASTRHT (SEQ ID NO: 64) | QQYYSVPPT (SEQ ID NO: 65) |
| aCD20 | YTFTSYNMH (SEQ ID NO: 66) | AIYPGNGDTSYNQKFKG (SEQ ID NO: 67) | STYYGGDWYFNV (SEQ ID NO: 68) | RASSSVSYIH (SEQ ID NO: 69) | ATSNLAS (SEQ ID NO: 70) | QQWTSNPPT (SEQ ID NO: 71) |
| aCD19 | YAFSSSWMD (SEQ ID NO: 72) | RIYPGDGDTNYNGKFKG (SEQ ID NO: 73) | SITTVVGWYFDV (SEQ ID NO: 74) | HASQGISSNIG (SEQ ID NO: 75) | HGTNLED (SEQ ID NO: 76) | VQYAQFPYT (SEQ ID NO: 77) |
| aCD70 1F6 | YTFTNYGMN (SEQ ID NO: 78) | WINTYTGEPTYADAFKG (SEQ ID NO: 79) | DYGDYGMDY (SEQ ID NO: 80) | RASKSVSTSGYSFMH (SEQ ID NO: 81) | LASNLES (SEQ ID NO: 82) | QHSREVPWT (SEQ ID NO: 83) |
| aFn14 PDL 192 | FTFSSYWMS (SEQ ID NO: 84) | EIRLKSDNYATHYAESVKG (SEQ ID NO: 85) | GYYADAMDY (SEQ ID NO: 86) | RASQSVSTSSYSYMH (SEQ ID NO: 87) | YASNLES (SEQ ID NO: 88) | QHSWEIPYT (SEQ ID NO: 89) |
| aCD70 2H5 | FTFSSYIMH (SEQ ID NO: 90) | VISYDGRNKYYADSVKG (SEQ ID NO: 91) | DTDGYDFDY (SEQ ID NO: 92) | RASQSVSSYLA (SEQ ID NO: 93) | DASNRAT (SEQ ID NO: 94) | QQRTNWPLT (SEQ ID NO: 95) |

SEQ ID NO: 96: scFv-anti-CD20 anchoring domain from protein construct of SEQ ID NO: 21:
QVQL QQPGAELVKP GASVKMSCKA SGYTFTSYNM HWVKQTPGRG LEWIGAIYPG

NGDTSYNQKF KGKATLTADK SSSTAYMQLS SLTSEDSAVY YCARSTYYGG DWYFNVWGAG

TTVTVSSGGG GSGGGGSGGG GSQIVLSQSP AILSASPGEK VTMTCRASSS VSYIHWFQQK

PGSSPKPWIY ATSNLASGVP VRFSGSGSGT SYSLTISRVE AEDAATYYCQ QWTSNPPTFG

GGTKLEIKR

SEQ ID NO: 97: Murine IL-2 anchoring domain from protein construct of SEQ ID NO: 24:
APTS SSTSSSTAEA QQQQQQQQQQ QQHLEQLLMD LQELLSRMEN YRNLKLPRML

TFKFYLPKQA TELKDLQCLE DELGPLRHVL DLTQSKSFQL EDAENFISNI RVTVVKLKGS

DNTFECQFDD ESATVVDFLR RWIAFCQSII STSPQ

SEQ ID NO: 98: scFv-anti-CD19 anchoring domain from protein construct of SEQ ID NO: 25:
DIQMTQS PSSMSVSLGD TVSITCHASQ GISSNIGWLQ QKPGKSFKGL IYHGTNLEDG

VPSRFSGSGS GADYSLTISS LESEDFADYY CVQYAQFPYT FGGGTKLELK RGGGGSGGGG

SGGGGSSGGG SQVQLQQSGP ELVKPGASVK ISCKASGYAF SSSWMDWVKQ RPGQGLEWIG

RIYPGDGDTN YNGKFKGKAT LTADKSSSTA YMQLSSLTSV DSAVYFCARS ITTVVGWYFD

VWGAGTTVTV SS

SEQ ID NO: 99: scFv-anti-CD20 anchoring domain from protein construct of SEQ ID NO: 26:
QVQLQQP GAELVKPGAS VKMSCKASGY TFTSYNMHWV KQTPGRGLEW IGAIYPGNGD

TSYNQKFKGK ATLTADKSSS TAYMQLSSLT SEDSAVYYCA RSTYYGGDWY FNVWGAGTTV

TVSSGGGGSG GGGSGGGGSQ IVLSQSPAIL SASPGEKVTM TCRASSSVSY IHWFQQKPGP

SSKPWIYATS NLASGVPVRF SGSGSGTSYS LTISRVEAED AATYYCQQWT SNPPTFGGGT

KLEIKR

SEQ ID NO: 100: scFv-anti-CD19 anchoring domain from protein construct of SEQ ID NO: 32:
DIQM TQSPSSMSVS LGDTVSITCH ASQGISSNIG

WLQQKPGKSF KGLIYHGTNL EDGVPSRFSG SGSGADYSLT ISSLESEDFA DYYCVQYAQF

PYTFGGGTKL ELKRGGGGSG GGGSGGGGSS GGGSQVQLQQ SGPELVKPGA SVKISCKASG

YAFSSSWMDW VKQRPGQGLE WIGRIYPGDG DTNYNGKFKG KATLTADKSS STAYMQLSSL

TSVDSAVYFC ARSITTVVGW YFDVWGAGTT VTVSS

SEQ ID NO: 101: scFv-anti-CD20 anchoring domain from protein construct of SEQ ID NO: 34:
QVQLQQPGAE

LVKPGASVKM SCKASGYTFT SYNMHWVKQT PGRGLEWIGA IYPGNGDTSY NQKFKGKATL

TADKSSSTAY MQLSSLTSED SAVYYCARST YYGGDWYFNV WGAGTTVTVS SGGGGSGGGG

SGGGGSQIVL SQSPAILSAS PGEKVTMTCR ASSSVSYIHW FQQKPGSSPK PWIYATSNLA

SGVPVRFSGS GSGTSYSLTI SRVEAEDAAT YYCQQWTSNP PTFGGGTKLE IKR

SEQ ID NO: 102: scTNF80(murine) anchoring domain from protein construct of SEQ ID NO: 19:
DKPVAHVVAN HQVEEQLEWL SQRANALLAN GMDLKDNQLV VPADGLYLVY

SQVLFKGQGC PDYVLLTHTV SRFAISYQEK VNLLSAVKSP CPKDTPEGAE LKPWYEPIYL

GGVFQLEKGD QLSAEVNLPK YLNFRESGQV YFGVIALGGG SGGGSGGGSG GGSDKPVAHV

VANHQVEEQL EWLSQRANAL LANGMDLKDN QLVVPADGLY LVYSQVLFKG QGCPDYVLLT

HTVSRFAISY QEKVNLLSAV KSPCPKDTPE GAELKPWYEP IYLGGVFQLE KGDQLSAEVN

LPKYLNFRES GQVYFGVIAL GGGSGGGSGG GSGGGSDKPV AHVVANHQVE EQLEWLSQRA

-continued

NALLANGMDL KDNQLVVPAD GLYLVYSQVL FKGQGCPDYV LLTHTVSRFA ISYQEKVNLL

SAVKSPCPKD TPEGAELKPW YEPIYLGGVF QLEKGDQLSA EVNLPKYLNF RESGQVYFGV

IAL

SEQ ID NO: 103: scBaff anchoring domain from protein construct of SEQ ID NO: 22:
GPEE TVTQDCLQLI ADSETPTIQK GSYTFVPWLL SFKRGSALEE KENKILVKET

GYFFIYGQVL YTDKTYAMGH LIQRKKVHVF GDELSLVTLF RCIQNMPETL PNNSCYSAGI

AKLEEGDELQ LAIPRENAQI SLDGDVTFFG ALKLLGGGGS GGGGSGPEET VTQDCLQLIA

DSETPTIQKG SYTFVPWLLS FKRGSALEEK ENKILVKETG YFFIYGQVLY TDKTYAMGHL

IQRKKVHVFG DELSLVTLFR CIQNMPETLP NNSCYSAGIA KLEEGDELQL AIPRENAQIS

LDGDVTFFGA LKLLGGGGSG GGGSQFAAGP EETVTQDCLQ LIADSETPTI QKGSYTFVPW

LLSFKRGSAL EEKENKILVK ETGYFFIYGQ VLYTDKTYAM GHLIQRKKVH VFGDELSLVT

LFRCIQNMPE TLPNNSCYSA GIAKLEEGDE LQLAIPRENA QISLDGDVTF FGALKLL

SEQ ID NO: 104: scGITRL anchoring domain from protein construct of SEQ ID NO: 28:
QL ETAKEPCMAK FGPLPSKWQM ASSEPPCVNK VSDWKLEILQ NGLYLIYGQV

APNANYNDVA PFEVRLYKNK DMIQTLTNKS KIQNVGGTYE LHVGDTIDLI FNSEHQVLKN

NTYWGIILLA NPQFISGGGS GGGSGGGSGG GSQLETAKEP CMAKFGPLPS KWQMASSEPP

CVNKVSDWKL EILQNGLYLI YGQVAPNANY NDVAPFEVRL YKNKDMIQTL TNKSKIQNVG

GTYELHVGDT IDLIFNSEHQ VLKNNTYWGI ILLANPQFIS GGGGSGGGSG GGSGGGSQFQ

LETAKEPCMA KFGPLPSKWQ MASSEPPCVN KVSDWKLEIL QNGLYLIYGQ VAPNANYNDV

APFEVRLYKN KDMIQTLTNK SKIQNVGGTY ELHVGDTIDL IFNSEHQVLK NNTYWGIILL

ANPQFIS

SEQ ID NO: 105: sc(murine)41BBL anchoring domain from protein construct of SEQ ID NO: 29:
TE PRPALTITTS PNLGTRENNA DQVTPVSHIG CPNTTQQGSP VFAKLLAKNQ

ASLCNTTLNW HSQDGAGSSY LSQGLRYEED KKELVVDSPG LYYVFLELKL SPTFTNTGHK

VQGWVSLVLQ AKPQVDDFDN LALTVELFPC SMENKLVDRS WSQLLLLKAG HRLSVGLRAY

LHGAQDAYRD WELSYPNTTS FGLFLVKPDN PWEGGGSGGG SGGGSGGGST EPRPALTITT

SPNLGTRENN ADQVTPVSHI GCPNTTQQGS PVFAKLLAKN QASLCNTTLN WHSQDGAGSS

YLSQGLRYEE DKKELVVDSP GLYYVFLELK LSPTFTNTGH KVQGWVSLVL QAKPQVDDFD

NLALTVELFP CSMENKLVDR SWSQLLLLKA GHRLSVGLRA YLHGAQDAYR DWELSYPNTT

SFGLFLVKPD NPWEGGGGSG GGSGGGSGGG STEPRPALTI TTSPNLGTRE NNADQVTPVS

HIGCPNTTQQ GSPVFAKLLA KNQASLCNTT LNWHSQDGAG SSYLSQGLRY EEDKKELVVD

SPGLYYVFLE LKLSPTFTNT GHKVQGWVSL VLQAKPQVDD FDNLALTVEL FPCSMENKLV

DRSWSQLLLL KAGHRLSVGL RAYLHGAQDA YRDWELSYPN TTSFGLFLVK PDNPWE

SEQ ID NO: 106: (murine)GITRL anchoring domain from protein construct of SEQ ID NO: 30:
PTAIESC MVKFELSSSK WHMTSPKPHC VNTTSDGKLK ILQSGTYLIY GQVIPVDKKY

IKDNAPFVVQ IYKKNDVLQT LMNDFQILPI GGVYELHAGD NIYLKFNSKD HIQKTNTYWG

IILMPDLPFI S

-continued

SEQ ID NO: 107: Human IL-2 anchoring domain:
APTSSSTKKT QLQLEHLLLD LQMILNGINN YKNPKLTRML TFKFYMPKKA TELKHLQCLE

EELKPLEEVL NLAQSKNFHL RPRDLISNIN VIVLELKEHK PSSQRKEEST C

SEQ ID NO: 108: anti-CD40(G28.5)-VH(1-114)
atgaacttcggcttcagcctgatcttcctggtgctggtgctgaagggcgtgcagtgcgaagtga agctggtgccccggcaattggactacaaggacgacgacgacaaagaattggatatccagctcca gcagtctggccctggactcgtcaaaccatctcagagcctgtctctcacctgttctgccaccgga tactccatcaccaccaactacaactggaattggattcggcagtttcctgggaacaaactcgaat ggatgggatacatccgatacgacggcactagtgaatacaccccatctctcaaaaatcgggtgtc cattacccgggacactcctatgaaccagttctttctccgactcacctctgtgacacctgaggat accgccacatactactgtgctagactggactactgggggcagggaacactggtgaccgtgtcat ctggatcctctagcgccagcacaaagggccccagcgtgttccctctggcccctagcagcaagag cacatctggcggaacagccgccctgggctgcctcgtgaaggactactttcccgagcccgtgaca gtgtcctggaactctggcgccctgacaagcggcgtgcacacctttccagccgtgctgcagagca gcggcctgtactctctgagcagcgtcgtgactgtgcccagcagcagcctgggcacccagaccta catctgcaacgtgaaccacaagcccagcaacaccaaggtggacaagaaggtggaacccaagagc tgcgacaagacccacacctgtccccccttgtcctgcctaa SEQ ID NO: 117: Protein construct expressed from SEQ ID NO: 108
MNFGFSLIFL VLVLKGVQCE VKLVPRQLDY KDDDDKELDI QLQQSGPGLV KPSQSLSLTC

SVTGYSITTN YNWNWIRQFP GNKLEWMGYI RYDGTSEYTP SLKNRVSITR DTSMNQFFLR

LTSVTPEDTA TYYCARLDYW GQGTLVTVSS GSSSASTKGP SVFPLAPSSK STSGGTAALG

CLVKDYFPEP VTVSWNSGAL TSGVHTFPAV LQSSGLYSLS SVVTVPSSSL GTQTYICNVN

HKPSNTKVDK KVEPKSCDKT HTCPPCPA*

SEQ ID NO: 109: anti-CD40(G28.5)-VH(1-114)-scBaff
atgaacttcggcttcagcctgatcttcctggtgctggtgctgaagggcgtgcagtgcgaagtga agctggtgccccggcaattggactacaaggacgacgacgacaaagaattggatatccagctcca gcagtctggccctggactcgtcaaaccatctcagagcctgtctctcacctgttctgtcaccgga tactccatcaccaccaactacaactggaattggattcggcagtttcctgggaaraaactcgaat ggatgggatacatccgatacgacggcactagtgaatacaccccatctctcaaaaatcgggtgtc cattacccgggacacttctatgaaccagttctttctccgactcacctctgtgacacctgaggat accgccacatactactgtgctagactggactactgggggcagggaacactggtgaccgtgtcat ctggatcctctagcgccagcacaaagggccccagcgtgttccctctggcccctagcagcaagag cacatctggcggaacagccgccctgggctgcctcgtgaaggactactttcccgagcccgtgaca gtgtcctggaactctggcgccctgacaagcggcgtgcacacctttccagccgtgctgcagagca gcggcctgtactctctgagcagcgtcgtgactgtgcccagcagcagcctgggcacccagaccta catctgcaacgtgaaccacaagcccagcaacaccaaggtggacaagaaggtggaacccaagagc tgcgacaagacccacacctgtccccccttgtcctgccctcgagggacccgaggaaactgtgactc aggactgtctccagctcattgccgatagtgaaacccctaccatccagaaaggctcttacacctt cgtgccatggctgctgtcattcaaacggggatctgctctggaggagaaggaaaacaaaatcctg gtcaaggaaaccggctacttcttcatctacggccaggtcctctacaccgacaaaacatacgcta tggggcatctcattcagcggaaaaaaagtccacgtgttcggcgacgaactctotctcgtgacact gttccggtgtattcagaacatgcccgagactctgcccaataatagctgctactctgctggcatt gccaaactggaggagggcgacgaactccagctggctattcctagggaaaatgcccagattagcc -continued tggacggggatgtgacatttttggcgccctgaaactgctgggaggcggagggagtggcggggg aggctctggacctgaggaaactgtgacccaggattgtctccagctcattgccgatagtgagact cctaccattcagaagggatcttacacctttgtgccttggctgctgtctttcaaacggggctctg ctctggaggaaaaggagaacaaaattctggtcaaagagactggctacttcttcatctacggcca ggtgctgtacaccgacaaaacatacgccatgggccatctcattcagcggaaaaaagtccacgtg ttcggcgacgaactctctctcgtgacactgttccggtgtatccagaacatgcccgagacactgc ccaataatagctgctactctgccggcattgctaaactggaggagggggacgaactccagctggc tattcctagggaaaatgcccagatttctctcgatggggatgtgacattcttcggggccctcaaa ctgctgggaggcggcggatctggcggaggcgggagtcaattcgcagcaggtccagaagaaacag tcactcaagactgcttgcaactgattgcagacagtgaaacaccaactatacaaaaaggatctta cacatttgttccatggcttctcagctttaaaaggggaagtgccctagaagaaaaagagaataaa atattggtcaaagaaactggttactttttatatatggtcaggttttatatactgataagacct acgccatgggacatctaattcagaggaagaaggtccatgtctttggggatgaattgagtctggt gactttgtttcgatgtattcaaaatatgcctgaaacactacccaataattcctgctattcagct ggcattgcaaaactggaagaaggagatgaactccaacttgcaataccaagagaaaatgcacaaa tatcactggatggagatgtcacatttttggtgcattgaaactgctgtga SEQ ID NO: 118: Protein construct expressed from SEQ ID NO: 109
MNFGFSLIFL VLVLKGVQCE VKLVPRQLDY KDDDDKELDI QLQQSGPGLV KPSQSLSLTC

SVTGYSITTN YNWNWIRQFP GNKLEWMGYI RYDGTSEYTP SLKNRVSITR DTSMNQFFLR

LTSVTPEDTA TYYCARLDYW GQGTLVTVSS GSSSASTKGP SVFPLAPSSK STSGGTAALG

CLVKDYFPEP VTVSWNSGAL TSGVHTFPAV LQSSGLYSLS SVVTVPSSSL GTQTYICNVN

HKPSNTKVDK KVEPKSCDKT HTCPPCPALE GPEETVTQDC LQLIADSETP TIQKGSYTFV

PWLLSFKRGS ALEEKENKIL VKETGYFFIY GQVLYTDKTY AMGHLIQRKK VHVFGDELSL

VTLFRCIQNM PETLPNNSCY SAGIAKLEEG DELQLAIPRE NAQISLDGDV TFFGALKLLG

GGGSGGGGSG PEETVTQDCL QLIADSETPT IQKGSYTFVP WLLSFKRGSA LEEKENKILV

KETGYFFIYG QVLYTDKTYA MGHLIQRKKV HVFGDELSLV TLFRCIQNMP ETLPNNSCYS

AGIAKLEEGD ELQLAIPREN AQISLDGDVT FFGALKLLGG GGSGGGGSQF AAGPEETVTQ

DCLQLIADSE TPTIQKGSYT FVPWLLSFKR GSALEEKENK ILVKETGYFF IYGQVLYTDK

TYAMGHLIQR KKVHVFGDEL SLVTLFRCIQ NMPETLPNNS CYSAGIAKLE EGDELQLAIP

RENAQISLDG DVTFFGALKL L*

SEQ ID NO: 110: anti-CD95(E09)-VH(1-114)-scBaff
atgaacttcggcttcagcctgatcttcctggtgctggtgctgaagggcgtgcagtgcgaagtga agctggtgccccggcaattggactacaaggacgacgacgacaaagaattgcagctgcagctgca ggaatctggccctggcctcgtgaagcccagcgagacactgagcctgacctgtaccgtgtccggc gccagcatcagcgccaacagctactatggcgtgtgggtgcgccagagccctggcaagggactgg aatgggtgggatctatcgcctaccggggcaacagcaacagcggcagcacctactacaaccccag cctgaagtcccgggccaccgtgtctgtggacaccagcaagaaccaggtgtccctgcggctgacc tctgtgacagccgccgataccgccctgtactactgcgccagaaggcagctgctggacgacggca caggatatcagtgggccgccttcgatgtgtggggccagggaacaatggtcaccgtgtcctccgg atcctctagcgccagcacaaagggccccagcgtgttccctctggcccctagcagcaagagcaca tctggcggaacagccgccctgggctgcctcgtgaaggactactttcccgagcccgtgacagtgt -continued cctggaactctggcgccctgacaagcggcgtgcacacctttccagccgtgctgcagagcagcgg cctgtactctctgagcagcgtcgtgactgtgcccagcagcagcctgggcacccagacctacatc tgcaacgtgaaccacaagcccagcaacaccaaggtggacaagaaggtggaacccaagagctgcg acaagacccacacctgtccccccttgtcctgcccctcgagggacccgaggaaactgtgactcagga ctgtctccagctcattgccgatagtgaaacccctaccatccagaaaggctcttacaccttcgtg ccatggctgctgtcattcaaacggggatctgctctggaggagaaggaaaacaaaatcctggtca aggaaaccggctacttcttcatctacggccaggtcctctacaccgacaaaacatacgctatggg gcatctcattcagcggaaaaaagtccacgtgttcggcgacgaactctctctcgtgacactgttc cggtgtattcagaacatgcccgagactctgcccaataatagctgctactctgctggcattgcca aactggaggagggcgacgaactccagctggctattcctagggaaaatgcccagattagcctgga cggggatgtgacatttttggcgccctgaaactgctgggaggcggagggagtggcgggggaggc tctggacctgaggaaactgtgacccaggattgtctccagctcattgccgatagtgagactccta ccattcagaagggatcttacacctttgtgccttggctgctgtctttcaaacggggctctgctct ggaggaaaaggagaacaaaattctggtcaaagagactggctacttcttcatctacggccaggtg ctgtacaccgacaaaacatacgccatgggccatctcattcagcggaaaaaagtccacgtgttcg gcgacgaactctctctcgtgacactgttccggtgtatccagaacatgcccgagacactgcccaa taatagctgctactctgccggcattgctaaactggaggagggggacgaactccagctggctatt cctagggaaaatgcccagatttctctcgatggggatgtgacattcttcggggccctcaaactgc tgggaggcggcggatctggcggaggcgggagtcaattcgcagcaggtccagaagaaacagtcac tcaagactgcttgcaactgattgcagacagtgaaacaccaactatacaaaaaggatcttacaca tttgttccatggcttctcagctttaaaaggggaagtgccctagaagaaaaagagaataaaatat tggtcaaagaaactggttactttttatatatggtcaggttttatatactgataagacctacgc catgggacatctaattcagaggaagaaggtccatgtctttggggatgaattgagtctggtgact ttgtttcgatgtattcaaaatatgcctgaaacactacccaataattcctgctattcagctggca ttgcaaaactggaagaaggagatgaactccaacttgcaataccaagagaaaatgcacaaatatc actggatggagatgtcacatttttggtgcattgaaactgctgtga SEQ ID NO: 119: Protein construct expressed from SEQ ID NO: 110

MNFGFSLIFL VLVLKGVQCE VKLVPRQLDY KDDDDKELQL QLQESGPGLV KPSETLSLTC

TVSGASISAN SYYGVWVRQS PGKGLEWVGS IAYRGNSNSG STYYNPSLKS RATVSVDTSK

NQVSLRLTSV TAADTALYYC ARRQLLDDGT GYQWAAFDVW GQGTMVTVSS GSSSASTKGP

SVFPLAPSSK STSGGTAALG CLVKDYFPEP VTVSWNSGAL TSGVHTFPAV LQSSGLYSLS

SVVTVPSSSL GTQTYICNVN HKPSNTKVDK KVEPKSCDKT HTCPPCPALE GPEETVTQDC

LQLIADSETP TIQKGSYTFV PWLLSFKRGS ALEEKENKIL VKETGYFFIY GQVLYTDKTY

AMGHLIQRKK VHVFGDELSL VTLFRCIQNM PETLPNNSCY SAGIAKLEEG DELQLAIPRE

NAQISLDGDV TFFGALKLLG GGGSGGGGSG PEETVTQDCL QLIADSETPT IQKGSYTFVP

WLLSFKRGSA LEEKENKILV KETGYFFIYG QVLYTDKTYA MGHLIQRKKV HVFGDELSLV

TLFRCIQNMP ETLPNNSCYS AGIAKLEEGD ELQLAIPREN AQISLDGDVT FFGALKLLGG

GGSGGGGSQF AAGPEETVTQ DCLQLIADSE TPTIQKGSYT FVPWLLSFKR GSALEEKENK

ILVKETGYFF IYGQVLYTDK TYAMGHLIQR KKVHVFGDEL SLVTLFRCIQ NMPETLPNNS

CYSAGIAKLE EGDELQLAIP RENAQISLDG DVTFFGALKL L*

-continued

SEQ ID NO: 111: anti-TNFR2(C4)-IgG2-VH-scFv:CD20 atgaacttcggcttcagcctgatcttcctggtgctggtgctgaagggcgtgcagtgcgaagtga agctggtgccccggcaattgcaggttcagctgctgcagtctggacctgagctggtgaagcctgg ggcttcagtgaagttgtcctgcaaggcttctggttatagtttcacaagttacgatattaactgg gtgaagcagaggcctggacagggacttgagtgggttggatggatttatcctagagatggtgata ctaagtacaatgagaaattcaagggcaaggccatattgactgtagacacatcctccaacacagc gtacatgaacctccacagcctgacatctgaggactctgcggtctatttctgtgcaagactaact gggccctactggtacttcgatgtctggggcacagggaccacggtcaccgtctcctcaggatcct cgagtgctagcaccaagggcccatcggtcttccccctggcgccctgctccaggagcacctccga gagcacagcggccctgggctgcctggtcaaggactacttccccgaaccggtgacggtgtcgtgg aactcaggcgctctgaccagcggcgtgcacaccttcccagctgtcctacagtcctcaggactct actccctcagcagcgtggtgaccgtgccctccagcaacttcggcacccagacctacacctgcaa cgtagatcacaagcccagcaacaccaaggtggacaagacagttgagcgcaaatgttgtgtcgag tgcccaccgtgcccagcaccacctgtggcaggaccgtcagtcttcctcttccccccaaaaccca aggacaccctcatgatctcccggacccctgaggtcacgtgcgtggtggtggacgtgagccacga agaccccgaggtccagttcaactggtacgtggacggcgtggaggtgcataatgccaagacaaag ccacgggaggagcagttcaacagcacgttccgtgtggtcagcgtcctcaccgttgtgcaccagg actggctgaacggcaaggagtacaagtgcaaggtctccaacaaaggcctcccagcccccatcga gaaaaccatctccaaaaccaaagggcagccccgagaaccacaggtgtacaccctgcccccatcc cgggaggagatgaccaagaaccaggtcagcctgacctgcctggtcaaaggcttctaccccagcg acatcgccgtggagtgggagagcaatgggcagccggagaacaactacaagaccacgcctcccat gctggactccgacggctccttcttcctctacagcaagctcaccgtggacaagagcaggtggcag caggggaacgtcttctcatgctccgtgatgcatgaggctctgcacaaccactacacgcagaaga gcctctccctgtctccgggtaaagaattccaggtacaactgcagcagcctggggctgagctggt gaagcctggggcctcagtgaagatgtcctgcaaggcttctggctacacatttaccagttacaat atgcactgggtaaaacagacacctggtcggggcctggaatggattggagctatttatcccggaa atggtgatacttcctacaatcagaagttcaaaggcaaggccacattgactgcagacaaatcctc cagcacagcctacatgcagctcagcagcctgacatctgaggactctgcggtctattactgtgca agatcgacttactacggcggtgactggtacttcaatgtctggggcgcagggaccacggtcaccg tctcttcaggaggaggcggatccggcggaggcggaagcggtggcggaggctctcaaattgttct ctcccagtctccagcaatcctgtctgcatctccaggggagaaggtcacaatgacttgcagggcc agctcaagtgtaagttacatccactggttccagcagaagccaggatcctcccccaaaccctgga tttatgccacatccaacctggcttctggagtccctgttcgcttcagtggcagtgggtctgggac ttcttactctctcacaatcagcagagtggaggctgaagatgctgccacttattactgccagcag tggactagtaacccacccacgttcggaggggggaccaagctggaaatcaaacgttaa SEQ ID NO: 120: Protein construct expressed from SEQ ID NO: 111

MNFGFSLIFL VLVLKGVQCE VKLVPRQLQV QLLQSGPELV KPGASVKLSC KASGYSFTSY

DINWVKQRPG QGLEWVGWIY PRDGDTKYNE KFKGKAILTV DTSSNTAYMN LHSLTSEDSA

VYFCARLTGP YWYFDVWGTG TTVTVSSGSS SASTKGPSVF PLAPCSRSTS ESTAALGCLV

KDYFPEPVTV SWNSGALTSG VHTFPAVLQS SGLYSLSSVV TVPSSNFGTQ TYTCNVDHKP

SNTKVDKTVE RKCCVECPPC PAPPVAGPSV FLFPPKPKDT LMISRTPEVT CVVVDVSHED

PEVQFNWYVD GVEVHNAKTK PREEQFNSTF RVVSVLTVVH QDWLNGKEYK CKVSNKGLPA

-continued

PIEKTISKTK GQPREPQVYT LPPSREEMTK NQVSLTCLVK GFYPSDIAVE WESNGQPENN

YKTTPPMLDS DGSFFLYSKL TVDKSRWQQG NVFSCSVMHE ALHNHYTQKS LSLSPGKEFQ

VQLQQPGAEL VKPGASVKMS CKASGYTFTS YNMHWVKQTP GRGLEWIGAI YPGNGDTSYN

QKFKGKATLT ADKSSSTAYM QLSSLTSEDS AVYYCARSTY YGGDWYFNVW GAGTTVTVSS

GGGGSGGGGS GGGGSQIVLS QSPAILSASP GEKVTMTCRA SSSVSYIHWF QQKPGSSPKP

WIYATSNLAS GVPVRFSGSG SGTSYSLTIS RVEAEDAATY YCQQWTSNPP TFGGGTKLEI

KR*

SEQ ID NO: 112: anti-TNFR2(C4)-IgG1(N297A)-VH-scFv:CD70(1F6)
atgaacttcggcttcagcctgatcttcctggtgctggtgctgaagggcgtgcagtgcgaagtga agctggtgccccggcaattgcaggttcagctgctgcagtctggacctgagctggtgaagcctgg ggcttcagtgaagttgtcctgcaaggcttctggttatagtttcacaagttacgatattaactgg gtgaagcagaggcctggacagggacttgagtgggttggatggatttatcctagagatggtgata ctaagtacaatgagaaattcaagggcaaggccatattgactgtagacacatcctccaacacagc gtacatgaacctccacagcctgacatctgaggactctgcggtctatttctgtgcaagactaact gggccctactggtacttcgatgtctggggcacagggaccacggtcaccgtctcctcaggatcca gcagcgcctctacaaagggccccagcgtgttccctctggcccctagcagcaagagcacatctgg cggaacagccgccctgggctgcctcgtgaaggactactttcccgagcccgtgaccgtgtcctgg aactctggcgctctgacaagcggcgtgcacacctttccagccgtgctgcagagcagcggcctgt actctctgagcagcgtcgtgacagtgcccagcagctctctgggcacccagacctacatctgcaa cgtgaaccacaagcccagcaacaccaaggtggacaagaaggtggaacccaagagctgcgacaag acccacacctgtcccccttgtcctgcccccgaactqctgggaggcccttccgtgttcctgttcc ccccaaagcccaaggacaccctgatgatcagccggacccccgaagtgacctgcgtggtggtgga tgtgtcccacgaggaccctgaagtgaagtttaattggtacgtggacggcgtggaagcgcacaac gccaagaccaagcctagagaggaacagtacgccagcacctaccgggtggtgtccgtgctgacag tgctgcaccaggactggctgaacggcaaagagtacaagtgcaaggtgtccaacaaggccctgcc tgcccccatcgagaaaaccatcagcaaggccaagggccagccccgcgaaccccaggtgtacaca ctgcccccaagcagggacgagctgaccaagaaccaggtgtccctgacctgtctcgtgaaaggct tctaccccagcgatatcgccgtggaatgggagagcaacggccagcccgagaacaactacaagac caccccccctgtgctggacagcgacggctcattcttcctgtacagcaagctgaccgtggacaag tcccggtggcagcagggcaacgtgttcagctgcagcgtgatgcacgaggccctgcacaaccact acacccagaagtccctgagcctgagccccggcaaggaattccagattcagctcgtccagtccgg acctgaagtgaaaaaacctggcgaaaccgtgaaaatttcctgtaaggcctctggctacaccttt accaactacggcatgaactgggtcaaacaggctcctgggaagggcctgaaatggatgggatgga tcaacacctacaccggcgaaccaacatacgccgatgcctttaagggacgctttgccttctctct ggaaacttccgcctctactgcttacctccagatcaataacctcaaaaacgaggacaccgccact tacttttgtgctcgggattacggggactacgggatggattactggggacagggaacatctgtga ccgtgtctagcgcttctacaaaggggcctaaactggaggagggcgagtttagcgaggctagagt ggatatcgtgctcacacagtctcccgcttctctggctgtctcactgggccagcgagcaacaatc tcttgtcgggcttccaaatccgtgtctactagcggctactcttttatgcactggtaccagcaga aacctgggcagcctccaaaactgctcatctacctggcttcaaacctcgaatccggagtgcctgc tcgattttctggctctggctccgggaccgactttacactgaacattcatcctgtcgaggaggag -continued gacgctgccacatactactgtcagcattctagggaggtgccatggacatttggcgggggaacaa aactggaaatcaaacggtaa SEQ ID NO: 121: Protein construct expressed from SEQ ID NO: 112
MNFGFSLIFL VLVLKGVQCE VKLVPRQLQV QLLQSGPELV KPGASVKLSC KASGYSFTSY

DINWVKQRPG QGLEWVGWIY PRDGDTKYNE KFKGKAILTV DTSSNTAYMN LHSLTSEDSA

VYFCARLTGP YWYFDVWGTG TTVTVSSGSS SASTKGPSVF PLAPSSKSTS GGTAALGCLV

KDYFPEPVTV SWNSGALTSG VHTFPAVLQS SGLYSLSSVV TVPSSSLGTQ TYICNVNHKP

SNTKVDKKVE PKSCDKTHTC PPCPAPELLG GPSVFLFPPK PKDTLMISRT PEVTCVVVDV

SHEDPEVKFN WYVDGVEVHN AKTKPREEQY ASTYRVVSVL TVLHQDWLNG KEYKCKVSNK

ALPAPIEKTI SKAKGQPREP QVYTLPPSRD ELTKNQVSLT CLVKGFYPSD IAVEWESNGQ

PENNYKTTPP VLDSDGSFFL YSKLTVDKSR WQQGNVFSCS VMHEALHNHY TQKSLSLSPG

KEFQIQLVQS GPEVKKPGET VKISCKASGY TFTNYGMNWV KQAPGKGLKW MGWINTYTGE

PTYADAFKGR FAFSLETSAS TAYLQINNLK NEDTATYFCA RDYGDYGMDY WGQGTSVTVS

SASTKGPKLE EGEFSEARVD IVLTQSPASL AVSLGQRATI SCRASKSVST SGYSFMHWYQ

QKPGQPPKLL IYLASNLESG VPARFSGSGS GTDFTLNIHP VEEEDAATYY CQHSREVPWT

FGGGTKLEIK R*

SEQ ID NO: 113: anti-TNFR2(C4)-IgG1(N297A)-VH-scFv:CD70(2H5)
atgaacttcggcttcagcctgatcttcctggtgctggtgctgaagggcgtgcagtgcgaagtga agctggtgccccggcaattgcaggttcagctgctgcagtctggacctgagctggtgaagcctgg ggcttcagtgaagttgtcctgcaaggcttctggttatagtttcacaagttacgatattaactgg gtgaagcagaggcctggacagggacttgagtgggttggacggatttatcctagagatggtgata ctaagtacaatgagaaattcaagggcaaggccatattgactgtagacacatcctccaacacagc gtacatgaacctccacagcctgacatctgaggactctgcggtctatttctgtgcaagactaact gggccctactggtacttcgatgtctggggcacagggaccacggtcaccgtctcctcaggatcca gcagcgcctctacaaagggccccagcgtgttccctctggcccctagcagcaagagcacatctgg cggaacagccgccctgggctgcctcgtgaaggactactttcccgagcccgtgaccgtgtcctgg aactctggcgctctgacaagcggcgtgcacacctttccagccgtgctgcagagcagcggcctgt actctctgagcagcgtcgtgacagtgcccagcagctctctgggcacccagacctacatctgcaa cgtgaaccacaagcccagcaacaccaaggtggacaagaaggtggaacccaagagctgcgacaag acccacacctgtccccccttgtcctgcccccgaactgctgggaggcccttccgtgttcctgttcc ccccaaagcccaaggacaccctgatgatcagccggacccccgaagtgacctgcgtggtggtgga tgtgtcccacgaggaccctgaagtgaagtttaattggtacgtggacggcgtggaagtgcacaac gccaagaccaagcctagagaggaacagtacgccagcacctaccgggtggtgtccgtgctgacag tgctgcaccaggactggctgaacggcaaagagtacaagtgcaaggtgtccaacaaggccctgcc tgcccccatcgagaaaaccatcagcaaggccaagggccagccccgcgaaccccaggtgtacaca ctscccccaagcagggacgagctgaccaagaaccaggtgtccccgacctgtctcgtgaaaggct tctaccccagcgatatcgccgtggaatgggagagcaacggccagcccgagaacaactacaagac cacccccccctgtgctggacagcgacggctcattcttcctgtacagcaagctgaccgtggacaag tcccggtggcagcagggcaacgtgttcagctgcagcgtgatgcacgaggccctgcacaaccact acacccagaagtccctgagcctgagccccggcaaggaattccaggtgcagctggtggaatctgg cggcggagtggtgcagcctggcagaagcctgagactgagctgtgccgccagcggcttcaccttc -continued agcagctacatcatgcactgggtgcgccaggcccctggcaagggactggaatgggtggccgtga tcagctacgacggccggaacaagtactacgccgacagcgtgaagggccggttcaccatctcccg ggacaacagcaagaacaccctgtacctgcagatgaacagcctqcgggccgaggacaccgccgtg tactactgtgccagagacaccgacggctacgacttcgactattggggccagggcaccctcgtga ccgtgtctagcggaggcggaggatctggcggagggggatcaggcgggggaggctctgaaatcgt gctgacacagagccccgccaccctgtcactgtctccaggcgaaagagccaccctgagctgcaga gccagccagagcgtgtccagctacctggcctggtatcagcagaagcccggacaggcccccagac tgctgatctacgacgccagcaatcgggccacaggcatccctgccagattttccggctctggcag cggcaccgacttcaccctgacaatcagcagcctggaacccgaggactttgccgtgtattattgc cagcagcggaccaactsgcccctgacctttggcggaggcaccaaggtggaaatcaaggccagca ccaagggctaa SEQ ID NO: 122: Protein construct expressed from SEQ ID NO: 113
MNFGFSLIFL VLVLKGVQCE VKLVPRQLQV QLLQSGPELV KPGASVKLSC KASGYSFTSY

DINWVKQRPG QGLEWVGWIY PRDGDTKYNE KFKGKAILTV DTSSNTAYMN LHSLTSEDSA

VYFCARLTGP YWYFDVWGTG TTVTVSSGSS SASTKGPSVF PLAPSSKSTS GGTAALGCLV

KDYFPEPVTV SWNSGALTSG VHTFPAVLQS SGLYSLSSVV TVPSSSLGTQ TYICNVNHKP

SNTKVDKKVE PKSCDKTHTC PPCPAPELLG GPSVFLFPPK PKDTLMISRT PEVTCVVVDV

SHEDPEVKFN WYVDGVEVHN AKTKPREEQY ASTYRVVSVL TVLHQDWLNG KEYKCKVSNK

ALPAPIEKTI SKAKGQPREP QVYTLPPSRD ELTKNQVSLT CLVKGFYPSD IAVEWESNGQ

PENNYKTTPP VLDSDGSFFL YSKLTVDKSR WQQGNVFSCS VMHEALHNHY TQKSLSLSPG

KEFQVQLVES GGGVVQPGRS LRLSCAASGF TFSSYIMHWV RQAPGKGLEW VAVISYDGRN

KYYADSVKGR FTISRDNSKN TLYLQMNSLR AEDTAVYYCA RDTDGYDFDY WGQGTLVTVS

SGGGGSGGGG SGGGGSEIVL TQSPATLSLS PGERATLSCR ASQSVSSYLA WYQQKPGQAP

RLLIYDASNR ATGIPARFSG SGSGTDFTLT ISSLEPEDFA VYYCQQRTNW PLTFGGGTKV

EIKASTKG*

SEQ ID NO: 114: anti-41BB(HBBK4)-IgG1(N297A)-VH-scFv:CD20
atgaacttcggcttcagcctgatcttcctggtgctggtgctgaagggcgtgcagtgcgaagtga agctggtgccccggcaattggactacaaggacgacgacgacaaagaattccaggtccagctgca gcagtctggcgccgaagttattaagcctggcgcctccgtgaagctgagctgtaaagccagcggc tacaccttcagcagctactggatgcactgggtccgacaggctccaggacaaggcctggaatgga tcggcgagatcaaccctggcaacggccacaccaactacaacgagaagttcaagagccgggccac actgaccggcgataccagcacaagcaccgtgtacatggaactgagcagcctgagaagcgaggac accgccgtgtactactgcgccagatcctttaccaccgccagagcctttgcctattggggccagg gaacactggtcaccgtgtccagcagatccagcagcgcctctacaaagggccccagcgtgttccc tctggcccctagcagcaagagcacatctggcggaacagccgccctgggctgcctcgtgaaggac tactttcccgagcccgtgaccgtgtcctggaactctggcgctctgacaagcggcgtgcacacct ttccagccgtgctgcagagcagcggcctgtactctctgagcagcgtcgtgacagtgcccagcag ctctctgggcacccagacctacatctgcaacgtgaaccacaagcccagcaacaccaaggtggac aagaaggtggaacccaagagctgcgacaagacccacacctgtccccttgtcctgcccccgaac tgctgggaggcccttccgtgttcctgttcccccaaagcccaaggacaccctgatgatcagccg gacccccgaagtgacctgcgtggtggtggatgtgtcccacgaggaccctgaagtgaagtttaat tggtacgtggacggcgtggaagtgcacaacgccaagaccaagcctagagaggaacagtacgcca -continued gcacctaccgggtggtgtccgtgctgacagtgctgcaccaggactggctgaacggcaaagagta caagtgcaaggtgtccaacaaggccctgcctgcccccatcgagaaaaccatcagcaaggccaag ggccagccccgcgaaccccaggtgtacacactgcccccaagcagggacgagctgaccaagaacc aggtgtccctgacctgtctcgtgaaaggcttctaccccagcgatatcgccgtggaatgggagag caacggccagcccgagaacaactacaagaccaccccccctgcgctggacagcgacggctcattc ttcctgcacagcaagctgaccgtggacaagtcccggtggcagcagggcaacgtgttcagctgca gcgtgatgcacgaggccctgcacaaccactacacccagaagtccctgagcctgagccccggcaa gctcgagcaggtacaactgcagcagcctggggctgagctggtgaagcctggggcctcagtgaag atgtcctgcaaggcttctggctacacatttaccagttacaatatgcactgggtaaaacagacac ctggtcggggcctggaatggattggagctatttatcccggaaatggtgatacttcctacaatca gaagttcaaaggcaaggccacattgactgcagacaaatcctccagcacagcctacatgcagctc agcagcctgacatctgaggactctgcggtctattactgtgcaagatcgacttactacggcggtg actggtacttcaatgtctggggcgcagggaccacggtcaccgtctcttcaggaggaggcggatc cggcggaggcggaagcggtggcggaggctctcaaattgttctctcccagtctccagcaatcctg tctgcatctccaggggagaaggtcacaatgacttgcagggccagctcaagtgtaagttacatcc actggttccagcagaagccaggatcctcccccaaaccctggatttatgccacatccaacctggc ttctggagtccctgttcgcttcagtggcagtgggtctgggactccttactctctcacaatcagc agagtggaggctgaagatgctgccacttattactgccagcagtggactagtaacccacccacgt tcggagggggggaccaagctggaaatcaaacgttaa SEQ ID NO: 123: Protein construct expressed from SEQ ID NO: 114

MNFGFSLIFL VLVLKGVQCE VKLVPRQLDY KDDDDKEFQV QLQQSGAEVI KPGASVKLSC

KASGYTFSSY WMHWVRQAPG QGLEWIGEIN PGNGHTNYNE KFKSRATLTG DTSTSTVYME

LSSLRSEDTA VYYCARSFTT ARAFAYWGQG TLVTVSSRSS SASTKGPSVF PLAPSSKSTS

GGTAALGCLV KDYFPEPVTV SWNSGALTSG VHTFPAVLQS SGLYSLSSVV TVPSSSLGTQ

TYICNVNHKP SNTKVDKKVE PKSCDKTHTC PPCPAPELLG GPSVFLFPPK PKDTLMISRT

PEVTCVVVDV SHEDPEVKFN WYVDGVEVHN AKTKPREEQY ASTYRVVSVL TVLHQDWLNG

KEYKCKVSNK ALPAPIEKTI SKAKGQPREP QVYTLPPSRD ELTKNQVSLT CLVKGFYPSD

IAVEWESNGQ PENNYKTTPP VLDSDGSFFL YSKLTVDKSR WQQGNVFSCS VMHEALHNHY

TQKSLSLSPG KLEQVQLQQP GAELVKPGAS VKMSCKASGY TFTSYNMHWV KQTPGRGLEW

IGAIYPGNGD TSYNQKFKGK ATLTADKSSS TAYMQLSSLT SEDSAVYYCA RSTYYGGDWY

FNVWGAGTTV TVSSGGGGSG GGGSGGGGSQ IVLSQSPAIL SASPGEKVTM TCRASSSVSY

IHWFQQKPGS SPKPWIYATS NLASGVPVRF SGSGSGTSYS LTISRVEAED AATYYCQQWT

SNPPTFGGGT KLEIKR*

SEQ ID NO: 115: anti-41BB(HBBK4)-VL atgaacttcggcttcagcctgatcttcctggtgctggtgctgaagggcgtgcagtgcgaagtga agctggtgccccggcaattggactacaaggacgacgacgacaaagaattggacatcgtgatgac tcagagccccgccttcctgtctgtgacccctggcgagaaagtgaccatcacctgtagagccagc cagaccatcagcgactacctgcactggtatcagcagaagcccgatcaggcccctaagctgctga ttaagtacgcctctcagagcatcagcggcatccccagcagattttctggcagcggctctggcac cgacttcacctttaccatcagctccctggaagccgaggatgccgccacctactattgtcaggac ggccacagcttccctccaacctttggacagggcacaaagctggaaatcaagggatccgaaatca -continued agcgtacggtggccgctcccagcgtgttcatcttcccacctagcgacgagcagctgaagtccgg cacagcctctgtcgtgtgcctgctgaacaacttctacccccgcgaggccaaggtgcagtggaag gtggacaatgccctgcagagcggcaacagccaggaaagcgtgaccgagcaggacagcaaggact ccacctacagcctgagcagcaccctgaccctgagcaaggccgactacgagaagcacaaggtgta cgcctgcgaagtgacccaccagggcctgtctagccccgtgaccaagagcttcaaccggggcgag tgctaa SEQ ID NO: 124: Protein construct expressed from SEQ ID NO: 115
MNFGFSLIFL VLVLKGVQCE VKLVPRQLDY KDDDDKELDI VMTQSPAFLS VTPGEKVTIT

CRASQTISDY LHWYQQKPDQ APKLLIKYAS QSISGIPSRF SGSGSGTDFT FTISSLEAED

AATYYCQDGH SFPPTFGQGT KLEIKGSEIK RTVAAPSVFI FPPSDEQLKS GTASVVCLLN

NFYPREAKVQ WKVDNALQSG NSQESVTEQD SKDSTYSLSS TLTLSKADYE KHKVYACEVT

HQGLSSPVTK SFNRGEC*

SEQ ID NO: 116: anti-CD95(E09)-IgG1(N297A)-VH-scFv:CD20
atgaacttcggcttcagcctgatcttcctggtgctggtgctgaagggcgtgcagtgcgaagtga agctggtgccccggcaattggactacaaggacgacgacgacaaagaattgcagctgcagctgca ggaatctggccctggcctcgtgaagcccagcgagacactgagcctgacctgtaccgtgtccggc gccagcatcagcgccaacagctactatggcgtgtgggtgcgccagagccctggcaagggactgg aatgggtgggatctatcgcctaccggggcaacagcaacagcggcagcacctactacaaccccag cctgaagtcccgggccaccgtgtctgtggacaccagcaagaaccaggtgtccctgcggctgacc tctgtgacagccgccgataccgccctgtactactgcgccagaaggcagctgctggacgacggca caggatatcagtgggccgccttcgatgtgtggggccagggaacaatggtcaccgtgtcctccgg atccagcagcgcctctacaaagggccccagcgtgttccctctggcccctagcagcaagagcaca tctggcggaacagccgccctgggctgcctcgtgaaggactactttcccgagcccgtgaccgtgt cctggaactctggcgctctgacaagcggcgtgcacacctttccagccgtgctgcagagcagcgg cctgtactctctgagcagcgtcgtgacagtgcccagcagctctctgggcacccagacctacatc tgcaacgtgaaccacaagcccagcaacaccaaggtggacaagaaggtggaacccaagagctgcg acaagacccacacctgtccccccttgtcctgcccccgaactgctgggaggcccttccgtgttcct gttcccccaaagcccaaggacaccctgatgatcagccggacccccgaagtgacctgcgtggtg gtggatgtgtcccacgaggaccctgaagtgaagtttaattggtacgtggacggcgtggaagtgc acaacgccaagaccaagcctagagaggaacagtacgccagcacctaccgggtggtgtccgtgct gacagtgctgcaccaggactggctgaacggcaaagagtacaagtgcaaggtgtccaacaaggcc ctgcctgcccccatcgagaaaaccatcagcaaggccaagggccagccccgcgaaccccaggtgt acacactgcccccaagcagggacgagctgaccaagaaccaggtgtccctgacctgtctcgtgaa aggcttctaccccagcgatatcgccgtggaatgggagagcaacggccagcccgagaacaactac aagaccacccccccctgtgctggacagcgacggctcattcttcctgtacagcaagctgaccgtgg acaagtcccggtggcagcagggcaacgtgttcagctgcagcgtgatgcacgaggccctgcacaa ccactacacccagaagtccctgagcctgagccccggcaaggaattccaggtacaactgcagcag cctggggctgagctggtgaagcctggggcctcagtgaagatgtcntgcaaggcttctggctaca catttaccagttacaatatgcactgggtaaaacagacacctggtcggggcctggaatggattgg agctatttatcccggaaatggtgatacttcctacaatcagaagttcaaaggcaaggccacattg actgcagacaaatcctccagcacagcctacatgcagctcagcagcctgacatctgaggactctg cggtctattactgtgcaagatcgacttactacggcggtgactggtacttcaatgtctggggcgc -continued

```
agggaccacggtcaccgtctcttcaggaggaggcggatccggcggaggcggaagcggtggcgga
ggctctcaaattgttctctcccagtctccagcaatcctgtctgcatctccaggggagaaggtca
caatgacttgcagggccagctcaagtgtaagttacatccactggttccagcagaagccaggatc
ctcccccaaaccctggatttatgccacatccaacctggcttctggagtccctgttcgcttcagt
ggcagtgggtctgggacttcttactctctcacaatcagcagagtggaggctgaagatgctgcca
cttattactgccagcagtggactagtaacccacccacgttcggaggggggaccaagctggaaat
caaacgttaa
```

```
SEQ ID NO: 125: Protein construct expressed from SEQ ID NO: 116
MNFGFSLIFL VLVLKGVQCE VKLVPRQLDY KDDDDKELQL QLQESGPGLV KPSETLSLTC
TVSGASISAN SYYGVWVRQS PGKGLEWVGS IAYRGNSNSG STYYNPSLKS RATVSVDTSK
NQVSLRLTSV TAADTALYYC ARRQLLDDGT GYQWAAFDVW GQGTMVTVSS GSSSASTKGP
SVFPLAPSSK STSGGTAALG CLVKDYFPEP VTVSWNSGAL TSGVHTFPAV LQSSGLYSLS
SVVTVPSSSL GTQTYICNVN HKPSNTKVDK KVEPKSCDKT HTCPPCPAPE LLGGPSVFLF
PPKPKDTLMI SRTPEVTCVV VDVSHEDPEV KFNWYVDGVE VHNAKTKPRE EQYASTYRVV
SVLTVLHQDW LNGKEYKCKV SNKALPAPIE KTISKAKGQP REPQVYTLPP SRDELTKNQV
SLTCLVKGFY PSDIAVEWES NGQPENNYKT TPPVLDSDGS FFLYSKLTVD KSRWQQGNVF
SCSVMHEALH NHYTQKSLSL SPGKEFQVQL QQPGAELVKP GASVKMSCKA SGYTFTSYNM
HWVKQTPGRG LEWIGAIYPG NGDTSYNQKF KGKATLTADK SSSTAYMQLS SLTSEDSAVY
YCARSTYYGG DWYFNVWGAG TTVTVSSGGG GSGGGGSGGG GSQIVLSQSP AILSASPGEK
VTMTCRASSS VSYIHWFQQK PGSSPKPWIY ATSNLASGVP VRFSGSGSGT SYSLTISRVE
AEDAATYYCQ QWTSNPPTFG GGTKLEIKR*
```

The following amino acid sequences of SEQ ID NOs 126 to 143 are CDR sequences of the anti-4-1BB monoclonal antibodies HBBK4 (which is used in non-limiting experiments of the present application), URELUMAB and UTOMILUMAB. Note that the terms “CDR1-H”, “CDR2-H” and “CDR3-H” refer to the heavy chain CDR1, CDR2 and CDR3 sequences, respectively, and that the terms “CDR1-L”, “CDR2-L” and “CDR3-L” refer to the light chain CDR1, CDR2 and CDR3 sequences, respectively:

```
SEQ ID NO: 126: HBBK4 CDR1-H:
YTFSSYWMH

SEQ ID NO: 127: HBBK4 CDR2-H:
EINPGNGHTNYNEKFKS

SEQ ID NO: 128: HBBK4 CDR3-H:
SFTTARAFAY

SEQ ID NO: 129: HBBK4 CDR1-L:
RASQTISDYLH

SEQ ID NO: 130: HBBK4 CDR2-L:
LASQSIS

SEQ ID NO: 131: HBBK4 CDR3-L:
QDGHSFPPT

SEQ ID NO: 132: URELUMAB CDR1-H:
GSFSGYYWS

SEQ ID NO: 133: URELUMAB CDR2-H:
EINHGGYVTYNPSLES
```

-continued

SEQ ID NO: 134: URELUMAB CDR3-H:
DYGPGNYDWYFDL

SEQ ID NO: 135: URELUMAB CDR1-L:
RASQSVSSYLA

SEQ ID NO: 136: URELUMAB CDR2-L:
DASNRAT

SEQ ID NO: 137: URELUMAB CDR3-L:
QQRSNWPPALT

SEQ ID NO: 138: UTOMILUMAB CDR1-H:
YSFSTYWIS

SEQ ID NO: 139: UTOMILUMAB CDR2-H:
KIYPGDSYTNYSPSFQG

SEQ ID NO: 140: UTOMILUMAB CDR3-H:
GYGIFDY

SEQ ID NO: 141: UTOMILUMAB CDR1-L:
SGDNIGDQYAH

SEQ ID NO: 142: UTOMILUMAB CDR2-L:
QDKNRPS

SEQ ID NO: 143: UTOMILUMAB CDR3-L:
ATYTGFGSLAV

SEQ ID NO: 144: scFv:CD70(1F6) anchoring domain from protein construct of SEQ ID NO: 121:
QIQLVQS GPEVKKPGET VKISCKASGY TFTNYGMNWV KQAPGKGLKW MGWINTYTGE

PTYADAFKGR FAFSLETSAS TAYLQINNLK NEDTATYFCA RDYGDYGMDY WGQGTSVTVS

SASTKGPKLE EGEFSEARVD IVLTQSPASL AVSLGQRATI SCRASKSVST SGYSFMHWYQ

QKPGQPPKLL IYLASNLESG VPARFSGSGS GTDFTLNIHP VEEEDAATYY CQHSREVPWT

FGGGTKLEIK R

SEQ ID NO: 145: scFv:CD70(2H5) anchoring domain from protein construct of SEQ ID NO: 122:
QVQLVES GGGVVQPGRS LRLSCAASGF TFSSYIMHWV RQAPGKGLEW VAVISYDGRN

KYYADSVKGR FTISRDNSKN TLYLQMNSLR AEDTAVYYCA RDTDGYDFDY WGQGTLVTVS

SGGGGSGGGG SGGGGSEIVL TQSPATLSLS PGERATLSCR ASQSVSSYLA WYQQKPGQAP

RLLIYDASNR ATGIPARFSG SGSGTDFTLT ISSLEPEDFA VYYCQQRTNW PLTFGGGTKV

EIKASTKG

SEQ ID NO: 146: anti-TRAILR2(Cona)-IgG1(N297A)-VH-scFv:CD70(9G2)
atgaacttcggcttcagcctgatcttcctggtgctggtgctgaagggcgtgcagtgcgaagtga agctggtgccccggcaattggactacaaggacgacgacgacaaagaattccaggtgcagctgca ggaatctggccctggcctcgtgaagcctagccagaccctgagcctgacctgtaccgtgtctggc ggcagcatcagcagcggcgactacttctggtcctggatcagacagctgcccggcaagggcctgg aatggatcggccacatccacaacagcggcaccacctactacaaccccagcctgaagtccagagt gaccatcagcgtggacaccagcaagaagcagttcagcctgcggctgagcagcgtgacagccgcc gatacagccgtgtactactgcgccagagacagaggcggcgattactactacggcatggacgtgt ggggccagggcaccaccgtgaccgtgtctagcagatccagcagcgcctctacaaagggccccag cgtgttccctctggcccctagcagcaagagcacatctggcggaacagccgccctgggctgcctc gtgaaggactactttcccgagcccgtgaccgtgtcctggaactctggcgctctgacaagcggcg tgcacacctttccagccgtgctgcagagcagcggcctgtactctctgagcagcgtcgtgacagt gcccagcagctctctgggcacccagacctacatctgcaacgtgaaccacaagcccagcaacacc aaggtggacaagaaggtggaacccaagagctgcgacaagacccacacctgtccccccttgtcctg -continued cccccgaactgctgggaggcccttccgtgttcctgttcccccccaaagcccaaggacaccctgat gatcagccggacccccgaagtgacctgcgtggtggtggatgtgtcccacgaggaccctgaagtg aagtttaattggtacgtggacggcgtggaagtgcacaacgccaagaccaagcctagagaggaac agtacgccagcacctaccgggtggtgtccgtgctgacagtgctgcaccaggactggctgaacgg caaagagtacaagtgcaaggtgtccaacaaggccctgcctgcccccatcgagaaaaccatcagc aaggccaagggccagccccgcgaaccccaggtgtacacactgcccccaagcagggacgagctga ccaagaaccaggtgtccctgacctgtctcgtgaaaggcttctaccccagcgatatcgccgtgga atgggagagcaacggccagcccgagaacaactacaagaccacccccccctgtgctggacagcgac ggctcattcttcctgtacagcaagctgaccgtggacaagtcccggtggcagcagggcaacgtgt tcagctgcagcgtgatgcacgaggccctgcacaaccactacacccagaagtccctgagccccgg caagctcgagcaggtgcagctggtggaatctggcggcggactgatgcagcctggcggctctctg agactgagctgtgccgccagcggcttcacctttagcagcagcgccatgagctgggtgcgccagg ctcctggaaagggcctggaatgggtgtccagcatctacagcgacagcagctacacctactacgc cgacagcgtgaagtcccggttcaccatcagcaccgacaacgccaagaacaccctgtacctgcag atgaacagcctgaagcccgacgacaccgccgtgtactactgtgccggcagcagcgattacgagg gcagctttgcctcttggggccagggcacacaagtgaccgtgtcctccagatctagcaccaaggg ccccaagctggaagagggcgagttcagcgaggcccaattgcagagcgtcgtgacccagcctcct agcctgtctgcctctcctggaagcagcgtgcggctgacctgtacactgagcagcggcaacagcg tgggcaactacgacatcagctggtatcagcagaaggccggcagccccccccagatacctgctgta ctactacagcgattccgtgaagcaccagggcagcggcgtgcccagcagattttccggaagctct gacgccagcgccaacgccggactgctgctgattcctggcctgcagcctgaggacgaggccgact actactgcagcgcctacaagagcggcagccacgtgttcggcggaggcaccaaactgacagtgct gggctaa SEQ ID NO: 157: Protein construct expressed from SEQ ID NO: 146
MNFGFSLIFL VLVLKGVQCE VKLVPRQLDY KDDDDKEFQV QLQESGPGLV KPSQTLSLTC

TVSGGSISSG DYFWSWIRQL PGKGLEWIGH IHNSGTTYYN PSLKSRVTIS VDTSKKQFSL

RLSSVTAADT AVYYCARDRG GDYYYGMDVW GQGTTVTVSS RSSSASTKGP SVFPLAPSSK

STSGGTAALG CLVKDYFPEP VTVSWNSGAL TSGVHTFPAV LQSSGLYSLS SVVTVPSSSL

GTQTYICNVN HKPSNTKVDK KVEPKSCDKT HTCPPCPAPE LLGGPSVFLF PPKPKDTLMI

SRTPEVTCVV VDVSHEDPEV KFNWYVDGVE VHNAKTKPRE EQYASTYRVV SVLTVLHQDW

LNGKEYKCKV SNKALPAPIE KTISKAKGQP REPQVYTLPP SRDELTKNQV SLTCLVKGFY

PSDIAVEWES NGQPENNYKT TPPVLDSDGS FFLYSKLTVD KSRWQQGNVF SCSVMHEALH

NHYTQKSLSL SPGKLEQVQL VESGGGLMQP GGSLRLSCAA SGFTFSSSAM SWVRQAPGKG

LEWVSSIYSD SSYTYYADSV KSRFTISTDN AKNTLYLQMN SLKPDDTAVY YCAGSSDYEG

SFASWGQGTQ VTVSSRSSTK GPKLEEGEFS EAQLQSVVTQ PPSLSASPGS SVRLTCTLSS

GNSVGNYDIS WYQQKAGSPP RYLLYYYSDS VKHQGSGVPS RFSGSSDASA NAGLLLISGL

QPEDEADYYC SAYKSGSHVF GGGTKLTVLG *

SEQ ID NO: 147: anti-TRAILR2(Cona)-VL
atgaacttcggcttcagcctgatcttcctggtgctggtgctgaagggcgtgcagtgcgaagtga agctggtgccccggcaattggactacaaggacgacgacgacaaagaattggagatcgtgctgac ccagagccctggcaccctgtcactgtctccaggcgagagagccaccctgagctgtagagccagc cagggcatcagccggtcttacctggcctggtatcagcagaagcccggccaggctcctagcctgc -continued tgatctacggcgccagcagcagagccaccggcatccccgatagattttccggcagcggctccgg caccgacttcaccctgacaatcagcagactggaacccgaggacttcgccgtgtattattgccag cagttcggcagcagcccctggacctttggccagggaacaaaagtgggatccgaaatcaagcgta cggtggccgctcccagcgtgttcatcttcccacctagcgacgagcagctgaagtccggcacagc ctctgtcgtgtgcctgctgaacaacttctacccccgcgaggccaaggtgcagtggaaggtggac aatgccctgcagagcggcaacagccaggaaagcgtgaccgagcaggacagcaaggactccacct acagcctgagcagcaccctgaccctgagcaaggccgactacgagaagcacaaggtgtacgcctg cgaagtgacccaccagggcctgtctagccccgtgaccaagagcttcaaccggggcgagtgctaa SEQ ID NO: 158: Protein construct expressed from SEQ ID NO: 147
MNFGFSLIFL VLVLKGVQCE VKLVPRQLDY KDDDDKELEI VLTQSPGTLS LSPGERATLS

CRASQGISRS YLAWYQQKPG QAPSLLIYGA SSRATGIPDR FSGSGSGTDF TLTISRLEPE

DFAVYYCQQF GSSPWTFGQG TKVGSEIKRT VAAPSVFIFP PSDEQLKSGT ASVVCLLNNF

YPREAKVQWK VDNALQSGNS QESVTEQDSK DSTYSLSSTL TLSKADYEKH KVYACEVTHQ

GLSSPVTKSF NRGEC*

SEQ ID NO: 148: anti-CD40(C)-IgG1(N297A)-VH-scFv:PD-L1(Ave)
atgaacttcggcttcagcctgatcttcctggtgctggtgctgaagggcgtgcagtgcgaagtga agctggtgccccggcaattggactacaaggacgacgacgacaaagaattccaggtgcagctggt tcagtctggcgccgaagtgaaaaagcctggcgcctctgtgaaggtgtcctgtacagccagcggc ttcaacatcaaggactactacgtgcactgggtcaagcaggcccctggacaaggactggaatgga tgggcagaatcgaccccgaggacggcgactctaagtacgcccctaagttccagggcaaagccac catgaccgccgataccagcacaagcaccgtgtacatggaactgagcagcctgagaagcgaggac accgccgtgtactactgcaccaccagctactatgtgggcacctacggctattggggccagggca cactggtcaccgtgtccagcagatccagcagcgcctctacaaagggccccagcgtgttccctct ggcccctagcagcaagagcacatctggcggaacagccgccctgggctgcctcgtgaaggactac tttcccgagcccgtgaccgtgtcctggaactctggcgctctgacaagcggcgtgcacacctttc cagccgtgctgcagagcagcggcctqtactctctgagcagcgtcgtgacagtgcccagcagctc tctgggcacccagacctacatctgcaacgtgaaccacaagcccagcaacaccaaggtggacaag aaggtggaacccaagagctgcgacaagacccacacctgtccccccttgtcctgcccccgaactgc tgggaggcccttccgtgttcctgttcccccaaagcccaaggacaccctgatgatcagccggac cccgaagtgacctgcgtggtggtggatgtgtcccacgaggaccctgaagtgaagtttaattgg tacgtggacggcgtggaagtgcacaacgccaagaccaagcctagagaggaacagtacgccagca cctaccgggtggtgtccgtgctgacagtgctgcaccaggactggctgaacggcaaagagtacaa gtgcaaggtgtccaacaaggccctgcctgcccccatcgagaaaaccatcagcaaggccaagggc cagccccgcgaaccccaggtgtacacactgcccccaagcagggacgagctgaccaagaaccagg tgtccctgacctgtctcgtgaaaggcttctaccccagcgatatcgccgtggaatgggagagcaa cggccagcccgagaacaactacaagaccaccccccctgtgctggacagcgacggctcattcttc ctgtacagcaagctgaccgtggacaagtcccggtggcagcagggcaacgtgttcagctgcagcg tgatgcacgaggccctgcacaaccactacacccagaagtccctgagcctgagccccggcaagct cgaggaggtgcagctgctggaatctggcggaggacttgttcagcctggcggctctctgagactg tcttgtgccgccagcggcttcaccttcagcagctatatcatgatgtgggtccgacaggcccctg gcaaaggccttgaatgggtgtccagcatctatcccagcggcggcatcaccttttacgccgacac -continued agtgaagggcagattcaccatcagccgggacaacagcaagaacaccctgtacctgcagatgaac agcctgagagccgaggacaccgccgtgtactactgcgccagaatcaagctgggcaccgtgacca ccgtggattattggggacagggcaccctggtcaccgtgtcctccagatcttctacaaagggccc caagctggaagagggcgagtttagcgaagcccaattgcagagcgccctgacacagcctgcatcc gtgtctggatctccaggccagagcatcaccatctcttgtaccggcacaagctccgatgtcggcg gctacaattacgtgtcctggtatcagcagcaccccggcaaggcccctaagctgatgatctacga cgtgtccaacagaccctccggcgtgtccaatagattcagcggcagcaagagcggcaacaccgcc agcctgacaattagcggactgcaggccgaggacgaggccgattactactgtagcagctacacca gctcctccaccagagtgtttggcaccggcaccaaagtgaccgtgctttaa SEQ ID NO: 159: Protein construct expressed from SEQ ID NO: 148

MNFGFSLIFL VLVLKGVQCE VKLVPRQLDY KDDDDKEFQV QLVQSGAEVK KPGASVKVSC

TASGFNIKDY YVHWVKQAPG QGLEWMGRID PEDGDSKYAP KFQGKATMTA DTSTSTVYME

LSSLRSEDTA VYYCTTSYYV GTYGYWGQGT LVTVSSRSSS ASTKGPSVFP LAPSSKSTSG

GTAALGCLVK DYFPEPVTVS WNSGALTSGV HTFPAVLQSS GLYSLSSVVT VPSSSLGTQT

YICNVNHKPS NTKVDKKVEP KSCDKTHTCP PCPAPELLGG PSVFLFPPKP KDTLMISRTP

EVTCVVVDVS HEDPEVKFNW YVDGVEVHNA KTKPREEQYA STYRVVSVLT VLHQDWLNGK

EYKCKVSNKA LPAPIEKTIS KAKGQPREPQ VYTLPPSRDE LTKNQVSLTC LVKGFYPSDI

AVEWESNGQP ENNYKTTPPV LDSDGSFFLY SKLTVDKSRW QQGNVFSCSV MHEALHNHYT

QKSLSLSPGK LEEVQLLESG GGLVQPGGSL RLSCAASGFT FSSYIMMWVR QAPGKGLEWV

SSIYPSGGIT FYADTVKGRF TISRDNSKNT LYLQMNSLRA EDTAVYYCAR IKLGTVTTVD

YWGQGTLVTV SSRSSTKGPK LEEGEFSEAQ LQSALTQPAS VSGSPGQSIT ISCTGTSSDV

GGYNYVSWYQ QHPGKAPKLM IYDVSNRPSG VSNRFSGSKS GNTASLTISG LQAEDEADYY

CSSYTSSSTR VFGTGTKVTV L*

SEQ ID NO: 149: anti-CD40(C)-VL atgaacttcggcttcagcctgatcttcctggtgctggtgctgaagggcgtgcagtgcgaagtga agctggtgccccggcaattggactacaaggacgacgacgacaaagaattggacatccagatgac acagagccccagcagcctgtctgccagcgtgggagatagagtgaccatcacctgtagcgccagc agcagcgtgtcctacatgctgtggttccagcagaagcctggcaaggcccctaagctgctgatct acagcacctccaatctggccagcggcgtgccaagcagattttctggctctggcagcggcaccga cttcaccctgaccatatctagcctgcagccagaggacttcgccacctactactgccagcagcgg acattctacccctacacctttggcggaggcaccaaggtggaaatcaagggatccgaaatcaagc gtacggtggccgctcccagcgtgttcatcttcccacctagcgacgagcagctgaagtccggcac agcctctgtcgtgtgcctgctgaacaacttctaccccgcgaggccaaggtgcagtggaaggtg gacaatgccctgcagagcggcaacagccaggaaagcgtgaccgagcaggacagcaaggactcca cctacagcctgagcagcaccctgaccctgagcaaggccgactacgagaagcacaaggtgtacgc ctgcgaagtgacccaccagggcctgtctagccccgtgaccaagagcttcaaccggggcgagtgc taa SEQ ID NO: 160: Protein construct expressed from SEQ ID NO: 149

MNFGFSLIFL VLVLKGVQCE VKLVPRQLDY KDDDDKELDI QMTQSPSSLS ASVGDRVTIT

CSASSSVSYM LWFQQKPGKA PKLLIYSTSN LASGVPSRFS GSGSGTDFTL TISSLQPEDF

ATYYCQQRTF YPYTFGGGTK VEIKGSEIKR TVAAPSVFIF PPSDEQLKSG TASVVCLLNN

FYPREAKVQW KVDNALQSGN SQESVTEQDS KDSTYSLSST LTLSKADYEK HKVYACEVTH

QGLSSPVTKS FNRGEC*

SEQ ID NO: 150: anti-CD40(C)-Fab2-scFv:PD-L1(Ave)
atgaacttcggcttcagcctgatcttcctggtgctggtgctgaagggcgtgcagtgcgaagtga agctggtgccccggcaattggactacaaggacgacgacgacaaagaattccaggtgcagctggt tcagtctggcgcogaagtgaaaaagcctggcgcctctgtgaaggtgtcctgtacagccagcggc ttcaacatcaaggactactacgtgcactgggtcaagcaggcccctggacaaggactggaatgga tgggcagaatcgaccccgaggacggcgactctaagtacgcccctaagttccagggcaaagccac catgaccgccgataccagcacaagcaccgtgtacatggaactgagcagcctgagaagcgaggac accgccgtgtactactgcaccaccagctactatgtgggcacctacggctattggggccagggca cactggtcaccgtgtccagcagatcctctagcgccagcacaaagggccccagcgtgttccctct ggcccctagcagcaagagcacatctggcggaacagccgccctgggctgcctcgtgaaggactac tttcccgagcccgtgacagtgtcctggaactctggcgccctgacaagcggcgtgcacacctttc cagccgtgctgcagagcagcggcctgtactctctgagcagcgtcgtgactgtgcccagcagcag cctgggcacccagacctacatctgcaacgtgaaccacaagcccagcaacaccaaggtggacaag aaggtggaacccaagagctgcgacaagacccacacctgtccccccttgtcctgccctcgaggagg tgcagctgctggaatctggcggaggacttgttcagcctggcggctctctgagactgtcttgtgc cgccagcggcttcaccttcagcagctatatcatgatgtgggtccgacaggcccctggcaaaggc cttgaatgggtgcccagcatctatcccagcggcggcatcaccttttacgccgacacagtgaagg gcagattcaccatcagccgggacaacagcaagaacaccctgtacctgcagatgaacagcctgag agccgaggacaccgccgtgtactactgcgccagaatcaagctgggcaccgtgaccaccgtggat tattggggacagggcaccctggtcaccgtgtcctccagatcttctacaaagggccccaagctgg aagagggcgagtttagcgaagcccaattgcagagcgccctgacacagcctgcatccgtgtctgg atctccaggccagagcatcaccatctcttgtaccggcacaagctccgatgtcggcggctacaat tacgtgtcctggtatcagcagcaccccggcaaggcccctaagctgatgatctacgacgtgtcca acagaccctccggcgtgtccaatagattcagcggcagcaagagcggcaacaccgccagcctgac aattagcggactgcaggccgaggacgaggccgattactactgtagcagctacaccagctcctcc accagagtgtttggcaccggcaccaaagtgaccgtgctttaa SEQ ID NO: 161: Protein construct expressed from SEQ ID NO: 150
MNFGESLIFL VLVLKGVQCE VKLVPRQLDY KDDDDKEFQV QLVQSGAEVK KPGASVKVSC

TASGFNIKDY YVHWVKQAPG QGLEWMGRID PEDGDSKYAP KFQGKATMTA DTSTSTVYME

LSSLRSEDTA VYYCTTSYYV GTYGYWGQGT LVTVSSRSSS ASTKGPSVFP LAPSSKSTSG

GTAALGCLVK DYFPEPVTVS WNSGALTSGV HTFPAVLQSS GLYSLSSVVT VPSSSLGTQT

YICNVNHKPS NTKVDKKVEP KSCDKTHTCP PCPALEEVQL LESGGGLVQP GGSLRLSCAA

SGFTFSSYIM MWVRQAPGKG LEWVSSIYPS GGITFYADTV KGRFTISRDN SKNTLYLQMN

SLRAEDTAVY YCARIKLGTV TTVDYWGQGT LVTVSSRSST KGPKLEEGEF SEAQLQSALT

QPASVSGSPG QSITISCTGT SSDVGGYNYV SWYQQHPGKA PKLMIYDVSN RPSGVSNRFS

GSKSGNTASL TISGLQAEDE ADYYCSSYTS SSTRVFGTGT KVTVL*

SEQ ID NO: 151: anti-41BB(HBBK)-IgG1(N297A)-VH-scFv:PD-L1(Ave)
atgaacttcggcttcagcctgatcttcctggtgctggtgctgaagggcgtgcagtgcgaagtga agctggtgccccggcaattggactacaaggacgacgacgacaaagaattccaggtccagctgca gcagtctggcgccgaagttattaagcctggcgcctccgtgaagctgagctgtaaagccagcggc tacaccttcagcagctactggatgcactgggtccgacaggctccaggacaaggcctggaatgga -continued tcggcgagatcaaccctggcaacggccacaccaactacaacgagaagttcaagagccgggccac actgaccggcgataccagcacaagcaccgtgtacatggaactgagcagcctgagaagcgaggac accgccgtgtactactgcgccagatcctttaccaccgccagagcctttgcctattggggccagg gaacactggtcaccgtgtccagcagatccagcagcgcctctacaaagggccccagcgtgttccc tctggcccctagcagcaagagcacatctggcggaacagccgccctgggctgcctcgtgaaggac tactttcccgagcccgtgaccgtgtcctggaactctggcgctctgacaagcggcgtgcacacct ttccagccgtgctgcagagcagcggcctgtactctctgagcagcgtcgtgacagtgcccagcag ctctctgggcacccagacctacatctgcaacgtgaaccacaagcccagcaacaccaaggtggac aagaaggtggaacccaagagctgcgacaagacccacacctgtcccccttgtcctgcccccgaac tgctgggaggcccttccgtgttcctgttcccccaaagcccaaggacaccctgatgatcagccg gacccccgaagtgacctgcgtggtggtggatgtgtcccacgaggaccctgaagtgaagtttaat tggtacgtggacggcgtggaagtgcacaacgccaagaccaagcctagagaggaacagtacgcca gcacctaccgggtggtgtccgtgctgacagtgctgcaccaggactggctgaacggcaaagagta caagtgcaaggtgtccaacaaggccctgcctgcccccatcgagaaaaccatcagcaaggccaag ggccagccccgcgaaccccaggtgtacacactgcccccaagcagggacgagctgaccaagaacc aggtgtccctgacctgtctcgtgaaaggcttctaccccagcgatatcgccgtggaatgggagag caacggccagcccgagaacaactacaagaccaccccccctgtgctggacagcgacggctcattc ttcctgtacagcaagctgaccgtggacaagtcccggtggcagcagggcaacgtgttcagctgca gcgtgatgcacgaggccctgcacaaccactacacccagaagtccctgagcctgagccccggcaa gctcgaggaggtgcagctgctggaatctggcggaggacttgttcagcctggcggctctctgaga ctgtcttgtgccgccagcggcttcaccttcagcagctatatcatgatgtgggtccgacaggccc ctggcaaaggccttgaatgggtgtccagcatctatcccagcggcggcatcaccttttacgccga cacagtgaagggcagattcaccatcagccgggacaacagcaagaacaccctgtacctgcagatg aacagcctgagagccgaggacaccgccgtgtactactgcgccagaatcaagctgggcaccgtga ccaccgtggattattggggacagggcaccctggtcaccgtgtcctccagatcttctacaaaggg ccccaagctggaagagggcgagtttagcgaagcccaattgcagagcgccctgacacagcctgca tccgtgtctggatctccaggccagagcatcaccatctcttgtaccggcacaagctccgatgtcg gcggctacaattacgtgtcctggtatcagcagcaccccggcaaggcccctaagctgatgatcta cgacgtgtccaacagaccctccggcgtgtccaatagattcagcggcagcaagagcggcaacacc gccagcctgacaattagcggactgcaggccgaggacgaggccgattactactgtagcagctaca ccagctcctccaccagagtgtttggcaccggcaccaaagtgaccgtgctttaa SEQ ID NO: 162: Protein construct expressed from SEQ ID NO: 151

MNFGFSLIFL VLVLKGVQCE VKLVPRQLDY KDDDDKEFQV QLQQSGAEVI KPGASVKLSC

KASGYTFSSY WMHWVRQAPG QGLEWIGEIN PGNGHTNYNE KFKSRATLTG DTSTSTVYME

LSSLRSEDTA VYYCARSFTT ARAFAYWGQG TLVTVSSRSS SASTKGPSVF PLAPSSKSTS

GGTAALGCLV KDYFPEPVTV SWNSGALTSG VHTFPAVLQS SGLYSLSSVV TVPSSSLGTQ

TYICNVNHKP SNTKVDKKVE PKSCDKTHTC PPCPAPELLG GPSVFLFPPK PKDTLMISRT

PEVTCVVVDV SHEDPEVKFN WYVDGVEVHN AKTKPREEQY ASTYRVVSVL TVLHQDWLNG

KEYKCKVSNK ALPAPIEKTI SKAKGQPREP QVYTLPPSRD ELTKNQVSLT CLVKGFYPSD

IAVEWESNGQ PENNYKTTPP VLDSDGSFFL YSKLTVDKSR WQQGNVFSCS VMHEALHNHY

TQKSLSLSPG KLEEVQLLES GGGLVQPGGS LRLSCAASGF TFSSYIMMWV RQAPGKGLEW

-continued

VSSIYPSGGI TFYADTVKGR FTISRDNSKN TLYLQMNSLR AEDTAVYYCA RIKLGTVTTV

DYWGQGTLVT VSSRSSTKGP KLEEGEFSEA QLQSALTQPA SVSGSPGQSI TISCTGTSSD

VGGYNYVSWY QQHPGKAPKL MIYDVSNRPS GVSNRFSGSK SGNTASLTIS GLQAEDEADY

YCSSYTSSST RVFGTGTKVT VL*

SEQ ID NO: 152: anti-41BB(HBBK)-Fab2-scFv:PD-L1(Ave)
atgaacttcggcttcagcctgatcttcctggtgctggtgctgaagggcgtgcagtgcgaagtga agctggtgccccggcaattggactacaaggacgacgacgacaaagaattccaggtccagctgca gcagtctggcgccgaagttattaagcctggcgcctccgtgaagctgagctgtaaagccagcggc tacaccttcagcagctactggatgcactgggtccgacaggctccaggacaaggcctggaatgga tcggcgagatcaaccctggcaacggccacaccaactacaacgagaagttcaagagccgggccac actgaccggcgataccagcacaagcaccgtgtacatggaactgagcagcctgagaagcgaggac accgccgtgtactactgcgccagatcctttaccaccgccagagcctttgcctattggggccagg gaacactggtcaccgtgtccagcagatcctctagcgccagcacaaagggccccagcgtgttccc tctggcccctagcagcaagagcacatctggcggaacagccgccctgggctgcctcgtgaaggac tactttcccgagcccgtgacagtgtcctggaactctggcgccctgacaagcggcgtgcacacct ttccagccgtgctgcagagcagcggcctgtactctctgagcagcgtcgtgactgtgcccagcag cagcctgggcacccagacctacatctgcaacgtgaaccacaagcccagcaacaccaaggtggac aagaaggtggaacccaagagctgcgacaagacccacacctgtccccccttgtcctgccctcgagg aggtgcagctgctggaatctggcggaggacttgttcagcctggcggctctctgagactgtcttg tgccgccagcggcttcaccttcagcagctatatcatgatgtgggtccgacaggcccctggcaaa ggccttgaatgggtgtccagcatctatcccagcggcggcatcaccttttacgccgacacagtga agggcagattcaccatcagccgggacaacagcaagaacaccctgtacctgcagatgaacagcct gagagccgaggacaccgccgtgtactactgcgccagaatcaagctgggcaccgtgaccaccgtg gattattggggacagggcaccctggtcaccgtgtcctccagatcttctacaaagggccccaagc tggaagagggcgagtttagcgaagcccaattgcagagcgccctgacacagcctgcatccgtgtc tggatctccaggccagagcatcaccatctcttgtaccggcacaagctccgatgtcggcggctac aattacgtgtcctggtatcagcagcaccccggcaaggcccctaagctgatgatctacgacgtgt ccaacagaccctccggcgtgtccaatagattcagcggcagcaagagcggcaacaccgccagcct gacaattagcggactgcaggccgaggacgaggccgattactactgtagcagctacaccagctcc tccaccagagtgtttggcaccggcaccaaagtgaccgtgctttaa SEQ ID NO: 163: Protein construct expressed from SEQ ID NO: 152
MNFGFSLIFL VLVLKGVQCE VKLVPRQLDY KDDDDKEFQV QLQQSGAEVI KPGASVKLSC

KASGYTFSSY WMHWVRQAPG QGLEWIGEIN PGNGHTNYNE KFKSRATLTG DTSTSTVYME

LSSLRSEDTA VYYCARSFTT ARAFAYWGQG TLVTVSSRSS SASTKGPSVF PLAPSSKSTS

GGTAALGCLV KDYFPEPVTV SWNSGALTSG VHTFPAVLQS SGLYSLSSVV TVPSSSLGTQ

TYICNVNHKP SNTKVDKKVE PKSCDKTHTC PPCPALEEVQ LLESGGGLVQ PGGSLRLSCA

ASGFTFSSYI MMWVRQAPGK GLEWVSSIYP SGGITFYADT VKGRFTISRD NSKNTLYLQM

NSLRAEDTAV YYCARIKLGT VTTVDYWGQG TLVTVSSRSS TKGPKLEEGE FSEAQLQSAL

-continued

TQPASVSGSP GQSITISCTG TSSDVGGYNY VSWYQQHPGK APKLMIYDVS NRPSGVSNRF

SGSKSGNTAS LTISGLQAED EADYYCSSYT SSSTRVFGTG TKVTVL*

SEQ ID NO: 153: anti-PD-L1(Ave)-IgG2-VH-scFv:41BB(HBBK)

atgaacttcggcttcagcctgatcttcctggtgctggtgctgaagggcgtgcagtgcgaagtga agctggtgccccggcaattggactacaaggacgacgacgacaaagaattcgaggtgcagctgct ggaatctggcggaggacttgttcagcctggcggctctctgagaccgtcttgtgccgccagcggc ttcaccttcagcagctatatcatgatgtgggtccgacaggcccctggcaaaggccttgaatggg tgtccagcatctatcccagcggcggcatcacctttttacgccgacacagtgaagggcagattcac catcagccgggacaacagcaagaacaccctgtacctgcagatgaacagcctgagagccgaggac accgccgtgtactactgcgccagaatcaagctgggcaccgtgaccaccgtggattattggggac agggcaccctggtcaccgtgtcctccagatcctcgagtgctagcaccaagggcccatcggtctt cccctggcgccctgctccaggagcacctccgagagcacagcggccctgggctgcctggtcaag gactacttccccgaaccggtgacggtgtcgtggaactcaggcgctctgaccagcggcgtgcaca ccttcccagctgtcctacagtcctcaggactctactccctcagcagcgtggtgaccgtgccctc cagcaacttcggcacccagacctacacctgcaacgtagatcacaagcccagcaacaccaaggtg gacaagacagttgagcgcaaatgttgtgtcgagtgcccaccgtgcccagcaccacctgtggcag gaccgtcagtcttcctcttccccccaaaacccaaggacaccctcatgatctcccggacccctga ggtcacgtgcgtggtggtggacgtgagccacgaagaccccgaggtccagttcaactggtacgtg gacggcgtggaggtgcataatgccaagacaaagccacgggaggagcagttcaacagcacgttcc gtgtggtcagcgtcctcaccgttgtgcaccaggartggctgaacggcaaggagtacaagtgcaa ggtctccaacaaaggcctcccagcccccatcgagaaaaccatctccaaaaccaaagggcagccc cgagaaccacaggtgtacaccctgcccccatcccgggaggagatgaccaagaaccaggtcagcc tgacctqcctggtcaaaggcttctaccccagcgacatcgccgtggagtgggagagcaatgggca gccggagaacaactacaagaccacgcctcccatgctggactccgacggctccttcttcctctac agcaagctcaccgtggacaagagcaggtggcagcaggggaacgtcttctcatgctccgtgatgc atgaggctctgcacaaccactacacgcagaagagcctctccctgtctccgggtaaagaattcca ggtccagctgcagcagtctggcgccgaagttattaagcctggcgcctccgtgaagctgagctgt aaagccagcggctacaccttcagcagctactggatgcactgggtccgacaggctccaggacaag gcctggaatggatcggcgagatcaaccctggcaacggccacaccaactacaacgagaagttcaa gagccgggccacactgaccggcgataccagcacaagcaccgtgtacatggaactgagcagcctg agaagcgaggacaccgccgtgtactactgcgccagatcctttaccaccgccagagcctttgcct attggggccagggaacactggtcaccgtgtccagcagatctagcacaaagggccccaagctgga agagggcgagtttagcgaggcccaattggacatcgtgatgactcagagccccgccttcctgtct gtgacccctggcgagaaagtgaccatcacctgtagagccagccagaccatcagcgactacctgc actggtatcagcagaagcccgatcaggcccctaagctgctgattaagtacgcctctcagagcat cagcggcatccccagcagattttctggcagcggctctggcaccgacttcacctttaccatcagc tccctggaagccgaggatgccgccacctactattgtcaggacggccacagcttccctccaacct ttggacagggcacaaagctggaaatcaagtaa SEQ ID NO: 164: Protein construct expressed from SEQ ID NO: 153

MNFGFSLIFL VLVLKGVQCE VKLVPRQLDY KDDDDKEFEV QLLESGGGLV QPGGSLRLSC

AASGFTFSSY IMMWVRQAPG KGLEWVSSIY PSGGITFYAD TVKGRFTISR DNSKNTLYLQ

MNSLRAEDTA VYYCARIKLG TVTTVDYWGQ GTLVTVSSRS SSASTKGPSV FPLAPCSRST

-continued

SESTAALGCL VKDYFPEPVT VSWNSGALTS GVHTFPAVLQ SSGLYSLSSV VTVPSSNFGT

QTYTCNVDHK PSNTKVDKTV ERKCCVECPP CRAPPVAGPS VFLFPPKPKD TLMISRTPEV

TCVVVDVSHE DPEVQFNWYV DGVEVHNAKT KPREEQFNST FRVVSVLTVV HQDWLNGKEY

KCKVSNKGLP APIEKTISKT KGQPREPQVY TLPPSREEMT KNQVSLTCLV KGFYPSDIAV

EWESNGQPEN NYKTTPPMLD SDGSFFLYSK LTVDKSRWQQ GNVFSCSVMH EALHNHYTQK

SLSLSPGKEF QVQLQQSGAE VIKPGASVKL SCKASGYTFS SYWMHWVRQA PGQGLEWIGE

INPGNGHTNY NEKFKSRATL TGDTSTSTVY MELSSLRSED TAVYYCARSF TTARAFAYWG

QGTLVTVSSR SSTKGPKLEE GEFSEAQLDI VMTQSPAFLS VTPGEKVTIT CRASQTISDY

LHWYQQKPDQ APKLLIKYAS QSISGIPSRF SGSGSGTDFT FTISSLEAED AATYYCQDGH

SFPPTFGQGT KLEIK*

SEQ ID NO: 154: anti-PD-L1(Ave)-VL
atgaacttcggcttcagcctgatcttcctggtgctggtgctgaagggcgtgcagtgcgaagtga agctggtgccccggcaattggactacaaggacgacgacgacaaagaattgcagagcgccctgac acagcctgcatccgtgtctggatctccaggccagagcatcaccatctcttgtaccggcacaagc tccgatgtcggcggctacaattacgtgtcctggtatcagcagcaccccggcaaggcccctaagc tgatgatctacgacgtgtccaacagaccctccggcgtgtccaatagattcagcggcagcaagag cggcaacaccgccagcctgacaattagcggactgcaggccgaggacgaggccgattactactgt agcagctacaccagctcctccaccagagtgtttggcaccggcaccaaagtgaccgtgcttggat ccgaaatcaagcgtacggtggccgctcccagcgtgttcatcttcccacctagcgacgagcagct gaagtccggcacagcctctgtogtgtgcctgctgaacaacttctacccccgcgaggccaaggtg cagtggaaggtggacaatgccctgcagagcggcaacagccaggaaagcgtgaccgagcaggaca gcaaggactccacctacagcctgagcagcaccctgaccctgagcaaggccgactacgagaagca caaggtgtacgcctgcgaagtgacccaccagggcctgtctagccccgtgaccaagagcttcaac cggggcgagtgctaa SEQ ID NO: 165: Protein construct expressed from SEQ ID NO: 154
MNFGFSLIFL VLVLKGVQCE VKLVPRQLDY KDDDDKELQS ALTQPASVSG SPGQSITISC

TGTSSDVGGY NYVSWYQQHP GKAPKLMIYD VSNRPSGVSN RFSGSKSGNT ASLTISGLQA

EDEADYYCSS YTSSSTRVFG TGTKVTVLGS EIKRTVAAPS VFIFPPSDEQ LKSGTASVVC

LLNNFYPREA KVQWKVDNAL QSGNSQESVT EQDSKDSTYS LSSTLTLSKA DYEKHKVYAC

EVTHQGLSSP VTKSFNRGEC *

SEQ ID NO: 155: anti-muCD27-IgG1(N297A)-VH-scFv:Fn14(18D1)
atgaacttcggcttcagcctgatcttcctggtgctggtgctgaagggcgtgcagtgcgaagtga agctggtgccccggcaattggactacaaggacgacgacgacaaagaattccaggtccagctgca gcagtctggcgccgaacttgtgaagcctggcagcagcgtgaagatcagctgtaaagccagcggc tacaccttcaccagctacgacatgcactggatcaagcagcagcccggcaaaggcctggaatgga tcggctggatctaccccggcaacggcaacaccaagtacaaccagaagttcaacggcaaggccac actgaccgccgacatctctagcagcacagcctacatgcagctgagcagcctgaccagcgaagat agcgccgtgtacttctgcgccaaatggggctacaacaacttcgactactggggccagggcgtga tggtcaccgtgtctagcagatccagcagcgcctctacaaagggccccagcgtgttccctctggc ccctagcagcaagagcacatctggcggaacagccgccctgggctgcctcgtgaaggactacttt cccgagcccgtgaccgtgtcctggaactctggcgctctgacaagcggcgtgcacacctttccag ccgtgctgcagagcagcggcctgtactctctgagcagcgtcgtgacagtgcccagcagctctct -continued gggcacccagacctacatctgcaacgtgaaccacaagcccagcaacaccaaggtggacaagaag gtggaacccaagagctgcgacaagacccacacctgtccccctgtcctgcccccgaactgctgg gaggcccttccgtgttcctgttcccccaaagcccaaggacaccctgatgatcagccggacccc cgaagtgacctgcgtggtggtggatgtgtcccacgaggaccctgaagtgaagtttaattggtac gtggacggcgtggaagtgcacaacgccaagaccaagcctagagaggaacagtacgccagcacct accgggtggtgtccgtgctgacagtgctgcaccaggactggctgaacggcaaagagtacaagtg caaggtgtccaacaaggccctgcctgcccccatcgagaaaaccatcagcaaggccaagggccag ccccgcgaaccccaggtgtacacactgcccccaagcagggacgagctgaccaagaaccaggtgt ccctgacctgtctcgtgaaaggcttctaccccagcgatatcgccgtggaatgggagagcaacgg ccagcccgagaacaactacaagaccacccccctgtgctggacagcgacggctcattcttcctg tacagcaagctgaccgtggacaagtcccggtggcagcagggcaacgtgttcagctgcagcgtga tgcacgaggccctgcacaaccactacacccagaagtccctgagcctgagccccggcaagctcga ggaggtgcagctggtggaatctggcggcggactggtgcagcctggcggatctctgagactgagc tgtgccgccagcggcttcaccttcagcaactactggatgagctgggtgcgccaggcccctggca aaggactggaatgggtgtccggcatcaacccaggcggcacctctacctactacgccgacagcgt gaagggccggttcaccatcagccgggacaacgccaagaacaccctgtacctgcagatgaacagc ctgaagtccgaggacaccgccgtgtactactgcgccaagcacctgggcaactggggcgagtaca attactggggccagggcacacaagtgaccgtgtccagtagatctagcaccaagggccccaagct ggaagagggcgagttcagcgaggcccaattgcagagcgccctgacccagcctccaagcgtgtca ggctctcctggcaagaccgtgaccatcagctgtgctggcaccggcggagatgtgggctacagaa acagcgtgtcctggtatcagcagctgcccggcatggcccccaaactgctgatctacgacgtgga caagcgggcctctggcatcaccgacagattcagcggcagcaagagcggcgataccgccagcctg acaatcagcggagtgcagagcgaggacgaggccgactactactgtgccagccagagaagcggaa tcgccgccgtgtttggcggaggcacacacctgacagtgctgggctaa SEQ ID NO: 166: Protein construct expressed from SEQ ID NO: 155
MNFGFSLIFL VLVLKGVQCE VKLVPRQLDY KDDDDKEFQV QLQQSGAELV KPGSSVKISC

KASGYTFTSY DMHWIKQQPG KGLEWIGWIY PGNGNTKYNQ KFNGKATLTA DISSSTAYMQ

LSSLTSEDSA VYFCAKWGYN NFDYWGQGVM VTVSSRSSSA STKGPSVFPL APSSKSTSGG

TAALGCLVKD YFPEPVTVSW NSGALTSGVH TFPAVLQSSG LYSLSSVVTV PSSSLGTQTY

ICNVNHKPSN TKVDKKVEPK SCDKTHTCPP CPAPELLGGP SVFLFPPKPK DTLMISRTPE

VTCVVVDVSH EDPEVKFNWY VDGVEVHNAK TKPREEQYAS TYRVVSVLTV LHQDWLNGKE

YKCKVSNKAL PAPIEKTISK AKGQPREPQV YTLPPSRDEL TKNQVSLTCL VKGFYPSDIA

VEWESNGQPE NNYKTTPPVL DSDGSFFLYS KLTVDKSRWQ QGNVFSCSVM HEALHNHYTQ

KSLSLSPGKL EEVQLVESGG GLVQPGGSLR LSCAASGFTF SNYWMSWVRQ APGKGLEWVS

GINPGGTSTY YADSVKGRFT ISRDNAKNTL YLQMNSLKSE DTAVYYCAKH LGNWGEYNYW

GQGTQVTVSS RSSTKGPKLE EGEFSEAQLQ SALTQPPSVS GSPGKTVTIS CAGTGGDVGY

RNSVSWYQQL PGMAPKLLIY DVDKRASGIT DRFSGSKSGD TASLTISGVQ SEDEADYYCA

SQRSGIAAVF GGGTHLTVLG *

SEQ ID NO: 156: anti-muCD27-VL
atgaacttcggcttcagcctgatcttcctggtgctggtgctgaagggcgtgcagtgcgaagtga agctggtgccccggcaattggactacaaggacgacgacgacaaagaattggacatccagatgac -continued

```
acagagccctgccagcctgtctgcctctctgggagagacagtgtccatcgattgtctggccagc

gagggcatcagcaacgacctggcttggtatcagcagaagtccggcaagagccctcagctgctga

tcaacagcgccagcagactggaagatggcgtgcccagcagattttctggctctggcagcggcac

ccggtacagcctgaagatttctggcatgcagcccgaggacgaggccgaatacttctgcctgcaa

agctacagaagcccctggacctttggcggaggcacaaagctggaactgaagggatccgaaatca

agcgtacggtggccgctcccagcgtgttcatcttcccacctagcgacgagcagctgaagtccgg

cacagcctctgtcgtgtgcctgctgaacaacttctacccccgcgaggccaaggtgcagtggaag

gtggacaatgccctgcagagcggcaacagccaggaaagcgtgaccgagcaggacagcaaggact

ccacctacagcctgagcagcaccctgaccctgagcaaggccgactacgagaagcacaaggtgta

cgcctgcgaagtgacccaccagggcctgtctagccccgtgaccaagagcttcaaccggggcgag

tgctaa

SEQ ID NO: 167: Protein construct expressed from SEQ ID NO: 156
MNFGFSLIFL VLVLKGVQCE VKLVPRQLDY KDDDDKELDI QMTQSPASLS ASLGETVSID

CLASEGISND LAWYQQKSGK SPQLLINSAS RLEDGVPSRF SGSGSGTRYS LKISGMQPED

EAEYFCLQSY RSPWTFGGGT KLELKGSEIK RTVAAPSVFI FPPSDEQLKS GTASVVCLLN

NFYPREAKVQ WKVDNALQSG NSQESVTEQD SKDSTYSLSS TLTLSKADYE KHKVYACEVT

HQGLSSPVTK SFNRGEC*
```

The present invention is further illustrated by the following non-limiting examples.

EXAMPLES

Figure 2:
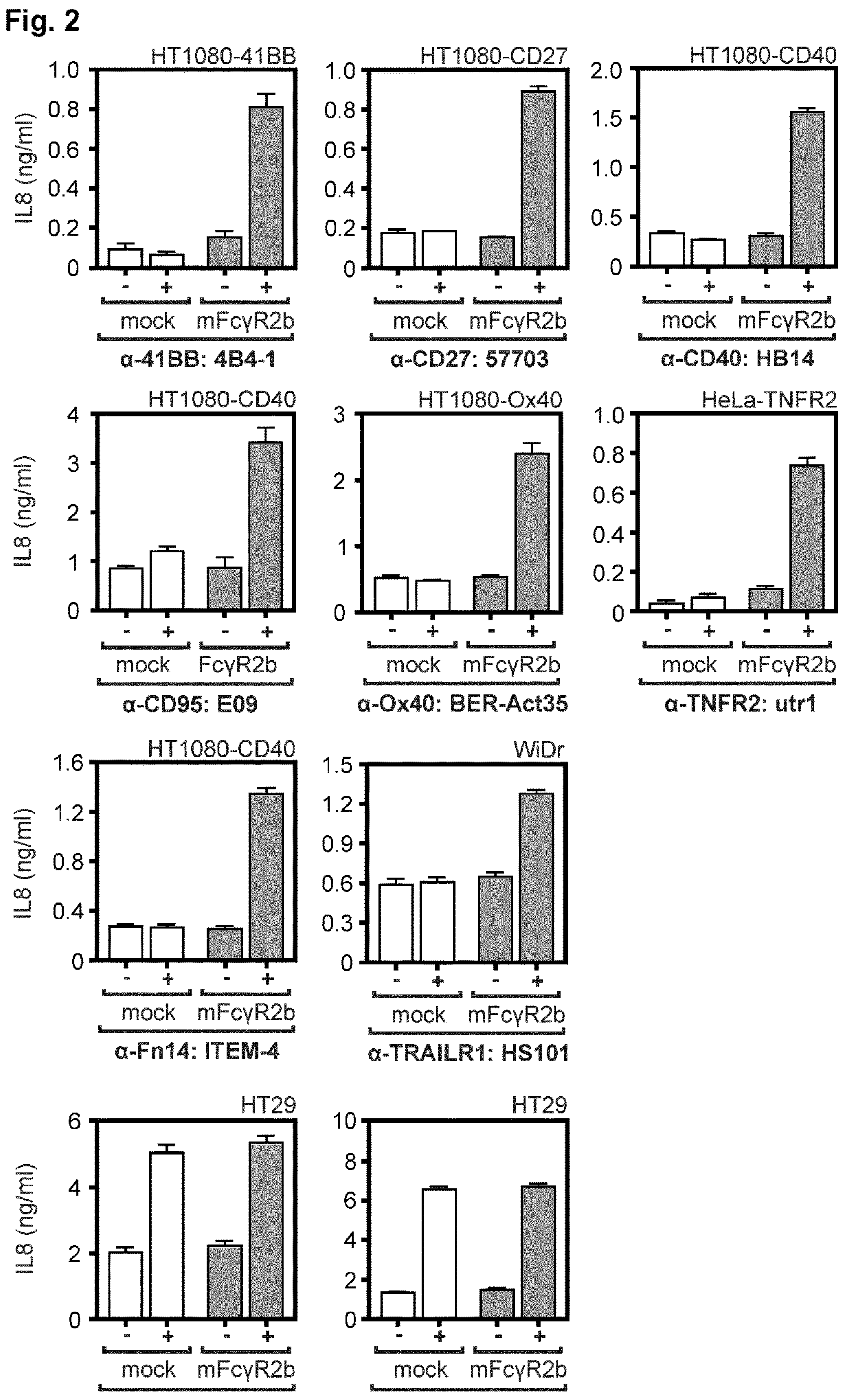
FIG. 2: FcγR-dependent stimulation of TNFRSF receptors by receptor-specific IgGs. Hek293 cells transfected either with an expression plasmid of murine FcγR2B or with an empty vector were co-cultured with cells of the indicated cell line in which the stimulation of the indicated TNFRSF receptors results in the production of IL8. After incubation with the various TNFRSF receptor-specific IgGs (clone name indicated) over night, the production of IL8 was captured using ELISA. Please note, TNFR1 and LTβR are examples of TNFRSF members already strongly activated by soluble ligand trimers and which can also be robustly activated by receptor-specific antibodies in the absence of FcγR expressing cells. The other TNFRSF receptors shown bind soluble TNF ligands without or only limited activation and become not or only inefficiently activated by antibodies in the absence of FcγR-binding. However, these anti-TNFRSF receptors become strongly activated upon FcγR-binding of the antibodies.

Example 1: A TNFR2-Binding Fusion Protein of the Anti-CD40 IgG1 G28.5 Exhibits an Increased CD40-Stimulating Activity after TNFR2 Binding During the analysis of a fusion protein (anti-CD40 (G28.5)-HC:scTNF80) of the IgG1 antibody G28.5, which recognizes the TNFRSF receptor CD40, with a single chain domain comprising three copies of a TNFR2-specific mutant of murine TNF connected by short peptide linkers (scTNF80 (mu) domain), wherein said copies intramolecularly form a trimeric ligand domain, the inventors made the following surprising observation:

If CD40-expressing cells or cell co-cultures, which do not exhibit FcγR or TNFR2 expression, are stimulated with anti-CD40(G28.5)-HC:scTNF80, this results in both cases in no or only in a very poor CD40 activation, which is, for instance, reflected by the production of IL8. By contrast, in the presence of FcγR-expressing cells, the molecules activate CD40 very well, as expected (see the above explanations). It now turned out that anti-CD40(G28.5)-HC: scTNF80 can—unlike the parental G28.5 antibody—also act in a strongly CD40-activating manner in the absence of FcγRs, if TNFR2 is expressed (FIG. 6). Evidently, the scTNF80 domain-mediated binding of anti-CD40(G28.5)-HC:scTNF80 to cell-bound TNFR2 is equally capable of generating an agonistic antibody effect as the Fc domain-mediated binding of G28.5 to FcγR-expressing cells (FIG. 2). This indicates that the mere antigen binding domain-independent binding of an anti-TNFRSF receptor antibody or antibody fusion protein to a cell is sufficient to confer a high agonistic activity to the antibody and the antibody fusion protein, respectively.

Example 2: Fusion Proteins of Antibodies Against the TNFRSF Receptors CD40, CD95 and TNFR2 and which were Fused with Protein Domains which Mediate the Binding to Cell-Bound Molecules, Act as Strong Agonists in an FcγR-Independent Manner In accordance with the idea that the mere antigen binding domain-independent binding of an anti-TNFRSF receptor antibody or antibody fusion protein to a cell is sufficient to confer a high agonistic activity to the antibody and the antibody fusion protein, respectively, the inventors were also able to demonstrate that also other antibody fusion proteins, which an antibody domain recognizing the TNFRSF receptors CD40, CD95 and TNFR2 which were fused with protein domains which mediate the binding to cell-bound molecules, act as strong agonists in an FcγR-independent manner. For details of these examples please see FIGS. 4, 5, 8 and 9 including figure legends.

Example 3: Fusion Proteins of Antibodies Against the TNFRSF Receptors CD40, CD95 and TNFR2 with Cell Surface Antigen-Targeting scFv Domains Act as Strong Agonists in an FcγR-Independent Manner Additionally, the inventors investigated fusion proteins of antibodies against the TNFRSF receptors CD40, CD95 and TNFR2 with cell surface antigen-targeting scFv domains targeting CD20 (FIGS. 10, 11 and 12), and CD19 (FIGS. 7 and 12), respectively. It was found that these fusion proteins act as strong agonists in an FcγR-independent manner. For details of these examples please see the cited figures and their figure legends.

Example 4: Fusion Proteins of Antibodies Against the TNFRSF Receptors CD40 and CD95 with scBaff Act as Strong Agonists in an FcγR-Independent Manner Additionally, the inventors investigated fusion proteins of antibodies, or fragments of antibodies, against the TNFRSF receptors CD40 (FIGS. 13, 14 and 15) and CD95 (FIGS. 16, 17 and 18) with scBaff. It was found that these fusion proteins act as strong agonists for CD40 and CD95 in an FcγR-independent manner provided that the fusion proteins have the possibility to bind to cell surface expressed receptors recognized by the scBaff domain of the fusion proteins. Details of these examples are given in the above-mentioned figures and their figure legends.

Example 5: scFv Fusion Proteins of Antibodies Against the TNFRSF Receptors CD40, CD95, TNFR2 and 4-1BB Act as Strong Agonists in an FcγR-Independent, scFv-Dependent, Manner Furthermore, the inventors investigated scFv fusion proteins of antibodies against the TNFRSF receptors TNFR2 (FIGS. 19 and 20), CD40 (FIGS. 21 and 22), CD95 (FIGS. 21 and 22) and 4-1BB (FIGS. 21 and 22). The scFv fragments used were scFv:CD20 (FIGS. 19, 21 and 22), scFv:CD70(2H5) (FIG. 20) and scFv:CD70(1F6) (FIG. 20). It was found that these fusion proteins act as strong agonists for the TNFRSF receptor recognized by the antibody part (TNFR2, CD40, CD95, 4-1BB) in an FcγR-independent manner provided the fusion proteins have the possibility to bind via their scFv domain to the cell surface antigen (CD20, CD70) recognized by the scFv domain. Details of these examples are given in the above-mentioned figures and their figure legends.

Example 6: A scFv Fusion Protein of the TNFRSF Receptor TRAILR2 (DR5) Acts as Strong Agonists in an FcγR-Independent, scFv-Dependent, Manner Furthermore, the inventors investigated a scFv fusion protein of an antibody (Conatumumab) against the TNFRSF receptors TRAILR2, also designated as DR5 (FIG. 23). The scFv fragment used was scFv:CD70. It was found that this fusion protein acts as a strong agonist for the TNFRSF receptor recognized by the antibody part (TRAILR2) in an FcγR-independent manner provided the fusion protein has the possibility to bind via their scFv domain to the cell surface antigen CD70 recognized by the scFv domain.

Example 7: Fusion Proteins of Antibodies Against the Antigen Presenting Cell-Stimulating TNFRSF Receptor CD40 or the T Cell-Stimulating TNFRSF Receptor 4-1BB Harboring as a Anchoring Domain a scFv Derived of the Checkpoint Inhibitor Avelumab which Blocks PD-1L PD-1 Interaction Act as Strong Agonists in an FcγR-Independent, scFv:PD-1L. Dependent Manner The inventors also investigated fusion proteins of antibodies, or fragments of antibodies, against the TNFRSF receptors CD40 (FIG. 24) and 4-1BB (FIG. 25) with scFv:PD-1L, a scFv derived of the checkpoint inhibitor Avelumab, an antibody blocking PD-1L binding to PD-1. It was found that these fusion proteins act as strong agonists for CD40 and 4-1BB in an FcγR-independent manner provided that the fusion proteins have the possibility to bind to cell surface expressed PD-1L recognized by the scFv:PD-1L domain of the fusion proteins. These fusion proteins are therefore examples for bifunctional antibodies which combine immune checkpoint blockade with checkpoint blockade-dependent restricted activation of immune stimulatory TNFRSF receptors. Details of these examples are given in the above-mentioned figures and their figure legends.

Example 8: scFv Specific for the TNFRSF Receptors Fn14 and 4-1BB Act as Strong Agonists in an FcγR-Independent Manner when Fused to a Complete Antibody which Anchors to a Cell Surface Antigen Additionally, the inventors investigated fusion proteins of scFvs, against the TNFRSF receptors 4-1BB (FIG. 26) and Fn14 (FIG. 27) with antibodies recognizing PD-1L. or murine CD27, It was found that these fusion proteins act as strong agonists for 4-1BB and Fn14 in an FcγR-independent manner provided that the antibody parts of fusion proteins have the possibility to bind to their cell surface expressed antigens PD-1L and murine CD27. These examples demonstrate that complete antibodies can be used as anchoring domains to enable anti-TNFRSF receptor antibody fragments (here scFvs) to act as agonists with anchoring dependent activity. Details of these examples are given in the above-mentioned figures and their figure legends.

CONCLUSIONS FROM THE EXAMPLES

The domain used for the FcγR- and antigen binding domain-independent cell interaction, which is hereinafter also referred to as immobilization domain, and which is fused to the antibody, is not particularly limited. Hence, the inventors were able to produce TRAAFFIAAs which utilize IL2 ligands or scTNFSF ligands for cell binding but also such TRAAFFIAAs, wherein a heterologous scFv antibody fragment was used for this purpose. In order to gain the agonistic activity, it also appears sufficient that the antigen-binding domains bind to a cell in an FcγR- and antigen-independent manner. For example, a $Fab_2$ fragment of the CD95-specific antibody E09 (FIG. 11), which had been genetically engineered by fusion with a CD20-specific scFv, showed a strongly increased TNFRSF receptor-stimulating activity depending on CD20.

From the work of the present inventors, is immediately evident that using an appropriately selected immobilization domain, which is used in a TRAAFFIAA, a local agonistic effect can be attained in vivo that is restricted to a target structure. It can thereby become possible to avoid systemic side effects that could be limiting to the therapy. TRAAFFIAAs therefore do not only advantageously stimulate TNFRSF receptors with antibodies in an FcγR-independent manner, but they also open up new fields of application, including clinical applications.

INDUSTRIAL APPLICABILITY

The antibody fusion proteins and the compositions related thereto according to the present invention may be industrially manufactured and sold as commercial products, e.g. as pharmaceutical drugs. Accordingly, the present invention is industrially applicable.

REFERENCES

Altschul et al. (1990) "Basic local alignment search tool," Journal of Molecular Biology 215. p. 403-410. Altschul et al.: (1997) Gapped BLAST and PSI-BLAST: a new generation of protein database search programs. Nucleic Acids Res. 25:3389-3402.

Arbabi Ghahroudi M et al.: "Selection and identification of single domain antibody fragments from camel heavy-chain antibodies," FEBS Lett. 1997 Sep. 15; 414(3):521-6.

Ausubel et al.: "Current Protocols in Molecular Biology." Greene Publishing Associates and Wiley Interscience; New York 1992.

Berg D, Lehne M, Müller N, Siegmund D, Münkel S, Sebald W, Pfizenmaier K, Wajant H. Enforced covalent trimerization increases the activity of the TNF ligand family members TRAIL and CD95L. Cell Death Differ. 2007 December; 14(12):2021-34. Epub 2007 Aug. 17

Chothia C et al.: Conformations of immunoglobulin hypervariable regions. Nature. 1989 Dec. 21-28; 342 (6252):877-83.

Clackson T et al.: "Making antibody fragments using phage display libraries," Nature. 1991 Aug. 15; 352 (6336):624-8.

Arbabi Ghahroudi M et al. "Selection and identification of single domain antibody fragments from camel heavy-chain antibodies." FEBS Lett. 1997 Sep. 15; 414(3): 521-6.

Giudicelli V et al.: IMGT/V-QUEST, an integrated software program for immunoglobulin and T cell receptor V-J and V-D-J rearrangement analysis. Nucleic Acids Res. 2004 Jul. 1; 32(Web Server issue):W435-40. Harlow and Lane: "Antibodies: A Laboratory Manual" Cold Spring Harbor Laboratory Press, Cold Spring Harbor, New York 1988.

Holliger P et al.: ""Diabodies": small bivalent and bispecific antibody fragments." Proc Natl Acad Sci USA. 1993 Jul. 15; 90(14):6444-8.

Holt L. J et al.: "Domain antibodies: proteins for therapy." Trends Biotechnol. 2003 November; 21(11):484-90.

Jones P T et al.: "Replacing the complementarity-determining regions in a human antibody with those from a mouse." Nature, 1986 May 29-June 4; 321(6069):522-5.

Kabat et al.: Sequences of proteins of immunological interest, U.S. Dept. of Health and Human Services, Public Health Service, National Institutes of Health, Bethesda, Md. 1983.

Köhler G and Milstein C: "Continuous cultures of fused cells secreting antibody of predefined specificity." Nature. 1975 Aug. 7; 256(5517):495-7.

Kums J, Nelke J, Ruth B, Schafer V, Siegmund D, Wajant H. Quantitative analysis of cell surface antigen-antibody interaction using *Gaussia princeps* luciferase antibody fusion proteins. MAbs. 2017 April; 9(3):506-520.

Marks J D et al.: "By-passing immunization. Human antibodies from V-gene libraries displayed on phage." J Mol Biol, 1991 Dec. 5; 222(3):581-97.

Paul, W. E. (Ed.).: "Fundamental Immunology" 2nd Ed. Raven Press, Ltd., New York 1989.

Remington's Pharmaceutical Sciences, Ed. A R Gennaro, 20th edition, 2000, Williams & Wilkins, PA, USA.

Riechmann L et al.: "Reshaping human antibodies for therapy." Nature. 1988 Mar. 24; 332(6162):323-7.

Saerens D et al.: "Single-domain antibodies as building blocks for novel therapeutics." Curr Opin Pharmacol. 2008 October; 8(5):600-8. Epub 2008 Aug. 22.

Sambrook et al.: "Molecular Cloning: A Laboratory Manual.", 2nd Ed., Cold Spring Harbor Laboratory Press, Cold Spring Harbor, New York 1989.

Siegel D L: "Recombinant monoclonal antibody technology." Transfus Clin Biol. 2002 January; 9(1):15-22.

Trebing J, Lang I, Chopra M, Salzmann S, Moshir M, Silence K, Riedel S S, Siegmund D, Beilhack A, Otto C, Wajant H. A novel llama antibody targeting Fn14 exhibits anti-metastatic activity in vivo. MAbs. 2014 January-February; 6(1):297-308.

Wajant et al., Cancer Left. 2013 May 28; 332(2):163-74.

Wajant 2015, Cell Death Differ. 2015 November; 22(11): 1727-41

Weiss T, Grell M, Hessabi B, Bourteele S, Müller G, Scheurich P, Wajant H. vEnhancement of TNF receptor p60-mediated cytotoxicity by TNF receptor p80: requirement of the TNF receptor-associated factor-2 binding site. J Immunol. 1997 Mar. 1; 158(5):2398-404.

Wyzgol A, Müller N, Fick A, Munkel 5, Grigoleit G U, Pfizenmaier K, Wajant H. Trimer stabilization, oligomerization, and antibody-mediated cell surface immobilization improve the activity of soluble trimers of CD27L, CD40L, 41BBL, and glucocorticoid-induced TNF receptor ligand. J Immunol. 2009 Aug. 1; 183(3):1851-61.

The invention claimed is:

1. A fusion protein, comprising, in an N- to C-terminal order:

(i) an anti-TNFRSF receptor antibody or an antigen-binding portion thereof selected from the group consisting of an anti-TNFR2 antibody or antigen-binding portion thereof, an anti-CD40 antibody or antigen-binding portion thereof, and an anti-Fn14 antibody or antigen-binding portion thereof, and (ii) a domain which is capable of binding to a structure of the cell surface in an FcγR-independent manner;

wherein the fusion protein is capable of an increased stimulation of the TNFRSF receptor as compared to a protein comprising the anti-TNFRSF receptor antibody or the antigen-binding portion thereof according to (i) but lacking the domain according to (ii);

wherein (i) comprises:

(a) an anti-TNFR2 antibody or an antigen-binding portion thereof comprising a heavy chain comprising a CDR1 amino acid sequence according to SEQ ID NO: 60, a CDR2 amino acid sequence according to SEQ ID NO: 61, and a CDR3 amino acid sequence according to SEQ ID NO: 62, and comprising a light chain comprising a CDR1 amino acid sequence according to SEQ ID NO: 63, a CDR2 amino acid sequence according to SEQ ID NO: 64, and a CDR3 amino acid sequence according to SEQ ID NO: 65;

(b) an anti-CD40 antibody or an antigen-binding portion thereof comprising a heavy chain comprising a CDR1 amino acid sequence according to SEQ ID NO: 37, a CDR2 amino acid sequence according to SEQ ID NO: 38, and the CDR3 amino acid sequence LDY, and comprising a light chain comprising a CDR1 amino acid sequence according to SEQ ID NO: 39, a CDR2 amino acid sequence according to SEQ ID NO: 40, and a CDR3 amino acid sequence according to SEQ ID NO: 41;

(c) an anti-Fn14 antibody or an antigen-binding portion thereof comprising a heavy chain comprising a CDR1 amino acid sequence according to SEQ ID NO: 54, a CDR2 amino acid sequence according to SEQ ID NO: 55, and a CDR3 amino acid sequence according to SEQ ID NO: 56, and comprising a light chain comprising a CDR1 amino acid sequence according to SEQ ID NO: 57, a CDR2 amino acid sequence according to SEQ ID NO: 58, and a CDR3 amino acid sequence according to SEQ ID NO: 59; or (d) an anti-Fn14 antibody or an antigen-binding portion thereof comprising a heavy chain comprising a CDR1 amino acid sequence according to SEQ ID NO: 84, a CDR2 amino acid sequence according to SEQ ID NO: 85, and a CDR3 amino acid sequence according to SEQ ID NO: 86, and comprising a light chain comprising a CDR1 amino acid sequence according to SEQ ID NO: 87, a CDR2 amino acid sequence according to SEQ ID NO: 88, and a CDR3 amino acid sequence according to SEQ ID NO: 89; and wherein the domain of (ii) is an Avelumab scFv.

2. The fusion protein according to claim 1, wherein the domain of (ii) binds to a structure of the cell surface of a TNFRSF receptor-expressing cell or a structure of the cell surface of a cell adjacent to a TNFRSF receptor-expressing cell.

3. The fusion protein according to claim 1, wherein the antibody or the antigen-binding portion thereof according to (i) is (A) monoclonal;

(B) a full-length antibody, an F(ab')2 fragment, an Fab fragment, or scFv fragments; and/or (C) does not comprise an Fc domain.

4. The fusion protein according to claim 1, wherein the antibody or the antigen-binding portion thereof according to (i) is an antibody variant with reduced ability to bind to one or more FcγR types compared to the antibody of which the antibody variant is a variant.

5. The fusion protein according to claim 1, wherein the antibody or the antigen-binding portion thereof according to (i) is an IgG1 antibody, an IgG2 antibody, or an IgG4 antibody, or antigen-binding portion of any of the foregoing; and/or the antibody or antigen-binding portion thereof according to (i) is a bivalent antibody or antigen-binding portion thereof.

6. The fusion protein according to claim 1, wherein said structure of the cell surface is a structure of the cell surface of an immune cell, a fibroblast, and/or a tumor cell.

7. A method of treating a subject in need thereof, the method comprising administering to the subject a composition comprising the fusion protein according to claim 1.

8. A nucleic acid, or a set of nucleic acids, encoding the fusion protein according to claim 1.

9. A method for producing a fusion protein, the method comprising expressing the nucleic acid or the set of nucleic acids according to claim 8 in at least one type of host cells, and harvesting the fusion protein.

* * * * *

SEQUENCE LISTING

```
<160> NUMBER OF SEQ ID NOS: 167

<210> SEQ ID NO 1
<211> LENGTH: 2892
<212> TYPE: DNA
<213> ORGANISM: Artificial Sequence
<220> FEATURE:
<223> OTHER INFORMATION: anti-CD40-Flag-VH-heavy-full-scTNF80(mu)-pCR3
      (N297A)

<400> SEQUENCE: 1

atgaacttcg gcttcagcct gatcttcctg gtgctggtgc tgaagggcgt gcagtgcgaa      60

gtgaagctgg tgccccggca attggactac aaggacgacg acgacaaaga attggatatc     120

cagctccagc agtctggccc tggactcgtc aaaccatctc agagcctgtc tctcacctgt     180

tctgtcaccg gatactccat caccaccaac tacaactgga attggattcg gcagtttcct     240

gggaacaaac tcgaatggat gggatacatc cgatacgacg gcactagtga atacacccca     300
```

```
tctctcaaaa atcgggtgtc cattacccgg gacacttcta tgaaccagtt ctttctccga    360
ctcacctctg tgacacctga ggataccgcc acatactact gtgctagact ggactactgg    420
gggcagggaa cactggtgac cgtgtcatct ggatccagca gcgcctctac aaagggcccc    480
agcgtgttcc ctctggcccc tagcagcaag agcacatctg gcggaacagc cgccctgggc    540
tgcctcgtga aggactactt tcccgagccc gtgaccgtgt cctggaactc tggcgctctg    600
acaagcggcg tgcacacctt tccagccgtg ctgcagagca gcggcctgta ctctctgagc    660
agcgtcgtga cagtgcccag cagctctctg ggcacccaga cctacatctg caacgtgaac    720
cacaagccca gcaacaccaa ggtggacaag aaggtggaac ccaagagctg cgacaagacc    780
cacacctgtc ccccttgtcc tgcccccgaa ctgctgggag gcccttccgt gttcctgttc    840
cccccaaagc ccaaggacac cctgatgatc agccggaccc ccgaagtgac ctgcgtggtg    900
gtggatgtgt cccacgagga ccctgaagtg aagtttaatt ggtacgtgga cggcgtggaa    960
gtgcacaacg ccaagaccaa gcctagagag gaacagtacg ccagcaccta ccgggtggtg   1020
tccgtgctga cagtgctgca ccaggactgg ctgaacggca aagagtacaa gtgcaaggtg   1080
tccaacaagg ccctgcctgc ccccatcgag aaaaccatca gcaaggccaa gggccagccc   1140
cgcgaacccc aggtgtacac actgcccccca agcagggacg agctgaccaa gaaccaggtg   1200
tccctgacct gtctcgtgaa aggcttctac cccagcgata tcgccgtgga atgggagagc   1260
aacggccagc ccgagaacaa ctacaagacc accccccctg tgctggacag cgacggctca   1320
ttcttcctgt acagcaagct gaccgtggac aagtcccggt ggcagcaggg caacgtgttc   1380
agctgcagcg tgatgcacga ggccctgcac aaccactaca cccagaagtc cctgagcctg   1440
agccccggca aggaattcga gttcacacgg gacaaacctg tggctcatgt ggtggccaat   1500
catcaggtgg aggaacagct ggaatggctg agtcagagag caaacgccct gctggcaaat   1560
gggatggacc tcaaagacaa tcagctcgtg gtgcctgccg atggactgta cctggtgtac   1620
tctcaggtcc tgtttaaggg acagggatgc cccgattacg tgctgctcac ccacactgtg   1680
tcacgcttcg ccatctcata ccaggagaaa gtcaatctcc tctccgccgt gaaatcacca   1740
tgtcctaagg atactcccga gggagccgaa ctgaaacctt ggtacgaacc catctacctg   1800
ggcggcgtgt ttcagctgga gaaaggcgat cagctctccg ccgaagtgaa tctgcccaaa   1860
tacctcaact ttagggaatc cggacaggtc tactttggcg tgattgccct gggaggcgga   1920
tctggaggag gctctggcgg gggatctggg ggcggatccg acaaacctgt ggcacacgtc   1980
gtggcaaacc atcaggtcga ggaacagctc gagtggctgt cacagagggc caatgccctg   2040
ctggcaaatg gaatggatct gaaggataat cagctcgtcg tgcctgccga cggcctctac   2100
ctcgtctact ctcaggtcct ctttaaggga cagggctgcc ccgactacgt cctgctcact   2160
cataccgtga gtcgcttcgc tatttcatac caggaaaaag tcaacctgct gagtgctgtg   2220
aaatctcctt gccctaagga taccccctgag ggagccgaac tcaaaccatg gtacgagcca   2280
atctacctcg gaggagtgtt tcagctggaa aaaggggatc agctctccgc cgaagtcaac   2340
ctccccaaat acctcaattt ccgggaatcc ggacaggtgt actttggagt cattgccctg   2400
ggaggcggct ctggcggggg atctggagga ggctccggag gaggcagtga caaacccgtc   2460
gctcacgtgg tggcaaatca tcaggtcgag gaacagctgg aatggctgtc tcagagagca   2520
aacgctctcc tcgccaatgg aatggatctc aaggacaacc agctcgtcgt ccctgccgat   2580
ggactctacc tggtctactc tcaggtgctc tttaagggac agggatgccc cgattacgtc   2640
```

```
ctgctcacac acaccgtgtc tcgctttgct atttcatacc aggagaaagt caatctgctg   2700

tctgccgtca aatctccttg tccaaaagac acacccgagg gagccgaact caaaccttgg   2760

tacgagccaa tctacctggg ggagtgtttt cagctggaga agggggatca gctctccgcc   2820

gaagtgaatc tcccaaaata cctcaatttt cgggaatccg gacaggtcta ctttggagtg   2880

attgccctgt ag                                                        2892
```

<210> SEQ ID NO 2
<211> LENGTH: 1455
<212> TYPE: DNA
<213> ORGANISM: Artificial Sequence
<220> FEATURE:
<223> OTHER INFORMATION: anti-CD40-Flag-VH-heavy-full-pCR3 (hIgG1)

<400> SEQUENCE: 2

```
atgaacttcg gcttcagcct gatcttcctg gtgctggtgc tgaagggcgt gcagtgcgaa     60

gtgaagctgg tgccccggca attggactac aaggacgacg acgacaaaga attggatatc    120

cagctccagc agtctggccc tggactcgtc aaaccatctc agagcctgtc tctcacctgt    180

tctgtcaccg gatactccat caccaccaac tacaactgga attggattcg gcagtttcct    240

gggaacaaac tcgaatggat gggatacatc cgatacgacg gcactagtga atacacccca    300

tctctcaaaa atcgggtgtc cattacccgg gacacttcta tgaaccagtt ctttctccga    360

ctcacctctg tgacacctga ggataccgcc acatactact gtgctagact ggactactgg    420

gggcagggaa cactggtgac cgtgtcatct ggatcctcta gcgccagcac aaagggcccc    480

agcgtgttcc ctctggcccc tagcagcaag agcacatctg gcggaacagc cgccctgggc    540

tgcctcgtga aggactactt tcccgagccc gtgacagtgt cctggaactc tggcgccctg    600

acaagcggcg tgcacacctt tccagccgtg ctgcagagca gcggcctgta ctctctgagc    660

agcgtcgtga ctgtgcccag cagcagcctg ggcacccaga cctacatctg caacgtgaac    720

cacaagccca gcaacaccaa ggtggacaag aaggtggaac ccaagagctg cgacaagacc    780

cacacctgtc cccctgtcc tgcccctgaa ctgctgggcg gaccttccgt gttcctgttc    840

cccccaaagc ccaaggacac cctgatgatc agccggaccc ccgaagtgac ctgcgtggtg    900

gtggatgtgt cccacgagga ccctgaagtg aagtttaatt ggtacgtgga cggcgtggaa    960

gtgcacaacg ccaagaccaa gcccagagag gaacagtaca acagcaccta ccgggtggtg   1020

tccgtgctga cagtgctgca ccaggactgg ctgaacggca aagagtacaa gtgcaaggtg   1080

tccaacaagg ccctgcctgc ccccatcgag aaaaccatca gcaaggccaa gggccagccc   1140

cgcgaacccc aggtgtacac actgcctccc agcagggacg agctgaccaa gaaccaggtg   1200

tccctgacct gtctcgtgaa aggcttctac cctccgata tcgccgtgga atgggagagc   1260

aacggccagc ccgagaacaa ctacaagacc acccccctg tgctggacag cgacggctca   1320

ttcttcctgt acagcaagct gaccgtggac aagtcccggt ggcagcaggg caacgtgttc   1380

agctgcagcg tgatgcacga ggccctgcac aaccactaca cccagaagtc cctgagcctg   1440

agccccggca agtaa                                                     1455
```

<210> SEQ ID NO 3
<211> LENGTH: 2189
<212> TYPE: DNA
<213> ORGANISM: Artificial Sequence
<220> FEATURE:
<223> OTHER INFORMATION: anti-CD40-Flag-VH-heavy-full-scFv-anti-CD20-
pCR3 (N297A)

<400> SEQUENCE: 3

```
atgaacttcg gcttcagcct gatcttcctg gtgctggtgc tgaagggcgt gcagtgcgaa      60
gtgaagctgg tgccccggca attggactac aaggacgacg acgacaaaga attggatatc     120
cagctccagc agtctggccc tggactcgtc aaaccatctc agagcctgtc tctcacctgt     180
tctgtcaccg gatactccat caccaccaac tacaactgga attggattcg gcagtttcct     240
gggaacaaac tcgaatggat gggatacatc cgatacgacg gcactagtga atacacccca     300
tctctcaaaa atcgggtgtc cattacccgg gacacttcta tgaaccagtt ctttctccga     360
ctcacctctg tgacacctga ggataccgcc acatactact gtgctagact ggactactgg     420
gggcagggaa cactggtgac cgtgtcatct ggatccagca gcgcctctac aaagggcccc     480
agcgtgttcc ctctggcccc tagcagcaag agcacatctg gcggaacagc cgccctgggc     540
tgcctcgtga aggactactt tcccgagccc gtgaccgtgt cctggaactc tggcgctctg     600
acaagcggcg tgcacacctt tccagccgtg ctgcagagca gcggcctgta ctctctgagc     660
agcgtcgtga cagtgcccag cagctctctg ggcacccaga cctacatctg caacgtgaac     720
cacaagccca gcaacaccaa ggtggacaag aaggtggaac ccaagagctg cgacaagacc     780
cacacctgtc cccccttgtcc tgcccccgaa ctgctgggag gcccttccgt gttcctgttc     840
cccccaaagc ccaaggacac cctgatgatc agccggaccc ccgaagtgac ctgcgtggtg     900
gtggatgtgt cccacgagga ccctgaagtg aagtttaatt ggtacgtgga cggcgtggaa     960
gtgcacaacg ccaagaccaa gcctagagag gaacagtacg ccagcaccta ccgggtggtg    1020
tccgtgctga cagtgctgca ccaggactgg ctgaacggca aagagtacaa gtgcaaggtg    1080
tccaacaagg ccctgcctgc ccccatcgag aaaaccatca gcaaggccaa gggccagccc    1140
cgcgaacccc aggtgtacac actgccccca agcagggacg agctgaccaa gaaccaggtg    1200
tccctgacct gtctcgtgaa aggcttctac cccagcgata tcgccgtgga atgggagagc    1260
aacggccagc ccgagaacaa ctacaagacc acccccccctg tgctggacag cgacggctca    1320
ttcttcctgt acagcaagct gaccgtggac aagtcccggt ggcagcaggg caacgtgttc    1380
agctgcagcg tgatgcacga ggccctgcac aaccactaca cccagaagtc cctgagcctg    1440
agccccggca aggaattcca ggtacaactg cagcagcctg gggctgagct ggtgaagcct    1500
ggggcctcag tgaagatgtc ctgcaaggct tctggctaca catttaccag ttacaatatg    1560
cactgggtaa aacagacacc tggtcggggc ctggaatgga ttggagctat ttatcccgga    1620
aatggtgata cttcctacaa tcagaagttc aaaggcaagg ccacattgac tgcagacaaa    1680
tcctccagca cagcctacat gcagctcagc agcctgacat ctgaggactc tgcggtctat    1740
tactgtgcaa gatcgactta ctacggcggt gactggtact tcaatgtctg gggcgcaggg    1800
accacggtca ccgtctcttc aggaggaggc ggatccggcg gaggcggaag cggtggcgga    1860
ggctctcaaa ttgttctctc ccagtctcca gcaatcctgt ctgcatctcc aggggagaag    1920
gtcacaatga cttgcagggc cagctcaagt gtaagttaca tccactggtt ccagcagaag    1980
ccaggatcct cccccaaacc ctggatttat gccacatcca acctggcttc tggagtccct    2040
gttcgcttca gtggcagtgg gtctgggact tcttactctc tcacaatcag cagagtggag    2100
gcgaagatgc tgccacttat tactgccagc agtggactag taacccaccc acgttcggag    2160
gggggaccaa gctggaaatc aaacgttaa                                       2189
```

<210> SEQ ID NO 4
<211> LENGTH: 2874

<212> TYPE: DNA
<213> ORGANISM: Artificial Sequence
<220> FEATURE:
<223> OTHER INFORMATION: anti-CD40-Flag-VH-heavy-full-scBaff-pCR3 (N297A)

<400> SEQUENCE: 4

```
atgaacttcg gcttcagcct gatcttcctg gtgctggtgc tgaagggcgt gcagtgcgaa     60
gtgaagctgg tgccccggca attggactac aaggacgacg acgacaaaga attggatatc    120
cagctccagc agtctggccc tggactcgtc aaaccatctc agagcctgtc tctcacctgt    180
tctgtcaccg gatactccat caccaccaac tacaactgga attggattcg gcagtttcct    240
gggaacaaac tcgaatggat gggatacatc cgatacgacg gcactagtga atacacccca    300
tctctcaaaa atcgggtgtc cattacccgg gacacttcta tgaaccagtt ctttctccga    360
ctcacctctg tgacacctga ggataccgcc acatactact gtgctagact ggactactgg    420
gggcagggaa cactggtgac cgtgtcatct ggatccagca gcgcctctac aaagggcccc    480
agcgtgttcc ctctggcccc tagcagcaag agcacatctg gcggaacagc cgccctgggc    540
tgcctcgtga aggactactt tcccgagccc gtgaccgtgt cctggaactc tggcgctctg    600
acaagcggcg tgcacacctt tccagccgtg ctgcagagca gcggcctgta ctctctgagc    660
agcgtcgtga cagtgcccag cagctctctg ggcacccaga cctacatctg caacgtgaac    720
cacaagccca gcaacaccaa ggtggacaag aaggtggaac ccaagagctg cgacaagacc    780
cacacctgtc ccccttgtcc tgcccccgaa ctgctgggag gcccttccgt gttcctgttc    840
cccccaaagc ccaaggacac cctgatgatc agccggaccc ccgaagtgac ctgcgtggtg    900
gtggatgtgt cccacgagga ccctgaagtg aagtttaatt ggtacgtgga cggcgtggaa    960
gtgcacaacg ccaagaccaa gcctagagag gaacagtacg ccagcaccta ccgggtggtg   1020
tccgtgctga cagtgctgca ccaggactgg ctgaacggca aagagtacaa gtgcaaggtg   1080
tccaacaagg ccctgcctgc ccccatcgag aaaaccatca gcaaggccaa gggccagccc   1140
cgcgaacccc aggtgtacac actgccccca agcagggacg agctgaccaa gaaccaggtg   1200
tccctgacct gtctcgtgaa aggcttctac cccagcgata tcgccgtgga atgggagagc   1260
aacggccagc ccgagaacaa ctacaagacc accccccctg tgctggacag cgacggctca   1320
ttcttcctgt acagcaagct gaccgtggac aagtcccggt ggcagcaggg caacgtgttc   1380
agctgcagcg tgatgcacga ggccctgcac aaccactaca cccagaagtc cctgagcctg   1440
agccccggca agctcgaggg acccgaggaa actgtgactc aggactgtct ccagctcatt   1500
gccgatagtg aaacccctac catccagaaa ggctcttaca ccttcgtgcc atggctgctg   1560
tcattcaaac ggggatctgc tctggaggag aaggaaaaca aaatcctggt caaggaaacc   1620
ggctacttct tcatctacgg ccaggtcctc tacaccgaca aaacatacgc tatggggcat   1680
ctcattcagc ggaaaaaagt ccacgtgttc ggcgacgaac tctctctcgt gacactgttc   1740
cggtgtattc agaacatgcc cgagactctg cccaataata gctgctactc tgctggcatt   1800
gccaaactgg aggagggcga cgaactccag ctggctattc ctagggaaaa tgcccagatt   1860
agcctggacg gggatgtgac attttttggc gccctgaaac tgctgggagg cggagggagt   1920
ggcgggggag gctctggacc tgaggaaact gtgacccagg attgtctcca gctcattgcc   1980
gatagtgaga ctcctaccat tcagaaggga tcttacacct ttgtgccttg gctgctgtct   2040
ttcaaacggg gctctgctct ggaggaaaag gagaacaaaa ttctggtcaa agagactggc   2100
tacttcttca tctacggcca ggtgctgtac accgacaaaa catacgccat gggccatctc   2160
```

```
attcagcgga aaaaagtcca cgtgttcggc gacgaactct ctctcgtgac actgttccgg   2220

tgtatccaga acatgcccga gacactgccc aataatagct gctactctgc cggcattgct   2280

aaactggagg agggggacga actccagctg gctattccta gggaaaatgc ccagatttct   2340

ctcgatgggg atgtgacatt cttcggggcc ctcaaactgc tgggaggcgg cggatctggc   2400

ggaggcggga gtcaattcgc agcaggtcca gaagaaacag tcactcaaga ctgcttgcaa   2460

ctgattgcag acagtgaaac accaactata caaaaaggat cttacacatt tgttccatgg   2520

cttctcagct ttaaaagggg aagtgcccta gaagaaaaag agaataaaat attggtcaaa   2580

gaaactggtt actttttat atatggtcag gttttatata ctgataagac ctacgccatg   2640

ggacatctaa ttcagaggaa gaaggtccat gtctttgggg atgaattgag tctggtgact   2700

ttgtttcgat gtattcaaaa tatgcctgaa acactaccca ataattcctg ctattcagct   2760

ggcattgcaa aactggaaga aggagatgaa ctccaacttg caataccaag agaaaatgca   2820

caaatatcac tggatggaga tgtcacattt tttggtgcat tgaaactgct gtga         2874
```

```
<210> SEQ ID NO 5
<211> LENGTH: 789
<212> TYPE: DNA
<213> ORGANISM: Artificial Sequence
<220> FEATURE:
<223> OTHER INFORMATION: anti-CD40-Flag-VL-light-full-pCR3

<400> SEQUENCE: 5

atgaacttcg gcttcagcct gatcttcctg gtgctggtgc tgaagggcgt gcagtgcgaa     60

gtgaagctgg tgccccggca attggactac aaggacgacg acgacaaaga attggacatc    120

gtgatgactc agaacccact gtctctgcct gtgtctctgg gggatgaggc tagcatttct    180

tgccgctcat ctcagtcact ggagaactcc aatggcaaca ccttcctgaa ttggtttttc    240

cagaaacccg gccagtcacc tcagctgctc atctaccgag tgagcaatcg gtttagcgga    300

gtgcccgatc gattctctgg ctccggatct gggaccgact ttaccctgaa aatctcacga    360

gtggaggccg aggatctggg agtgtacttc tgtctccagg tcacacatgt gccttacaca    420

tttggcggcg gaacaactct cgaaatcaaa ggatccgaaa tcaagcgtac ggtggccgct    480

cccagcgtgt tcatcttccc acctagcgac gagcagctga agtccggcac agcctctgtc    540

gtgtgcctgc tgaacaactt ctacccccgc gaggccaagg tgcagtggaa ggtggacaat    600

gccctgcaga gcggcaacag ccaggaaagc gtgaccgagc aggacagcaa ggactccacc    660

tacagcctga gcagcaccct gaccctgagc aaggccgact acgagaagca caaggtgtac    720

gcctgcgaag tgacccacca gggcctgtct agccccgtga ccaagagctt caaccggggc    780

gagtgctaa                                                            789
```

```
<210> SEQ ID NO 6
<211> LENGTH: 1908
<212> TYPE: DNA
<213> ORGANISM: Artificial Sequence
<220> FEATURE:
<223> OTHER INFORMATION: C4-HC-full-IL2(mu)-pCR3  (hIgG1) ( Flagless)

<400> SEQUENCE: 6

atgaacttcg gcttcagcct gatcttcctg gtgctggtgc tgaagggcgt gcagtgcgaa     60

gtgaagctgg tgccccggca attgcaggtt cagctgctgc agtctggacc tgagctggtg    120

aagcctgggg cttcagtgaa gttgtcctgc aaggcttctg gttatagttt cacaagttac    180
```

```
gatattaact gggtgaagca gaggcctgga cagggacttg agtgggttgg atggatttat    240
cctagagatg gtgatactaa gtacaatgag aaattcaagg gcaaggccat attgactgta    300
gacacatcct ccaacacagc gtacatgaac ctccacagcc tgacatctga ggactctgcg    360
gtctatttct gtgcaagact aactgggccc tactggtact tcgatgtctg gggcacaggg    420
accacggtca ccgtctcctc aggatcctct agcgccagca caaagggccc cagcgtgttc    480
cctctggccc ctagcagcaa gagcacatct ggcggaacag ccgccctggg ctgcctcgtg    540
aaggactact tcccgagcc cgtgacagtg tcctggaact ctggcgccct gacaagcggc    600
gtgcacacct ttccagccgt gctgcagagc agcggcctgt actctctgag cagcgtcgtg    660
actgtgccca gcagcagcct gggcacccag acctacatct gcaacgtgaa ccacaagccc    720
agcaacacca aggtggacaa gaaggtggaa cccaagagct gcgacaagac ccacacctgt    780
ccccccttgtc ctgcccctga actgctgggc ggaccttccg tgttcctgtt cccccaaag    840
cccaaggaca ccctgatgat cagccggacc cccgaagtga cctgcgtggt ggtggatgtg    900
tcccacgagg accctgaagt gaagtttaat tggtacgtgg acggcgtgga agtgcacaac    960
gccaagacca agcccagaga ggaacagtac aacagcacct accgggtggt gtccgtgctg   1020
acagtgctgc accaggactg gctgaacggc aaagagtaca agtgcaaggt gtccaacaag   1080
gccctgcctg cccccatcga gaaaaccatc agcaaggcca agggccagcc ccgcgaaccc   1140
caggtgtaca cactgcctcc cagcagggac gagctgacca agaaccaggt gtccctgacc   1200
tgtctcgtga aaggcttcta cccctccgat atcgccgtgg aatgggagag caacggccag   1260
cccgagaaca actacaagac cacccccccct gtgctggaca gcgacggctc attcttcctg   1320
tacagcaagc tgaccgtgga caagtcccgg tggcagcagg gcaacgtgtt cagctgcagc   1380
gtgatgcacg aggccctgca caaccactac acccagaagt ccctgagcct gagccccggc   1440
aaggaattgc ccggtaccgc ccctaccagc agcagcacct ctagctctac agccgaggct   1500
caacaacaac aacaacagca acagcagcag cagcagcacc tggaacagct gctgatggac   1560
ctgcaggaac tgctgagccg gatggaaaac taccggaacc tgaagctgcc ccggatgctg   1620
accttcaagt tctacctgcc caagcaggcc accgagctga aggatctgca gtgcctggaa   1680
gatgagctgg gcccccctgag acacgtgctg gatctgaccc agagcaagag ctttcagctg   1740
gaagatgccg agaacttcat cagcaacatc agagtgaccg tcgtgaagct gaagggcagc   1800
gacaacacct tcgagtgcca gttcgacgac gagagcgcta ccgtggtgga cttcctgcgg   1860
agatggatcg ccttctgcca gagcatcatc agcaccagcc cccagtaa                1908
```

<210> SEQ ID NO 7
<211> LENGTH: 2199
<212> TYPE: DNA
<213> ORGANISM: Artificial Sequence
<220> FEATURE:
<223> OTHER INFORMATION: C4-HC-heavy-konst-full-scFv-anti-CD19-pCR3 (N297A) (Flagless)

<400> SEQUENCE: 7

```
atgaacttcg gcttcagcct gatcttcctg gtgctggtgc tgaagggcgt gcagtgcgaa     60
gtgaagctgg tgccccggca attgcaggtt cagctgctgc agtctggacc tgagctggtg    120
aagcctgggg cttcagtgaa gttgtcctgc aaggcttctg gttatagttt cacaagttac    180
gatattaact gggtgaagca gaggcctgga cagggacttg agtgggttgg atggatttat    240
cctagagatg gtgatactaa gtacaatgag aaattcaagg gcaaggccat attgactgta    300
```

```
gacacatcct ccaacacagc gtacatgaac ctccacagcc tgacatctga ggactctgcg    360

gtctatttct gtgcaagact aactgggccc tactggtact tcgatgtctg gggcacaggg    420

accacggtca ccgtctcctc aggatccagc agcgcctcta caaagggccc cagcgtgttc    480

cctctggccc ctagcagcaa gagcacatct ggcggaacag ccgccctggg ctgcctcgtg    540

aaggactact ttcccgagcc cgtgaccgtg tcctggaact ctggcgctct gacaagcggc    600

gtgcacacct ttccagccgt gctgcagagc agcggcctgt actctctgag cagcgtcgtg    660

acagtgccca gcagctctct gggcacccag acctacatct gcaacgtgaa ccacaagccc    720

agcaacacca aggtggacaa gaaggtggaa cccaagagct gcgacaagac ccacacctgt    780

ccccttgtc ctgcccccga actgctggga ggcccttccg tgttcctgtt ccccccaaag    840

cccaaggaca ccctgatgat cagccggacc cccgaagtga cctgcgtggt ggtggatgtg    900

tcccacgagg accctgaagt gaagtttaat tggtacgtgg acggcgtgga agtgcacaac    960

gccaagacca agcctagaga ggaacagtac gccagcacct accgggtggt gtccgtgctg   1020

acagtgctgc accaggactg gctgaacggc aaagagtaca agtgcaaggt gtccaacaag   1080

gccctgcctg cccccatcga gaaaaccatc agcaaggcca agggccagcc ccgcgaaccc   1140

caggtgtaca cactgccccc aagcagggac gagctgacca agaaccaggt gtccctgacc   1200

tgtctcgtga aaggcttcta ccccagcgat atcgccgtgg aatgggagag caacggccag   1260

cccgagaaca actacaagac cacccccccct gtgctggaca gcgacggctc attcttcctg   1320

tacagcaagc tgaccgtgga caagtcccgg tggcagcagg gcaacgtgtt cagctgcagc   1380

gtgatgcacg aggccctgca caaccactac acccagaagt ccctgagcct gagccccggc   1440

aaggaattcg acattcagat gacgcagtct ccatcctcca tgtctgtatc tctgggagac   1500

acagtcagca tcacttgcca tgcaagtcag ggcattagca gtaatatagg gtggttgcag   1560

cagaaaccag ggaaatcatt taagggcctg atctatcatg gaaccaactt ggaagatgga   1620

gttccatcaa ggttcagtgg cagtggatct ggagcagatt attctctcac catcagcagc   1680

ctggaatctg aagattttgc agactattac tgtgtacagt atgctcagtt tccgtacacg   1740

ttcggagggg ggaccaagct ggagctgaaa cgtggtggtg gtggttctgg tggtggtggt   1800

tctggcggcg gcggctccag tggtggtgga tcccaggttc agctgcagca atctggacct   1860

gagctggtga agcctggggc ctcagtgaag atttcctgca aagcttctgg ctacgcattc   1920

agtagctctt ggatggactg ggtgaagcag aggcctggac agggtcttga gtggattgga   1980

cggatttatc ctggagatgg agatactaac tacaatggga agttcaaggg caaggccaca   2040

ctgactgcag acaaatcctc cagcacagcc tacatgcagc tcagcagcct gacctctgtg   2100

gactctgcgg tctatttctg tgcaaggtcc attactacgg tagtagggtg gtacttcgat   2160

gtctggggcg cagggaccac ggtcaccgtt tcctcctaa                          2199
```

```
<210> SEQ ID NO 8
<211> LENGTH: 2181
<212> TYPE: DNA
<213> ORGANISM: Artificial Sequence
<220> FEATURE:
<223> OTHER INFORMATION: C4-HC-heavy-konst-full-scFv-anti-CD20-pCR3
      (N297A) (Flagless)

<400> SEQUENCE: 8

atgaacttcg gcttcagcct gatcttcctg gtgctggtgc tgaagggcgt gcagtgcgaa     60

gtgaagctgg tgccccggca attgcaggtt cagctgctgc agtctggacc tgagctggtg    120
```

```
aagcctgggg cttcagtgaa gttgtcctgc aaggcttctg gttatagttt cacaagttac    180
gatattaact gggtgaagca gaggcctgga cagggacttg agtgggttgg atggatttat    240
cctagagatg gtgatactaa gtacaatgag aaattcaagg gcaaggccat attgactgta    300
gacacatcct ccaacacagc gtacatgaac ctccacagcc tgacatctga ggactctgcg    360
gtctatttct gtgcaagact aactgggccc tactggtact tcgatgtctg gggcacaggg    420
accacggtca ccgtctcctc aggatccagc agcgcctcta caaagggccc cagcgtgttc    480
cctctggccc ctagcagcaa gagcacatct ggcggaacag ccgccctggg ctgcctcgtg    540
aaggactact ttcccgagcc cgtgaccgtg tcctggaact ctggcgctct gacaagcggc    600
gtgcacacct ttccagccgt gctgcagagc agcggcctgt actctctgag cagcgtcgtg    660
acagtgccca gcagctctct gggcacccag acctacatct gcaacgtgaa ccacaagccc    720
agcaacacca aggtggacaa gaaggtggaa cccaagagct gcgacaagac ccacacctgt    780
cccccttgtc ctgcccccga actgctggga ggcccttccg tgttcctgtt ccccccaaag    840
cccaaggaca ccctgatgat cagccggacc cccgaagtga cctgcgtggt ggtggatgtg    900
tcccacgagg accctgaagt gaagtttaat tggtacgtgg acggcgtgga agtgcacaac    960
gccaagacca agcctagaga ggaacagtac gccagcacct accgggtggt gtccgtgctg   1020
acagtgctgc accaggactg gctgaacggc aaagagtaca agtgcaaggt gtccaacaag   1080
gccctgcctg cccccatcga gaaaaccatc agcaaggcca agggccagcc ccgcgaaccc   1140
caggtgtaca cactgccccc aagcagggac gagctgacca agaaccaggt gtccctgacc   1200
tgtctcgtga aaggcttcta ccccagcgat atcgccgtgg aatgggagag caacggccag   1260
cccgagaaca actacaagac cacccccccct gtgctggaca gcgacggctc attcttcctg   1320
tacagcaagc tgaccgtgga caagtcccgg tggcagcagg gcaacgtgtt cagctgcagc   1380
gtgatgcacg aggccctgca caaccactac acccagaagt ccctgagcct gagccccggc   1440
aaggaattcc aggtacaact gcagcagcct ggggctgagc tggtgaagcc tggggcctca   1500
gtgaagatgt cctgcaaggc ttctggctac acatttacca gttacaatat gcactgggta   1560
aaacagacac ctggtcgggg cctggaatgg attggagcta tttatcccgg aaatggtgat   1620
acttcctaca atcagaagtt caaaggcaag gccacattga ctgcagacaa atcctccagc   1680
acagcctaca tgcagctcag cagcctgaca tctgaggact ctgcggtcta ttactgtgca   1740
agatcgactt actacggcgg tgactggtac ttcaatgtct ggggcgcagg gaccacggtc   1800
accgtctctt caggaggagg cggatccggc ggaggcggaa gcggtggcgg aggctctcaa   1860
attgttctct cccagtctcc agcaatcctg tctgcatctc caggggagaa ggtcacaatg   1920
acttgcaggg ccagctcaag tgtaagttac atccactggt tccagcagaa gccaggaccc   1980
tcccccaaac cctggattta tgccacatcc aacctggctt ctggagtccc tgttcgcttc   2040
agtggcagtg ggtctgggac ttcttactct ctcacaatca gcagagtgga ggctgaagat   2100
gctgccactt attactgcca gcagtggact agtaacccac ccacgttcgg aggggggacc   2160
aagctggaaa tcaaacgtta a                                              2181
```

<210> SEQ ID NO 9
<211> LENGTH: 1446
<212> TYPE: DNA
<213> ORGANISM: Artificial Sequence
<220> FEATURE:
<223> OTHER INFORMATION: C4-HC-heavy-full-pCR3 (IgG1) (Flagless)

<400> SEQUENCE: 9

```
atgaacttcg gcttcagcct gatcttcctg gtgctggtgc tgaagggcgt gcagtgcgaa     60

gtgaagctgg tgccccggca attgcaggtt cagctgctgc agtctggacc tgagctggtg    120

aagcctgggg cttcagtgaa gttgtcctgc aaggcttctg gttatagttt cacaagttac    180

gatattaact gggtgaagca gaggcctgga cagggacttg agtgggttgg atggatttat    240

cctagagatg gtgatactaa gtacaatgag aaattcaagg gcaaggccat attgactgta    300

gacacatcct ccaacacagc gtacatgaac ctccacagcc tgacatctga ggactctgcg    360

gtctatttct gtgcaagact aactgggccc tactggtact tcgatgtctg gggcacaggg    420

accacggtca ccgtctcctc aggatcctct agcgccagca caaagggccc cagcgtgttc    480

cctctggccc ctagcagcaa gagcacatct ggcggaacag ccgccctggg ctgcctcgtg    540

aaggactact tcccgagccc cgtgacagtg tcctggaact ctggcgccct gacaagcggc    600

gtgcacacct ttccagccgt gctgcagagc agcggcctgt actctctgag cagcgtcgtg    660

actgtgccca gcagcagcct gggcacccag acctacatct gcaacgtgaa ccacaagccc    720

agcaacacca aggtggacaa gaaggtggaa cccaagagct gcgacaagac ccacacctgt    780

ccccccttgtc ctgcccctga actgctgggc ggaccttccg tgttcctgtt ccccccaaag    840

cccaaggaca ccctgatgat cagccggacc cccgaagtga cctgcgtggt ggtggatgtg    900

tcccacgagg accctgaagt gaagtttaat tggtacgtgg acggcgtgga agtgcacaac    960

gccaagacca agcccagaga ggaacagtac aacagcacct accgggtggt gtccgtgctg   1020

acagtgctgc accaggactg gctgaacggc aaagagtaca agtgcaaggt gtccaacaag   1080

gccctgcctg cccccatcga gaaaaccatc agcaaggcca agggccagcc ccgcgaaccc   1140

caggtgtaca cactgcctcc cagcagggac gagctgacca agaaccaggt gtccctgacc   1200

tgtctcgtga aaggcttcta cccctccgat atcgccgtgg aatgggagag caacggccag   1260

cccgagaaca actacaagac caccccccct gtgctggaca gcgacggctc attcttcctg   1320

tacagcaagc tgaccgtgga caagtcccgg tggcagcagg gcaacgtgtt cagctgcagc   1380

gtgatgcacg aggccctgca caaccactac acccagaagt ccctgagcct gagccccggc   1440

aagtaa                                                               1446
```

```
<210> SEQ ID NO 10
<211> LENGTH: 2724
<212> TYPE: DNA
<213> ORGANISM: Artificial Sequence
<220> FEATURE:
<223> OTHER INFORMATION: C4-HC-heavy-full-scGITRL-pCR3 (N297A)

<400> SEQUENCE: 10
```

```
atgaacttcg gcttcagcct gatcttcctg gtgctggtgc tgaagggcgt gcagtgcgaa     60

gtgaagctgg tgccccggca attgcaggtt cagctgctgc agtctggacc tgagctggtg    120

aagcctgggg cttcagtgaa gttgtcctgc aaggcttctg gttatagttt cacaagttac    180

gatattaact gggtgaagca gaggcctgga cagggacttg agtgggttgg atggatttat    240

cctagagatg gtgatactaa gtacaatgag aaattcaagg gcaaggccat attgactgta    300

gacacatcct ccaacacagc gtacatgaac ctccacagcc tgacatctga ggactctgcg    360

gtctatttct gtgcaagact aactgggccc tactggtact tcgatgtctg gggcacaggg    420

accacggtca ccgtctcctc aggatccagc agcgcctcta caaagggccc cagcgtgttc    480

cctctggccc ctagcagcaa gagcacatct ggcggaacag ccgccctggg ctgcctcgtg    540
```

```
aaggactact ttcccgagcc cgtgaccgtg tcctggaact ctggcgctct gacaagcggc    600
gtgcacacct ttccagccgt gctgcagagc agcggcctgt actctctgag cagcgtcgtg    660
acagtgccca gcagctctct gggcacccag acctacatct gcaacgtgaa ccacaagccc    720
agcaacacca aggtggacaa gaaggtggaa cccaagagct gcgacaagac ccacacctgt    780
ccccccttgtc ctgcccccga actgctggga ggcccttccg tgttcctgtt cccccccaaag    840
cccaaggaca ccctgatgat cagccggacc cccgaagtga cctgcgtggt ggtggatgtg    900
tcccacgagg accctgaagt gaagtttaat tggtacgtgg acggcgtgga agtgcacaac    960
gccaagacca agcctagaga ggaacagtac gccagcacct accgggtggt gtccgtgctg   1020
acagtgctgc accaggactg gctgaacggc aaagagtaca agtgcaaggt gtccaacaag   1080
gccctgcctg cccccatcga gaaaaccatc agcaaggcca agggccagcc ccgcgaaccc   1140
caggtgtaca cactgccccc aagcagggac gagctgacca agaaccaggt gtccctgacc   1200
tgtctcgtga aaggcttcta ccccagcgat atcgccgtgg aatgggagag caacggccag   1260
cccgagaaca actacaagac cacccccccct gtgctggaca gcgacggctc attcttcctg   1320
tacagcaagc tgaccgtgga caagtcccgg tggcagcagg gcaacgtgtt cagctgcagc   1380
gtgatgcacg aggccctgca caaccactac acccagaagt ccctgagcct gagccccggc   1440
aaggaattcg gcggagggag cggacagctg gaaactgcca aagaaccctg tatggccaaa   1500
ttcggaccac tgcctagcaa atggcagatg gctagtagcg aacctccatg tgtgaacaaa   1560
gtgagcgatt ggaaactcga gatcctccag aatggactgt acctcatcta cggacaggtc   1620
gccccaaatg ccaattacaa tgatgtggcc ccctttgaag tccggctcta caaaaacaag   1680
gatatgatcc agaccctcac caacaaatcc aaaatccaga atgtgggcgg cacatacgaa   1740
ctccatgtcg gcgataccat cgatctcatt ttcaactctg aacaccaggt gctcaaaaac   1800
aacacctact ggggaatcat cctgctggca aaccctcagt tcatctccgg cggcggctct   1860
ggcggcggat ctggcggagg gagtggcgga ggctcacagc tggagactgc taaagaaccc   1920
tgtatggcaa aattcgggcc cctgccctca aaatggcaga tggcctcctc tgaaccaccc   1980
tgtgtgaaca aagtgagtga ttggaaactg gaaatcctcc agaacggcct ctacctcatc   2040
tacggacagg tggcacccaa tgccaattac aacgacgtgg caccccttcga agtgagactg   2100
tacaaaaaca aggatatgat ccagaccctc accaacaaat caaaaatcca gaatgtcgga   2160
gggacatacg aactccatgt gggagacact atcgacctca ttttcaattc cgaacatcag   2220
gtcctgaaaa acaacactta ctggggcatt attctgctcg ccaatccaca gtttattagt   2280
ggaggcgggg gatctggggg aggctccggc ggagggagtg gaggcggatc tcaattccaa   2340
ttagagactg ctaaggagcc ctgtatggct aagtttggac cattaccctc aaaatggcaa   2400
atggcatctt ctgaacctcc ttgcgtgaat aaggtgtctg actggaagct ggagatactt   2460
cagaatggct tatatttaat ttatggccaa gtggctccca atgcaaacta caatgatgta   2520
gctccttttg aggtgcggct gtataaaaac aaagacatga tacaaactct aacaaacaaa   2580
tctaaaatcc aaaatgtagg agggacttat gaattgcatg ttggggacac catagacttg   2640
atattcaact ctgagcatca ggttctaaaa aataatacat actggggtat cattttacta   2700
gcaaatcccc aattcatctc ctag                                          2724
```

<210> SEQ ID NO 11
<211> LENGTH: 3411
<212> TYPE: DNA
<213> ORGANISM: Artificial Sequence
<220> FEATURE:
<223> OTHER INFORMATION: C4-HC-heavy-full-sc(mu)41BBL-pCR3 (N297A)

<400> SEQUENCE: 11

```
atgaacttcg gcttcagcct gatcttcctg gtgctggtgc tgaagggcgt gcagtgcgaa     60
gtgaagctgg tgccccggca attgcaggtt cagctgctgc agtctggacc tgagctggtg    120
aagcctgggg cttcagtgaa gttgtcctgc aaggcttctg gttatagttt cacaagttac    180
gatattaact gggtgaagca gaggcctgga cagggacttg agtgggttgg atggatttat    240
cctagagatg gtgatactaa gtacaatgag aaattcaagg gcaaggccat attgactgta    300
gacacatcct ccaacacagc gtacatgaac ctccacagcc tgacatctga ggactctgcg    360
gtctatttct gtgcaagact aactgggccc tactggtact tcgatgtctg gggcacaggg    420
accacggtca ccgtctcctc aggatccagc agcgcctcta caaagggccc cagcgtgttc    480
cctctggccc ctagcagcaa gagcacatct ggcggaacag ccgccctggg ctgcctcgtg    540
aaggactact tcccgagcc cgtgaccgtg tcctggaact ctggcgctct gacaagcggc    600
gtgcacacct ttccagccgt gctgcagagc agcggcctgt actctctgag cagcgtcgtg    660
acagtgccca gcagctctct gggcacccag acctacatct gcaacgtgaa ccacaagccc    720
agcaacacca aggtggacaa gaaggtggaa cccaagagct gcgacaagac ccacacctgt    780
cccccttgtc ctgcccccga actgctggga ggcccttccg tgttcctgtt cccccaaag    840
cccaaggaca ccctgatgat cagccggacc cccgaagtga cctgcgtggt ggtggatgtg    900
tcccacgagg accctgaagt gaagtttaat tggtacgtgg acggcgtgga agtgcacaac    960
gccaagacca agcctagaga ggaacagtac gccagcacct accgggtggt gtccgtgctg   1020
acagtgctgc accaggactg gctgaacggc aaagagtaca agtgcaaggt gtccaacaag   1080
gccctgcctg cccccatcga gaaaaccatc agcaaggcca agggccagcc ccgcgaaccc   1140
caggtgtaca cactgccccc aagcagggac gagctgacca agaaccaggt gtccctgacc   1200
tgtctcgtga aaggcttcta ccccagcgat atcgccgtgg aatgggagag caacggccag   1260
cccgagaaca actacaagac caccccccct gtgctggaca gcgacggctc attcttcctg   1320
tacagcaagc tgaccgtgga caagtcccgg tggcagcagg gcaacgtgtt cagctgcagc   1380
gtgatgcacg aggccctgca caaccactac acccagaagt ccctgagcct gagccccggc   1440
aaggaattcg gcggtggaag tggtactgaa ccgcgacccg ctctcactat aaccaccagc   1500
cctaacttgg gaacgcggga gaataacgcg gatcaagtaa ccccagtttc ccatatcggg   1560
tgtccaaata ccactcaaca aggatcaccg gtctttgcta agctcctggc gaaaaaccaa   1620
gcgtccctct gtaatacaac ccttaattgg cactcccaag atggggcggg ttcttcatac   1680
ctctcacagg ggctccgata cgaagaagac aaaaaggagt tggtggtcga ctcaccagga   1740
ctttactatg tattcctgga gttgaagctc tctcctacat tcaccaatac cggtcacaaa   1800
gtacagggtt gggtgagcct tgtgctccag gcgaagccgc aggtggacga cttcgacaac   1860
cttgcactca ctgtagagct gttcccttgt tccatggaga ataaattggt ggaccgctct   1920
tggagtcagc tcctcctcct caaggcgggt catcgattga gcgttggcct tcgggcatat   1980
cttcatgggg cgcaagatgc ataccgcgat tgggaattgt catacccaa cacgacctct   2040
tttggcctgt ttctggtcaa acccgacaat ccgtgggaag gtgggggaag cggagggggt   2100
tcaggaggag gatctggggg aggttcaact gaaccgaggc ccgcgcttac tatcacgact   2160
tccccaaatc tggggactag ggaaaacaat gccgatcagg tcactcctgt tagtcacatt   2220
```

```
ggttgtccta atacgaccca gcaaggctct ccggtgtttg ccaaactgtt ggccaaaaat   2280

caggcgtcac tttgtaatac aacgctcaac tggcatagtc aggatggggc cggctcctca   2340

tacttgtctc aaggtcttag gtacgaagaa gataagaagg agctggtggt agacagcccc   2400

gggctctact atgtgttcct ggagctcaaa ctgtcaccga cgttcactaa caccggtcat   2460

aaggtacagg gttgggtatc cttggtgttg caagcaaaac cccaggtgga cgatttcgat   2520

aatcttgcgc ttactgtaga gctctttcca tgttcaatgg aaaataaact ggtcgatagg   2580

agctggtccc aacttctcct tcttaaagct ggccatcgcc tgagtgttgg cctgagagcg   2640

tatcttcatg gggcgcagga cgcttaccgg gattgggaac tgtcataccc aaacaccacc   2700

agctttgggc tcttccttgt aaagccagac aatccgtggg aggggggagg cgggagtggg   2760

ggcgggtctg gagggggcag tgggggggt agtacggagc cgcgccccgc cctgaccatc   2820

acaacgtcac ccaatcttgg gactcgggag aataacgccg accaggttac ccctgtatcc   2880

catatcggtt gtcctaatac gacacaacaa ggcagtcctg tattcgctaa actcttggca   2940

aaaaaccagg ccagtctttg taatacgacg cttaattggc atagccagga cggtgcgggc   3000

agctcctacc tttcccaggg gctcaggtat gaagaagata agaaagaact cgttgtagac   3060

agtcccggat tgtattacgt ttttttggaa ctcaagctct ctccaacctt caccaatacg   3120

ggacataagg tccagggctg ggtgagcctc gtactccagg ctaagccgca agttgacgat   3180

ttcgataatc tcgctcttac agtggagttg tttccctgta gtatggagaa taagctcgtc   3240

gaccggtctt ggagccaact tctgctgctt aaggctggtc accggctcag tgtaggcctc   3300

cgagcgtatt tgcatggggc gcaggacgcc tatcgagact gggagctttc ctaccctaac   3360

acgaccagct ttggactctt cttggtgaaa cctgacaatc cgtgggaata a             3411
```

```
<210> SEQ ID NO 12
<211> LENGTH: 1836
<212> TYPE: DNA
<213> ORGANISM: Artificial Sequence
<220> FEATURE:
<223> OTHER INFORMATION: C4-HC-heavy-full-(mu)GITRL-pCR3 (N297A)

<400> SEQUENCE: 12
```

```
atgaacttcg gcttcagcct gatcttcctg gtgctggtgc tgaagggcgt gcagtgcgaa     60

gtgaagctgg tgccccggca attgcaggtt cagctgctgc agtctggacc tgagctggtg    120

aagcctgggg cttcagtgaa gttgtcctgc aaggcttctg gttatagttt cacaagttac    180

gatattaact gggtgaagca gaggcctgga cagggacttg agtgggttgg atggatttat    240

cctagagatg gtgatactaa gtacaatgag aaattcaagg gcaaggccat attgactgta    300

gacacatcct ccaacacagc gtacatgaac ctccacagcc tgacatctga ggactctgcg    360

gtctatttct gtgcaagact aactgggccc tactggtact tcgatgtctg gggcacaggg    420

accacggtca ccgtctcctc aggatccagc agcgcctcta caaagggccc cagcgtgttc    480

cctctggccc ctagcagcaa gagcacatct ggcggaacag ccgccctggg ctgcctcgtg    540

aaggactact tcccgagcc cgtgaccgtg tcctggaact ctggcgctct gacaagcggc    600

gtgcacacct ttccagccgt gctgcagagc agcggcctgt actctctgag cagcgtcgtg    660

acagtgccca gcagctctct gggcacccag acctacatct gcaacgtgaa ccacaagccc    720

agcaacacca aggtggacaa gaaggtggaa cccaagagct gcgacaagac ccacacctgt    780

ccccccttgtc ctgcccccga actgctggga ggcccttccg tgttcctgtt ccccccaaag    840

cccaaggaca ccctgatgat cagccggacc cccgaagtga cctgcgtggt ggtggatgtg    900
```

```
tcccacgagg accctgaagt gaagtttaat tggtacgtgg acggcgtgga agtgcacaac    960

gccaagacca agcctagaga ggaacagtac gccagcacct accgggtggt gtccgtgctg   1020

acagtgctgc accaggactg gctgaacggc aaagagtaca agtgcaaggt gtccaacaag   1080

gccctgcctg cccccatcga gaaaaccatc agcaaggcca agggccagcc ccgcgaaccc   1140

caggtgtaca cactgccccc aagcagggac gagctgacca agaaccaggt gtccctgacc   1200

tgtctcgtga aaggcttcta ccccagcgat atcgccgtgg aatgggagag caacggccag   1260

cccgagaaca actacaagac cacccccccct gtgctggaca gcgacggctc attcttcctg   1320

tacagcaagc tgaccgtgga caagtcccgg tggcagcagg gcaacgtgtt cagctgcagc   1380

gtgatgcacg aggccctgca caaccactac acccagaagt ccctgagcct gagccccggc   1440

aaggaattcc caactgccat cgagtcctgc atggttaagt ttgaactatc atcctcaaaa   1500

tggcacatga catctcccaa acctcactgt gtgaatacga catctgatgg gaagctgaag   1560

atactgcaga gtggcacata tttaatctac ggccaagtga ttcctgtgga taagaaatac   1620

ataaaagaca atgccccctt cgtagtacag atatataaaa agaatgatgt cctacaaact   1680

ctaatgaatg attttcaaat cttgcctata ggaggggttt atgaactgca tgctggagat   1740

aacatatatc tgaagttcaa ctctaaagac catattcaga aaactaacac atactggggg   1800

atcatcttaa tgcctgatct accattcatc tcttag                             1836
```

<210> SEQ ID NO 13
<211> LENGTH: 735
<212> TYPE: DNA
<213> ORGANISM: Artificial Sequence
<220> FEATURE:
<223> OTHER INFORMATION: C4-LC-light-full-pCR3 (Flagless)

<400> SEQUENCE: 13

```
atgaacttcg gcttcagcct gatcttcctg gtgctggtgc tgaagggcgt gcagtgcgaa     60

gtgaagctgg tgccccggca attggacatt gtgatgaccc agtctcacaa attcatgtcc    120

acatcagtag gagacagggt cagcatcacc tgcaaggcca gtcaggatgt ggatactgct    180

gtagcctggt atcaacaaaa accagggcaa tctcctaaac tactgattta ctgggcatcc    240

acccggcaca ctggagtccc tgatcgcttc acaggcagtg gatctgggac agattatact    300

ctcaccatca gcagtgtgca ggctgaagac ctggcgcgtt attactgtca gcaatattat    360

agtgttcctc cgacgttcgg tggaggcacc aagctgggat ccgaaatcaa gcgtacggtg    420

gccgctccca gcgtgttcat cttcccacct agcgacgagc agctgaagtc cggcacagcc    480

tctgtcgtgt gcctgctgaa caacttctac ccccgcgagg ccaaggtgca gtggaaggtg    540

gacaatgccc tgcagagcgg caacagccag gaaagcgtga ccgagcagga cagcaaggac    600

tccacctaca gcctgagcag caccctgacc ctgagcaagg ccgactacga gaagcacaag    660

gtgtacgcct gcgaagtgac ccaccagggc ctgtctagcc ccgtgaccaa gagcttcaac    720

cggggcgagt gctaa                                                     735
```

<210> SEQ ID NO 14
<211> LENGTH: 2268
<212> TYPE: DNA
<213> ORGANISM: Artificial Sequence
<220> FEATURE:
<223> OTHER INFORMATION: anti-CD95(E09)-Flag-VH-full-scFv-anti-CD19-pCR3
      (IgG1)

<400> SEQUENCE: 14

```
atgaacttcg gcttcagcct gatcttcctg gtgctggtgc tgaagggcgt gcagtgcgaa     60
gtgaagctgg tgccccggca attggactac aaggacgacg acgacaaaga attccagctg    120
cagctgcagg aatctggccc tggcctcgtg aagcccagcg agacactgag cctgacctgt    180
accgtgtccg gcgccagcat cagcgccaac agctactatg gcgtgtgggt gcgccagagc    240
cctggcaagg gactggaatg ggtgggatct atcgcctacc ggggcaacag caacagcggc    300
agcacctact acaaccccag cctgaagtcc cgggccaccg tgtctgtgga caccagcaag    360
aaccaggtgt ccctgcggct gacctctgtg acagccgccg ataccgccct gtactactgc    420
gccagaaggc agctgctgga cgacggcaca ggatatcagt gggccgcctt cgatgtgtgg    480
ggccagggaa caatggtcac cgtgtcctcc agatcctcta gcgccagcac aaagggcccc    540
agcgtgttcc ctctggcccc tagcagcaag agcacatctg gcggaacagc cgccctgggc    600
tgcctcgtga aggactactt tcccgagccc gtgacagtgt cctggaactc tggcgccctg    660
acaagcggcg tgcacacctt tccagccgtg ctgcagagca gcggcctgta ctctctgagc    720
agcgtcgtga ctgtgcccag cagcagcctg ggcacccaga cctacatctg caacgtgaac    780
cacaagccca gcaacaccaa ggtggacaag aaggtggaac ccaagagctg cgacaagacc    840
cacacctgtc cccccttgtcc tgcccctgaa ctgctgggcg gaccttccgt gttcctgttc    900
cccccaaagc ccaaggacac cctgatgatc agccggaccc ccgaagtgac ctgcgtggtg    960
gtggatgtgt cccacgagga ccctgaagtg aagtttaatt ggtacgtgga cggcgtggaa   1020
gtgcacaacg ccaagaccaa gcccagagag gaacagtaca acagcaccta ccgggtggtg   1080
tccgtgctga cagtgctgca ccaggactgg ctgaacggca aagagtacaa gtgcaaggtg   1140
tccaacaagg ccctgcctgc ccccatcgag aaaaccatca gcaaggccaa gggccagccc   1200
cgcgaacccc aggtgtacac actgcctccc agcagggacg agctgaccaa gaaccaggtg   1260
tccctgacct gtctcgtgaa aggcttctac ccctccgata tcgccgtgga atgggagagc   1320
aacggccagc ccgagaacaa ctacaagacc acccccccctg tgctggacag cgacggctca   1380
ttcttcctgt acagcaagct gaccgtggac aagtcccggt ggcagcaggg caacgtgttc   1440
agctgcagcg tgatgcacga ggccctgcac aaccactaca cccagaagtc cctgagcctg   1500
agccccggca agctcgagga cattcagatg acgcagtctc catcctccat gtctgtatct   1560
ctgggagaca cagtcagcat cacttgccat gcaagtcagg gcattagcag taatataggg   1620
tggttgcagc agaaaccagg gaaatcattt aagggcctga tctatcatgg aaccaacttg   1680
gaagatggag ttccatcaag gttcagtggc agtggatctg gagcagatta ttctctcacc   1740
atcagcagcc tggaatctga agattttgca gactattact gtgtacagta tgctcagttt   1800
ccgtacacgt tcggaggggg gaccaagctg gagctgaaac gtggtggtgg tggttctggt   1860
ggtggtggtt ctggcggcgg cggctccagt ggtggtggat cccaggttca gctgcagcaa   1920
tctggacctg agctggtgaa gcctggggcc tcagtgaaga tttcctgcaa agcttctggc   1980
tacgcattca gtagctcttg gatggactgg gtgaagcaga ggcctggaca gggtcttgag   2040
tggattggac ggatttatcc tggagatgga gatactaact acaatgggaa gttcaagggc   2100
aaggccacac tgactgcaga caaatcctcc agcacagcct acatgcagct cagcagcctg   2160
acctctgtgg actctgcggt ctatttctgt gcaaggtcca ttactacggt agtagggtgg   2220
tacttcgatg tctggggcgc agggaccacg gtcaccgttt cctcctaa                2268
```

<210> SEQ ID NO 15

<211> LENGTH: 1515
<212> TYPE: DNA
<213> ORGANISM: Artificial Sequence
<220> FEATURE:
<223> OTHER INFORMATION: anti-CD95-E09-Flag-VH-heavy-full-pCR3 (IgG1)

<400> SEQUENCE: 15

```
atgaacttcg gcttcagcct gatcttcctg gtgctggtgc tgaagggcgt gcagtgcgaa     60
gtgaagctgg tgccccggca attggactac aaggacgacg acgacaaaga attccagctg    120
cagctgcagg aatctggccc tggcctcgtg aagcccagcg agacactgag cctgacctgt    180
accgtgtccg gcgccagcat cagcgccaac agctactatg gcgtgtgggt gcgccagagc    240
cctggcaagg gactggaatg ggtgggatct atcgcctacc ggggcaacag caacagcggc    300
agcacctact acaaccccag cctgaagtcc cgggccaccg tgtctgtgga caccagcaag    360
aaccaggtgt ccctgcggct gacctctgtg acagccgccg ataccgccct gtactactgc    420
gccagaaggc agctgctgga cgacggcaca ggatatcagt gggccgcctt cgatgtgtgg    480
ggccagggaa caatggtcac cgtgtcctcc agatcctcta gcgccagcac aaagggcccc    540
agcgtgttcc ctctggcccc tagcagcaag agcacatctg gcggaacagc cgccctgggc    600
tgcctcgtga aggactactt tcccgagccc gtgacagtgt cctggaactc tggcgccctg    660
acaagcggcg tgcacacctt tccagccgtg ctgcagagca gcggcctgta ctctctgagc    720
agcgtcgtga ctgtgcccag cagcagcctg ggcacccaga cctacatctg caacgtgaac    780
cacaagccca gcaacaccaa ggtggacaag aaggtggaac ccaagagctg cgacaagacc    840
cacacctgtc cccccttgtcc tgcccctgaa ctgctgggcg gaccttccgt gttcctgttc    900
cccccaaagc ccaaggacac cctgatgatc agccggaccc ccgaagtgac ctgcgtggtg    960
gtggatgtgt cccacgagga ccctgaagtg aagtttaatt ggtacgtgga cggcgtggaa   1020
gtgcacaacg ccaagaccaa gcccagagag gaacagtaca acagcaccta ccgggtggtg   1080
tccgtgctga cagtgctgca ccaggactgg ctgaacggca aagagtacaa gtgcaaggtg   1140
tccaacaagg ccctgcctgc ccccatcgag aaaaccatca gcaaggccaa gggccagccc   1200
cgcgaacccc aggtgtacac actgcctccc agcagggacg agctgaccaa gaaccaggtg   1260
tccctgacct gtctcgtgaa aggcttctac cctccgata tcgccgtgga atgggagagc   1320
aacggccagc ccgagaacaa ctacaagacc accccccctg tgctggacag cgacggctca   1380
ttcttcctgt acagcaagct gaccgtggac aagtcccggt ggcagcaggg caacgtgttc   1440
agctgcagcg tgatgcacga ggccctgcac aaccactaca cccagaagtc cctgagcctg   1500
agccccggca agtaa                                                    1515
```

<210> SEQ ID NO 16
<211> LENGTH: 1602
<212> TYPE: DNA
<213> ORGANISM: Artificial Sequence
<220> FEATURE:
<223> OTHER INFORMATION: anti-CD95(E09)-Flag-VH-FAB2(1-114)-scFv-anti-CD20-pCR3 (IgG1)

<400> SEQUENCE: 16

```
atgaacttcg gcttcagcct gatcttcctg gtgctggtgc tgaagggcgt gcagtgcgaa     60
gtgaagctgg tgccccggca attggactac aaggacgacg acgacaaaga attgcagctg    120
cagctgcagg aatctggccc tggcctcgtg aagcccagcg agacactgag cctgacctgt    180
accgtgtccg gcgccagcat cagcgccaac agctactatg gcgtgtgggt gcgccagagc    240
```

```
cctggcaagg gactggaatg ggtgggatct atcgcctacc ggggcaacag caacagcggc    300

agcacctact acaaccccag cctgaagtcc cgggccaccg tgtctgtgga caccagcaag    360

aaccaggtgt ccctgcggct gacctctgtg acagccgccg ataccgccct gtactactgc    420

gccagaaggc agctgctgga cgacggcaca ggatatcagt gggccgcctt cgatgtgtgg    480

ggccagggaa caatggtcac cgtgtcctcc ggatcctcta gcgccagcac aaagggcccc    540

agcgtgttcc ctctggcccc tagcagcaag agcacatctg gcggaacagc cgccctgggc    600

tgcctcgtga aggactactt tcccgagccc gtgacagtgt cctggaactc tggcgccctg    660

acaagcggcg tgcacacctt tccagccgtg ctgcagagca gcggcctgta ctctctgagc    720

agcgtcgtga ctgtgcccag cagcagcctg ggcacccaga cctacatctg caacgtgaac    780

cacaagccca gcaacaccaa ggtggacaag aaggtggaac ccaagagctg cgacaagacc    840

cacacctgtc cccccttgtcc tgccctcgag caggtacaac tgcagcagcc tggggctgag   900

ctggtgaagc ctggggcctc agtgaagatg tcctgcaagg cttctggcta cacatttacc    960

agttacaata tgcactgggt aaaacagaca cctggtcggg gcctggaatg gattggagct   1020

atttatcccg gaaatggtga tacttcctac aatcagaagt tcaaaggcaa ggccacattg   1080

actgcagaca aatcctccag cacagcctac atgcagctca gcagcctgac atctgaggac   1140

tctgcggtct attactgtgc aagatcgact tactacggcg gtgactggta cttcaatgtc   1200

tggggcgcag ggaccacggt caccgtctct tcaggaggag gcggatccgg cggaggcgga   1260

agcggtggcg gaggctctca aattgttctc tcccagtctc cagcaatcct gtctgcatct   1320

ccaggggaga aggtcacaat gacttgcagg gccagctcaa gtgtaagtta catccactgg   1380

ttccagcaga agccaggatc ctcccccaaa ccctggattt atgccacatc caacctggct   1440

tctggagtcc ctgttcgctt cagtggcagt gggtctggga cttcttactc tctcacaatc   1500

agcagagtgg aggctgaaga tgctgccact tattactgcc agcagtggac tagtaaccca   1560

cccacgttcg gagggggggac caagctggaa atcaaacgtt aa                     1602
```

<210> SEQ ID NO 17
<211> LENGTH: 2934
<212> TYPE: DNA
<213> ORGANISM: Artificial Sequence
<220> FEATURE:
<223> OTHER INFORMATION: anti-CD95-E09-Flag-VH-heavy-full-scBaff-pCR3
(N297A)

<400> SEQUENCE: 17

```
atgaacttcg gcttcagcct gatcttcctg gtgctggtgc tgaagggcgt gcagtgcgaa     60

gtgaagctgg tgccccggca attggactac aaggacgacg acgacaaaga attgcagctg    120

cagctgcagg aatctggccc tggcctcgtg aagcccagcg agacactgag cctgacctgt    180

accgtgtccg gcgccagcat cagcgccaac agctactatg gcgtgtgggt gcgccagagc    240

cctggcaagg gactggaatg ggtgggatct atcgcctacc ggggcaacag caacagcggc    300

agcacctact acaaccccag cctgaagtcc cgggccaccg tgtctgtgga caccagcaag    360

aaccaggtgt ccctgcggct gacctctgtg acagccgccg ataccgccct gtactactgc    420

gccagaaggc agctgctgga cgacggcaca ggatatcagt gggccgcctt cgatgtgtgg    480

ggccagggaa caatggtcac cgtgtcctcc ggatccagca gcgcctctac aaagggcccc    540

agcgtgttcc ctctggcccc tagcagcaag agcacatctg gcggaacagc cgccctgggc    600

tgcctcgtga aggactactt tcccgagccc gtgaccgtgt cctggaactc tggcgctctg    660
```

```
acaagcggcg tgcacacctt tccagccgtg ctgcagagca gcggcctgta ctctctgagc    720

agcgtcgtga cagtgcccag cagctctctg ggcacccaga cctacatctg caacgtgaac    780

cacaagccca gcaacaccaa ggtggacaag aaggtggaac ccaagagctg cgacaagacc    840

cacacctgtc cccctgtcc tgcccccgaa ctgctgggag gcccttccgt gttcctgttc    900

cccccaaagc ccaaggacac cctgatgatc agccggaccc ccgaagtgac ctgcgtggtg    960

gtggatgtgt cccacgagga ccctgaagtg aagtttaatt ggtacgtgga cggcgtggaa   1020

gtgcacaacg ccaagaccaa gcctagagag gaacagtacg ccagcaccta ccgggtggtg   1080

tccgtgctga cagtgctgca ccaggactgg ctgaacggca aagagtacaa gtgcaaggtg   1140

tccaacaagg ccctgcctgc ccccatcgag aaaaccatca gcaaggccaa gggccagccc   1200

cgcgaacccc aggtgtacac actgccccca agcagggacg agctgaccaa gaaccaggtg   1260

tccctgacct gtctcgtgaa aggcttctac cccagcgata tcgccgtgga atgggagagc   1320

aacggccagc ccgagaacaa ctacaagacc acccccccctg tgctggacag cgacggctca   1380

ttcttcctgt acagcaagct gaccgtggac aagtcccggt ggcagcaggg caacgtgttc   1440

agctgcagcg tgatgcacga ggccctgcac aaccactaca cccagaagtc cctgagcctg   1500

agccccggca agctcgaggg acccgaggaa actgtgactc aggactgtct ccagctcatt   1560

gccgatagtg aaacccctac catccagaaa ggctcttaca ccttcgtgcc atggctgctg   1620

tcattcaaac ggggatctgc tctggaggag aaggaaaaca aaatcctggt caaggaaacc   1680

ggctacttct tcatctacgg ccaggtcctc tacaccgaca aaacatacgc tatggggcat   1740

ctcattcagc ggaaaaaagt ccacgtgttc ggcgacgaac tctctctcgt gacactgttc   1800

cggtgtattc agaacatgcc cgagactctg cccaataata gctgctactc tgctggcatt   1860

gccaaactgg aggagggcga cgaactccag ctggctattc ctagggaaaa tgcccagatt   1920

agcctggacg gggatgtgac attttttggc gccctgaaac tgctgggagg cggagggagt   1980

ggcgggggag gctctggacc tgaggaaact gtgacccagg attgtctcca gctcattgcc   2040

gatagtgaga ctcctaccat tcagaaggga tcttacacct ttgtgccttg gctgctgtct   2100

ttcaaacggg gctctgctct ggaggaaaag gagaacaaaa ttctggtcaa agagactggc   2160

tacttcttca tctacggcca ggtgctgtac accgacaaaa catacgccat gggccatctc   2220

attcagcgga aaaaagtcca cgtgttcggc gacgaactct ctctcgtgac actgttccgg   2280

tgtatccaga acatgcccga gacactgccc aataatagct gctactctgc cggcattgct   2340

aaactggagg agggggacga actccagctg gctattccta gggaaaatgc ccagatttct   2400

ctcgatgggg atgtgacatt cttcggggcc ctcaaactgc tgggaggcgg cggatctggc   2460

ggaggcggga gtcaattcgc agcaggtcca gaagaaacag tcactcaaga ctgcttgcaa   2520

ctgattgcag acagtgaaac accaactata caaaaaggat cttacacatt tgttccatgg   2580

cttctcagct ttaaaagggg aagtgcccta gaagaaaaag agaataaaat attggtcaaa   2640

gaaactggtt actttttat atatggtcag gttttatata ctgataagac ctacgccatg   2700

ggacatctaa ttcagaggaa gaaggtccat gtctttgggg atgaattgag tctggtgact   2760

ttgtttcgat gtattcaaaa tatgcctgaa acactaccca ataattcctg ctattcagct   2820

ggcattgcaa aactggaaga aggagatgaa ctccaacttg caataccaag agaaaatgca   2880

caaatatcac tggatggaga tgtcacattt tttggtgcat tgaaactgct gtga         2934
```

<210> SEQ ID NO 18
<211> LENGTH: 786

```
<212> TYPE: DNA
<213> ORGANISM: Artificial Sequence
<220> FEATURE:
<223> OTHER INFORMATION: anti-CD95-E09-Flag-VL-light-full-pCR3

<400> SEQUENCE: 18

atgaacttcg gcttcagcct gatcttcctg gtgctggtgc tgaagggcgt gcagtgcgaa     60

gtgaagctgg tgccccggca attggactac aaggacgacg acgacaaaga attgcagagc    120

gtgctgaccc agcctcctag cgtgtccgaa gcccctagac agaccgtgac catcagctgc    180

tccggcaaca gcttcaacat cggcagatac cccgtgaact ggtatcagca gctgccaggc    240

aaggccccta aactgctgat ctactataac aacctgcggt tcagcggagt gtccgaccgg    300

ttctctggca gcaagtctgg cacatctgcc agcctggcca tccgggatct gctgtctgag    360

gacgaggccg actactactg cagcacctgg gacgacaccc tgaagggctg ggtgttcggc    420

ggaggcacca aagtgacagt gctgggcgga tccgaaatca agcgtacggt ggccgctccc    480

agcgtgttca tcttcccacc tagcgacgag cagctgaagt ccggcacagc ctctgtcgtg    540

tgcctgctga acaacttcta cccccgcgag gccaaggtgc agtggaaggt ggacaatgcc    600

ctgcagagcg gcaacagcca ggaaagcgtg accgagcagg acagcaagga ctccacctac    660

agcctgagca gcaccctgac cctgagcaag gccgactacg agaagcacaa ggtgtacgcc    720

tgcgaagtga cccaccaggg cctgtctagc cccgtgacca agagcttcaa ccggggcgag    780

tgctaa                                                               786


<210> SEQ ID NO 19
<211> LENGTH: 963
<212> TYPE: PRT
<213> ORGANISM: Artificial Sequence
<220> FEATURE:
<223> OTHER INFORMATION: Protein construct expressed from SEQ ID NO: 1

<400> SEQUENCE: 19

Met Asn Phe Gly Phe Ser Leu Ile Phe Leu Val Leu Val Leu Lys Gly
1               5                   10                  15

Val Gln Cys Glu Val Lys Leu Val Pro Arg Gln Leu Asp Tyr Lys Asp
            20                  25                  30

Asp Asp Asp Lys Glu Leu Asp Ile Gln Leu Gln Gln Ser Gly Pro Gly
        35                  40                  45

Leu Val Lys Pro Ser Gln Ser Leu Ser Leu Thr Cys Ser Val Thr Gly
    50                  55                  60

Tyr Ser Ile Thr Thr Asn Tyr Asn Trp Asn Trp Ile Arg Gln Phe Pro
65                  70                  75                  80

Gly Asn Lys Leu Glu Trp Met Gly Tyr Ile Arg Tyr Asp Gly Thr Ser
                85                  90                  95

Glu Tyr Thr Pro Ser Leu Lys Asn Arg Val Ser Ile Thr Arg Asp Thr
            100                 105                 110

Ser Met Asn Gln Phe Phe Leu Arg Leu Thr Ser Val Thr Pro Glu Asp
        115                 120                 125

Thr Ala Thr Tyr Tyr Cys Ala Arg Leu Asp Tyr Trp Gly Gln Gly Thr
    130                 135                 140

Leu Val Thr Val Ser Ser Gly Ser Ser Ser Ala Ser Thr Lys Gly Pro
145                 150                 155                 160

Ser Val Phe Pro Leu Ala Pro Ser Ser Lys Ser Thr Ser Gly Gly Thr
                165                 170                 175

Ala Ala Leu Gly Cys Leu Val Lys Asp Tyr Phe Pro Glu Pro Val Thr
```

```
            180                 185                 190

Val Ser Trp Asn Ser Gly Ala Leu Thr Ser Gly Val His Thr Phe Pro
        195                 200                 205

Ala Val Leu Gln Ser Ser Gly Leu Tyr Ser Leu Ser Ser Val Val Thr
    210                 215                 220

Val Pro Ser Ser Ser Leu Gly Thr Gln Thr Tyr Ile Cys Asn Val Asn
225                 230                 235                 240

His Lys Pro Ser Asn Thr Lys Val Asp Lys Lys Val Glu Pro Lys Ser
                245                 250                 255

Cys Asp Lys Thr His Thr Cys Pro Pro Cys Pro Ala Pro Glu Leu Leu
            260                 265                 270

Gly Gly Pro Ser Val Phe Leu Phe Pro Pro Lys Pro Lys Asp Thr Leu
        275                 280                 285

Met Ile Ser Arg Thr Pro Glu Val Thr Cys Val Val Val Asp Val Ser
    290                 295                 300

His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Ala Ser Thr
                325                 330                 335

Tyr Arg Val Val Ser Val Leu Thr Val Leu His Gln Asp Trp Leu Asn
            340                 345                 350

Gly Lys Glu Tyr Lys Cys Lys Val Ser Asn Lys Ala Leu Pro Ala Pro
        355                 360                 365

Ile Glu Lys Thr Ile Ser Lys Ala Lys Gly Gln Pro Arg Glu Pro Gln
    370                 375                 380

Val Tyr Thr Leu Pro Pro Ser Arg Asp Glu Leu Thr Lys Asn Gln Val
385                 390                 395                 400

Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Lys Leu Thr
        435                 440                 445

Val Asp Lys Ser Arg Trp Gln Gln Gly Asn Val Phe Ser Cys Ser Val
    450                 455                 460

Met His Glu Ala Leu His Asn His Tyr Thr Gln Lys Ser Leu Ser Leu
465                 470                 475                 480

Ser Pro Gly Lys Glu Phe Glu Phe Thr Arg Asp Lys Pro Val Ala His
                485                 490                 495

Val Val Ala Asn His Gln Val Glu Glu Gln Leu Glu Trp Leu Ser Gln
            500                 505                 510

Arg Ala Asn Ala Leu Leu Ala Asn Gly Met Asp Leu Lys Asp Asn Gln
        515                 520                 525

Leu Val Val Pro Ala Asp Gly Leu Tyr Leu Val Tyr Ser Gln Val Leu
    530                 535                 540

Phe Lys Gly Gln Gly Cys Pro Asp Tyr Val Leu Leu Thr His Thr Val
545                 550                 555                 560

Ser Arg Phe Ala Ile Ser Tyr Gln Glu Lys Val Asn Leu Leu Ser Ala
                565                 570                 575

Val Lys Ser Pro Cys Pro Lys Asp Thr Pro Glu Gly Ala Glu Leu Lys
            580                 585                 590

Pro Trp Tyr Glu Pro Ile Tyr Leu Gly Gly Val Phe Gln Leu Glu Lys
        595                 600                 605
```

```
Gly Asp Gln Leu Ser Ala Glu Val Asn Leu Pro Lys Tyr Leu Asn Phe
    610                 615                 620

Arg Glu Ser Gly Gln Val Tyr Phe Gly Val Ile Ala Leu Gly Gly Gly
625                 630                 635                 640

Ser Gly Gly Gly Ser Gly Gly Gly Ser Gly Gly Gly Ser Asp Lys Pro
                645                 650                 655

Val Ala His Val Val Ala Asn His Gln Val Glu Glu Gln Leu Glu Trp
            660                 665                 670

Leu Ser Gln Arg Ala Asn Ala Leu Leu Ala Asn Gly Met Asp Leu Lys
        675                 680                 685

Asp Asn Gln Leu Val Val Pro Ala Asp Gly Leu Tyr Leu Val Tyr Ser
    690                 695                 700

Gln Val Leu Phe Lys Gly Gln Gly Cys Pro Asp Tyr Val Leu Leu Thr
705                 710                 715                 720

His Thr Val Ser Arg Phe Ala Ile Ser Tyr Gln Glu Lys Val Asn Leu
                725                 730                 735

Leu Ser Ala Val Lys Ser Pro Cys Pro Lys Asp Thr Pro Glu Gly Ala
            740                 745                 750

Glu Leu Lys Pro Trp Tyr Glu Pro Ile Tyr Leu Gly Gly Val Phe Gln
        755                 760                 765

Leu Glu Lys Gly Asp Gln Leu Ser Ala Glu Val Asn Leu Pro Lys Tyr
    770                 775                 780

Leu Asn Phe Arg Glu Ser Gly Gln Val Tyr Phe Gly Val Ile Ala Leu
785                 790                 795                 800

Gly Gly Gly Ser Gly Gly Gly Ser Gly Gly Gly Ser Gly Gly Gly Ser
                805                 810                 815

Asp Lys Pro Val Ala His Val Val Ala Asn His Gln Val Glu Glu Gln
            820                 825                 830

Leu Glu Trp Leu Ser Gln Arg Ala Asn Ala Leu Leu Ala Asn Gly Met
        835                 840                 845

Asp Leu Lys Asp Asn Gln Leu Val Val Pro Ala Asp Gly Leu Tyr Leu
    850                 855                 860

Val Tyr Ser Gln Val Leu Phe Lys Gly Gln Gly Cys Pro Asp Tyr Val
865                 870                 875                 880

Leu Leu Thr His Thr Val Ser Arg Phe Ala Ile Ser Tyr Gln Glu Lys
                885                 890                 895

Val Asn Leu Leu Ser Ala Val Lys Ser Pro Cys Pro Lys Asp Thr Pro
            900                 905                 910

Glu Gly Ala Glu Leu Lys Pro Trp Tyr Glu Pro Ile Tyr Leu Gly Gly
        915                 920                 925

Val Phe Gln Leu Glu Lys Gly Asp Gln Leu Ser Ala Glu Val Asn Leu
    930                 935                 940

Pro Lys Tyr Leu Asn Phe Arg Glu Ser Gly Gln Val Tyr Phe Gly Val
945                 950                 955                 960

Ile Ala Leu
```

<210> SEQ ID NO 20
<211> LENGTH: 484
<212> TYPE: PRT
<213> ORGANISM: Artificial Sequence
<220> FEATURE:
<223> OTHER INFORMATION: Protein construct expressed from SEQ ID NO: 2

<400> SEQUENCE: 20

```
Met Asn Phe Gly Phe Ser Leu Ile Phe Leu Val Leu Val Leu Lys Gly
1               5                   10                  15

Val Gln Cys Glu Val Lys Leu Val Pro Arg Gln Leu Asp Tyr Lys Asp
            20                  25                  30

Asp Asp Asp Lys Glu Leu Asp Ile Gln Leu Gln Gln Ser Gly Pro Gly
        35                  40                  45

Leu Val Lys Pro Ser Gln Ser Leu Ser Leu Thr Cys Ser Val Thr Gly
    50                  55                  60

Tyr Ser Ile Thr Thr Asn Tyr Asn Trp Asn Trp Ile Arg Gln Phe Pro
65                  70                  75                  80

Gly Asn Lys Leu Glu Trp Met Gly Tyr Ile Arg Tyr Asp Gly Thr Ser
                85                  90                  95

Glu Tyr Thr Pro Ser Leu Lys Asn Arg Val Ser Ile Thr Arg Asp Thr
            100                 105                 110

Ser Met Asn Gln Phe Phe Leu Arg Leu Thr Ser Val Thr Pro Glu Asp
        115                 120                 125

Thr Ala Thr Tyr Tyr Cys Ala Arg Leu Asp Tyr Trp Gly Gln Gly Thr
    130                 135                 140

Leu Val Thr Val Ser Ser Gly Ser Ser Ser Ala Ser Thr Lys Gly Pro
145                 150                 155                 160

Ser Val Phe Pro Leu Ala Pro Ser Ser Lys Ser Thr Ser Gly Gly Thr
                165                 170                 175

Ala Ala Leu Gly Cys Leu Val Lys Asp Tyr Phe Pro Glu Pro Val Thr
            180                 185                 190

Val Ser Trp Asn Ser Gly Ala Leu Thr Ser Gly Val His Thr Phe Pro
        195                 200                 205

Ala Val Leu Gln Ser Ser Gly Leu Tyr Ser Leu Ser Ser Val Val Thr
    210                 215                 220

Val Pro Ser Ser Ser Leu Gly Thr Gln Thr Tyr Ile Cys Asn Val Asn
225                 230                 235                 240

His Lys Pro Ser Asn Thr Lys Val Asp Lys Lys Val Glu Pro Lys Ser
                245                 250                 255

Cys Asp Lys Thr His Thr Cys Pro Pro Cys Pro Ala Pro Glu Leu Leu
            260                 265                 270

Gly Gly Pro Ser Val Phe Leu Phe Pro Pro Lys Pro Lys Asp Thr Leu
        275                 280                 285

Met Ile Ser Arg Thr Pro Glu Val Thr Cys Val Val Val Asp Val Ser
    290                 295                 300

His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Asn Ser Thr
                325                 330                 335

Tyr Arg Val Val Ser Val Leu Thr Val Leu His Gln Asp Trp Leu Asn
            340                 345                 350

Gly Lys Glu Tyr Lys Cys Lys Val Ser Asn Lys Ala Leu Pro Ala Pro
        355                 360                 365

Ile Glu Lys Thr Ile Ser Lys Ala Lys Gly Gln Pro Arg Glu Pro Gln
    370                 375                 380

Val Tyr Thr Leu Pro Pro Ser Arg Asp Glu Leu Thr Lys Asn Gln Val
385                 390                 395                 400

Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
```

```
            420                 425                 430

Pro Val Leu Asp Ser Asp Gly Ser Phe Phe Leu Tyr Ser Lys Leu Thr
        435                 440                 445

Val Asp Lys Ser Arg Trp Gln Gln Gly Asn Val Phe Ser Cys Ser Val
    450                 455                 460

Met His Glu Ala Leu His Asn His Tyr Thr Gln Lys Ser Leu Ser Leu
465                 470                 475                 480

Ser Pro Gly Lys


<210> SEQ ID NO 21
<211> LENGTH: 729
<212> TYPE: PRT
<213> ORGANISM: Artificial Sequence
<220> FEATURE:
<223> OTHER INFORMATION: Protein construct expressed from SEQ ID NO: 3

<400> SEQUENCE: 21

Met Asn Phe Gly Phe Ser Leu Ile Phe Leu Val Leu Val Leu Lys Gly
1               5                   10                  15

Val Gln Cys Glu Val Lys Leu Val Pro Arg Gln Leu Asp Tyr Lys Asp
            20                  25                  30

Asp Asp Asp Lys Glu Leu Asp Ile Gln Leu Gln Gln Ser Gly Pro Gly
        35                  40                  45

Leu Val Lys Pro Ser Gln Ser Leu Ser Leu Thr Cys Ser Val Thr Gly
    50                  55                  60

Tyr Ser Ile Thr Thr Asn Tyr Asn Trp Asn Trp Ile Arg Gln Phe Pro
65                  70                  75                  80

Gly Asn Lys Leu Glu Trp Met Gly Tyr Ile Arg Tyr Asp Gly Thr Ser
                85                  90                  95

Glu Tyr Thr Pro Ser Leu Lys Asn Arg Val Ser Ile Thr Arg Asp Thr
            100                 105                 110

Ser Met Asn Gln Phe Phe Leu Arg Leu Thr Ser Val Thr Pro Glu Asp
        115                 120                 125

Thr Ala Thr Tyr Tyr Cys Ala Arg Leu Asp Tyr Trp Gly Gln Gly Thr
    130                 135                 140

Leu Val Thr Val Ser Ser Gly Ser Ser Ser Ala Ser Thr Lys Gly Pro
145                 150                 155                 160

Ser Val Phe Pro Leu Ala Pro Ser Ser Lys Ser Thr Ser Gly Gly Thr
                165                 170                 175

Ala Ala Leu Gly Cys Leu Val Lys Asp Tyr Phe Pro Glu Pro Val Thr
            180                 185                 190

Val Ser Trp Asn Ser Gly Ala Leu Thr Ser Gly Val His Thr Phe Pro
        195                 200                 205

Ala Val Leu Gln Ser Ser Gly Leu Tyr Ser Leu Ser Ser Val Val Thr
    210                 215                 220

Val Pro Ser Ser Ser Leu Gly Thr Gln Thr Tyr Ile Cys Asn Val Asn
225                 230                 235                 240

His Lys Pro Ser Asn Thr Lys Val Asp Lys Lys Val Glu Pro Lys Ser
                245                 250                 255

Cys Asp Lys Thr His Thr Cys Pro Pro Cys Pro Ala Pro Glu Leu Leu
            260                 265                 270

Gly Gly Pro Ser Val Phe Leu Phe Pro Pro Lys Pro Lys Asp Thr Leu
        275                 280                 285

Met Ile Ser Arg Thr Pro Glu Val Thr Cys Val Val Val Asp Val Ser
    290                 295                 300
```

```
His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Ala Ser Thr
                325                 330                 335

Tyr Arg Val Val Ser Val Leu Thr Val Leu His Gln Asp Trp Leu Asn
            340                 345                 350

Gly Lys Glu Tyr Lys Cys Lys Val Ser Asn Lys Ala Leu Pro Ala Pro
        355                 360                 365

Ile Glu Lys Thr Ile Ser Lys Ala Lys Gly Gln Pro Arg Glu Pro Gln
    370                 375                 380

Val Tyr Thr Leu Pro Pro Ser Arg Asp Glu Leu Thr Lys Asn Gln Val
385                 390                 395                 400

Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Lys Leu Thr
        435                 440                 445

Val Asp Lys Ser Arg Trp Gln Gln Gly Asn Val Phe Ser Cys Ser Val
    450                 455                 460

Met His Glu Ala Leu His Asn His Tyr Thr Gln Lys Ser Leu Ser Leu
465                 470                 475                 480

Ser Pro Gly Lys Glu Phe Gln Val Gln Leu Gln Gln Pro Gly Ala Glu
                485                 490                 495

Leu Val Lys Pro Gly Ala Ser Val Lys Met Ser Cys Lys Ala Ser Gly
            500                 505                 510

Tyr Thr Phe Thr Ser Tyr Asn Met His Trp Val Lys Gln Thr Pro Gly
        515                 520                 525

Arg Gly Leu Glu Trp Ile Gly Ala Ile Tyr Pro Gly Asn Gly Asp Thr
    530                 535                 540

Ser Tyr Asn Gln Lys Phe Lys Gly Lys Ala Thr Leu Thr Ala Asp Lys
545                 550                 555                 560

Ser Ser Ser Thr Ala Tyr Met Gln Leu Ser Ser Leu Thr Ser Glu Asp
                565                 570                 575

Ser Ala Val Tyr Tyr Cys Ala Arg Ser Thr Tyr Tyr Gly Gly Asp Trp
            580                 585                 590

Tyr Phe Asn Val Trp Gly Ala Gly Thr Thr Val Thr Val Ser Ser Gly
        595                 600                 605

Gly Gly Gly Ser Gly Gly Gly Gly Ser Gly Gly Gly Gly Ser Gln Ile
    610                 615                 620

Val Leu Ser Gln Ser Pro Ala Ile Leu Ser Ala Ser Pro Gly Glu Lys
625                 630                 635                 640

Val Thr Met Thr Cys Arg Ala Ser Ser Ser Val Ser Tyr Ile His Trp
                645                 650                 655

Phe Gln Gln Lys Pro Gly Ser Ser Pro Lys Pro Trp Ile Tyr Ala Thr
            660                 665                 670

Ser Asn Leu Ala Ser Gly Val Pro Val Arg Phe Ser Gly Ser Gly Ser
        675                 680                 685

Gly Thr Ser Tyr Ser Leu Thr Ile Ser Arg Val Glu Ala Glu Asp Ala
    690                 695                 700

Ala Thr Tyr Tyr Cys Gln Gln Trp Thr Ser Asn Pro Pro Thr Phe Gly
705                 710                 715                 720
```

```
Gly Gly Thr Lys Leu Glu Ile Lys Arg
                725


<210> SEQ ID NO 22
<211> LENGTH: 957
<212> TYPE: PRT
<213> ORGANISM: Artificial Sequence
<220> FEATURE:
<223> OTHER INFORMATION: Protein construct expressed from SEQ ID NO: 4

<400> SEQUENCE: 22

Met Asn Phe Gly Phe Ser Leu Ile Phe Leu Val Leu Val Leu Lys Gly
1               5                   10                  15

Val Gln Cys Glu Val Lys Leu Val Pro Arg Gln Leu Asp Tyr Lys Asp
            20                  25                  30

Asp Asp Asp Lys Glu Leu Asp Ile Gln Leu Gln Gln Ser Gly Pro Gly
        35                  40                  45

Leu Val Lys Pro Ser Gln Ser Leu Ser Leu Thr Cys Ser Val Thr Gly
    50                  55                  60

Tyr Ser Ile Thr Thr Asn Tyr Asn Trp Asn Trp Ile Arg Gln Phe Pro
65                  70                  75                  80

Gly Asn Lys Leu Glu Trp Met Gly Tyr Ile Arg Tyr Asp Gly Thr Ser
                85                  90                  95

Glu Tyr Thr Pro Ser Leu Lys Asn Arg Val Ser Ile Thr Arg Asp Thr
            100                 105                 110

Ser Met Asn Gln Phe Phe Leu Arg Leu Thr Ser Val Thr Pro Glu Asp
        115                 120                 125

Thr Ala Thr Tyr Tyr Cys Ala Arg Leu Asp Tyr Trp Gly Gln Gly Thr
    130                 135                 140

Leu Val Thr Val Ser Ser Gly Ser Ser Ser Ala Ser Thr Lys Gly Pro
145                 150                 155                 160

Ser Val Phe Pro Leu Ala Pro Ser Ser Lys Ser Thr Ser Gly Gly Thr
                165                 170                 175

Ala Ala Leu Gly Cys Leu Val Lys Asp Tyr Phe Pro Glu Pro Val Thr
            180                 185                 190

Val Ser Trp Asn Ser Gly Ala Leu Thr Ser Gly Val His Thr Phe Pro
        195                 200                 205

Ala Val Leu Gln Ser Ser Gly Leu Tyr Ser Leu Ser Ser Val Val Thr
    210                 215                 220

Val Pro Ser Ser Ser Leu Gly Thr Gln Thr Tyr Ile Cys Asn Val Asn
225                 230                 235                 240

His Lys Pro Ser Asn Thr Lys Val Asp Lys Lys Val Glu Pro Lys Ser
                245                 250                 255

Cys Asp Lys Thr His Thr Cys Pro Pro Cys Pro Ala Pro Glu Leu Leu
            260                 265                 270

Gly Gly Pro Ser Val Phe Leu Phe Pro Pro Lys Pro Lys Asp Thr Leu
        275                 280                 285

Met Ile Ser Arg Thr Pro Glu Val Thr Cys Val Val Val Asp Val Ser
    290                 295                 300

His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Ala Ser Thr
                325                 330                 335

Tyr Arg Val Val Ser Val Leu Thr Val Leu His Gln Asp Trp Leu Asn
            340                 345                 350
```

```
Gly Lys Glu Tyr Lys Cys Lys Val Ser Asn Lys Ala Leu Pro Ala Pro
        355                 360                 365

Ile Glu Lys Thr Ile Ser Lys Ala Lys Gly Gln Pro Arg Glu Pro Gln
    370                 375                 380

Val Tyr Thr Leu Pro Pro Ser Arg Asp Glu Leu Thr Lys Asn Gln Val
385                 390                 395                 400

Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Lys Leu Thr
        435                 440                 445

Val Asp Lys Ser Arg Trp Gln Gln Gly Asn Val Phe Ser Cys Ser Val
    450                 455                 460

Met His Glu Ala Leu His Asn His Tyr Thr Gln Lys Ser Leu Ser Leu
465                 470                 475                 480

Ser Pro Gly Lys Leu Glu Gly Pro Glu Glu Thr Val Thr Gln Asp Cys
                485                 490                 495

Leu Gln Leu Ile Ala Asp Ser Glu Thr Pro Thr Ile Gln Lys Gly Ser
            500                 505                 510

Tyr Thr Phe Val Pro Trp Leu Leu Ser Phe Lys Arg Gly Ser Ala Leu
        515                 520                 525

Glu Glu Lys Glu Asn Lys Ile Leu Val Lys Glu Thr Gly Tyr Phe Phe
    530                 535                 540

Ile Tyr Gly Gln Val Leu Tyr Thr Asp Lys Thr Tyr Ala Met Gly His
545                 550                 555                 560

Leu Ile Gln Arg Lys Lys Val His Val Phe Gly Asp Glu Leu Ser Leu
                565                 570                 575

Val Thr Leu Phe Arg Cys Ile Gln Asn Met Pro Glu Thr Leu Pro Asn
            580                 585                 590

Asn Ser Cys Tyr Ser Ala Gly Ile Ala Lys Leu Glu Glu Gly Asp Glu
        595                 600                 605

Leu Gln Leu Ala Ile Pro Arg Glu Asn Ala Gln Ile Ser Leu Asp Gly
    610                 615                 620

Asp Val Thr Phe Phe Gly Ala Leu Lys Leu Leu Gly Gly Gly Gly Ser
625                 630                 635                 640

Gly Gly Gly Gly Ser Gly Pro Glu Glu Thr Val Thr Gln Asp Cys Leu
                645                 650                 655

Gln Leu Ile Ala Asp Ser Glu Thr Pro Thr Ile Gln Lys Gly Ser Tyr
            660                 665                 670

Thr Phe Val Pro Trp Leu Leu Ser Phe Lys Arg Gly Ser Ala Leu Glu
        675                 680                 685

Glu Lys Glu Asn Lys Ile Leu Val Lys Glu Thr Gly Tyr Phe Phe Ile
    690                 695                 700

Tyr Gly Gln Val Leu Tyr Thr Asp Lys Thr Tyr Ala Met Gly His Leu
705                 710                 715                 720

Ile Gln Arg Lys Lys Val His Val Phe Gly Asp Glu Leu Ser Leu Val
                725                 730                 735

Thr Leu Phe Arg Cys Ile Gln Asn Met Pro Glu Thr Leu Pro Asn Asn
            740                 745                 750

Ser Cys Tyr Ser Ala Gly Ile Ala Lys Leu Glu Glu Gly Asp Glu Leu
        755                 760                 765

Gln Leu Ala Ile Pro Arg Glu Asn Ala Gln Ile Ser Leu Asp Gly Asp
```

```
    770                 775                 780

Val Thr Phe Phe Gly Ala Leu Lys Leu Leu Gly Gly Gly Gly Ser Gly
785                 790                 795                 800

Gly Gly Gly Ser Gln Phe Ala Ala Gly Pro Glu Glu Thr Val Thr Gln
                805                 810                 815

Asp Cys Leu Gln Leu Ile Ala Asp Ser Glu Thr Pro Thr Ile Gln Lys
            820                 825                 830

Gly Ser Tyr Thr Phe Val Pro Trp Leu Leu Ser Phe Lys Arg Gly Ser
        835                 840                 845

Ala Leu Glu Glu Lys Glu Asn Lys Ile Leu Val Lys Glu Thr Gly Tyr
    850                 855                 860

Phe Phe Ile Tyr Gly Gln Val Leu Tyr Thr Asp Lys Thr Tyr Ala Met
865                 870                 875                 880

Gly His Leu Ile Gln Arg Lys Lys Val His Val Phe Gly Asp Glu Leu
                885                 890                 895

Ser Leu Val Thr Leu Phe Arg Cys Ile Gln Asn Met Pro Glu Thr Leu
            900                 905                 910

Pro Asn Asn Ser Cys Tyr Ser Ala Gly Ile Ala Lys Leu Glu Glu Gly
        915                 920                 925

Asp Glu Leu Gln Leu Ala Ile Pro Arg Glu Asn Ala Gln Ile Ser Leu
    930                 935                 940

Asp Gly Asp Val Thr Phe Phe Gly Ala Leu Lys Leu Leu
945                 950                 955


<210> SEQ ID NO 23
<211> LENGTH: 262
<212> TYPE: PRT
<213> ORGANISM: Artificial Sequence
<220> FEATURE:
<223> OTHER INFORMATION: Protein construct expressed from SEQ ID NO: 5

<400> SEQUENCE: 23

Met Asn Phe Gly Phe Ser Leu Ile Phe Leu Val Leu Val Leu Lys Gly
1               5                   10                  15

Val Gln Cys Glu Val Lys Leu Val Pro Arg Gln Leu Asp Tyr Lys Asp
            20                  25                  30

Asp Asp Asp Lys Glu Leu Asp Ile Val Met Thr Gln Asn Pro Leu Ser
        35                  40                  45

Leu Pro Val Ser Leu Gly Asp Glu Ala Ser Ile Ser Cys Arg Ser Ser
    50                  55                  60

Gln Ser Leu Glu Asn Ser Asn Gly Asn Thr Phe Leu Asn Trp Phe Phe
65                  70                  75                  80

Gln Lys Pro Gly Gln Ser Pro Gln Leu Leu Ile Tyr Arg Val Ser Asn
                85                  90                  95

Arg Phe Ser Gly Val Pro Asp Arg Phe Ser Gly Ser Gly Ser Gly Thr
            100                 105                 110

Asp Phe Thr Leu Lys Ile Ser Arg Val Glu Ala Glu Asp Leu Gly Val
        115                 120                 125

Tyr Phe Cys Leu Gln Val Thr His Val Pro Tyr Thr Phe Gly Gly Gly
    130                 135                 140

Thr Thr Leu Glu Ile Lys Gly Ser Glu Ile Lys Arg Thr Val Ala Ala
145                 150                 155                 160

Pro Ser Val Phe Ile Phe Pro Pro Ser Asp Glu Gln Leu Lys Ser Gly
                165                 170                 175

Thr Ala Ser Val Val Cys Leu Leu Asn Asn Phe Tyr Pro Arg Glu Ala
```

```
            180                 185                 190

Lys Val Gln Trp Lys Val Asp Asn Ala Leu Gln Ser Gly Asn Ser Gln
        195                 200                 205

Glu Ser Val Thr Glu Gln Asp Ser Lys Asp Ser Thr Tyr Ser Leu Ser
    210                 215                 220

Ser Thr Leu Thr Leu Ser Lys Ala Asp Tyr Glu Lys His Lys Val Tyr
225                 230                 235                 240

Ala Cys Glu Val Thr His Gln Gly Leu Ser Ser Pro Val Thr Lys Ser
                245                 250                 255

Phe Asn Arg Gly Glu Cys
            260


<210> SEQ ID NO 24
<211> LENGTH: 635
<212> TYPE: PRT
<213> ORGANISM: Artificial Sequence
<220> FEATURE:
<223> OTHER INFORMATION: Protein construct expressed from SEQ ID NO: 6

<400> SEQUENCE: 24

Met Asn Phe Gly Phe Ser Leu Ile Phe Leu Val Leu Val Leu Lys Gly
1               5                   10                  15

Val Gln Cys Glu Val Lys Leu Val Pro Arg Gln Leu Gln Val Gln Leu
            20                  25                  30

Leu Gln Ser Gly Pro Glu Leu Val Lys Pro Gly Ala Ser Val Lys Leu
        35                  40                  45

Ser Cys Lys Ala Ser Gly Tyr Ser Phe Thr Ser Tyr Asp Ile Asn Trp
    50                  55                  60

Val Lys Gln Arg Pro Gly Gln Gly Leu Glu Trp Val Gly Trp Ile Tyr
65                  70                  75                  80

Pro Arg Asp Gly Asp Thr Lys Tyr Asn Glu Lys Phe Lys Gly Lys Ala
                85                  90                  95

Ile Leu Thr Val Asp Thr Ser Ser Asn Thr Ala Tyr Met Asn Leu His
            100                 105                 110

Ser Leu Thr Ser Glu Asp Ser Ala Val Tyr Phe Cys Ala Arg Leu Thr
        115                 120                 125

Gly Pro Tyr Trp Tyr Phe Asp Val Trp Gly Thr Gly Thr Thr Val Thr
    130                 135                 140

Val Ser Ser Gly Ser Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
```

```
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

Lys Glu Leu Pro Gly Thr Ala Pro Thr Ser Ser Ser Thr Ser Ser Ser
                485                 490                 495

Thr Ala Glu Ala Gln Gln Gln Gln Gln Gln Gln Gln Gln Gln Gln Gln
            500                 505                 510

His Leu Glu Gln Leu Leu Met Asp Leu Gln Glu Leu Leu Ser Arg Met
        515                 520                 525

Glu Asn Tyr Arg Asn Leu Lys Leu Pro Arg Met Leu Thr Phe Lys Phe
    530                 535                 540

Tyr Leu Pro Lys Gln Ala Thr Glu Leu Lys Asp Leu Gln Cys Leu Glu
545                 550                 555                 560

Asp Glu Leu Gly Pro Leu Arg His Val Leu Asp Leu Thr Gln Ser Lys
                565                 570                 575

Ser Phe Gln Leu Glu Asp Ala Glu Asn Phe Ile Ser Asn Ile Arg Val
            580                 585                 590

Thr Val Val Lys Leu Lys Gly Ser Asp Asn Thr Phe Glu Cys Gln Phe
        595                 600                 605

Asp Asp Glu Ser Ala Thr Val Val Asp Phe Leu Arg Arg Trp Ile Ala
    610                 615                 620

Phe Cys Gln Ser Ile Ile Ser Thr Ser Pro Gln
625                 630                 635
```

```
<210> SEQ ID NO 25
<211> LENGTH: 732
<212> TYPE: PRT
<213> ORGANISM: Artificial Sequence
<220> FEATURE:
<223> OTHER INFORMATION: Protein construct expressed from SEQ ID NO: 7

<400> SEQUENCE: 25

Met Asn Phe Gly Phe Ser Leu Ile Phe Leu Val Leu Val Leu Lys Gly
```

```
1               5                   10                  15

Val Gln Cys Glu Val Lys Leu Val Pro Arg Gln Leu Gln Val Gln Leu
            20                  25                  30

Leu Gln Ser Gly Pro Glu Leu Val Lys Pro Gly Ala Ser Val Lys Leu
        35                  40                  45

Ser Cys Lys Ala Ser Gly Tyr Ser Phe Thr Ser Tyr Asp Ile Asn Trp
    50                  55                  60

Val Lys Gln Arg Pro Gly Gln Gly Leu Glu Trp Val Gly Trp Ile Tyr
65                  70                  75                  80

Pro Arg Asp Gly Asp Thr Lys Tyr Asn Glu Lys Phe Lys Gly Lys Ala
                85                  90                  95

Ile Leu Thr Val Asp Thr Ser Ser Asn Thr Ala Tyr Met Asn Leu His
            100                 105                 110

Ser Leu Thr Ser Glu Asp Ser Ala Val Tyr Phe Cys Ala Arg Leu Thr
        115                 120                 125

Gly Pro Tyr Trp Tyr Phe Asp Val Trp Gly Thr Gly Thr Thr Val Thr
    130                 135                 140

Val Ser Ser Gly Ser Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Ala Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430
```

```
Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

Lys Glu Phe Asp Ile Gln Met Thr Gln Ser Pro Ser Ser Met Ser Val
                485                 490                 495

Ser Leu Gly Asp Thr Val Ser Ile Thr Cys His Ala Ser Gln Gly Ile
            500                 505                 510

Ser Ser Asn Ile Gly Trp Leu Gln Gln Lys Pro Gly Lys Ser Phe Lys
        515                 520                 525

Gly Leu Ile Tyr His Gly Thr Asn Leu Glu Asp Gly Val Pro Ser Arg
    530                 535                 540

Phe Ser Gly Ser Gly Ser Gly Ala Asp Tyr Ser Leu Thr Ile Ser Ser
545                 550                 555                 560

Leu Glu Ser Glu Asp Phe Ala Asp Tyr Tyr Cys Val Gln Tyr Ala Gln
                565                 570                 575

Phe Pro Tyr Thr Phe Gly Gly Gly Thr Lys Leu Glu Leu Lys Arg Gly
            580                 585                 590

Gly Gly Gly Ser Gly Gly Gly Gly Ser Gly Gly Gly Gly Ser Ser Gly
        595                 600                 605

Gly Gly Ser Gln Val Gln Leu Gln Gln Ser Gly Pro Glu Leu Val Lys
    610                 615                 620

Pro Gly Ala Ser Val Lys Ile Ser Cys Lys Ala Ser Gly Tyr Ala Phe
625                 630                 635                 640

Ser Ser Ser Trp Met Asp Trp Val Lys Gln Arg Pro Gly Gln Gly Leu
                645                 650                 655

Glu Trp Ile Gly Arg Ile Tyr Pro Gly Asp Gly Asp Thr Asn Tyr Asn
            660                 665                 670

Gly Lys Phe Lys Gly Lys Ala Thr Leu Thr Ala Asp Lys Ser Ser Ser
        675                 680                 685

Thr Ala Tyr Met Gln Leu Ser Ser Leu Thr Ser Val Asp Ser Ala Val
    690                 695                 700

Tyr Phe Cys Ala Arg Ser Ile Thr Thr Val Val Gly Trp Tyr Phe Asp
705                 710                 715                 720

Val Trp Gly Ala Gly Thr Thr Val Thr Val Ser Ser
                725                 730


<210> SEQ ID NO 26
<211> LENGTH: 726
<212> TYPE: PRT
<213> ORGANISM: Artificial Sequence
<220> FEATURE:
<223> OTHER INFORMATION: Protein construct expressed from SEQ ID NO: 8

<400> SEQUENCE: 26

Met Asn Phe Gly Phe Ser Leu Ile Phe Leu Val Leu Val Leu Lys Gly
1               5                   10                  15

Val Gln Cys Glu Val Lys Leu Val Pro Arg Gln Leu Gln Val Gln Leu
            20                  25                  30

Leu Gln Ser Gly Pro Glu Leu Val Lys Pro Gly Ala Ser Val Lys Leu
        35                  40                  45

Ser Cys Lys Ala Ser Gly Tyr Ser Phe Thr Ser Tyr Asp Ile Asn Trp
    50                  55                  60
```

```
Val Lys Gln Arg Pro Gly Gln Gly Leu Glu Trp Val Gly Trp Ile Tyr
65                  70                  75                  80

Pro Arg Asp Gly Asp Thr Lys Tyr Asn Glu Lys Phe Lys Gly Lys Ala
                85                  90                  95

Ile Leu Thr Val Asp Thr Ser Ser Asn Thr Ala Tyr Met Asn Leu His
            100                 105                 110

Ser Leu Thr Ser Glu Asp Ser Ala Val Tyr Phe Cys Ala Arg Leu Thr
        115                 120                 125

Gly Pro Tyr Trp Tyr Phe Asp Val Trp Gly Thr Gly Thr Thr Val Thr
    130                 135                 140

Val Ser Ser Gly Ser Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Ala Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480
```

```
Lys Glu Phe Gln Val Gln Leu Gln Gln Pro Gly Ala Glu Leu Val Lys
                485                 490                 495

Pro Gly Ala Ser Val Lys Met Ser Cys Lys Ala Ser Gly Tyr Thr Phe
            500                 505                 510

Thr Ser Tyr Asn Met His Trp Val Lys Gln Thr Pro Gly Arg Gly Leu
        515                 520                 525

Glu Trp Ile Gly Ala Ile Tyr Pro Gly Asn Gly Asp Thr Ser Tyr Asn
    530                 535                 540

Gln Lys Phe Lys Gly Lys Ala Thr Leu Thr Ala Asp Lys Ser Ser Ser
545                 550                 555                 560

Thr Ala Tyr Met Gln Leu Ser Ser Leu Thr Ser Glu Asp Ser Ala Val
                565                 570                 575

Tyr Tyr Cys Ala Arg Ser Thr Tyr Tyr Gly Gly Asp Trp Tyr Phe Asn
            580                 585                 590

Val Trp Gly Ala Gly Thr Thr Val Thr Val Ser Ser Gly Gly Gly Gly
        595                 600                 605

Ser Gly Gly Gly Gly Ser Gly Gly Gly Gly Ser Gln Ile Val Leu Ser
    610                 615                 620

Gln Ser Pro Ala Ile Leu Ser Ala Ser Pro Gly Glu Lys Val Thr Met
625                 630                 635                 640

Thr Cys Arg Ala Ser Ser Ser Val Ser Tyr Ile His Trp Phe Gln Gln
                645                 650                 655

Lys Pro Gly Pro Ser Ser Lys Pro Trp Ile Tyr Ala Thr Ser Asn Leu
            660                 665                 670

Ala Ser Gly Val Pro Val Arg Phe Ser Gly Ser Gly Ser Gly Thr Ser
        675                 680                 685

Tyr Ser Leu Thr Ile Ser Arg Val Glu Ala Glu Asp Ala Ala Thr Tyr
    690                 695                 700

Tyr Cys Gln Gln Trp Thr Ser Asn Pro Pro Thr Phe Gly Gly Gly Thr
705                 710                 715                 720

Lys Leu Glu Ile Lys Arg
                725


<210> SEQ ID NO 27
<211> LENGTH: 481
<212> TYPE: PRT
<213> ORGANISM: Artificial Sequence
<220> FEATURE:
<223> OTHER INFORMATION: Protein construct expressed from SEQ ID NO: 9

<400> SEQUENCE: 27

Met Asn Phe Gly Phe Ser Leu Ile Phe Leu Val Leu Val Leu Lys Gly
1               5                   10                  15

Val Gln Cys Glu Val Lys Leu Val Pro Arg Gln Leu Gln Val Gln Leu
            20                  25                  30

Leu Gln Ser Gly Pro Glu Leu Val Lys Pro Gly Ala Ser Val Lys Leu
        35                  40                  45

Ser Cys Lys Ala Ser Gly Tyr Ser Phe Thr Ser Tyr Asp Ile Asn Trp
    50                  55                  60

Val Lys Gln Arg Pro Gly Gln Gly Leu Glu Trp Val Gly Trp Ile Tyr
65                  70                  75                  80

Pro Arg Asp Gly Asp Thr Lys Tyr Asn Glu Lys Phe Lys Gly Lys Ala
                85                  90                  95

Ile Leu Thr Val Asp Thr Ser Ser Asn Thr Ala Tyr Met Asn Leu His
            100                 105                 110
```

```
Ser Leu Thr Ser Glu Asp Ser Ala Val Tyr Phe Cys Ala Arg Leu Thr
        115                 120                 125

Gly Pro Tyr Trp Tyr Phe Asp Val Trp Gly Thr Gly Thr Thr Val Thr
    130                 135                 140

Val Ser Ser Gly Ser Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

Lys
```

<210> SEQ ID NO 28
<211> LENGTH: 907
<212> TYPE: PRT
<213> ORGANISM: Artificial Sequence
<220> FEATURE:
<223> OTHER INFORMATION: Protein construct expressed from SEQ ID NO: 10

<400> SEQUENCE: 28

```
Met Asn Phe Gly Phe Ser Leu Ile Phe Leu Val Leu Val Leu Lys Gly
1               5                   10                  15

Val Gln Cys Glu Val Lys Leu Val Pro Arg Gln Leu Gln Val Gln Leu
            20                  25                  30

Leu Gln Ser Gly Pro Glu Leu Val Lys Pro Gly Ala Ser Val Lys Leu
        35                  40                  45

Ser Cys Lys Ala Ser Gly Tyr Ser Phe Thr Ser Tyr Asp Ile Asn Trp
    50                  55                  60

Val Lys Gln Arg Pro Gly Gln Gly Leu Glu Trp Val Gly Trp Ile Tyr
65                  70                  75                  80

Pro Arg Asp Gly Asp Thr Lys Tyr Asn Glu Lys Phe Lys Gly Lys Ala
                85                  90                  95

Ile Leu Thr Val Asp Thr Ser Ser Asn Thr Ala Tyr Met Asn Leu His
            100                 105                 110

Ser Leu Thr Ser Glu Asp Ser Ala Val Tyr Phe Cys Ala Arg Leu Thr
        115                 120                 125

Gly Pro Tyr Trp Tyr Phe Asp Val Trp Gly Thr Gly Thr Thr Val Thr
    130                 135                 140

Val Ser Ser Gly Ser Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Ala Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415
```

```
Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

Lys Glu Phe Gly Gly Gly Ser Gly Gln Leu Glu Thr Ala Lys Glu Pro
                485                 490                 495

Cys Met Ala Lys Phe Gly Pro Leu Pro Ser Lys Trp Gln Met Ala Ser
            500                 505                 510

Ser Glu Pro Pro Cys Val Asn Lys Val Ser Asp Trp Lys Leu Glu Ile
        515                 520                 525

Leu Gln Asn Gly Leu Tyr Leu Ile Tyr Gly Gln Val Ala Pro Asn Ala
    530                 535                 540

Asn Tyr Asn Asp Val Ala Pro Phe Glu Val Arg Leu Tyr Lys Asn Lys
545                 550                 555                 560

Asp Met Ile Gln Thr Leu Thr Asn Lys Ser Lys Ile Gln Asn Val Gly
                565                 570                 575

Gly Thr Tyr Glu Leu His Val Gly Asp Thr Ile Asp Leu Ile Phe Asn
            580                 585                 590

Ser Glu His Gln Val Leu Lys Asn Asn Thr Tyr Trp Gly Ile Ile Leu
        595                 600                 605

Leu Ala Asn Pro Gln Phe Ile Ser Gly Gly Gly Ser Gly Gly Gly Ser
    610                 615                 620

Gly Gly Gly Ser Gly Gly Gly Ser Gln Leu Glu Thr Ala Lys Glu Pro
625                 630                 635                 640

Cys Met Ala Lys Phe Gly Pro Leu Pro Ser Lys Trp Gln Met Ala Ser
                645                 650                 655

Ser Glu Pro Pro Cys Val Asn Lys Val Ser Asp Trp Lys Leu Glu Ile
            660                 665                 670

Leu Gln Asn Gly Leu Tyr Leu Ile Tyr Gly Gln Val Ala Pro Asn Ala
        675                 680                 685

Asn Tyr Asn Asp Val Ala Pro Phe Glu Val Arg Leu Tyr Lys Asn Lys
    690                 695                 700

Asp Met Ile Gln Thr Leu Thr Asn Lys Ser Lys Ile Gln Asn Val Gly
705                 710                 715                 720

Gly Thr Tyr Glu Leu His Val Gly Asp Thr Ile Asp Leu Ile Phe Asn
                725                 730                 735

Ser Glu His Gln Val Leu Lys Asn Asn Thr Tyr Trp Gly Ile Ile Leu
            740                 745                 750

Leu Ala Asn Pro Gln Phe Ile Ser Gly Gly Gly Gly Ser Gly Gly Gly
        755                 760                 765

Ser Gly Gly Gly Ser Gly Gly Gly Ser Gln Phe Gln Leu Glu Thr Ala
    770                 775                 780

Lys Glu Pro Cys Met Ala Lys Phe Gly Pro Leu Pro Ser Lys Trp Gln
785                 790                 795                 800

Met Ala Ser Ser Glu Pro Pro Cys Val Asn Lys Val Ser Asp Trp Lys
                805                 810                 815

Leu Glu Ile Leu Gln Asn Gly Leu Tyr Leu Ile Tyr Gly Gln Val Ala
            820                 825                 830
```

```
Pro Asn Ala Asn Tyr Asn Asp Val Ala Pro Phe Glu Val Arg Leu Tyr
        835                 840                 845

Lys Asn Lys Asp Met Ile Gln Thr Leu Thr Asn Lys Ser Lys Ile Gln
    850                 855                 860

Asn Val Gly Gly Thr Tyr Glu Leu His Val Gly Asp Thr Ile Asp Leu
865                 870                 875                 880

Ile Phe Asn Ser Glu His Gln Val Leu Lys Asn Asn Thr Tyr Trp Gly
                885                 890                 895

Ile Ile Leu Leu Ala Asn Pro Gln Phe Ile Ser
            900                 905


<210> SEQ ID NO 29
<211> LENGTH: 1136
<212> TYPE: PRT
<213> ORGANISM: Artificial Sequence
<220> FEATURE:
<223> OTHER INFORMATION: Protein construct expressed from SEQ ID NO: 11

<400> SEQUENCE: 29

Met Asn Phe Gly Phe Ser Leu Ile Phe Leu Val Leu Val Leu Lys Gly
1               5                   10                  15

Val Gln Cys Glu Val Lys Leu Val Pro Arg Gln Leu Gln Val Gln Leu
            20                  25                  30

Leu Gln Ser Gly Pro Glu Leu Val Lys Pro Gly Ala Ser Val Lys Leu
        35                  40                  45

Ser Cys Lys Ala Ser Gly Tyr Ser Phe Thr Ser Tyr Asp Ile Asn Trp
    50                  55                  60

Val Lys Gln Arg Pro Gly Gln Gly Leu Glu Trp Val Gly Trp Ile Tyr
65                  70                  75                  80

Pro Arg Asp Gly Asp Thr Lys Tyr Asn Glu Lys Phe Lys Gly Lys Ala
                85                  90                  95

Ile Leu Thr Val Asp Thr Ser Ser Asn Thr Ala Tyr Met Asn Leu His
            100                 105                 110

Ser Leu Thr Ser Glu Asp Ser Ala Val Tyr Phe Cys Ala Arg Leu Thr
        115                 120                 125

Gly Pro Tyr Trp Tyr Phe Asp Val Trp Gly Thr Gly Thr Thr Val Thr
    130                 135                 140

Val Ser Ser Gly Ser Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285
```

```
Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Ala Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

Lys Glu Phe Gly Gly Gly Ser Gly Thr Glu Pro Arg Pro Ala Leu Thr
                485                 490                 495

Ile Thr Thr Ser Pro Asn Leu Gly Thr Arg Glu Asn Asn Ala Asp Gln
            500                 505                 510

Val Thr Pro Val Ser His Ile Gly Cys Pro Asn Thr Thr Gln Gln Gly
        515                 520                 525

Ser Pro Val Phe Ala Lys Leu Leu Ala Lys Asn Gln Ala Ser Leu Cys
    530                 535                 540

Asn Thr Thr Leu Asn Trp His Ser Gln Asp Gly Ala Gly Ser Ser Tyr
545                 550                 555                 560

Leu Ser Gln Gly Leu Arg Tyr Glu Glu Asp Lys Lys Glu Leu Val Val
                565                 570                 575

Asp Ser Pro Gly Leu Tyr Tyr Val Phe Leu Glu Leu Lys Leu Ser Pro
            580                 585                 590

Thr Phe Thr Asn Thr Gly His Lys Val Gln Gly Trp Val Ser Leu Val
        595                 600                 605

Leu Gln Ala Lys Pro Gln Val Asp Asp Phe Asp Asn Leu Ala Leu Thr
    610                 615                 620

Val Glu Leu Phe Pro Cys Ser Met Glu Asn Lys Leu Val Asp Arg Ser
625                 630                 635                 640

Trp Ser Gln Leu Leu Leu Leu Lys Ala Gly His Arg Leu Ser Val Gly
                645                 650                 655

Leu Arg Ala Tyr Leu His Gly Ala Gln Asp Ala Tyr Arg Asp Trp Glu
            660                 665                 670

Leu Ser Tyr Pro Asn Thr Thr Ser Phe Gly Leu Phe Leu Val Lys Pro
        675                 680                 685

Asp Asn Pro Trp Glu Gly Gly Gly Ser Gly Gly Gly Ser Gly Gly Gly
    690                 695                 700

Ser Gly Gly Gly Ser Thr Glu Pro Arg Pro Ala Leu Thr Ile Thr Thr
```

```
705                 710                 715                 720

Ser Pro Asn Leu Gly Thr Arg Glu Asn Asn Ala Asp Gln Val Thr Pro
                725                 730                 735

Val Ser His Ile Gly Cys Pro Asn Thr Thr Gln Gln Gly Ser Pro Val
            740                 745                 750

Phe Ala Lys Leu Leu Ala Lys Asn Gln Ala Ser Leu Cys Asn Thr Thr
        755                 760                 765

Leu Asn Trp His Ser Gln Asp Gly Ala Gly Ser Ser Tyr Leu Ser Gln
    770                 775                 780

Gly Leu Arg Tyr Glu Glu Asp Lys Lys Glu Leu Val Val Asp Ser Pro
785                 790                 795                 800

Gly Leu Tyr Tyr Val Phe Leu Glu Leu Lys Leu Ser Pro Thr Phe Thr
                805                 810                 815

Asn Thr Gly His Lys Val Gln Gly Trp Val Ser Leu Val Leu Gln Ala
            820                 825                 830

Lys Pro Gln Val Asp Asp Phe Asp Asn Leu Ala Leu Thr Val Glu Leu
        835                 840                 845

Phe Pro Cys Ser Met Glu Asn Lys Leu Val Asp Arg Ser Trp Ser Gln
    850                 855                 860

Leu Leu Leu Leu Lys Ala Gly His Arg Leu Ser Val Gly Leu Arg Ala
865                 870                 875                 880

Tyr Leu His Gly Ala Gln Asp Ala Tyr Arg Asp Trp Glu Leu Ser Tyr
                885                 890                 895

Pro Asn Thr Thr Ser Phe Gly Leu Phe Leu Val Lys Pro Asp Asn Pro
            900                 905                 910

Trp Glu Gly Gly Gly Gly Ser Gly Gly Gly Ser Gly Gly Gly Ser Gly
        915                 920                 925

Gly Gly Ser Thr Glu Pro Arg Pro Ala Leu Thr Ile Thr Thr Ser Pro
    930                 935                 940

Asn Leu Gly Thr Arg Glu Asn Asn Ala Asp Gln Val Thr Pro Val Ser
945                 950                 955                 960

His Ile Gly Cys Pro Asn Thr Thr Gln Gln Gly Ser Pro Val Phe Ala
                965                 970                 975

Lys Leu Leu Ala Lys Asn Gln Ala Ser Leu Cys Asn Thr Thr Leu Asn
            980                 985                 990

Trp His Ser Gln Asp Gly Ala Gly  Ser Ser Tyr Leu Ser  Gln Gly Leu
        995                 1000                1005

Arg Tyr  Glu Glu Asp Lys Lys  Glu Leu Val Val Asp  Ser Pro Gly
    1010                1015                1020

Leu Tyr  Tyr Val Phe Leu Glu  Leu Lys Leu Ser Pro  Thr Phe Thr
    1025                1030                1035

Asn Thr  Gly His Lys Val Gln  Gly Trp Val Ser Leu  Val Leu Gln
    1040                1045                1050

Ala Lys  Pro Gln Val Asp Asp  Phe Asp Asn Leu Ala  Leu Thr Val
    1055                1060                1065

Glu Leu  Phe Pro Cys Ser Met  Glu Asn Lys Leu Val  Asp Arg Ser
    1070                1075                1080

Trp Ser  Gln Leu Leu Leu Leu  Lys Ala Gly His Arg  Leu Ser Val
    1085                1090                1095

Gly Leu  Arg Ala Tyr Leu His  Gly Ala Gln Asp Ala  Tyr Arg Asp
    1100                1105                1110

Trp Glu  Leu Ser Tyr Pro Asn  Thr Thr Ser Phe Gly  Leu Phe Leu
    1115                1120                1125
```

```
Val Lys  Pro Asp Asn Pro Trp  Glu
    1130                 1135


<210> SEQ ID NO 30
<211> LENGTH: 611
<212> TYPE: PRT
<213> ORGANISM: Artificial Sequence
<220> FEATURE:
<223> OTHER INFORMATION: Protein construct expressed from SEQ ID NO: 12

<400> SEQUENCE: 30

Met Asn Phe Gly Phe Ser Leu Ile Phe Leu Val Leu Val Leu Lys Gly
1               5                   10                  15

Val Gln Cys Glu Val Lys Leu Val Pro Arg Gln Leu Gln Val Gln Leu
            20                  25                  30

Leu Gln Ser Gly Pro Glu Leu Val Lys Pro Gly Ala Ser Val Lys Leu
        35                  40                  45

Ser Cys Lys Ala Ser Gly Tyr Ser Phe Thr Ser Tyr Asp Ile Asn Trp
    50                  55                  60

Val Lys Gln Arg Pro Gly Gln Gly Leu Glu Trp Val Gly Trp Ile Tyr
65                  70                  75                  80

Pro Arg Asp Gly Asp Thr Lys Tyr Asn Glu Lys Phe Lys Gly Lys Ala
                85                  90                  95

Ile Leu Thr Val Asp Thr Ser Ser Asn Thr Ala Tyr Met Asn Leu His
            100                 105                 110

Ser Leu Thr Ser Glu Asp Ser Ala Val Tyr Phe Cys Ala Arg Leu Thr
        115                 120                 125

Gly Pro Tyr Trp Tyr Phe Asp Val Trp Gly Thr Gly Thr Thr Val Thr
    130                 135                 140

Val Ser Ser Gly Ser Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Ala Ser Thr Tyr Arg Val
                325                 330                 335

Val Ser Val Leu Thr Val Leu His Gln Asp Trp Leu Asn Gly Lys Glu
            340                 345                 350
```

```
Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

Lys Glu Phe Pro Thr Ala Ile Glu Ser Cys Met Val Lys Phe Glu Leu
                485                 490                 495

Ser Ser Ser Lys Trp His Met Thr Ser Pro Lys Pro His Cys Val Asn
            500                 505                 510

Thr Thr Ser Asp Gly Lys Leu Lys Ile Leu Gln Ser Gly Thr Tyr Leu
        515                 520                 525

Ile Tyr Gly Gln Val Ile Pro Val Asp Lys Lys Tyr Ile Lys Asp Asn
    530                 535                 540

Ala Pro Phe Val Val Gln Ile Tyr Lys Lys Asn Asp Val Leu Gln Thr
545                 550                 555                 560

Leu Met Asn Asp Phe Gln Ile Leu Pro Ile Gly Gly Val Tyr Glu Leu
                565                 570                 575

His Ala Gly Asp Asn Ile Tyr Leu Lys Phe Asn Ser Lys Asp His Ile
            580                 585                 590

Gln Lys Thr Asn Thr Tyr Trp Gly Ile Ile Leu Met Pro Asp Leu Pro
        595                 600                 605

Phe Ile Ser
    610
```

<210> SEQ ID NO 31
<211> LENGTH: 244
<212> TYPE: PRT
<213> ORGANISM: Artificial Sequence
<220> FEATURE:
<223> OTHER INFORMATION: Protein construct expressed from SEQ ID NO: 13

<400> SEQUENCE: 31

```
Met Asn Phe Gly Phe Ser Leu Ile Phe Leu Val Leu Val Leu Lys Gly
1               5                   10                  15

Val Gln Cys Glu Val Lys Leu Val Pro Arg Gln Leu Asp Ile Val Met
            20                  25                  30

Thr Gln Ser His Lys Phe Met Ser Thr Ser Val Gly Asp Arg Val Ser
        35                  40                  45

Ile Thr Cys Lys Ala Ser Gln Asp Val Asp Thr Ala Val Ala Trp Tyr
    50                  55                  60

Gln Gln Lys Pro Gly Gln Ser Pro Lys Leu Leu Ile Tyr Trp Ala Ser
65                  70                  75                  80

Thr Arg His Thr Gly Val Pro Asp Arg Phe Thr Gly Ser Gly Ser Gly
                85                  90                  95
```

```
Thr Asp Tyr Thr Leu Thr Ile Ser Ser Val Gln Ala Glu Asp Leu Ala
            100                 105                 110

Arg Tyr Tyr Cys Gln Gln Tyr Tyr Ser Val Pro Pro Thr Phe Gly Gly
        115                 120                 125

Gly Thr Lys Leu Gly Ser Glu Ile Lys Arg Thr Val Ala Ala Pro Ser
    130                 135                 140

Val Phe Ile Phe Pro Pro Ser Asp Glu Gln Leu Lys Ser Gly Thr Ala
145                 150                 155                 160

Ser Val Val Cys Leu Leu Asn Asn Phe Tyr Pro Arg Glu Ala Lys Val
                165                 170                 175

Gln Trp Lys Val Asp Asn Ala Leu Gln Ser Gly Asn Ser Gln Glu Ser
            180                 185                 190

Val Thr Glu Gln Asp Ser Lys Asp Ser Thr Tyr Ser Leu Ser Ser Thr
        195                 200                 205

Leu Thr Leu Ser Lys Ala Asp Tyr Glu Lys His Lys Val Tyr Ala Cys
    210                 215                 220

Glu Val Thr His Gln Gly Leu Ser Ser Pro Val Thr Lys Ser Phe Asn
225                 230                 235                 240

Arg Gly Glu Cys


<210> SEQ ID NO 32
<211> LENGTH: 755
<212> TYPE: PRT
<213> ORGANISM: Artificial Sequence
<220> FEATURE:
<223> OTHER INFORMATION: Protein construct expressed from SEQ ID NO: 14

<400> SEQUENCE: 32

Met Asn Phe Gly Phe Ser Leu Ile Phe Leu Val Leu Val Leu Lys Gly
1               5                   10                  15

Val Gln Cys Glu Val Lys Leu Val Pro Arg Gln Leu Asp Tyr Lys Asp
            20                  25                  30

Asp Asp Asp Lys Glu Phe Gln Leu Gln Leu Gln Glu Ser Gly Pro Gly
        35                  40                  45

Leu Val Lys Pro Ser Glu Thr Leu Ser Leu Thr Cys Thr Val Ser Gly
    50                  55                  60

Ala Ser Ile Ser Ala Asn Ser Tyr Tyr Gly Val Trp Val Arg Gln Ser
65                  70                  75                  80

Pro Gly Lys Gly Leu Glu Trp Val Gly Ser Ile Ala Tyr Arg Gly Asn
                85                  90                  95

Ser Asn Ser Gly Ser Thr Tyr Tyr Asn Pro Ser Leu Lys Ser Arg Ala
            100                 105                 110

Thr Val Ser Val Asp Thr Ser Lys Asn Gln Val Ser Leu Arg Leu Thr
        115                 120                 125

Ser Val Thr Ala Ala Asp Thr Ala Leu Tyr Tyr Cys Ala Arg Arg Gln
    130                 135                 140

Leu Leu Asp Asp Gly Thr Gly Tyr Gln Trp Ala Ala Phe Asp Val Trp
145                 150                 155                 160

Gly Gln Gly Thr Met Val Thr Val Ser Ser Arg Ser Ser Ser Ala Ser
                165                 170                 175

Thr Lys Gly Pro Ser Val Phe Pro Leu Ala Pro Ser Ser Lys Ser Thr
            180                 185                 190

Ser Gly Gly Thr Ala Ala Leu Gly Cys Leu Val Lys Asp Tyr Phe Pro
        195                 200                 205
```

```
Glu Pro Val Thr Val Ser Trp Asn Ser Gly Ala Leu Thr Ser Gly Val
    210                 215                 220

His Thr Phe Pro Ala Val Leu Gln Ser Ser Gly Leu Tyr Ser Leu Ser
225                 230                 235                 240

Ser Val Val Thr Val Pro Ser Ser Ser Leu Gly Thr Gln Thr Tyr Ile
                245                 250                 255

Cys Asn Val Asn His Lys Pro Ser Asn Thr Lys Val Asp Lys Lys Val
            260                 265                 270

Glu Pro Lys Ser Cys Asp Lys Thr His Thr Cys Pro Pro Cys Pro Ala
        275                 280                 285

Pro Glu Leu Leu Gly Gly Pro Ser Val Phe Leu Phe Pro Pro Lys Pro
    290                 295                 300

Lys Asp Thr Leu Met Ile Ser Arg Thr Pro Glu Val Thr Cys Val Val
305                 310                 315                 320

Val Asp Val Ser His Glu Asp Pro Glu Val Lys Phe Asn Trp Tyr Val
                325                 330                 335

Asp Gly Val Glu Val His Asn Ala Lys Thr Lys Pro Arg Glu Glu Gln
            340                 345                 350

Tyr Asn Ser Thr Tyr Arg Val Val Ser Val Leu Thr Val Leu His Gln
        355                 360                 365

Asp Trp Leu Asn Gly Lys Glu Tyr Lys Cys Lys Val Ser Asn Lys Ala
    370                 375                 380

Leu Pro Ala Pro Ile Glu Lys Thr Ile Ser Lys Ala Lys Gly Gln Pro
385                 390                 395                 400

Arg Glu Pro Gln Val Tyr Thr Leu Pro Pro Ser Arg Asp Glu Leu Thr
                405                 410                 415

Lys Asn Gln Val Ser Leu Thr Cys Leu Val Lys Gly Phe Tyr Pro Ser
            420                 425                 430

Asp Ile Ala Val Glu Trp Glu Ser Asn Gly Gln Pro Glu Asn Asn Tyr
        435                 440                 445

Lys Thr Thr Pro Pro Val Leu Asp Ser Asp Gly Ser Phe Phe Leu Tyr
    450                 455                 460

Ser Lys Leu Thr Val Asp Lys Ser Arg Trp Gln Gln Gly Asn Val Phe
465                 470                 475                 480

Ser Cys Ser Val Met His Glu Ala Leu His Asn His Tyr Thr Gln Lys
                485                 490                 495

Ser Leu Ser Leu Ser Pro Gly Lys Leu Glu Asp Ile Gln Met Thr Gln
            500                 505                 510

Ser Pro Ser Ser Met Ser Val Ser Leu Gly Asp Thr Val Ser Ile Thr
        515                 520                 525

Cys His Ala Ser Gln Gly Ile Ser Ser Asn Ile Gly Trp Leu Gln Gln
    530                 535                 540

Lys Pro Gly Lys Ser Phe Lys Gly Leu Ile Tyr His Gly Thr Asn Leu
545                 550                 555                 560

Glu Asp Gly Val Pro Ser Arg Phe Ser Gly Ser Gly Ser Gly Ala Asp
                565                 570                 575

Tyr Ser Leu Thr Ile Ser Ser Leu Glu Ser Glu Asp Phe Ala Asp Tyr
            580                 585                 590

Tyr Cys Val Gln Tyr Ala Gln Phe Pro Tyr Thr Phe Gly Gly Gly Thr
        595                 600                 605

Lys Leu Glu Leu Lys Arg Gly Gly Gly Gly Ser Gly Gly Gly Gly Ser
    610                 615                 620

Gly Gly Gly Gly Ser Ser Gly Gly Gly Ser Gln Val Gln Leu Gln Gln
```

```
625                 630                 635                 640

Ser Gly Pro Glu Leu Val Lys Pro Gly Ala Ser Val Lys Ile Ser Cys
                645                 650                 655

Lys Ala Ser Gly Tyr Ala Phe Ser Ser Ser Trp Met Asp Trp Val Lys
            660                 665                 670

Gln Arg Pro Gly Gln Gly Leu Glu Trp Ile Gly Arg Ile Tyr Pro Gly
        675                 680                 685

Asp Gly Asp Thr Asn Tyr Asn Gly Lys Phe Lys Gly Lys Ala Thr Leu
    690                 695                 700

Thr Ala Asp Lys Ser Ser Ser Thr Ala Tyr Met Gln Leu Ser Ser Leu
705                 710                 715                 720

Thr Ser Val Asp Ser Ala Val Tyr Phe Cys Ala Arg Ser Ile Thr Thr
                725                 730                 735

Val Val Gly Trp Tyr Phe Asp Val Trp Gly Ala Gly Thr Thr Val Thr
            740                 745                 750

Val Ser Ser
        755


<210> SEQ ID NO 33
<211> LENGTH: 504
<212> TYPE: PRT
<213> ORGANISM: Artificial Sequence
<220> FEATURE:
<223> OTHER INFORMATION: Protein construct expressed from SEQ ID NO: 15

<400> SEQUENCE: 33

Met Asn Phe Gly Phe Ser Leu Ile Phe Leu Val Leu Val Leu Lys Gly
1               5                   10                  15

Val Gln Cys Glu Val Lys Leu Val Pro Arg Gln Leu Asp Tyr Lys Asp
            20                  25                  30

Asp Asp Asp Lys Glu Phe Gln Leu Gln Leu Gln Glu Ser Gly Pro Gly
        35                  40                  45

Leu Val Lys Pro Ser Glu Thr Leu Ser Leu Thr Cys Thr Val Ser Gly
    50                  55                  60

Ala Ser Ile Ser Ala Asn Ser Tyr Tyr Gly Val Trp Val Arg Gln Ser
65                  70                  75                  80

Pro Gly Lys Gly Leu Glu Trp Val Gly Ser Ile Ala Tyr Arg Gly Asn
                85                  90                  95

Ser Asn Ser Gly Ser Thr Tyr Tyr Asn Pro Ser Leu Lys Ser Arg Ala
            100                 105                 110

Thr Val Ser Val Asp Thr Ser Lys Asn Gln Val Ser Leu Arg Leu Thr
        115                 120                 125

Ser Val Thr Ala Ala Asp Thr Ala Leu Tyr Tyr Cys Ala Arg Arg Gln
    130                 135                 140

Leu Leu Asp Asp Gly Thr Gly Tyr Gln Trp Ala Ala Phe Asp Val Trp
145                 150                 155                 160

Gly Gln Gly Thr Met Val Thr Val Ser Ser Arg Ser Ser Ser Ala Ser
                165                 170                 175

Thr Lys Gly Pro Ser Val Phe Pro Leu Ala Pro Ser Ser Lys Ser Thr
            180                 185                 190

Ser Gly Gly Thr Ala Ala Leu Gly Cys Leu Val Lys Asp Tyr Phe Pro
        195                 200                 205

Glu Pro Val Thr Val Ser Trp Asn Ser Gly Ala Leu Thr Ser Gly Val
    210                 215                 220

His Thr Phe Pro Ala Val Leu Gln Ser Ser Gly Leu Tyr Ser Leu Ser
```

```
225                 230                 235                 240

Ser Val Val Thr Val Pro Ser Ser Ser Leu Gly Thr Gln Thr Tyr Ile
                245                 250                 255

Cys Asn Val Asn His Lys Pro Ser Asn Thr Lys Val Asp Lys Lys Val
            260                 265                 270

Glu Pro Lys Ser Cys Asp Lys Thr His Thr Cys Pro Pro Cys Pro Ala
        275                 280                 285

Pro Glu Leu Leu Gly Gly Pro Ser Val Phe Leu Phe Pro Pro Lys Pro
    290                 295                 300

Lys Asp Thr Leu Met Ile Ser Arg Thr Pro Glu Val Thr Cys Val Val
305                 310                 315                 320

Val Asp Val Ser His Glu Asp Pro Glu Val Lys Phe Asn Trp Tyr Val
                325                 330                 335

Asp Gly Val Glu Val His Asn Ala Lys Thr Lys Pro Arg Glu Glu Gln
            340                 345                 350

Tyr Asn Ser Thr Tyr Arg Val Val Ser Val Leu Thr Val Leu His Gln
        355                 360                 365

Asp Trp Leu Asn Gly Lys Glu Tyr Lys Cys Lys Val Ser Asn Lys Ala
    370                 375                 380

Leu Pro Ala Pro Ile Glu Lys Thr Ile Ser Lys Ala Lys Gly Gln Pro
385                 390                 395                 400

Arg Glu Pro Gln Val Tyr Thr Leu Pro Pro Ser Arg Asp Glu Leu Thr
                405                 410                 415

Lys Asn Gln Val Ser Leu Thr Cys Leu Val Lys Gly Phe Tyr Pro Ser
            420                 425                 430

Asp Ile Ala Val Glu Trp Glu Ser Asn Gly Gln Pro Glu Asn Asn Tyr
        435                 440                 445

Lys Thr Thr Pro Pro Val Leu Asp Ser Asp Gly Ser Phe Phe Leu Tyr
    450                 455                 460

Ser Lys Leu Thr Val Asp Lys Ser Arg Trp Gln Gln Gly Asn Val Phe
465                 470                 475                 480

Ser Cys Ser Val Met His Glu Ala Leu His Asn His Tyr Thr Gln Lys
                485                 490                 495

Ser Leu Ser Leu Ser Pro Gly Lys
            500


<210> SEQ ID NO 34
<211> LENGTH: 533
<212> TYPE: PRT
<213> ORGANISM: Artificial Sequence
<220> FEATURE:
<223> OTHER INFORMATION: Protein construct expressed from SEQ ID NO: 16

<400> SEQUENCE: 34

Met Asn Phe Gly Phe Ser Leu Ile Phe Leu Val Leu Val Leu Lys Gly
1               5                   10                  15

Val Gln Cys Glu Val Lys Leu Val Pro Arg Gln Leu Asp Tyr Lys Asp
            20                  25                  30

Asp Asp Asp Lys Glu Leu Gln Leu Gln Leu Gln Glu Ser Gly Pro Gly
        35                  40                  45

Leu Val Lys Pro Ser Glu Thr Leu Ser Leu Thr Cys Thr Val Ser Gly
    50                  55                  60

Ala Ser Ile Ser Ala Asn Ser Tyr Tyr Gly Val Trp Val Arg Gln Ser
65                  70                  75                  80

Pro Gly Lys Gly Leu Glu Trp Val Gly Ser Ile Ala Tyr Arg Gly Asn
```

```
                85                  90                  95

Ser Asn Ser Gly Ser Thr Tyr Tyr Asn Pro Ser Leu Lys Ser Arg Ala
            100                 105                 110

Thr Val Ser Val Asp Thr Ser Lys Asn Gln Val Ser Leu Arg Leu Thr
        115                 120                 125

Ser Val Thr Ala Ala Asp Thr Ala Leu Tyr Tyr Cys Ala Arg Arg Gln
    130                 135                 140

Leu Leu Asp Asp Gly Thr Gly Tyr Gln Trp Ala Ala Phe Asp Val Trp
145                 150                 155                 160

Gly Gln Gly Thr Met Val Thr Val Ser Ser Gly Ser Ser Ser Ala Ser
                165                 170                 175

Thr Lys Gly Pro Ser Val Phe Pro Leu Ala Pro Ser Ser Lys Ser Thr
            180                 185                 190

Ser Gly Gly Thr Ala Ala Leu Gly Cys Leu Val Lys Asp Tyr Phe Pro
        195                 200                 205

Glu Pro Val Thr Val Ser Trp Asn Ser Gly Ala Leu Thr Ser Gly Val
    210                 215                 220

His Thr Phe Pro Ala Val Leu Gln Ser Ser Gly Leu Tyr Ser Leu Ser
225                 230                 235                 240

Ser Val Val Thr Val Pro Ser Ser Ser Leu Gly Thr Gln Thr Tyr Ile
                245                 250                 255

Cys Asn Val Asn His Lys Pro Ser Asn Thr Lys Val Asp Lys Lys Val
            260                 265                 270

Glu Pro Lys Ser Cys Asp Lys Thr His Thr Cys Pro Pro Cys Pro Ala
        275                 280                 285

Leu Glu Gln Val Gln Leu Gln Gln Pro Gly Ala Glu Leu Val Lys Pro
    290                 295                 300

Gly Ala Ser Val Lys Met Ser Cys Lys Ala Ser Gly Tyr Thr Phe Thr
305                 310                 315                 320

Ser Tyr Asn Met His Trp Val Lys Gln Thr Pro Gly Arg Gly Leu Glu
                325                 330                 335

Trp Ile Gly Ala Ile Tyr Pro Gly Asn Gly Asp Thr Ser Tyr Asn Gln
            340                 345                 350

Lys Phe Lys Gly Lys Ala Thr Leu Thr Ala Asp Lys Ser Ser Ser Thr
        355                 360                 365

Ala Tyr Met Gln Leu Ser Ser Leu Thr Ser Glu Asp Ser Ala Val Tyr
    370                 375                 380

Tyr Cys Ala Arg Ser Thr Tyr Tyr Gly Gly Asp Trp Tyr Phe Asn Val
385                 390                 395                 400

Trp Gly Ala Gly Thr Thr Val Thr Val Ser Ser Gly Gly Gly Gly Ser
                405                 410                 415

Gly Gly Gly Gly Ser Gly Gly Gly Gly Ser Gln Ile Val Leu Ser Gln
            420                 425                 430

Ser Pro Ala Ile Leu Ser Ala Ser Pro Gly Glu Lys Val Thr Met Thr
        435                 440                 445

Cys Arg Ala Ser Ser Ser Val Ser Tyr Ile His Trp Phe Gln Gln Lys
    450                 455                 460

Pro Gly Ser Ser Pro Lys Pro Trp Ile Tyr Ala Thr Ser Asn Leu Ala
465                 470                 475                 480

Ser Gly Val Pro Val Arg Phe Ser Gly Ser Gly Ser Gly Thr Ser Tyr
                485                 490                 495

Ser Leu Thr Ile Ser Arg Val Glu Ala Glu Asp Ala Ala Thr Tyr Tyr
            500                 505                 510
```

```
Cys Gln Gln Trp Thr Ser Asn Pro Pro Thr Phe Gly Gly Gly Thr Lys
        515                 520                 525

Leu Glu Ile Lys Arg
    530


<210> SEQ ID NO 35
<211> LENGTH: 977
<212> TYPE: PRT
<213> ORGANISM: Artificial Sequence
<220> FEATURE:
<223> OTHER INFORMATION: Protein construct expressed from SEQ ID NO: 17

<400> SEQUENCE: 35

Met Asn Phe Gly Phe Ser Leu Ile Phe Leu Val Leu Val Leu Lys Gly
1               5                   10                  15

Val Gln Cys Glu Val Lys Leu Val Pro Arg Gln Leu Asp Tyr Lys Asp
            20                  25                  30

Asp Asp Asp Lys Glu Leu Gln Leu Gln Leu Gln Glu Ser Gly Pro Gly
        35                  40                  45

Leu Val Lys Pro Ser Glu Thr Leu Ser Leu Thr Cys Thr Val Ser Gly
    50                  55                  60

Ala Ser Ile Ser Ala Asn Ser Tyr Tyr Gly Val Trp Val Arg Gln Ser
65                  70                  75                  80

Pro Gly Lys Gly Leu Glu Trp Val Gly Ser Ile Ala Tyr Arg Gly Asn
                85                  90                  95

Ser Asn Ser Gly Ser Thr Tyr Tyr Asn Pro Ser Leu Lys Ser Arg Ala
            100                 105                 110

Thr Val Ser Val Asp Thr Ser Lys Asn Gln Val Ser Leu Arg Leu Thr
        115                 120                 125

Ser Val Thr Ala Ala Asp Thr Ala Leu Tyr Tyr Cys Ala Arg Arg Gln
    130                 135                 140

Leu Leu Asp Asp Gly Thr Gly Tyr Gln Trp Ala Ala Phe Asp Val Trp
145                 150                 155                 160

Gly Gln Gly Thr Met Val Thr Val Ser Ser Gly Ser Ser Ser Ala Ser
                165                 170                 175

Thr Lys Gly Pro Ser Val Phe Pro Leu Ala Pro Ser Ser Lys Ser Thr
            180                 185                 190

Ser Gly Gly Thr Ala Ala Leu Gly Cys Leu Val Lys Asp Tyr Phe Pro
        195                 200                 205

Glu Pro Val Thr Val Ser Trp Asn Ser Gly Ala Leu Thr Ser Gly Val
    210                 215                 220

His Thr Phe Pro Ala Val Leu Gln Ser Ser Gly Leu Tyr Ser Leu Ser
225                 230                 235                 240

Ser Val Val Thr Val Pro Ser Ser Ser Leu Gly Thr Gln Thr Tyr Ile
                245                 250                 255

Cys Asn Val Asn His Lys Pro Ser Asn Thr Lys Val Asp Lys Lys Val
            260                 265                 270

Glu Pro Lys Ser Cys Asp Lys Thr His Thr Cys Pro Pro Cys Pro Ala
        275                 280                 285

Pro Glu Leu Leu Gly Gly Pro Ser Val Phe Leu Phe Pro Pro Lys Pro
    290                 295                 300

Lys Asp Thr Leu Met Ile Ser Arg Thr Pro Glu Val Thr Cys Val Val
305                 310                 315                 320

Val Asp Val Ser His Glu Asp Pro Glu Val Lys Phe Asn Trp Tyr Val
                325                 330                 335
```

```
Asp Gly Val Glu Val His Asn Ala Lys Thr Lys Pro Arg Glu Glu Gln
            340                 345                 350

Tyr Ala Ser Thr Tyr Arg Val Val Ser Val Leu Thr Val Leu His Gln
        355                 360                 365

Asp Trp Leu Asn Gly Lys Glu Tyr Lys Cys Lys Val Ser Asn Lys Ala
    370                 375                 380

Leu Pro Ala Pro Ile Glu Lys Thr Ile Ser Lys Ala Lys Gly Gln Pro
385                 390                 395                 400

Arg Glu Pro Gln Val Tyr Thr Leu Pro Pro Ser Arg Asp Glu Leu Thr
                405                 410                 415

Lys Asn Gln Val Ser Leu Thr Cys Leu Val Lys Gly Phe Tyr Pro Ser
            420                 425                 430

Asp Ile Ala Val Glu Trp Glu Ser Asn Gly Gln Pro Glu Asn Asn Tyr
        435                 440                 445

Lys Thr Thr Pro Pro Val Leu Asp Ser Asp Gly Ser Phe Phe Leu Tyr
    450                 455                 460

Ser Lys Leu Thr Val Asp Lys Ser Arg Trp Gln Gln Gly Asn Val Phe
465                 470                 475                 480

Ser Cys Ser Val Met His Glu Ala Leu His Asn His Tyr Thr Gln Lys
                485                 490                 495

Ser Leu Ser Leu Ser Pro Gly Lys Leu Glu Gly Pro Glu Glu Thr Val
            500                 505                 510

Thr Gln Asp Cys Leu Gln Leu Ile Ala Asp Ser Glu Thr Pro Thr Ile
        515                 520                 525

Gln Lys Gly Ser Tyr Thr Phe Val Pro Trp Leu Leu Ser Phe Lys Arg
    530                 535                 540

Gly Ser Ala Leu Glu Glu Lys Glu Asn Lys Ile Leu Val Lys Glu Thr
545                 550                 555                 560

Gly Tyr Phe Phe Ile Tyr Gly Gln Val Leu Tyr Thr Asp Lys Thr Tyr
                565                 570                 575

Ala Met Gly His Leu Ile Gln Arg Lys Lys Val His Val Phe Gly Asp
            580                 585                 590

Glu Leu Ser Leu Val Thr Leu Phe Arg Cys Ile Gln Asn Met Pro Glu
        595                 600                 605

Thr Leu Pro Asn Asn Ser Cys Tyr Ser Ala Gly Ile Ala Lys Leu Glu
    610                 615                 620

Glu Gly Asp Glu Leu Gln Leu Ala Ile Pro Arg Glu Asn Ala Gln Ile
625                 630                 635                 640

Ser Leu Asp Gly Asp Val Thr Phe Phe Gly Ala Leu Lys Leu Leu Gly
                645                 650                 655

Gly Gly Gly Ser Gly Gly Gly Gly Ser Gly Pro Glu Glu Thr Val Thr
            660                 665                 670

Gln Asp Cys Leu Gln Leu Ile Ala Asp Ser Glu Thr Pro Thr Ile Gln
        675                 680                 685

Lys Gly Ser Tyr Thr Phe Val Pro Trp Leu Leu Ser Phe Lys Arg Gly
    690                 695                 700

Ser Ala Leu Glu Glu Lys Glu Asn Lys Ile Leu Val Lys Glu Thr Gly
705                 710                 715                 720

Tyr Phe Phe Ile Tyr Gly Gln Val Leu Tyr Thr Asp Lys Thr Tyr Ala
                725                 730                 735

Met Gly His Leu Ile Gln Arg Lys Lys Val His Val Phe Gly Asp Glu
            740                 745                 750
```

```
Leu Ser Leu Val Thr Leu Phe Arg Cys Ile Gln Asn Met Pro Glu Thr
        755                 760                 765

Leu Pro Asn Asn Ser Cys Tyr Ser Ala Gly Ile Ala Lys Leu Glu Glu
    770                 775                 780

Gly Asp Glu Leu Gln Leu Ala Ile Pro Arg Glu Asn Ala Gln Ile Ser
785                 790                 795                 800

Leu Asp Gly Asp Val Thr Phe Phe Gly Ala Leu Lys Leu Leu Gly Gly
                805                 810                 815

Gly Gly Ser Gly Gly Gly Gly Ser Gln Phe Ala Ala Gly Pro Glu Glu
            820                 825                 830

Thr Val Thr Gln Asp Cys Leu Gln Leu Ile Ala Asp Ser Glu Thr Pro
        835                 840                 845

Thr Ile Gln Lys Gly Ser Tyr Thr Phe Val Pro Trp Leu Leu Ser Phe
    850                 855                 860

Lys Arg Gly Ser Ala Leu Glu Glu Lys Glu Asn Lys Ile Leu Val Lys
865                 870                 875                 880

Glu Thr Gly Tyr Phe Phe Ile Tyr Gly Gln Val Leu Tyr Thr Asp Lys
                885                 890                 895

Thr Tyr Ala Met Gly His Leu Ile Gln Arg Lys Lys Val His Val Phe
            900                 905                 910

Gly Asp Glu Leu Ser Leu Val Thr Leu Phe Arg Cys Ile Gln Asn Met
        915                 920                 925

Pro Glu Thr Leu Pro Asn Asn Ser Cys Tyr Ser Ala Gly Ile Ala Lys
    930                 935                 940

Leu Glu Glu Gly Asp Glu Leu Gln Leu Ala Ile Pro Arg Glu Asn Ala
945                 950                 955                 960

Gln Ile Ser Leu Asp Gly Asp Val Thr Phe Phe Gly Ala Leu Lys Leu
                965                 970                 975

Leu
```

<210> SEQ ID NO 36
<211> LENGTH: 261
<212> TYPE: PRT
<213> ORGANISM: Artificial Sequence
<220> FEATURE:
<223> OTHER INFORMATION: Protein construct expressed from SEQ ID NO: 18

<400> SEQUENCE: 36

```
Met Asn Phe Gly Phe Ser Leu Ile Phe Leu Val Leu Val Leu Lys Gly
1               5                   10                  15

Val Gln Cys Glu Val Lys Leu Val Pro Arg Gln Leu Asp Tyr Lys Asp
            20                  25                  30

Asp Asp Asp Lys Glu Leu Gln Ser Val Leu Thr Gln Pro Pro Ser Val
        35                  40                  45

Ser Glu Ala Pro Arg Gln Thr Val Thr Ile Ser Cys Ser Gly Asn Ser
    50                  55                  60

Phe Asn Ile Gly Arg Tyr Pro Val Asn Trp Tyr Gln Gln Leu Pro Gly
65                  70                  75                  80

Lys Ala Pro Lys Leu Leu Ile Tyr Tyr Asn Asn Leu Arg Phe Ser Gly
                85                  90                  95

Val Ser Asp Arg Phe Ser Gly Ser Lys Ser Gly Thr Ser Ala Ser Leu
            100                 105                 110

Ala Ile Arg Asp Leu Leu Ser Glu Asp Glu Ala Asp Tyr Tyr Cys Ser
        115                 120                 125

Thr Trp Asp Asp Thr Leu Lys Gly Trp Val Phe Gly Gly Gly Thr Lys
```

```
    130                 135                 140

Val Thr Val Leu Gly Gly Ser Glu Ile Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260


<210> SEQ ID NO 37
<211> LENGTH: 10
<212> TYPE: PRT
<213> ORGANISM: Artificial Sequence
<220> FEATURE:
<223> OTHER INFORMATION: CDR1-H of aCD40 G28.5

<400> SEQUENCE: 37

Tyr Ser Ile Thr Thr Asn Tyr Asn Trp Asn
1               5                   10


<210> SEQ ID NO 38
<211> LENGTH: 16
<212> TYPE: PRT
<213> ORGANISM: Artificial Sequence
<220> FEATURE:
<223> OTHER INFORMATION: CDR2-H of aCD40 G28.5

<400> SEQUENCE: 38

Tyr Ile Arg Tyr Asp Gly Thr Ser Glu Tyr Thr Pro Ser Leu Lys Asn
1               5                   10                  15


<210> SEQ ID NO 39
<211> LENGTH: 15
<212> TYPE: PRT
<213> ORGANISM: Artificial Sequence
<220> FEATURE:
<223> OTHER INFORMATION: CDR1-L of aCD40 G28.5

<400> SEQUENCE: 39

Ser Ser Gln Ser Leu Glu Asn Ser Asn Gly Asn Thr Phe Leu Asn
1               5                   10                  15


<210> SEQ ID NO 40
<211> LENGTH: 7
<212> TYPE: PRT
<213> ORGANISM: Artificial Sequence
<220> FEATURE:
<223> OTHER INFORMATION: CDR2-L of aCD40 G28.5

<400> SEQUENCE: 40

Arg Val Ser Asn Arg Phe Ser
1               5
```

<210> SEQ ID NO 41
<211> LENGTH: 9
<212> TYPE: PRT
<213> ORGANISM: Artificial Sequence
<220> FEATURE:
<223> OTHER INFORMATION: CDR3-L of aCD40 G28.5

<400> SEQUENCE: 41

Leu Gln Val Thr His Val Pro Tyr Thr
1               5

<210> SEQ ID NO 42
<211> LENGTH: 11
<212> TYPE: PRT
<213> ORGANISM: Artificial Sequence
<220> FEATURE:
<223> OTHER INFORMATION: CDR1-H of aCD95 E09

<400> SEQUENCE: 42

Ala Ser Ile Ser Ala Asn Ser Tyr Tyr Gly Val
1               5                   10

<210> SEQ ID NO 43
<211> LENGTH: 21
<212> TYPE: PRT
<213> ORGANISM: Artificial Sequence
<220> FEATURE:
<223> OTHER INFORMATION: CDR2-H of aCD95 E09

<400> SEQUENCE: 43

Ser Ile Ala Tyr Arg Gly Asn Ser Asn Ser Gly Ser Thr Tyr Tyr Asn
1               5                   10                  15

Pro Ser Leu Lys Ser
            20

<210> SEQ ID NO 44
<211> LENGTH: 17
<212> TYPE: PRT
<213> ORGANISM: Artificial Sequence
<220> FEATURE:
<223> OTHER INFORMATION: CDR3-H of aCD95 E09

<400> SEQUENCE: 44

Arg Gln Leu Leu Asp Asp Gly Thr Gly Tyr Gln Trp Ala Ala Phe Asp
1               5                   10                  15

Val

<210> SEQ ID NO 45
<211> LENGTH: 13
<212> TYPE: PRT
<213> ORGANISM: Artificial Sequence
<220> FEATURE:
<223> OTHER INFORMATION: CDR1-L of aCD95 E09

<400> SEQUENCE: 45

Ser Gly Asn Ser Phe Asn Ile Gly Arg Tyr Pro Val Asn
1               5                   10

<210> SEQ ID NO 46
<211> LENGTH: 7
<212> TYPE: PRT
<213> ORGANISM: Artificial Sequence
<220> FEATURE:
<223> OTHER INFORMATION: CDR2-L of aCD95 E09

<400> SEQUENCE: 46

Tyr Asn Asn Leu Arg Phe Ser
1 5

<210> SEQ ID NO 47
<211> LENGTH: 11
<212> TYPE: PRT
<213> ORGANISM: Artificial Sequence
<220> FEATURE:
<223> OTHER INFORMATION: CDR3-L of aCD95 E09

<400> SEQUENCE: 47

Ser Thr Trp Asp Asp Thr Leu Lys Gly Trp Val
1 5 10

<210> SEQ ID NO 48
<211> LENGTH: 11
<212> TYPE: PRT
<213> ORGANISM: Artificial Sequence
<220> FEATURE:
<223> OTHER INFORMATION: CDR1-H of aDR5 Conatu

<400> SEQUENCE: 48

Gly Ser Ile Ser Ser Gly Asp Tyr Phe Trp Ser
1 5 10

<210> SEQ ID NO 49
<211> LENGTH: 16
<212> TYPE: PRT
<213> ORGANISM: Artificial Sequence
<220> FEATURE:
<223> OTHER INFORMATION: CDR2-H of aDR5 Conatu

<400> SEQUENCE: 49

His Ile His Asn Ser Gly Thr Thr Tyr Tyr Asn Pro Ser Leu Lys Ser
1 5 10 15

<210> SEQ ID NO 50
<211> LENGTH: 12
<212> TYPE: PRT
<213> ORGANISM: Artificial Sequence
<220> FEATURE:
<223> OTHER INFORMATION: CDR3-H of aDR5 Conatu

<400> SEQUENCE: 50

Asp Arg Gly Gly Asp Tyr Tyr Tyr Gly Met Asp Val
1 5 10

<210> SEQ ID NO 51
<211> LENGTH: 12
<212> TYPE: PRT
<213> ORGANISM: Artificial Sequence
<220> FEATURE:
<223> OTHER INFORMATION: CDR1-L of aDR5 Conatu

<400> SEQUENCE: 51

Arg Ala Ser Gln Gly Ile Ser Arg Ser Tyr Leu Ala
1 5 10

<210> SEQ ID NO 52
<211> LENGTH: 7
<212> TYPE: PRT
<213> ORGANISM: Artificial Sequence
<220> FEATURE:
<223> OTHER INFORMATION: CDR2-L of aDR5 Conatu

<400> SEQUENCE: 52

Gly Ala Ser Ser Arg Ala Thr 1 5

<210> SEQ ID NO 53
<211> LENGTH: 9
<212> TYPE: PRT
<213> ORGANISM: Artificial Sequence
<220> FEATURE:
<223> OTHER INFORMATION: CDR3-L of aDR5 Conatu

<400> SEQUENCE: 53

Gln Gln Phe Gly Ser Ser Pro Trp Thr
1 5

<210> SEQ ID NO 54
<211> LENGTH: 9
<212> TYPE: PRT
<213> ORGANISM: Artificial Sequence
<220> FEATURE:
<223> OTHER INFORMATION: CDR1-H of aFn14 P4A8

<400> SEQUENCE: 54

Tyr Thr Phe Thr Asp Tyr Gly Met His
1 5

<210> SEQ ID NO 55
<211> LENGTH: 17
<212> TYPE: PRT
<213> ORGANISM: Artificial Sequence
<220> FEATURE:
<223> OTHER INFORMATION: CDR2-H of aFn14 P4A8

<400> SEQUENCE: 55

Val Ile Ser Thr Tyr Asn Gly Tyr Thr Asn Tyr Asn Gln Lys Phe Lys
1 5 10 15

Gly

<210> SEQ ID NO 56
<211> LENGTH: 12
<212> TYPE: PRT
<213> ORGANISM: Artificial Sequence
<220> FEATURE:
<223> OTHER INFORMATION: CDR3-H of aFn14 P4A8

<400> SEQUENCE: 56

Ala Tyr Tyr Gly Asn Leu Tyr Tyr Ala Met Asp Tyr
1 5 10

<210> SEQ ID NO 57
<211> LENGTH: 15
<212> TYPE: PRT
<213> ORGANISM: Artificial Sequence
<220> FEATURE:
<223> OTHER INFORMATION: CDR1-L of aFn14 P4A8

<400> SEQUENCE: 57

Arg Ala Ser Lys Ser Val Ser Thr Ser Ser Tyr Ser Tyr Met His
1 5 10 15

<210> SEQ ID NO 58
<211> LENGTH: 7
<212> TYPE: PRT
<213> ORGANISM: Artificial Sequence
<220> FEATURE:
<223> OTHER INFORMATION: CDR2-L of aFn14 P4A8

<400> SEQUENCE: 58

Tyr Ala Ser Asn Leu Glu Ser
1               5

<210> SEQ ID NO 59
<211> LENGTH: 9
<212> TYPE: PRT
<213> ORGANISM: Artificial Sequence
<220> FEATURE:
<223> OTHER INFORMATION: CDR3-L of aFn14 P4A8

<400> SEQUENCE: 59

Gln His Ser Arg Glu Leu Pro Phe Thr
1               5

<210> SEQ ID NO 60
<211> LENGTH: 9
<212> TYPE: PRT
<213> ORGANISM: Artificial Sequence
<220> FEATURE:
<223> OTHER INFORMATION: CDR1-H of aTNFR2 C4

<400> SEQUENCE: 60

Tyr Ser Phe Thr Ser Tyr Asp Ile Asn
1               5

<210> SEQ ID NO 61
<211> LENGTH: 17
<212> TYPE: PRT
<213> ORGANISM: Artificial Sequence
<220> FEATURE:
<223> OTHER INFORMATION: CDR2-H of aTNFR2 C4

<400> SEQUENCE: 61

Trp Ile Tyr Pro Arg Asp Gly Asp Thr Lys Tyr Asn Glu Lys Phe Lys
1               5                   10                  15

Gly

<210> SEQ ID NO 62
<211> LENGTH: 10
<212> TYPE: PRT
<213> ORGANISM: Artificial Sequence
<220> FEATURE:
<223> OTHER INFORMATION: CDR3-H of aTNFR2 C4

<400> SEQUENCE: 62

Leu Thr Gly Pro Tyr Trp Tyr Phe Asp Val
1               5                   10

<210> SEQ ID NO 63
<211> LENGTH: 11
<212> TYPE: PRT
<213> ORGANISM: Artificial Sequence
<220> FEATURE:
<223> OTHER INFORMATION: CDR1-L of aTNFR2 C4

<400> SEQUENCE: 63

Lys Ala Ser Gln Asp Val Asp Thr Ala Val Ala
1               5                   10

<210> SEQ ID NO 64
<211> LENGTH: 7
<212> TYPE: PRT
<213> ORGANISM: Artificial Sequence
<220> FEATURE:
<223> OTHER INFORMATION: CDR2-L of aTNFR2 C4

<400> SEQUENCE: 64

Trp Ala Ser Thr Arg His Thr
1 5

<210> SEQ ID NO 65
<211> LENGTH: 9
<212> TYPE: PRT
<213> ORGANISM: Artificial Sequence
<220> FEATURE:
<223> OTHER INFORMATION: CDR3-L of aTNFR2 C4

<400> SEQUENCE: 65

Gln Gln Tyr Tyr Ser Val Pro Pro Thr
1 5

<210> SEQ ID NO 66
<211> LENGTH: 9
<212> TYPE: PRT
<213> ORGANISM: Artificial Sequence
<220> FEATURE:
<223> OTHER INFORMATION: CDR1-H of aCD20

<400> SEQUENCE: 66

Tyr Thr Phe Thr Ser Tyr Asn Met His
1 5

<210> SEQ ID NO 67
<211> LENGTH: 17
<212> TYPE: PRT
<213> ORGANISM: Artificial Sequence
<220> FEATURE:
<223> OTHER INFORMATION: CDR2-H of aCD20

<400> SEQUENCE: 67

Ala Ile Tyr Pro Gly Asn Gly Asp Thr Ser Tyr Asn Gln Lys Phe Lys
1 5 10 15

Gly

<210> SEQ ID NO 68
<211> LENGTH: 12
<212> TYPE: PRT
<213> ORGANISM: Artificial Sequence
<220> FEATURE:
<223> OTHER INFORMATION: CDR3-H of aCD20

<400> SEQUENCE: 68

Ser Thr Tyr Tyr Gly Gly Asp Trp Tyr Phe Asn Val
1 5 10

<210> SEQ ID NO 69
<211> LENGTH: 10
<212> TYPE: PRT
<213> ORGANISM: Artificial Sequence
<220> FEATURE:
<223> OTHER INFORMATION: CDR1-L of aCD20

<400> SEQUENCE: 69

Arg Ala Ser Ser Ser Val Ser Tyr Ile His
1 5 10

<210> SEQ ID NO 70
<211> LENGTH: 7
<212> TYPE: PRT
<213> ORGANISM: Artificial Sequence
<220> FEATURE:
<223> OTHER INFORMATION: CDR2-L of aCD20

<400> SEQUENCE: 70

```
Ala Thr Ser Asn Leu Ala Ser
1               5
```

<210> SEQ ID NO 71
<211> LENGTH: 9
<212> TYPE: PRT
<213> ORGANISM: Artificial Sequence
<220> FEATURE:
<223> OTHER INFORMATION: CDR3-L of aCD20

<400> SEQUENCE: 71

```
Gln Gln Trp Thr Ser Asn Pro Pro Thr
1               5
```

<210> SEQ ID NO 72
<211> LENGTH: 9
<212> TYPE: PRT
<213> ORGANISM: Artificial Sequence
<220> FEATURE:
<223> OTHER INFORMATION: CDR1-H of aCD19

<400> SEQUENCE: 72

```
Tyr Ala Phe Ser Ser Ser Trp Met Asp
1               5
```

<210> SEQ ID NO 73
<211> LENGTH: 17
<212> TYPE: PRT
<213> ORGANISM: Artificial Sequence
<220> FEATURE:
<223> OTHER INFORMATION: CDR2-H of aCD19

<400> SEQUENCE: 73

```
Arg Ile Tyr Pro Gly Asp Gly Asp Thr Asn Tyr Asn Gly Lys Phe Lys
1               5                   10                  15

Gly
```

<210> SEQ ID NO 74
<211> LENGTH: 12
<212> TYPE: PRT
<213> ORGANISM: Artificial Sequence
<220> FEATURE:
<223> OTHER INFORMATION: CDR3-H of aCD19

<400> SEQUENCE: 74

```
Ser Ile Thr Thr Val Val Gly Trp Tyr Phe Asp Val
1               5                   10
```

<210> SEQ ID NO 75
<211> LENGTH: 11
<212> TYPE: PRT
<213> ORGANISM: Artificial Sequence
<220> FEATURE:
<223> OTHER INFORMATION: CDR1-L of aCD19

<400> SEQUENCE: 75

```
His Ala Ser Gln Gly Ile Ser Ser Asn Ile Gly
1               5                   10
```

<210> SEQ ID NO 76
<211> LENGTH: 7
<212> TYPE: PRT
<213> ORGANISM: Artificial Sequence
<220> FEATURE:
<223> OTHER INFORMATION: CDR2-L of aCD19

<400> SEQUENCE: 76

His Gly Thr Asn Leu Glu Asp
1 5

<210> SEQ ID NO 77
<211> LENGTH: 9
<212> TYPE: PRT
<213> ORGANISM: Artificial Sequence
<220> FEATURE:
<223> OTHER INFORMATION: CDR3-L of aCD19

<400> SEQUENCE: 77

Val Gln Tyr Ala Gln Phe Pro Tyr Thr
1 5

<210> SEQ ID NO 78
<211> LENGTH: 9
<212> TYPE: PRT
<213> ORGANISM: Artificial Sequence
<220> FEATURE:
<223> OTHER INFORMATION: CDR1-H of aCD70 1F6

<400> SEQUENCE: 78

Tyr Thr Phe Thr Asn Tyr Gly Met Asn
1 5

<210> SEQ ID NO 79
<211> LENGTH: 17
<212> TYPE: PRT
<213> ORGANISM: Artificial Sequence
<220> FEATURE:
<223> OTHER INFORMATION: CDR2-H of aCD70 1F6

<400> SEQUENCE: 79

Trp Ile Asn Thr Tyr Thr Gly Glu Pro Thr Tyr Ala Asp Ala Phe Lys
1 5 10 15

Gly

<210> SEQ ID NO 80
<211> LENGTH: 9
<212> TYPE: PRT
<213> ORGANISM: Artificial Sequence
<220> FEATURE:
<223> OTHER INFORMATION: CDR3-H of aCD70 1F6

<400> SEQUENCE: 80

Asp Tyr Gly Asp Tyr Gly Met Asp Tyr
1 5

<210> SEQ ID NO 81
<211> LENGTH: 15
<212> TYPE: PRT
<213> ORGANISM: Artificial Sequence
<220> FEATURE:
<223> OTHER INFORMATION: CDR1-L of aCD70 1F6

<400> SEQUENCE: 81

Arg Ala Ser Lys Ser Val Ser Thr Ser Gly Tyr Ser Phe Met His
1 5 10 15

<210> SEQ ID NO 82
<211> LENGTH: 7
<212> TYPE: PRT
<213> ORGANISM: Artificial Sequence
<220> FEATURE:

<223> OTHER INFORMATION: CDR2-L of aCD70 1F6

<400> SEQUENCE: 82

Leu Ala Ser Asn Leu Glu Ser
1 5

<210> SEQ ID NO 83
<211> LENGTH: 9
<212> TYPE: PRT
<213> ORGANISM: Artificial Sequence
<220> FEATURE:
<223> OTHER INFORMATION: CDR3-L of aCD70 1F6

<400> SEQUENCE: 83

Gln His Ser Arg Glu Val Pro Trp Thr
1 5

<210> SEQ ID NO 84
<211> LENGTH: 9
<212> TYPE: PRT
<213> ORGANISM: Artificial Sequence
<220> FEATURE:
<223> OTHER INFORMATION: CDR1-H of aFn14 PDL192

<400> SEQUENCE: 84

Phe Thr Phe Ser Ser Tyr Trp Met Ser
1 5

<210> SEQ ID NO 85
<211> LENGTH: 19
<212> TYPE: PRT
<213> ORGANISM: Artificial Sequence
<220> FEATURE:
<223> OTHER INFORMATION: CDR2-H of aFn14 PDL192

<400> SEQUENCE: 85

Glu Ile Arg Leu Lys Ser Asp Asn Tyr Ala Thr His Tyr Ala Glu Ser
1 5 10 15

Val Lys Gly

<210> SEQ ID NO 86
<211> LENGTH: 9
<212> TYPE: PRT
<213> ORGANISM: Artificial Sequence
<220> FEATURE:
<223> OTHER INFORMATION: CDR3-H of aFn14 PDL192

<400> SEQUENCE: 86

Gly Tyr Tyr Ala Asp Ala Met Asp Tyr
1 5

<210> SEQ ID NO 87
<211> LENGTH: 15
<212> TYPE: PRT
<213> ORGANISM: Artificial Sequence
<220> FEATURE:
<223> OTHER INFORMATION: CDR1-L of aFn14 PDL192

<400> SEQUENCE: 87

Arg Ala Ser Gln Ser Val Ser Thr Ser Ser Tyr Ser Tyr Met His
1 5 10 15

<210> SEQ ID NO 88
<211> LENGTH: 7
<212> TYPE: PRT
<213> ORGANISM: Artificial Sequence

```
<220> FEATURE:
<223> OTHER INFORMATION: CDR2-L of aFn14 PDL192

<400> SEQUENCE: 88

Tyr Ala Ser Asn Leu Glu Ser
1               5


<210> SEQ ID NO 89
<211> LENGTH: 9
<212> TYPE: PRT
<213> ORGANISM: Artificial Sequence
<220> FEATURE:
<223> OTHER INFORMATION: CDR3-L of aFn14 PDL192

<400> SEQUENCE: 89

Gln His Ser Trp Glu Ile Pro Tyr Thr
1               5


<210> SEQ ID NO 90
<211> LENGTH: 9
<212> TYPE: PRT
<213> ORGANISM: Artificial Sequence
<220> FEATURE:
<223> OTHER INFORMATION: CDR1-H of aCD70 2H5

<400> SEQUENCE: 90

Phe Thr Phe Ser Ser Tyr Ile Met His
1               5


<210> SEQ ID NO 91
<211> LENGTH: 17
<212> TYPE: PRT
<213> ORGANISM: Artificial Sequence
<220> FEATURE:
<223> OTHER INFORMATION: CDR2-H of aCD70 2H5

<400> SEQUENCE: 91

Val Ile Ser Tyr Asp Gly Arg Asn Lys Tyr Tyr Ala Asp Ser Val Lys
1               5                   10                  15

Gly


<210> SEQ ID NO 92
<211> LENGTH: 9
<212> TYPE: PRT
<213> ORGANISM: Artificial Sequence
<220> FEATURE:
<223> OTHER INFORMATION: CDR3-H of aCD70 2H5

<400> SEQUENCE: 92

Asp Thr Asp Gly Tyr Asp Phe Asp Tyr
1               5


<210> SEQ ID NO 93
<211> LENGTH: 11
<212> TYPE: PRT
<213> ORGANISM: Artificial Sequence
<220> FEATURE:
<223> OTHER INFORMATION: CDR1-L of aCD70 2H5

<400> SEQUENCE: 93

Arg Ala Ser Gln Ser Val Ser Ser Tyr Leu Ala
1               5                   10


<210> SEQ ID NO 94
<211> LENGTH: 7
<212> TYPE: PRT
```

<213> ORGANISM: Artificial Sequence
<220> FEATURE:
<223> OTHER INFORMATION: CDR2-L of aCD70 2H5

<400> SEQUENCE: 94

Asp Ala Ser Asn Arg Ala Thr
1 5

<210> SEQ ID NO 95
<211> LENGTH: 9
<212> TYPE: PRT
<213> ORGANISM: Artificial Sequence
<220> FEATURE:
<223> OTHER INFORMATION: CDR3-L of aCD70 2H5

<400> SEQUENCE: 95

Gln Gln Arg Thr Asn Trp Pro Leu Thr
1 5

<210> SEQ ID NO 96
<211> LENGTH: 243
<212> TYPE: PRT
<213> ORGANISM: Artificial Sequence
<220> FEATURE:
<223> OTHER INFORMATION: scFv-anti-CD20 anchoring domain from protein construct of SEQ ID NO: 21

<400> SEQUENCE: 96

Gln Val Gln Leu Gln Gln Pro Gly Ala Glu Leu Val Lys Pro Gly Ala
1 5 10 15

Ser Val Lys Met Ser Cys Lys Ala Ser Gly Tyr Thr Phe Thr Ser Tyr
20 25 30

Asn Met His Trp Val Lys Gln Thr Pro Gly Arg Gly Leu Glu Trp Ile
35 40 45

Gly Ala Ile Tyr Pro Gly Asn Gly Asp Thr Ser Tyr Asn Gln Lys Phe
50 55 60

Lys Gly Lys Ala Thr Leu Thr Ala Asp Lys Ser Ser Ser Thr Ala Tyr
65 70 75 80

Met Gln Leu Ser Ser Leu Thr Ser Glu Asp Ser Ala Val Tyr Tyr Cys
85 90 95

Ala Arg Ser Thr Tyr Tyr Gly Gly Asp Trp Tyr Phe Asn Val Trp Gly
100 105 110

Ala Gly Thr Thr Val Thr Val Ser Ser Gly Gly Gly Gly Ser Gly Gly
115 120 125

Gly Gly Ser Gly Gly Gly Gly Ser Gln Ile Val Leu Ser Gln Ser Pro
130 135 140

Ala Ile Leu Ser Ala Ser Pro Gly Glu Lys Val Thr Met Thr Cys Arg
145 150 155 160

Ala Ser Ser Ser Val Ser Tyr Ile His Trp Phe Gln Gln Lys Pro Gly
165 170 175

Ser Ser Pro Lys Pro Trp Ile Tyr Ala Thr Ser Asn Leu Ala Ser Gly
180 185 190

Val Pro Val Arg Phe Ser Gly Ser Gly Ser Gly Thr Ser Tyr Ser Leu
195 200 205

Thr Ile Ser Arg Val Glu Ala Glu Asp Ala Ala Thr Tyr Tyr Cys Gln
210 215 220

Gln Trp Thr Ser Asn Pro Pro Thr Phe Gly Gly Gly Thr Lys Leu Glu
225 230 235 240

Ile Lys Arg

<210> SEQ ID NO 97
<211> LENGTH: 149
<212> TYPE: PRT
<213> ORGANISM: Artificial Sequence
<220> FEATURE:
<223> OTHER INFORMATION: Murine IL-2 anchoring domain from protein construct of SEQ ID NO: 24

<400> SEQUENCE: 97

```
Ala Pro Thr Ser Ser Ser Thr Ser Ser Ser Thr Ala Glu Ala Gln Gln
1               5                   10                  15

Gln Gln Gln Gln Gln Gln Gln Gln Gln Gln His Leu Glu Gln Leu Leu
            20                  25                  30

Met Asp Leu Gln Glu Leu Leu Ser Arg Met Glu Asn Tyr Arg Asn Leu
        35                  40                  45

Lys Leu Pro Arg Met Leu Thr Phe Lys Phe Tyr Leu Pro Lys Gln Ala
    50                  55                  60

Thr Glu Leu Lys Asp Leu Gln Cys Leu Glu Asp Glu Leu Gly Pro Leu
65                  70                  75                  80

Arg His Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Ser Ala Thr
        115                 120                 125

Val Val Asp Phe Leu Arg Arg Trp Ile Ala Phe Cys Gln Ser Ile Ile
    130                 135                 140

Ser Thr Ser Pro Gln
145
```

<210> SEQ ID NO 98
<211> LENGTH: 249
<212> TYPE: PRT
<213> ORGANISM: Artificial Sequence
<220> FEATURE:
<223> OTHER INFORMATION: scFv-anti-CD19 anchoring domain from protein construct of SEQ ID NO: 25

<400> SEQUENCE: 98

```
Asp Ile Gln Met Thr Gln Ser Pro Ser Ser Met Ser Val Ser Leu Gly
1               5                   10                  15

Asp Thr Val Ser Ile Thr Cys His Ala Ser Gln Gly Ile Ser Ser Asn
            20                  25                  30

Ile Gly Trp Leu Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Ala Asp Tyr Ser Leu Thr Ile Ser Ser Leu Glu Ser
65                  70                  75                  80

Glu Asp Phe Ala Asp Tyr Tyr Cys Val Gln Tyr Ala Gln Phe Pro Tyr
                85                  90                  95

Thr Phe Gly Gly Gly Thr Lys Leu Glu Leu Lys Arg Gly Gly Gly Gly
            100                 105                 110

Ser Gly Gly Gly Gly Ser Gly Gly Gly Gly Ser Ser Gly Gly Gly Ser
        115                 120                 125

Gln Val Gln Leu Gln Gln Ser Gly Pro Glu Leu Val Lys Pro Gly Ala
    130                 135                 140
```

```
Ser Val Lys Ile Ser Cys Lys Ala Ser Gly Tyr Ala Phe Ser Ser Ser
145                 150                 155                 160

Trp Met Asp Trp Val Lys Gln Arg Pro Gly Gln Gly Leu Glu Trp Ile
                165                 170                 175

Gly Arg Ile Tyr Pro Gly Asp Gly Asp Thr Asn Tyr Asn Gly Lys Phe
            180                 185                 190

Lys Gly Lys Ala Thr Leu Thr Ala Asp Lys Ser Ser Ser Thr Ala Tyr
        195                 200                 205

Met Gln Leu Ser Ser Leu Thr Ser Val Asp Ser Ala Val Tyr Phe Cys
    210                 215                 220

Ala Arg Ser Ile Thr Thr Val Val Gly Trp Tyr Phe Asp Val Trp Gly
225                 230                 235                 240

Ala Gly Thr Thr Val Thr Val Ser Ser
                245


<210> SEQ ID NO 99
<211> LENGTH: 243
<212> TYPE: PRT
<213> ORGANISM: Artificial Sequence
<220> FEATURE:
<223> OTHER INFORMATION: scFv-anti-CD20 anchoring domain from protein
      construct of SEQ ID NO: 26

<400> SEQUENCE: 99

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ser Gly Gly Gly Gly Ser Gly Gly
        115                 120                 125

Gly Gly Ser Gly Gly Gly Gly Ser Gln Ile Val Leu Ser Gln Ser Pro
    130                 135                 140

Ala Ile Leu Ser Ala Ser Pro Gly Glu Lys Val Thr Met Thr Cys Arg
145                 150                 155                 160

Ala Ser Ser Ser Val Ser Tyr Ile His Trp Phe Gln Gln Lys Pro Gly
                165                 170                 175

Pro Ser Ser Lys Pro Trp Ile Tyr Ala Thr Ser Asn Leu Ala Ser Gly
            180                 185                 190

Val Pro Val Arg Phe Ser Gly Ser Gly Ser Gly Thr Ser Tyr Ser Leu
        195                 200                 205

Thr Ile Ser Arg Val Glu Ala Glu Asp Ala Ala Thr Tyr Tyr Cys Gln
    210                 215                 220

Gln Trp Thr Ser Asn Pro Pro Thr Phe Gly Gly Gly Thr Lys Leu Glu
225                 230                 235                 240

Ile Lys Arg
```

<210> SEQ ID NO 100
<211> LENGTH: 249
<212> TYPE: PRT
<213> ORGANISM: Artificial Sequence
<220> FEATURE:
<223> OTHER INFORMATION: scFv-anti-CD19 anchoring domain from protein construct of SEQ ID NO: 32

<400> SEQUENCE: 100

```
Asp Ile Gln Met Thr Gln Ser Pro Ser Ser Met Ser Val Ser Leu Gly
1               5                   10                  15

Asp Thr Val Ser Ile Thr Cys His Ala Ser Gln Gly Ile Ser Ser Asn
            20                  25                  30

Ile Gly Trp Leu Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Ala Asp Tyr Ser Leu Thr Ile Ser Ser Leu Glu Ser
65                  70                  75                  80

Glu Asp Phe Ala Asp Tyr Tyr Cys Val Gln Tyr Ala Gln Phe Pro Tyr
                85                  90                  95

Thr Phe Gly Gly Gly Thr Lys Leu Glu Leu Lys Arg Gly Gly Gly Gly
            100                 105                 110

Ser Gly Gly Gly Gly Ser Gly Gly Gly Gly Ser Ser Gly Gly Gly Ser
        115                 120                 125

Gln Val Gln Leu Gln Gln Ser Gly Pro Glu Leu Val Lys Pro Gly Ala
    130                 135                 140

Ser Val Lys Ile Ser Cys Lys Ala Ser Gly Tyr Ala Phe Ser Ser Ser
145                 150                 155                 160

Trp Met Asp Trp Val Lys Gln Arg Pro Gly Gln Gly Leu Glu Trp Ile
                165                 170                 175

Gly Arg Ile Tyr Pro Gly Asp Gly Asp Thr Asn Tyr Asn Gly Lys Phe
            180                 185                 190

Lys Gly Lys Ala Thr Leu Thr Ala Asp Lys Ser Ser Ser Thr Ala Tyr
        195                 200                 205

Met Gln Leu Ser Ser Leu Thr Ser Val Asp Ser Ala Val Tyr Phe Cys
    210                 215                 220

Ala Arg Ser Ile Thr Thr Val Val Gly Trp Tyr Phe Asp Val Trp Gly
225                 230                 235                 240

Ala Gly Thr Thr Val Thr Val Ser Ser
                245
```

<210> SEQ ID NO 101
<211> LENGTH: 243
<212> TYPE: PRT
<213> ORGANISM: Artificial Sequence
<220> FEATURE:
<223> OTHER INFORMATION: scFv-anti-CD20 anchoring domain from protein construct of SEQ ID NO: 34

<400> SEQUENCE: 101

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45
```

```
Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ser Gly Gly Gly Gly Ser Gly Gly
        115                 120                 125

Gly Gly Ser Gly Gly Gly Gly Ser Gln Ile Val Leu Ser Gln Ser Pro
    130                 135                 140

Ala Ile Leu Ser Ala Ser Pro Gly Glu Lys Val Thr Met Thr Cys Arg
145                 150                 155                 160

Ala Ser Ser Ser Val Ser Tyr Ile His Trp Phe Gln Gln Lys Pro Gly
                165                 170                 175

Ser Ser Pro Lys Pro Trp Ile Tyr Ala Thr Ser Asn Leu Ala Ser Gly
            180                 185                 190

Val Pro Val Arg Phe Ser Gly Ser Gly Ser Gly Thr Ser Tyr Ser Leu
        195                 200                 205

Thr Ile Ser Arg Val Glu Ala Glu Asp Ala Ala Thr Tyr Tyr Cys Gln
    210                 215                 220

Gln Trp Thr Ser Asn Pro Pro Thr Phe Gly Gly Gly Thr Lys Leu Glu
225                 230                 235                 240

Ile Lys Arg
```

<210> SEQ ID NO 102
<211> LENGTH: 473
<212> TYPE: PRT
<213> ORGANISM: Artificial Sequence
<220> FEATURE:
<223> OTHER INFORMATION: scTNF80(murine) anchoring domain from protein construct of SEQ ID NO: 19

<400> SEQUENCE: 102

```
Asp Lys Pro Val Ala His Val Val Ala Asn His Gln Val Glu Glu Gln
1               5                   10                  15

Leu Glu Trp Leu Ser Gln Arg Ala Asn Ala Leu Leu Ala Asn Gly Met
            20                  25                  30

Asp Leu Lys Asp Asn Gln Leu Val Val Pro Ala Asp Gly Leu Tyr Leu
        35                  40                  45

Val Tyr Ser Gln Val Leu Phe Lys Gly Gln Gly Cys Pro Asp Tyr Val
    50                  55                  60

Leu Leu Thr His Thr Val Ser Arg Phe Ala Ile Ser Tyr Gln Glu Lys
65                  70                  75                  80

Val Asn Leu Leu Ser Ala Val Lys Ser Pro Cys Pro Lys Asp Thr Pro
                85                  90                  95

Glu Gly Ala Glu Leu Lys Pro Trp Tyr Glu Pro Ile Tyr Leu Gly Gly
            100                 105                 110

Val Phe Gln Leu Glu Lys Gly Asp Gln Leu Ser Ala Glu Val Asn Leu
        115                 120                 125

Pro Lys Tyr Leu Asn Phe Arg Glu Ser Gly Gln Val Tyr Phe Gly Val
    130                 135                 140

Ile Ala Leu Gly Gly Gly Ser Gly Gly Gly Ser Gly Gly Gly Ser Gly
145                 150                 155                 160
```

```
Gly Gly Ser Asp Lys Pro Val Ala His Val Val Ala Asn His Gln Val
                165                 170                 175

Glu Glu Gln Leu Glu Trp Leu Ser Gln Arg Ala Asn Ala Leu Leu Ala
            180                 185                 190

Asn Gly Met Asp Leu Lys Asp Asn Gln Leu Val Val Pro Ala Asp Gly
        195                 200                 205

Leu Tyr Leu Val Tyr Ser Gln Val Leu Phe Lys Gly Gln Gly Cys Pro
    210                 215                 220

Asp Tyr Val Leu Leu Thr His Thr Val Ser Arg Phe Ala Ile Ser Tyr
225                 230                 235                 240

Gln Glu Lys Val Asn Leu Leu Ser Ala Val Lys Ser Pro Cys Pro Lys
                245                 250                 255

Asp Thr Pro Glu Gly Ala Glu Leu Lys Pro Trp Tyr Glu Pro Ile Tyr
            260                 265                 270

Leu Gly Gly Val Phe Gln Leu Glu Lys Gly Asp Gln Leu Ser Ala Glu
        275                 280                 285

Val Asn Leu Pro Lys Tyr Leu Asn Phe Arg Glu Ser Gly Gln Val Tyr
    290                 295                 300

Phe Gly Val Ile Ala Leu Gly Gly Gly Ser Gly Gly Gly Ser Gly Gly
305                 310                 315                 320

Gly Ser Gly Gly Gly Ser Asp Lys Pro Val Ala His Val Val Ala Asn
                325                 330                 335

His Gln Val Glu Glu Gln Leu Glu Trp Leu Ser Gln Arg Ala Asn Ala
            340                 345                 350

Leu Leu Ala Asn Gly Met Asp Leu Lys Asp Asn Gln Leu Val Val Pro
        355                 360                 365

Ala Asp Gly Leu Tyr Leu Val Tyr Ser Gln Val Leu Phe Lys Gly Gln
    370                 375                 380

Gly Cys Pro Asp Tyr Val Leu Leu Thr His Thr Val Ser Arg Phe Ala
385                 390                 395                 400

Ile Ser Tyr Gln Glu Lys Val Asn Leu Leu Ser Ala Val Lys Ser Pro
                405                 410                 415

Cys Pro Lys Asp Thr Pro Glu Gly Ala Glu Leu Lys Pro Trp Tyr Glu
            420                 425                 430

Pro Ile Tyr Leu Gly Gly Val Phe Gln Leu Glu Lys Gly Asp Gln Leu
        435                 440                 445

Ser Ala Glu Val Asn Leu Pro Lys Tyr Leu Asn Phe Arg Glu Ser Gly
    450                 455                 460

Gln Val Tyr Phe Gly Val Ile Ala Leu
465                 470


<210> SEQ ID NO 103
<211> LENGTH: 471
<212> TYPE: PRT
<213> ORGANISM: Artificial Sequence
<220> FEATURE:
<223> OTHER INFORMATION: scBaff anchoring domain from protein construct
      of SEQ ID NO: 22

<400> SEQUENCE: 103

Gly Pro Glu Glu Thr Val Thr Gln Asp Cys Leu Gln Leu Ile Ala Asp
1               5                   10                  15

Ser Glu Thr Pro Thr Ile Gln Lys Gly Ser Tyr Thr Phe Val Pro Trp
            20                  25                  30

Leu Leu Ser Phe Lys Arg Gly Ser Ala Leu Glu Glu Lys Glu Asn Lys
```

```
        35                  40                  45

Ile Leu Val Lys Glu Thr Gly Tyr Phe Phe Ile Tyr Gly Gln Val Leu
    50                  55                  60

Tyr Thr Asp Lys Thr Tyr Ala Met Gly His Leu Ile Gln Arg Lys Lys
65                  70                  75                  80

Val His Val Phe Gly Asp Glu Leu Ser Leu Val Thr Leu Phe Arg Cys
                85                  90                  95

Ile Gln Asn Met Pro Glu Thr Leu Pro Asn Asn Ser Cys Tyr Ser Ala
            100                 105                 110

Gly Ile Ala Lys Leu Glu Glu Gly Asp Glu Leu Gln Leu Ala Ile Pro
        115                 120                 125

Arg Glu Asn Ala Gln Ile Ser Leu Asp Gly Asp Val Thr Phe Phe Gly
    130                 135                 140

Ala Leu Lys Leu Leu Gly Gly Gly Gly Ser Gly Gly Gly Gly Ser Gly
145                 150                 155                 160

Pro Glu Glu Thr Val Thr Gln Asp Cys Leu Gln Leu Ile Ala Asp Ser
                165                 170                 175

Glu Thr Pro Thr Ile Gln Lys Gly Ser Tyr Thr Phe Val Pro Trp Leu
            180                 185                 190

Leu Ser Phe Lys Arg Gly Ser Ala Leu Glu Glu Lys Glu Asn Lys Ile
        195                 200                 205

Leu Val Lys Glu Thr Gly Tyr Phe Phe Ile Tyr Gly Gln Val Leu Tyr
    210                 215                 220

Thr Asp Lys Thr Tyr Ala Met Gly His Leu Ile Gln Arg Lys Lys Val
225                 230                 235                 240

His Val Phe Gly Asp Glu Leu Ser Leu Val Thr Leu Phe Arg Cys Ile
                245                 250                 255

Gln Asn Met Pro Glu Thr Leu Pro Asn Asn Ser Cys Tyr Ser Ala Gly
            260                 265                 270

Ile Ala Lys Leu Glu Glu Gly Asp Glu Leu Gln Leu Ala Ile Pro Arg
        275                 280                 285

Glu Asn Ala Gln Ile Ser Leu Asp Gly Asp Val Thr Phe Phe Gly Ala
    290                 295                 300

Leu Lys Leu Leu Gly Gly Gly Gly Ser Gly Gly Gly Gly Ser Gln Phe
305                 310                 315                 320

Ala Ala Gly Pro Glu Glu Thr Val Thr Gln Asp Cys Leu Gln Leu Ile
                325                 330                 335

Ala Asp Ser Glu Thr Pro Thr Ile Gln Lys Gly Ser Tyr Thr Phe Val
            340                 345                 350

Pro Trp Leu Leu Ser Phe Lys Arg Gly Ser Ala Leu Glu Glu Lys Glu
        355                 360                 365

Asn Lys Ile Leu Val Lys Glu Thr Gly Tyr Phe Phe Ile Tyr Gly Gln
    370                 375                 380

Val Leu Tyr Thr Asp Lys Thr Tyr Ala Met Gly His Leu Ile Gln Arg
385                 390                 395                 400

Lys Lys Val His Val Phe Gly Asp Glu Leu Ser Leu Val Thr Leu Phe
                405                 410                 415

Arg Cys Ile Gln Asn Met Pro Glu Thr Leu Pro Asn Asn Ser Cys Tyr
            420                 425                 430

Ser Ala Gly Ile Ala Lys Leu Glu Glu Gly Asp Glu Leu Gln Leu Ala
        435                 440                 445

Ile Pro Arg Glu Asn Ala Gln Ile Ser Leu Asp Gly Asp Val Thr Phe
    450                 455                 460
```

```
Phe Gly Ala Leu Lys Leu Leu
465                 470


<210> SEQ ID NO 104
<211> LENGTH: 419
<212> TYPE: PRT
<213> ORGANISM: Artificial Sequence
<220> FEATURE:
<223> OTHER INFORMATION: scGITRL anchoring domain from protein construct
      of SEQ ID NO: 28

<400> SEQUENCE: 104

Gln Leu Glu Thr Ala Lys Glu Pro Cys Met Ala Lys Phe Gly Pro Leu
1               5                   10                  15

Pro Ser Lys Trp Gln Met Ala Ser Ser Glu Pro Pro Cys Val Asn Lys
            20                  25                  30

Val Ser Asp Trp Lys Leu Glu Ile Leu Gln Asn Gly Leu Tyr Leu Ile
        35                  40                  45

Tyr Gly Gln Val Ala Pro Asn Ala Asn Tyr Asn Asp Val Ala Pro Phe
    50                  55                  60

Glu Val Arg Leu Tyr Lys Asn Lys Asp Met Ile Gln Thr Leu Thr Asn
65                  70                  75                  80

Lys Ser Lys Ile Gln Asn Val Gly Gly Thr Tyr Glu Leu His Val Gly
                85                  90                  95

Asp Thr Ile Asp Leu Ile Phe Asn Ser Glu His Gln Val Leu Lys Asn
            100                 105                 110

Asn Thr Tyr Trp Gly Ile Ile Leu Leu Ala Asn Pro Gln Phe Ile Ser
        115                 120                 125

Gly Gly Gly Ser Gly Gly Gly Ser Gly Gly Gly Ser Gly Gly Gly Ser
    130                 135                 140

Gln Leu Glu Thr Ala Lys Glu Pro Cys Met Ala Lys Phe Gly Pro Leu
145                 150                 155                 160

Pro Ser Lys Trp Gln Met Ala Ser Ser Glu Pro Pro Cys Val Asn Lys
                165                 170                 175

Val Ser Asp Trp Lys Leu Glu Ile Leu Gln Asn Gly Leu Tyr Leu Ile
            180                 185                 190

Tyr Gly Gln Val Ala Pro Asn Ala Asn Tyr Asn Asp Val Ala Pro Phe
        195                 200                 205

Glu Val Arg Leu Tyr Lys Asn Lys Asp Met Ile Gln Thr Leu Thr Asn
    210                 215                 220

Lys Ser Lys Ile Gln Asn Val Gly Gly Thr Tyr Glu Leu His Val Gly
225                 230                 235                 240

Asp Thr Ile Asp Leu Ile Phe Asn Ser Glu His Gln Val Leu Lys Asn
                245                 250                 255

Asn Thr Tyr Trp Gly Ile Ile Leu Leu Ala Asn Pro Gln Phe Ile Ser
            260                 265                 270

Gly Gly Gly Gly Ser Gly Gly Gly Ser Gly Gly Gly Ser Gly Gly Gly
        275                 280                 285

Ser Gln Phe Gln Leu Glu Thr Ala Lys Glu Pro Cys Met Ala Lys Phe
    290                 295                 300

Gly Pro Leu Pro Ser Lys Trp Gln Met Ala Ser Ser Glu Pro Pro Cys
305                 310                 315                 320

Val Asn Lys Val Ser Asp Trp Lys Leu Glu Ile Leu Gln Asn Gly Leu
                325                 330                 335

Tyr Leu Ile Tyr Gly Gln Val Ala Pro Asn Ala Asn Tyr Asn Asp Val
```

```
            340                 345                 350

Ala Pro Phe Glu Val Arg Leu Tyr Lys Asn Lys Asp Met Ile Gln Thr
        355                 360                 365

Leu Thr Asn Lys Ser Lys Ile Gln Asn Val Gly Gly Thr Tyr Glu Leu
    370                 375                 380

His Val Gly Asp Thr Ile Asp Leu Ile Phe Asn Ser Glu His Gln Val
385                 390                 395                 400

Leu Lys Asn Asn Thr Tyr Trp Gly Ile Ile Leu Leu Ala Asn Pro Gln
                405                 410                 415

Phe Ile Ser


<210> SEQ ID NO 105
<211> LENGTH: 648
<212> TYPE: PRT
<213> ORGANISM: Artificial Sequence
<220> FEATURE:
<223> OTHER INFORMATION: sc(murine)41BBL anchoring domain from protein
      construct of SEQ ID NO: 29

<400> SEQUENCE: 105

Thr Glu Pro Arg Pro Ala Leu Thr Ile Thr Thr Ser Pro Asn Leu Gly
1               5                   10                  15

Thr Arg Glu Asn Asn Ala Asp Gln Val Thr Pro Val Ser His Ile Gly
            20                  25                  30

Cys Pro Asn Thr Thr Gln Gln Gly Ser Pro Val Phe Ala Lys Leu Leu
        35                  40                  45

Ala Lys Asn Gln Ala Ser Leu Cys Asn Thr Thr Leu Asn Trp His Ser
    50                  55                  60

Gln Asp Gly Ala Gly Ser Ser Tyr Leu Ser Gln Gly Leu Arg Tyr Glu
65                  70                  75                  80

Glu Asp Lys Lys Glu Leu Val Val Asp Ser Pro Gly Leu Tyr Tyr Val
                85                  90                  95

Phe Leu Glu Leu Lys Leu Ser Pro Thr Phe Thr Asn Thr Gly His Lys
            100                 105                 110

Val Gln Gly Trp Val Ser Leu Val Leu Gln Ala Lys Pro Gln Val Asp
        115                 120                 125

Asp Phe Asp Asn Leu Ala Leu Thr Val Glu Leu Phe Pro Cys Ser Met
    130                 135                 140

Glu Asn Lys Leu Val Asp Arg Ser Trp Ser Gln Leu Leu Leu Leu Lys
145                 150                 155                 160

Ala Gly His Arg Leu Ser Val Gly Leu Arg Ala Tyr Leu His Gly Ala
                165                 170                 175

Gln Asp Ala Tyr Arg Asp Trp Glu Leu Ser Tyr Pro Asn Thr Thr Ser
            180                 185                 190

Phe Gly Leu Phe Leu Val Lys Pro Asp Asn Pro Trp Glu Gly Gly Gly
        195                 200                 205

Ser Gly Gly Gly Ser Gly Gly Gly Ser Gly Gly Gly Ser Thr Glu Pro
    210                 215                 220

Arg Pro Ala Leu Thr Ile Thr Thr Ser Pro Asn Leu Gly Thr Arg Glu
225                 230                 235                 240

Asn Asn Ala Asp Gln Val Thr Pro Val Ser His Ile Gly Cys Pro Asn
                245                 250                 255

Thr Thr Gln Gln Gly Ser Pro Val Phe Ala Lys Leu Leu Ala Lys Asn
            260                 265                 270

Gln Ala Ser Leu Cys Asn Thr Thr Leu Asn Trp His Ser Gln Asp Gly
```

```
        275                 280                 285

Ala Gly Ser Ser Tyr Leu Ser Gln Gly Leu Arg Tyr Glu Glu Asp Lys
    290                 295                 300

Lys Glu Leu Val Val Asp Ser Pro Gly Leu Tyr Tyr Val Phe Leu Glu
305                 310                 315                 320

Leu Lys Leu Ser Pro Thr Phe Thr Asn Thr Gly His Lys Val Gln Gly
                325                 330                 335

Trp Val Ser Leu Val Leu Gln Ala Lys Pro Gln Val Asp Asp Phe Asp
            340                 345                 350

Asn Leu Ala Leu Thr Val Glu Leu Phe Pro Cys Ser Met Glu Asn Lys
        355                 360                 365

Leu Val Asp Arg Ser Trp Ser Gln Leu Leu Leu Leu Lys Ala Gly His
    370                 375                 380

Arg Leu Ser Val Gly Leu Arg Ala Tyr Leu His Gly Ala Gln Asp Ala
385                 390                 395                 400

Tyr Arg Asp Trp Glu Leu Ser Tyr Pro Asn Thr Thr Ser Phe Gly Leu
                405                 410                 415

Phe Leu Val Lys Pro Asp Asn Pro Trp Glu Gly Gly Gly Gly Ser Gly
            420                 425                 430

Gly Gly Ser Gly Gly Gly Ser Gly Gly Gly Ser Thr Glu Pro Arg Pro
        435                 440                 445

Ala Leu Thr Ile Thr Thr Ser Pro Asn Leu Gly Thr Arg Glu Asn Asn
    450                 455                 460

Ala Asp Gln Val Thr Pro Val Ser His Ile Gly Cys Pro Asn Thr Thr
465                 470                 475                 480

Gln Gln Gly Ser Pro Val Phe Ala Lys Leu Leu Ala Lys Asn Gln Ala
                485                 490                 495

Ser Leu Cys Asn Thr Thr Leu Asn Trp His Ser Gln Asp Gly Ala Gly
            500                 505                 510

Ser Ser Tyr Leu Ser Gln Gly Leu Arg Tyr Glu Glu Asp Lys Lys Glu
        515                 520                 525

Leu Val Val Asp Ser Pro Gly Leu Tyr Tyr Val Phe Leu Glu Leu Lys
    530                 535                 540

Leu Ser Pro Thr Phe Thr Asn Thr Gly His Lys Val Gln Gly Trp Val
545                 550                 555                 560

Ser Leu Val Leu Gln Ala Lys Pro Gln Val Asp Asp Phe Asp Asn Leu
                565                 570                 575

Ala Leu Thr Val Glu Leu Phe Pro Cys Ser Met Glu Asn Lys Leu Val
            580                 585                 590

Asp Arg Ser Trp Ser Gln Leu Leu Leu Leu Lys Ala Gly His Arg Leu
        595                 600                 605

Ser Val Gly Leu Arg Ala Tyr Leu His Gly Ala Gln Asp Ala Tyr Arg
    610                 615                 620

Asp Trp Glu Leu Ser Tyr Pro Asn Thr Thr Ser Phe Gly Leu Phe Leu
625                 630                 635                 640

Val Lys Pro Asp Asn Pro Trp Glu
                645
```

<210> SEQ ID NO 106
<211> LENGTH: 128
<212> TYPE: PRT
<213> ORGANISM: Artificial Sequence
<220> FEATURE:
<223> OTHER INFORMATION: (murine)GITRL anchoring domain from protein construct of SEQ ID NO: 30

<400> SEQUENCE: 106

Pro Thr Ala Ile Glu Ser Cys Met Val Lys Phe Glu Leu Ser Ser Ser
1 5 10 15

Lys Trp His Met Thr Ser Pro Lys Pro His Cys Val Asn Thr Thr Ser
20 25 30

Asp Gly Lys Leu Lys Ile Leu Gln Ser Gly Thr Tyr Leu Ile Tyr Gly
35 40 45

Gln Val Ile Pro Val Asp Lys Lys Tyr Ile Lys Asp Asn Ala Pro Phe
50 55 60

Val Val Gln Ile Tyr Lys Lys Asn Asp Val Leu Gln Thr Leu Met Asn
65 70 75 80

Asp Phe Gln Ile Leu Pro Ile Gly Gly Val Tyr Glu Leu His Ala Gly
85 90 95

Asp Asn Ile Tyr Leu Lys Phe Asn Ser Lys Asp His Ile Gln Lys Thr
100 105 110

Asn Thr Tyr Trp Gly Ile Ile Leu Met Pro Asp Leu Pro Phe Ile Ser
115 120 125

<210> SEQ ID NO 107
<211> LENGTH: 111
<212> TYPE: PRT
<213> ORGANISM: Artificial Sequence
<220> FEATURE:
<223> OTHER INFORMATION: Human IL-2 anchoring domain

<400> SEQUENCE: 107

Ala Pro Thr Ser Ser Ser Thr Lys Lys Thr Gln Leu Gln Leu Glu His
1 5 10 15

Leu Leu Leu Asp Leu Gln Met Ile Leu Asn Gly Ile Asn Asn Tyr Lys
20 25 30

Asn Pro Lys Leu Thr Arg Met Leu Thr Phe Lys Phe Tyr Met Pro Lys
35 40 45

Lys Ala Thr Glu Leu Lys His Leu Gln Cys Leu Glu Glu Glu Leu Lys
50 55 60

Pro Leu Glu Glu Val Leu Asn Leu Ala Gln Ser Lys Asn Phe His Leu
65 70 75 80

Arg Pro Arg Asp Leu Ile Ser Asn Ile Asn Val Ile Val Leu Glu Leu
85 90 95

Lys Glu His Lys Pro Ser Ser Gln Arg Lys Glu Glu Ser Thr Cys
100 105 110

<210> SEQ ID NO 108
<211> LENGTH: 807
<212> TYPE: DNA
<213> ORGANISM: Artificial Sequence
<220> FEATURE:
<223> OTHER INFORMATION: anti-CD40(G28.5)-VH(1-114)

<400> SEQUENCE: 108
atgaacttcg gcttcagcct gatcttcctg gtgctggtgc tgaagggcgt gcagtgcgaa 60
gtgaagctgg tgccccggca attggactac aaggacgacg acgacaaaga attggatatc 120
cagctccagc agtctggccc tggactcgtc aaaccatctc agagcctgtc tctcacctgt 180
tctgtcaccg gatactccat caccaccaac tacaactgga attggattcg gcagtttcct 240
gggaacaaac tcgaatggat gggatacatc cgatacgacg gcactagtga atacacccca 300
tctctcaaaa atcgggtgtc cattacccgg gacacttcta tgaaccagtt ctttctccga 360

```
ctcacctctg tgacacctga ggataccgcc acatactact gtgctagact ggactactgg    420

gggcagggaa cactggtgac cgtgtcatct ggatcctcta gcgccagcac aaagggcccc    480

agcgtgttcc ctctggcccc tagcagcaag agcacatctg gcggaacagc cgccctgggc    540

tgcctcgtga aggactactt tcccgagccc gtgacagtgt cctggaactc tggcgccctg    600

acaagcggcg tgcacacctt tccagccgtg ctgcagagca gcggcctgta ctctctgagc    660

agcgtcgtga ctgtgcccag cagcagcctg ggcacccaga cctacatctg caacgtgaac    720

cacaagccca gcaacaccaa ggtggacaag aaggtggaac ccaagagctg cgacaagacc    780

cacacctgtc ccccttgtcc tgcctaa                                          807
```

<210> SEQ ID NO 109
<211> LENGTH: 2226
<212> TYPE: DNA
<213> ORGANISM: Artificial Sequence
<220> FEATURE:
<223> OTHER INFORMATION: anti-CD40(G28.5)-VH(1-114)-scBaff

<400> SEQUENCE: 109

```
atgaacttcg gcttcagcct gatcttcctg gtgctggtgc tgaagggcgt gcagtgcgaa     60

gtgaagctgg tgccccggca attggactac aaggacgacg acgacaaaga attggatatc    120

cagctccagc agtctggccc tggactcgtc aaaccatctc agagcctgtc tctcacctgt    180

tctgtcaccg gatactccat caccaccaac tacaactgga attggattcg gcagtttcct    240

gggaacaaac tcgaatggat gggatacatc cgatacgacg gcactagtga atacacccca    300

tctctcaaaa atcgggtgtc cattacccgg gacacttcta tgaaccagtt ctttctccga    360

ctcacctctg tgacacctga ggataccgcc acatactact gtgctagact ggactactgg    420

gggcagggaa cactggtgac cgtgtcatct ggatcctcta gcgccagcac aaagggcccc    480

agcgtgttcc ctctggcccc tagcagcaag agcacatctg gcggaacagc cgccctgggc    540

tgcctcgtga aggactactt tcccgagccc gtgacagtgt cctggaactc tggcgccctg    600

acaagcggcg tgcacacctt tccagccgtg ctgcagagca gcggcctgta ctctctgagc    660

agcgtcgtga ctgtgcccag cagcagcctg ggcacccaga cctacatctg caacgtgaac    720

cacaagccca gcaacaccaa ggtggacaag aaggtggaac ccaagagctg cgacaagacc    780

cacacctgtc cccttgtcc tgccctcgag ggacccgagg aaactgtgac tcaggactgt     840

ctccagctca ttgccgatag tgaaacccct accatccaga aaggctctta caccttcgtg    900

ccatggctgc tgtcattcaa acggggatct gctctggagg agaaggaaaa caaaatcctg    960

gtcaaggaaa ccggctactt cttcatctac ggccaggtcc tctacaccga caaaacatac   1020

gctatggggc atctcattca gcggaaaaaa gtccacgtgt tcggcgacga actctctctc   1080

gtgacactgt tccggtgtat tcagaacatg cccgagactc tgcccaataa tagctgctac   1140

tctgctggca ttgccaaact ggaggagggc gacgaactcc agctggctat tcctagggaa   1200

aatgcccaga ttagcctgga cggggatgtg acatttttg gcgccctgaa actgctggga    1260

ggcggaggga gtggcggggg aggctctgga cctgaggaaa ctgtgaccca ggattgtctc   1320

cagctcattg ccgatagtga gactcctacc attcagaagg gatcttacac ctttgtgcct   1380

tggctgctgt ctttcaaacg gggctctgct ctggaggaaa aggagaacaa aattctggtc   1440

aaagagactg gctacttctt catctacggc caggtgctgt acaccgacaa aacatacgcc   1500

atgggccatc tcattcagcg gaaaaaagtc cacgtgttcg gcgacgaact ctctctcgtg   1560
```

```
acactgttcc ggtgtatcca gaacatgccc gagacactgc ccaataatag ctgctactct   1620

gccggcattg ctaaactgga ggagggggac gaactccagc tggctattcc tagggaaaat   1680

gcccagattt ctctcgatgg ggatgtgaca ttcttcgggg ccctcaaact gctgggaggc   1740

ggcggatctg gcggaggcgg gagtcaattc gcagcaggtc cagaagaaac agtcactcaa   1800

gactgcttgc aactgattgc agacagtgaa acaccaacta tacaaaaagg atcttacaca   1860

tttgttccat ggcttctcag ctttaaaagg ggaagtgccc tagaagaaaa agagaataaa   1920

atattggtca aagaaactgg ttactttttt atatatggtc aggttttata tactgataag   1980

acctacgcca tgggacatct aattcagagg aagaaggtcc atgtctttgg ggatgaattg   2040

agtctggtga ctttgtttcg atgtattcaa aatatgcctg aaacactacc caataattcc   2100

tgctattcag ctggcattgc aaaactggaa gaaggagatg aactccaact tgcaatacca   2160

agagaaaatg cacaaatatc actggatgga gatgtcacat tttttggtgc attgaaactg   2220

ctgtga                                                              2226
```

<210> SEQ ID NO 110
<211> LENGTH: 2286
<212> TYPE: DNA
<213> ORGANISM: Artificial Sequence
<220> FEATURE:
<223> OTHER INFORMATION: anti-CD95(E09)-VH(1-114)-scBaff

<400> SEQUENCE: 110

```
atgaacttcg gcttcagcct gatcttcctg gtgctggtgc tgaagggcgt gcagtgcgaa     60

gtgaagctgg tgccccggca attggactac aaggacgacg acgacaaaga attgcagctg    120

cagctgcagg aatctggccc tggcctcgtg aagcccagcg agacactgag cctgacctgt    180

accgtgtccg gcgccagcat cagcgccaac agctactatg gcgtgtgggt gcgccagagc    240

cctggcaagg gactggaatg ggtgggatct atcgcctacc ggggcaacag caacagcggc    300

agcacctact acaaccccag cctgaagtcc cgggccaccg tgtctgtgga caccagcaag    360

aaccaggtgt ccctgcggct gacctctgtg acagccgccg ataccgccct gtactactgc    420

gccagaaggc agctgctgga cgacggcaca ggatatcagt gggccgcctt cgatgtgtgg    480

ggccagggaa caatggtcac cgtgtcctcc ggatcctcta gcgccagcac aaagggcccc    540

agcgtgttcc ctctggcccc tagcagcaag agcacatctg gcggaacagc cgccctgggc    600

tgcctcgtga aggactactt tcccgagccc gtgacagtgt cctggaactc tggcgccctg    660

acaagcggcg tgcacacctt tccagccgtg ctgcagagca gcggcctgta ctctctgagc    720

agcgtcgtga ctgtgcccag cagcagcctg ggcacccaga cctacatctg caacgtgaac    780

cacaagccca gcaacaccaa ggtggacaag aaggtggaac ccaagagctg cgacaagacc    840

cacacctgtc cccccttgtcc tgccctcgag ggacccgagg aaactgtgac tcaggactgt    900

ctccagctca ttgccgatag tgaaacccct accatccaga aaggctctta caccttcgtg    960

ccatggctgc tgtcattcaa acggggatct gctctggagg agaaggaaaa caaaatcctg   1020

gtcaaggaaa ccggctactt cttcatctac ggccaggtcc tctacaccga caaaacatac   1080

gctatggggc atctcattca gcggaaaaaa gtccacgtgt tcggcgacga actctctctc   1140

gtgacactgt tccggtgtat tcagaacatg cccgagactc tgcccaataa tagctgctac   1200

tctgctggca ttgccaaact ggaggagggc gacgaactcc agctggctat tcctagggaa   1260

aatgcccaga ttagcctgga cggggatgtg acatttttttg gcgccctgaa actgctggga   1320

ggcggaggga gtggcggggg aggctctgga cctgaggaaa ctgtgaccca ggattgtctc   1380
```

```
cagctcattg ccgatagtga gactcctacc attcagaagg gatcttacac ctttgtgcct   1440
tggctgctgt ctttcaaacg gggctctgct ctggaggaaa aggagaacaa aattctggtc   1500
aaagagactg gctacttctt catctacggc caggtgctgt acaccgacaa aacatacgcc   1560
atgggccatc tcattcagcg gaaaaaagtc cacgtgttcg gcgacgaact ctctctcgtg   1620
acactgttcc ggtgtatcca gaacatgccc gagacactgc ccaataatag ctgctactct   1680
gccggcattg ctaaactgga ggagggggac gaactccagc tggctattcc tagggaaaat   1740
gcccagattt ctctcgatgg ggatgtgaca ttcttcgggg ccctcaaact gctgggaggc   1800
ggcggatctg gcggaggcgg gagtcaattc gcagcaggtc cagaagaaac agtcactcaa   1860
gactgcttgc aactgattgc agacagtgaa acaccaacta tacaaaaagg atcttacaca   1920
tttgttccat ggcttctcag ctttaaaagg ggaagtgccc tagaagaaaa agagaataaa   1980
atattggtca aagaaactgg ttactttttt atatatggtc aggttttata tactgataag   2040
acctacgcca tgggacatct aattcagagg aagaaggtcc atgtctttgg ggatgaattg   2100
agtctggtga ctttgtttcg atgtattcaa aatatgcctg aaacactacc caataattcc   2160
tgctattcag ctggcattgc aaaactggaa gaaggagatg aactccaact tgcaatacca   2220
agagaaaatg cacaaatatc actggatgga gatgtcacat tttttggtgc attgaaactg   2280
ctgtga                                                              2286
```

<210> SEQ ID NO 111
<211> LENGTH: 2169
<212> TYPE: DNA
<213> ORGANISM: Artificial Sequence
<220> FEATURE:
<223> OTHER INFORMATION: anti-TNFR2(C4)-IgG2-VH-scFv:CD20

<400> SEQUENCE: 111

```
atgaacttcg gcttcagcct gatcttcctg gtgctggtgc tgaagggcgt gcagtgcgaa     60
gtgaagctgg tgccccggca attgcaggtt cagctgctgc agtctggacc tgagctggtg    120
aagcctgggg cttcagtgaa gttgtcctgc aaggcttctg gttatagttt cacaagttac    180
gatattaact gggtgaagca gaggcctgga cagggacttg agtgggttgg atggatttat    240
cctagagatg gtgatactaa gtacaatgag aaattcaagg gcaaggccat attgactgta    300
gacacatcct ccaacacagc gtacatgaac ctccacagcc tgacatctga ggactctgcg    360
gtctatttct gtgcaagact aactgggccc tactggtact tcgatgtctg gggcacaggg    420
accacggtca ccgtctcctc aggatcctcg agtgctagca ccaagggccc atcggtcttc    480
cccctggcgc cctgctccag gagcacctcc gagagcacag cggccctggg ctgcctggtc    540
aaggactact tccccgaacc ggtgacggtg tcgtggaact caggcgctct gaccagcggc    600
gtgcacacct tcccagctgt cctacagtcc tcaggactct actccctcag cagcgtggtg    660
accgtgccct ccagcaactt cggcacccag acctacacct gcaacgtaga tcacaagccc    720
agcaacacca aggtggacaa gacagttgag cgcaaatgtt gtgtcgagtg cccaccgtgc    780
ccagcaccac ctgtggcagg accgtcagtc ttcctcttcc ccccaaaacc caaggacacc    840
ctcatgatct cccggacccc tgaggtcacg tgcgtggtgg tggacgtgag ccacgaagac    900
cccgaggtcc agttcaactg gtacgtggac ggcgtggagg tgcataatgc caagacaaag    960
ccacgggagg agcagttcaa cagcacgttc cgtgtggtca gcgtcctcac cgttgtgcac   1020
caggactggc tgaacggcaa ggagtacaag tgcaaggtct ccaacaaagg cctcccagcc   1080
```

```
cccatcgaga aaaccatctc caaaaccaaa gggcagcccc gagaaccaca ggtgtacacc   1140
ctgcccccat cccgggagga gatgaccaag aaccaggtca gcctgacctg cctggtcaaa   1200
ggcttctacc ccagcgacat cgccgtggag tgggagagca atgggcagcc ggagaacaac   1260
tacaagacca cgcctcccat gctggactcc gacggctcct tcttcctcta cagcaagctc   1320
accgtggaca agagcaggtg gcagcagggg aacgtcttct catgctccgt gatgcatgag   1380
gctctgcaca accactacac gcagaagagc ctctccctgt ctccgggtaa agaattccag   1440
gtacaactgc agcagcctgg ggctgagctg gtgaagcctg gggcctcagt gaagatgtcc   1500
tgcaaggctt ctggctacac atttaccagt tacaatatgc actgggtaaa acagacacct   1560
ggtcggggcc tggaatggat tggagctatt tatcccggaa atggtgatac ttcctacaat   1620
cagaagttca aaggcaaggc cacattgact gcagacaaat cctccagcac agcctacatg   1680
cagctcagca gcctgacatc tgaggactct gcggtctatt actgtgcaag atcgacttac   1740
tacggcggtg actggtactt caatgtctgg ggcgcaggga ccacggtcac cgtctcttca   1800
ggaggaggcg gatccggcgg aggcggaagc ggtggcggag gctctcaaat tgttctctcc   1860
cagtctccag caatcctgtc tgcatctcca ggggagaagg tcacaatgac ttgcagggcc   1920
agctcaagtg taagttacat ccactggttc cagcagaagc caggatcctc ccccaaaccc   1980
tggatttatg ccacatccaa cctggcttct ggagtccctg ttcgcttcag tggcagtggg   2040
tctgggactt cttactctct cacaatcagc agagtggagg ctgaagatgc tgccacttat   2100
tactgccagc agtggactag taacccaccc acgttcggag gggggaccaa gctggaaatc   2160
aaacgttaa                                                           2169
```

<210> SEQ ID NO 112
<211> LENGTH: 2196
<212> TYPE: DNA
<213> ORGANISM: Artificial Sequence
<220> FEATURE:
<223> OTHER INFORMATION: anti-TNFR2(C4)-IgG1(N297A)-VH-scFv:CD70(1F6)

<400> SEQUENCE: 112

```
atgaacttcg gcttcagcct gatcttcctg gtgctggtgc tgaagggcgt gcagtgcgaa     60
gtgaagctgg tgccccggca attgcaggtt cagctgctgc agtctggacc tgagctggtg    120
aagcctgggg cttcagtgaa gttgtcctgc aaggcttctg gttatagttt cacaagttac    180
gatattaact gggtgaagca gaggcctgga cagggacttg agtgggttgg atggatttat    240
cctagagatg gtgatactaa gtacaatgag aaattcaagg gcaaggccat attgactgta    300
gacacatcct ccaacacagc gtacatgaac ctccacagcc tgacatctga ggactctgcg    360
gtctatttct gtgcaagact aactgggccc tactggtact tcgatgtctg gggcacaggg    420
accacggtca ccgtctcctc aggatccagc agcgcctcta caaagggccc cagcgtgttc    480
cctctggccc ctagcagcaa gagcacatct ggcggaacag ccgccctggg ctgcctcgtg    540
aaggactact tcccgagccc cgtgaccgtg tcctggaact ctggcgctct gacaagcggc    600
gtgcacacct ttccagccgt gctgcagagc agcggcctgt actctctgag cagcgtcgtg    660
acagtgccca gcagctctct gggcacccag acctacatct gcaacgtgaa ccacaagccc    720
agcaacacca aggtggacaa gaaggtggaa cccaagagct gcgacaagac ccacacctgt    780
ccccccttgtc ctgcccccga actgctggga ggcccttccg tgttcctgtt cccccccaaag    840
cccaaggaca ccctgatgat cagccggacc cccgaagtga cctgcgtggt ggtggatgtg    900
tcccacgagg accctgaagt gaagtttaat tggtacgtgg acggcgtgga agtgcacaac    960
```

```
gccaagacca agcctagaga ggaacagtac gccagcacct accgggtggt gtccgtgctg   1020

acagtgctgc accaggactg gctgaacggc aaagagtaca agtgcaaggt gtccaacaag   1080

gccctgcctg cccccatcga gaaaaccatc agcaaggcca agggccagcc ccgcgaaccc   1140

caggtgtaca cactgccccc aagcagggac gagctgacca agaaccaggt gtccctgacc   1200

tgtctcgtga aaggcttcta ccccagcgat atcgccgtgg aatgggagag caacggccag   1260

cccgagaaca actacaagac cacccccccct gtgctggaca gcgacggctc attcttcctg   1320

tacagcaagc tgaccgtgga caagtcccgg tggcagcagg gcaacgtgtt cagctgcagc   1380

gtgatgcacg aggccctgca caaccactac acccagaagt ccctgagcct gagccccggc   1440

aaggaattcc agattcagct cgtccagtcc ggacctgaag tgaaaaaacc tggcgaaacc   1500

gtgaaaattt cctgtaaggc ctctggctac acctttacca actacggcat gaactgggtc   1560

aaacaggctc ctgggaaggg cctgaaatgg atgggatgga tcaacaccta caccggcgaa   1620

ccaacatacg ccgatgcctt taagggacgc tttgccttct ctctggaaac ttccgcctct   1680

actgcttacc tccagatcaa taacctcaaa aacgaggaca ccgccactta cttttgtgct   1740

cgggattacg gggactacgg gatggattac tggggacagg gaacatctgt gaccgtgtct   1800

agcgcttcta caaagggggcc taaactggag gagggcgagt ttagcgaggc tagagtggat   1860

atcgtgctca cacagtctcc cgcttctctg gctgtctcac tgggccagcg agcaacaatc   1920

tcttgtcggg cttccaaatc cgtgtctact agcggctact cttttatgca ctggtaccag   1980

cagaaacctg gcagcctcc aaaactgctc atctacctgg cttcaaacct cgaatccgga   2040

gtgcctgctc gattttctgg ctctggctcc gggaccgact ttacactgaa cattcatcct   2100

gtcgaggagg aggacgctgc cacatactac tgtcagcatt ctagggaggt gccatggaca   2160

tttggcgggg gaacaaaact ggaaatcaaa cggtaa                             2196
```

```
<210> SEQ ID NO 113
<211> LENGTH: 2187
<212> TYPE: DNA
<213> ORGANISM: Artificial Sequence
<220> FEATURE:
<223> OTHER INFORMATION: anti-TNFR2(C4)-IgG1(N297A)-VH-scFv:CD70(2H5)

<400> SEQUENCE: 113

atgaacttcg gcttcagcct gatcttcctg gtgctggtgc tgaagggcgt gcagtgcgaa     60

gtgaagctgg tgccccggca attgcaggtt cagctgctgc agtctggacc tgagctggtg    120

aagcctgggg cttcagtgaa gttgtcctgc aaggcttctg gttatagttt cacaagttac    180

gatattaact gggtgaagca gaggcctgga cagggacttg agtgggttgg atggatttat    240

cctagagatg gtgatactaa gtacaatgag aaattcaagg gcaaggccat attgactgta    300

gacacatcct ccaacacagc gtacatgaac ctccacagcc tgacatctga ggactctgcg    360

gtctatttct gtgcaagact aactgggccc tactggtact tcgatgtctg gggcacaggg    420

accacggtca ccgtctcctc aggatccagc agcgcctcta caaagggccc cagcgtgttc    480

cctctggccc ctagcagcaa gagcacatct ggcggaacag ccgccctggg ctgcctcgtg    540

aaggactact tcccgagcc cgtgaccgtg tcctggaact ctggcgctct gacaagcggc    600

gtgcacacct ttccagccgt gctgcagagc agcggcctgt actctctgag cagcgtcgtg    660

acagtgccca gcagctctct gggcacccag acctacatct gcaacgtgaa ccacaagccc    720

agcaacacca aggtggacaa gaaggtggaa cccaagagct gcgacaagac ccacacctgt    780
```

```
ccccccttgtc ctgcccccga actgctggga ggcccttccg tgttcctgtt ccccccaaag    840

cccaaggaca ccctgatgat cagccggacc cccgaagtga cctgcgtggt ggtggatgtg    900

tcccacgagg accctgaagt gaagtttaat tggtacgtgg acggcgtgga agtgcacaac    960

gccaagacca agcctagaga ggaacagtac gccagcacct accgggtggt gtccgtgctg   1020

acagtgctgc accaggactg gctgaacggc aaagagtaca agtgcaaggt gtccaacaag   1080

gccctgcctg cccccatcga gaaaaccatc agcaaggcca agggccagcc ccgcgaaccc   1140

caggtgtaca cactgccccc aagcagggac gagctgacca agaaccaggt gtccctgacc   1200

tgtctcgtga aaggcttcta ccccagcgat atcgccgtgg aatgggagag caacggccag   1260

cccgagaaca actacaagac cacccccccct gtgctggaca gcgacggctc attcttcctg   1320

tacagcaagc tgaccgtgga caagtcccgg tggcagcagg gcaacgtgtt cagctgcagc   1380

gtgatgcacg aggccctgca caaccactac acccagaagt ccctgagcct gagccccggc   1440

aaggaattcc aggtgcagct ggtggaatct ggcggcggag tggtgcagcc tggcagaagc   1500

ctgagactga gctgtgccgc cagcggcttc accttcagca gctacatcat gcactgggtg   1560

cgccaggccc ctggcaaggg actggaatgg gtggccgtga tcagctacga cggccggaac   1620

aagtactacg ccgacagcgt gaagggccgg ttcaccatct cccgggacaa cagcaagaac   1680

accctgtacc tgcagatgaa cagcctgcgg gccgaggaca ccgccgtgta ctactgtgcc   1740

agagacaccg acggctacga cttcgactat tggggccagg gcaccctcgt gaccgtgtct   1800

agcggaggcg gaggatctgg cggagggggga tcaggcgggg gaggctctga aatcgtgctg   1860

acacagagcc ccgccaccct gtcactgtct ccaggcgaaa gagccaccct gagctgcaga   1920

gccagccaga gcgtgtccag ctacctggcc tggtatcagc agaagcccgg acaggccccc   1980

agactgctga tctacgacgc cagcaatcgg gccacaggca tccctgccag attttccggc   2040

tctggcagcg gcaccgactt caccctgaca atcagcagcc tggaacccga ggactttgcc   2100

gtgtattatt gccagcagcg gaccaactgg cccctgacct ttggcggagg caccaaggtg   2160

gaaatcaagg ccagcaccaa gggctaa                                        2187
```

```
<210> SEQ ID NO 114
<211> LENGTH: 2211
<212> TYPE: DNA
<213> ORGANISM: Artificial Sequence
<220> FEATURE:
<223> OTHER INFORMATION: anti-41BB(HBBK4)-IgG1(N297A)-VH-scFv:CD20

<400> SEQUENCE: 114
```

```
atgaacttcg gcttcagcct gatcttcctg gtgctggtgc tgaagggcgt gcagtgcgaa     60

gtgaagctgg tgccccggca attggactac aaggacgacg acgacaaaga attccaggtc    120

cagctgcagc agtctggcgc cgaagttatt aagcctggcg cctccgtgaa gctgagctgt    180

aaagccagcg gctacacctt cagcagctac tggatgcact gggtccgaca ggctccagga    240

caaggcctgg aatggatcgg cgagatcaac cctggcaacg gccacaccaa ctacaacgag    300

aagttcaaga gccgggccac actgaccggc gataccagca caagcaccgt gtacatggaa    360

ctgagcagcc tgagaagcga ggacaccgcc gtgtactact gcgccagatc ctttaccacc    420

gccagagcct ttgcctattg gggccaggga acactggtca ccgtgtccag cagatccagc    480

agcgcctcta caaagggccc cagcgtgttc cctctggccc ctagcagcaa gagcacatct    540

ggcggaacag ccgccctggg ctgcctcgtg aaggactact ttcccgagcc cgtgaccgtg    600

tcctggaact ctggcgctct gacaagcggc gtgcacacct ttccagccgt gctgcagagc    660
```

```
agcggcctgt actctctgag cagcgtcgtg acagtgccca gcagctctct gggcacccag    720
acctacatct gcaacgtgaa ccacaagccc agcaacacca aggtggacaa gaaggtggaa    780
cccaagagct gcgacaagac ccacacctgt ccccccttgtc ctgcccccga actgctggga   840
ggcccttccg tgttcctgtt ccccccaaag cccaaggaca ccctgatgat cagccggacc    900
cccgaagtga cctgcgtggt ggtggatgtg tcccacgagg accctgaagt gaagtttaat    960
tggtacgtgg acggcgtgga agtgcacaac gccaagacca agcctagaga ggaacagtac   1020
gccagcacct accgggtggt gtccgtgctg acagtgctgc accaggactg gctgaacggc   1080
aaagagtaca agtgcaaggt gtccaacaag gccctgcctg cccccatcga gaaaaccatc   1140
agcaaggcca agggccagcc ccgcgaaccc caggtgtaca cactgccccc aagcagggac   1200
gagctgacca agaaccaggt gtccctgacc tgtctcgtga aaggcttcta ccccagcgat   1260
atcgccgtgg aatgggagag caacggccag cccgagaaca actacaagac cacccccccct  1320
gtgctggaca gcgacggctc attcttcctg tacagcaagc tgaccgtgga caagtcccgg   1380
tggcagcagg gcaacgtgtt cagctgcagc gtgatgcacg aggccctgca caaccactac   1440
acccagaagt ccctgagcct gagccccggc aagctcgagc aggtacaact gcagcagcct   1500
ggggctgagc tggtgaagcc tggggcctca gtgaagatgt cctgcaaggc ttctggctac   1560
acatttacca gttacaatat gcactgggta aaacagacac ctggtcgggg cctggaatgg   1620
attggagcta tttatcccgg aaatggtgat acttcctaca atcagaagtt caaaggcaag   1680
gccacattga ctgcagacaa atcctccagc acagcctaca tgcagctcag cagcctgaca   1740
tctgaggact ctgcggtcta ttactgtgca agatcgactt actacggcgg tgactggtac   1800
ttcaatgtct ggggcgcagg gaccacggtc accgtctctt caggaggagg cggatccggc   1860
ggaggcggaa gcggtggcgg aggctctcaa attgttctct cccagtctcc agcaatcctg   1920
tctgcatctc caggggagaa ggtcacaatg acttgcaggg ccagctcaag tgtaagttac   1980
atccactggt tccagcagaa gccaggatcc tcccccaaac cctggattta tgccacatcc   2040
aacctggctt ctggagtccc tgttcgcttc agtggcagtg ggtctgggac ttcttactct   2100
ctcacaatca gcagagtgga ggctgaagat gctgccactt attactgcca gcagtggact   2160
agtaacccac ccacgttcgg agggggggacc aagctggaaa tcaaacgtta a            2211
```

<210> SEQ ID NO 115
<211> LENGTH: 774
<212> TYPE: DNA
<213> ORGANISM: Artificial Sequence
<220> FEATURE:
<223> OTHER INFORMATION: anti-41BB(HBBK4)-VL

<400> SEQUENCE: 115

```
atgaacttcg gcttcagcct gatcttcctg gtgctggtgc tgaagggcgt gcagtgcgaa     60
gtgaagctgg tgccccggca attggactac aaggacgacg acgacaaaga attggacatc    120
gtgatgactc agagccccgc cttcctgtct gtgacccctg gcgagaaagt gaccatcacc    180
tgtagagcca gccagaccat cagcgactac ctgcactggt atcagcagaa gcccgatcag    240
gcccctaagc tgctgattaa gtacgcctct cagagcatca gcggcatccc cagcagattt    300
tctggcagcg gctctggcac cgacttcacc tttaccatca gctccctgga agccgaggat    360
gccgccacct actattgtca ggacggccac agcttccctc caacctttgg acagggcaca    420
aagctggaaa tcaagggatc cgaaatcaag cgtacggtgg ccgctcccag cgtgttcatc    480
```

```
ttcccaccta gcgacgagca gctgaagtcc ggcacagcct ctgtcgtgtg cctgctgaac    540

aacttctacc cccgcgaggc caaggtgcag tggaaggtgg acaatgccct gcagagcggc    600

aacagccagg aaagcgtgac cgagcaggac agcaaggact ccacctacag cctgagcagc    660

accctgaccc tgagcaaggc cgactacgag aagcacaagg tgtacgcctg cgaagtgacc    720

caccagggcc tgtctagccc cgtgaccaag agcttcaacc ggggcgagtg ctaa          774
```

```
<210> SEQ ID NO 116
<211> LENGTH: 2250
<212> TYPE: DNA
<213> ORGANISM: Artificial Sequence
<220> FEATURE:
<223> OTHER INFORMATION: anti-CD95(E09)-IgG1(N297A)-VH-scFv:CD20
<220> FEATURE:
<221> NAME/KEY: misc_feature
<222> LOCATION: (1581)..(1581)
<223> OTHER INFORMATION: n is a, c, g, or t

<400> SEQUENCE: 116

atgaacttcg gcttcagcct gatcttcctg gtgctggtgc tgaagggcgt gcagtgcgaa     60

gtgaagctgg tgccccggca attggactac aaggacgacg acgacaaaga attgcagctg    120

cagctgcagg aatctggccc tggcctcgtg aagcccagcg agacactgag cctgacctgt    180

accgtgtccg gcgccagcat cagcgccaac agctactatg gcgtgtgggt gcgccagagc    240

cctggcaagg gactggaatg ggtgggatct atcgcctacc ggggcaacag caacagcggc    300

agcacctact acaaccccag cctgaagtcc cgggccaccg tgtctgtgga caccagcaag    360

aaccaggtgt ccctgcggct gacctctgtg acagccgccg ataccgccct gtactactgc    420

gccagaaggc agctgctgga cgacggcaca ggatatcagt gggccgcctt cgatgtgtgg    480

ggccagggaa caatggtcac cgtgtcctcc ggatccagca gcgcctctac aaagggcccc    540

agcgtgttcc ctctggcccc tagcagcaag agcacatctg gcggaacagc cgccctgggc    600

tgcctcgtga aggactactt tcccgagccc gtgaccgtgt cctggaactc tggcgctctg    660

acaagcggcg tgcacacctt tccagccgtg ctgcagagca gcggcctgta ctctctgagc    720

agcgtcgtga cagtgcccag cagctctctg ggcacccaga cctacatctg caacgtgaac    780

cacaagccca gcaacaccaa ggtggacaag aaggtggaac ccaagagctg cgacaagacc    840

cacacctgtc cccctttgtcc tgcccccgaa ctgctgggag gcccttccgt gttcctgttc    900

cccccaaagc ccaaggacac cctgatgatc agccggaccc ccgaagtgac ctgcgtggtg    960

gtggatgtgt cccacgagga ccctgaagtg aagtttaatt ggtacgtgga cggcgtggaa   1020

gtgcacaacg ccaagaccaa gcctagagag gaacagtacg ccagcaccta ccgggtggtg   1080

tccgtgctga cagtgctgca ccaggactgg ctgaacggca aagagtacaa gtgcaaggtg   1140

tccaacaagg ccctgcctgc ccccatcgag aaaaccatca gcaaggccaa gggccagccc   1200

cgcgaacccc aggtgtacac actgccccca agcagggacg agctgaccaa gaaccaggtg   1260

tccctgacct gtctcgtgaa aggcttctac cccagcgata tcgccgtgga atgggagagc   1320

aacggccagc ccgagaacaa ctacaagacc acccccccctg tgctggacag cgacggctca   1380

ttcttcctgt acagcaagct gaccgtggac aagtcccggt ggcagcaggg caacgtgttc   1440

agctgcagcg tgatgcacga ggccctgcac aaccactaca cccagaagtc cctgagcctg   1500

agccccggca aggaattcca ggtacaactg cagcagcctg gggctgagct ggtgaagcct   1560

ggggcctcag tgaagatgtc ntgcaaggct tctggctaca catttaccag ttacaatatg   1620

cactgggtaa aacagacacc tggtcggggc ctggaatgga ttggagctat ttatcccgga   1680
```

```
aatggtgata cttcctacaa tcagaagttc aaaggcaagg ccacattgac tgcagacaaa   1740

tcctccagca cagcctacat gcagctcagc agcctgacat ctgaggactc tgcggtctat   1800

tactgtgcaa gatcgactta ctacggcggt gactggtact tcaatgtctg gggcgcaggg   1860

accacggtca ccgtctcttc aggaggaggc ggatccggcg gaggcggaag cggtggcgga   1920

ggctctcaaa ttgttctctc ccagtctcca gcaatcctgt ctgcatctcc aggggagaag   1980

gtcacaatga cttgcagggc cagctcaagt gtaagttaca tccactggtt ccagcagaag   2040

ccaggatcct cccccaaacc ctggatttat gccacatcca acctggcttc tggagtccct   2100

gttcgcttca gtggcagtgg gtctgggact tcttactctc tcacaatcag cagagtggag   2160

gctgaagatg ctgccactta ttactgccag cagtggacta gtaacccacc cacgttcgga   2220

ggggggacca agctggaaat caaacgttaa                                    2250
```

<210> SEQ ID NO 117
<211> LENGTH: 268
<212> TYPE: PRT
<213> ORGANISM: Artificial Sequence
<220> FEATURE:
<223> OTHER INFORMATION: Protein construct expressed from SEQ ID NO: 108

<400> SEQUENCE: 117

```
Met Asn Phe Gly Phe Ser Leu Ile Phe Leu Val Leu Val Leu Lys Gly
1               5                   10                  15

Val Gln Cys Glu Val Lys Leu Val Pro Arg Gln Leu Asp Tyr Lys Asp
            20                  25                  30

Asp Asp Asp Lys Glu Leu Asp Ile Gln Leu Gln Gln Ser Gly Pro Gly
        35                  40                  45

Leu Val Lys Pro Ser Gln Ser Leu Ser Leu Thr Cys Ser Val Thr Gly
    50                  55                  60

Tyr Ser Ile Thr Thr Asn Tyr Asn Trp Asn Trp Ile Arg Gln Phe Pro
65                  70                  75                  80

Gly Asn Lys Leu Glu Trp Met Gly Tyr Ile Arg Tyr Asp Gly Thr Ser
                85                  90                  95

Glu Tyr Thr Pro Ser Leu Lys Asn Arg Val Ser Ile Thr Arg Asp Thr
            100                 105                 110

Ser Met Asn Gln Phe Phe Leu Arg Leu Thr Ser Val Thr Pro Glu Asp
        115                 120                 125

Thr Ala Thr Tyr Tyr Cys Ala Arg Leu Asp Tyr Trp Gly Gln Gly Thr
    130                 135                 140

Leu Val Thr Val Ser Ser Gly Ser Ser Ser Ala Ser Thr Lys Gly Pro
145                 150                 155                 160

Ser Val Phe Pro Leu Ala Pro Ser Ser Lys Ser Thr Ser Gly Gly Thr
                165                 170                 175

Ala Ala Leu Gly Cys Leu Val Lys Asp Tyr Phe Pro Glu Pro Val Thr
            180                 185                 190

Val Ser Trp Asn Ser Gly Ala Leu Thr Ser Gly Val His Thr Phe Pro
        195                 200                 205

Ala Val Leu Gln Ser Ser Gly Leu Tyr Ser Leu Ser Ser Val Val Thr
    210                 215                 220

Val Pro Ser Ser Ser Leu Gly Thr Gln Thr Tyr Ile Cys Asn Val Asn
225                 230                 235                 240

His Lys Pro Ser Asn Thr Lys Val Asp Lys Lys Val Glu Pro Lys Ser
                245                 250                 255
```

```
Cys Asp Lys Thr His Thr Cys Pro Pro Cys Pro Ala
            260                 265


<210> SEQ ID NO 118
<211> LENGTH: 741
<212> TYPE: PRT
<213> ORGANISM: Artificial Sequence
<220> FEATURE:
<223> OTHER INFORMATION: Protein construct expressed from SEQ ID NO: 109

<400> SEQUENCE: 118

Met Asn Phe Gly Phe Ser Leu Ile Phe Leu Val Leu Val Leu Lys Gly
1               5                   10                  15

Val Gln Cys Glu Val Lys Leu Val Pro Arg Gln Leu Asp Tyr Lys Asp
            20                  25                  30

Asp Asp Asp Lys Glu Leu Asp Ile Gln Leu Gln Gln Ser Gly Pro Gly
        35                  40                  45

Leu Val Lys Pro Ser Gln Ser Leu Ser Leu Thr Cys Ser Val Thr Gly
    50                  55                  60

Tyr Ser Ile Thr Thr Asn Tyr Asn Trp Asn Trp Ile Arg Gln Phe Pro
65                  70                  75                  80

Gly Asn Lys Leu Glu Trp Met Gly Tyr Ile Arg Tyr Asp Gly Thr Ser
                85                  90                  95

Glu Tyr Thr Pro Ser Leu Lys Asn Arg Val Ser Ile Thr Arg Asp Thr
            100                 105                 110

Ser Met Asn Gln Phe Phe Leu Arg Leu Thr Ser Val Thr Pro Glu Asp
        115                 120                 125

Thr Ala Thr Tyr Tyr Cys Ala Arg Leu Asp Tyr Trp Gly Gln Gly Thr
    130                 135                 140

Leu Val Thr Val Ser Ser Gly Ser Ser Ser Ala Ser Thr Lys Gly Pro
145                 150                 155                 160

Ser Val Phe Pro Leu Ala Pro Ser Ser Lys Ser Thr Ser Gly Gly Thr
                165                 170                 175

Ala Ala Leu Gly Cys Leu Val Lys Asp Tyr Phe Pro Glu Pro Val Thr
            180                 185                 190

Val Ser Trp Asn Ser Gly Ala Leu Thr Ser Gly Val His Thr Phe Pro
        195                 200                 205

Ala Val Leu Gln Ser Ser Gly Leu Tyr Ser Leu Ser Ser Val Val Thr
    210                 215                 220

Val Pro Ser Ser Ser Leu Gly Thr Gln Thr Tyr Ile Cys Asn Val Asn
225                 230                 235                 240

His Lys Pro Ser Asn Thr Lys Val Asp Lys Lys Val Glu Pro Lys Ser
                245                 250                 255

Cys Asp Lys Thr His Thr Cys Pro Pro Cys Pro Ala Leu Glu Gly Pro
            260                 265                 270

Glu Glu Thr Val Thr Gln Asp Cys Leu Gln Leu Ile Ala Asp Ser Glu
        275                 280                 285

Thr Pro Thr Ile Gln Lys Gly Ser Tyr Thr Phe Val Pro Trp Leu Leu
    290                 295                 300

Ser Phe Lys Arg Gly Ser Ala Leu Glu Glu Lys Glu Asn Lys Ile Leu
305                 310                 315                 320

Val Lys Glu Thr Gly Tyr Phe Phe Ile Tyr Gly Gln Val Leu Tyr Thr
                325                 330                 335

Asp Lys Thr Tyr Ala Met Gly His Leu Ile Gln Arg Lys Lys Val His
            340                 345                 350
```

```
Val Phe Gly Asp Glu Leu Ser Leu Val Thr Leu Phe Arg Cys Ile Gln
        355                 360                 365

Asn Met Pro Glu Thr Leu Pro Asn Asn Ser Cys Tyr Ser Ala Gly Ile
    370                 375                 380

Ala Lys Leu Glu Glu Gly Asp Glu Leu Gln Leu Ala Ile Pro Arg Glu
385                 390                 395                 400

Asn Ala Gln Ile Ser Leu Asp Gly Asp Val Thr Phe Phe Gly Ala Leu
                405                 410                 415

Lys Leu Leu Gly Gly Gly Gly Ser Gly Gly Gly Gly Ser Gly Pro Glu
            420                 425                 430

Glu Thr Val Thr Gln Asp Cys Leu Gln Leu Ile Ala Asp Ser Glu Thr
        435                 440                 445

Pro Thr Ile Gln Lys Gly Ser Tyr Thr Phe Val Pro Trp Leu Leu Ser
    450                 455                 460

Phe Lys Arg Gly Ser Ala Leu Glu Glu Lys Glu Asn Lys Ile Leu Val
465                 470                 475                 480

Lys Glu Thr Gly Tyr Phe Phe Ile Tyr Gly Gln Val Leu Tyr Thr Asp
                485                 490                 495

Lys Thr Tyr Ala Met Gly His Leu Ile Gln Arg Lys Lys Val His Val
            500                 505                 510

Phe Gly Asp Glu Leu Ser Leu Val Thr Leu Phe Arg Cys Ile Gln Asn
        515                 520                 525

Met Pro Glu Thr Leu Pro Asn Asn Ser Cys Tyr Ser Ala Gly Ile Ala
    530                 535                 540

Lys Leu Glu Glu Gly Asp Glu Leu Gln Leu Ala Ile Pro Arg Glu Asn
545                 550                 555                 560

Ala Gln Ile Ser Leu Asp Gly Asp Val Thr Phe Phe Gly Ala Leu Lys
                565                 570                 575

Leu Leu Gly Gly Gly Gly Ser Gly Gly Gly Gly Ser Gln Phe Ala Ala
            580                 585                 590

Gly Pro Glu Glu Thr Val Thr Gln Asp Cys Leu Gln Leu Ile Ala Asp
        595                 600                 605

Ser Glu Thr Pro Thr Ile Gln Lys Gly Ser Tyr Thr Phe Val Pro Trp
    610                 615                 620

Leu Leu Ser Phe Lys Arg Gly Ser Ala Leu Glu Glu Lys Glu Asn Lys
625                 630                 635                 640

Ile Leu Val Lys Glu Thr Gly Tyr Phe Phe Ile Tyr Gly Gln Val Leu
                645                 650                 655

Tyr Thr Asp Lys Thr Tyr Ala Met Gly His Leu Ile Gln Arg Lys Lys
            660                 665                 670

Val His Val Phe Gly Asp Glu Leu Ser Leu Val Thr Leu Phe Arg Cys
        675                 680                 685

Ile Gln Asn Met Pro Glu Thr Leu Pro Asn Asn Ser Cys Tyr Ser Ala
    690                 695                 700

Gly Ile Ala Lys Leu Glu Glu Gly Asp Glu Leu Gln Leu Ala Ile Pro
705                 710                 715                 720

Arg Glu Asn Ala Gln Ile Ser Leu Asp Gly Asp Val Thr Phe Phe Gly
                725                 730                 735

Ala Leu Lys Leu Leu
            740
```

<210> SEQ ID NO 119
<211> LENGTH: 761
<212> TYPE: PRT

<213> ORGANISM: Artificial Sequence
<220> FEATURE:
<223> OTHER INFORMATION: Protein construct expressed from SEQ ID NO: 110

<400> SEQUENCE: 119

```
Met Asn Phe Gly Phe Ser Leu Ile Phe Leu Val Leu Val Leu Lys Gly
1               5                   10                  15

Val Gln Cys Glu Val Lys Leu Val Pro Arg Gln Leu Asp Tyr Lys Asp
            20                  25                  30

Asp Asp Asp Lys Glu Leu Gln Leu Gln Leu Gln Glu Ser Gly Pro Gly
        35                  40                  45

Leu Val Lys Pro Ser Glu Thr Leu Ser Leu Thr Cys Thr Val Ser Gly
    50                  55                  60

Ala Ser Ile Ser Ala Asn Ser Tyr Tyr Gly Val Trp Val Arg Gln Ser
65                  70                  75                  80

Pro Gly Lys Gly Leu Glu Trp Val Gly Ser Ile Ala Tyr Arg Gly Asn
                85                  90                  95

Ser Asn Ser Gly Ser Thr Tyr Tyr Asn Pro Ser Leu Lys Ser Arg Ala
            100                 105                 110

Thr Val Ser Val Asp Thr Ser Lys Asn Gln Val Ser Leu Arg Leu Thr
        115                 120                 125

Ser Val Thr Ala Ala Asp Thr Ala Leu Tyr Tyr Cys Ala Arg Arg Gln
    130                 135                 140

Leu Leu Asp Asp Gly Thr Gly Tyr Gln Trp Ala Ala Phe Asp Val Trp
145                 150                 155                 160

Gly Gln Gly Thr Met Val Thr Val Ser Ser Gly Ser Ser Ser Ala Ser
                165                 170                 175

Thr Lys Gly Pro Ser Val Phe Pro Leu Ala Pro Ser Ser Lys Ser Thr
            180                 185                 190

Ser Gly Gly Thr Ala Ala Leu Gly Cys Leu Val Lys Asp Tyr Phe Pro
        195                 200                 205

Glu Pro Val Thr Val Ser Trp Asn Ser Gly Ala Leu Thr Ser Gly Val
    210                 215                 220

His Thr Phe Pro Ala Val Leu Gln Ser Ser Gly Leu Tyr Ser Leu Ser
225                 230                 235                 240

Ser Val Val Thr Val Pro Ser Ser Ser Leu Gly Thr Gln Thr Tyr Ile
                245                 250                 255

Cys Asn Val Asn His Lys Pro Ser Asn Thr Lys Val Asp Lys Lys Val
            260                 265                 270

Glu Pro Lys Ser Cys Asp Lys Thr His Thr Cys Pro Pro Cys Pro Ala
        275                 280                 285

Leu Glu Gly Pro Glu Glu Thr Val Thr Gln Asp Cys Leu Gln Leu Ile
    290                 295                 300

Ala Asp Ser Glu Thr Pro Thr Ile Gln Lys Gly Ser Tyr Thr Phe Val
305                 310                 315                 320

Pro Trp Leu Leu Ser Phe Lys Arg Gly Ser Ala Leu Glu Glu Lys Glu
                325                 330                 335

Asn Lys Ile Leu Val Lys Glu Thr Gly Tyr Phe Phe Ile Tyr Gly Gln
            340                 345                 350

Val Leu Tyr Thr Asp Lys Thr Tyr Ala Met Gly His Leu Ile Gln Arg
        355                 360                 365

Lys Lys Val His Val Phe Gly Asp Glu Leu Ser Leu Val Thr Leu Phe
    370                 375                 380

Arg Cys Ile Gln Asn Met Pro Glu Thr Leu Pro Asn Asn Ser Cys Tyr
```

```
385                 390                 395                 400

Ser Ala Gly Ile Ala Lys Leu Glu Glu Gly Asp Glu Leu Gln Leu Ala
                405                 410                 415

Ile Pro Arg Glu Asn Ala Gln Ile Ser Leu Asp Gly Asp Val Thr Phe
            420                 425                 430

Phe Gly Ala Leu Lys Leu Leu Gly Gly Gly Gly Ser Gly Gly Gly Gly
        435                 440                 445

Ser Gly Pro Glu Glu Thr Val Thr Gln Asp Cys Leu Gln Leu Ile Ala
    450                 455                 460

Asp Ser Glu Thr Pro Thr Ile Gln Lys Gly Ser Tyr Thr Phe Val Pro
465                 470                 475                 480

Trp Leu Leu Ser Phe Lys Arg Gly Ser Ala Leu Glu Glu Lys Glu Asn
                485                 490                 495

Lys Ile Leu Val Lys Glu Thr Gly Tyr Phe Phe Ile Tyr Gly Gln Val
            500                 505                 510

Leu Tyr Thr Asp Lys Thr Tyr Ala Met Gly His Leu Ile Gln Arg Lys
        515                 520                 525

Lys Val His Val Phe Gly Asp Glu Leu Ser Leu Val Thr Leu Phe Arg
    530                 535                 540

Cys Ile Gln Asn Met Pro Glu Thr Leu Pro Asn Asn Ser Cys Tyr Ser
545                 550                 555                 560

Ala Gly Ile Ala Lys Leu Glu Glu Gly Asp Glu Leu Gln Leu Ala Ile
                565                 570                 575

Pro Arg Glu Asn Ala Gln Ile Ser Leu Asp Gly Asp Val Thr Phe Phe
            580                 585                 590

Gly Ala Leu Lys Leu Leu Gly Gly Gly Gly Ser Gly Gly Gly Gly Ser
        595                 600                 605

Gln Phe Ala Ala Gly Pro Glu Glu Thr Val Thr Gln Asp Cys Leu Gln
    610                 615                 620

Leu Ile Ala Asp Ser Glu Thr Pro Thr Ile Gln Lys Gly Ser Tyr Thr
625                 630                 635                 640

Phe Val Pro Trp Leu Leu Ser Phe Lys Arg Gly Ser Ala Leu Glu Glu
                645                 650                 655

Lys Glu Asn Lys Ile Leu Val Lys Glu Thr Gly Tyr Phe Phe Ile Tyr
            660                 665                 670

Gly Gln Val Leu Tyr Thr Asp Lys Thr Tyr Ala Met Gly His Leu Ile
        675                 680                 685

Gln Arg Lys Lys Val His Val Phe Gly Asp Glu Leu Ser Leu Val Thr
    690                 695                 700

Leu Phe Arg Cys Ile Gln Asn Met Pro Glu Thr Leu Pro Asn Asn Ser
705                 710                 715                 720

Cys Tyr Ser Ala Gly Ile Ala Lys Leu Glu Glu Gly Asp Glu Leu Gln
                725                 730                 735

Leu Ala Ile Pro Arg Glu Asn Ala Gln Ile Ser Leu Asp Gly Asp Val
            740                 745                 750

Thr Phe Phe Gly Ala Leu Lys Leu Leu
        755                 760


<210> SEQ ID NO 120
<211> LENGTH: 722
<212> TYPE: PRT
<213> ORGANISM: Artificial Sequence
<220> FEATURE:
<223> OTHER INFORMATION: Protein construct expressed from SEQ ID NO: 111
```

<400> SEQUENCE: 120

```
Met Asn Phe Gly Phe Ser Leu Ile Phe Leu Val Leu Val Leu Lys Gly
1               5                   10                  15

Val Gln Cys Glu Val Lys Leu Val Pro Arg Gln Leu Gln Val Gln Leu
            20                  25                  30

Leu Gln Ser Gly Pro Glu Leu Val Lys Pro Gly Ala Ser Val Lys Leu
        35                  40                  45

Ser Cys Lys Ala Ser Gly Tyr Ser Phe Thr Ser Tyr Asp Ile Asn Trp
    50                  55                  60

Val Lys Gln Arg Pro Gly Gln Gly Leu Glu Trp Val Gly Trp Ile Tyr
65                  70                  75                  80

Pro Arg Asp Gly Asp Thr Lys Tyr Asn Glu Lys Phe Lys Gly Lys Ala
                85                  90                  95

Ile Leu Thr Val Asp Thr Ser Ser Asn Thr Ala Tyr Met Asn Leu His
            100                 105                 110

Ser Leu Thr Ser Glu Asp Ser Ala Val Tyr Phe Cys Ala Arg Leu Thr
        115                 120                 125

Gly Pro Tyr Trp Tyr Phe Asp Val Trp Gly Thr Gly Thr Thr Val Thr
    130                 135                 140

Val Ser Ser Gly Ser Ser Ser Ala Ser Thr Lys Gly Pro Ser Val Phe
145                 150                 155                 160

Pro Leu Ala Pro Cys Ser Arg Ser Thr Ser Glu Ser Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Asn Phe Gly Thr Gln Thr Tyr Thr Cys Asn Val Asp His Lys Pro
225                 230                 235                 240

Ser Asn Thr Lys Val Asp Lys Thr Val Glu Arg Lys Cys Cys Val Glu
                245                 250                 255

Cys Pro Pro Cys Pro Ala Pro Pro Val Ala Gly Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Gln
    290                 295                 300

Phe Asn Trp Tyr Val Asp Gly Val Glu Val His Asn Ala Lys Thr Lys
305                 310                 315                 320

Pro Arg Glu Glu Gln Phe Asn Ser Thr Phe Arg Val Val Ser Val Leu
                325                 330                 335

Thr Val Val His Gln Asp Trp Leu Asn Gly Lys Glu Tyr Lys Cys Lys
            340                 345                 350

Val Ser Asn Lys Gly Leu Pro Ala Pro Ile Glu Lys Thr Ile Ser Lys
        355                 360                 365

Thr Lys Gly Gln Pro Arg Glu Pro Gln Val Tyr Thr Leu Pro Pro Ser
    370                 375                 380

Arg Glu Glu Met Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415
```

```
Pro Glu Asn Asn Tyr Lys Thr Thr Pro Pro Met Leu Asp Ser Asp Gly
            420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Lys Glu Phe Gln
465                 470                 475                 480

Val Gln Leu Gln Gln Pro Gly Ala Glu Leu Val Lys Pro Gly Ala Ser
                485                 490                 495

Val Lys Met Ser Cys Lys Ala Ser Gly Tyr Thr Phe Thr Ser Tyr Asn
            500                 505                 510

Met His Trp Val Lys Gln Thr Pro Gly Arg Gly Leu Glu Trp Ile Gly
        515                 520                 525

Ala Ile Tyr Pro Gly Asn Gly Asp Thr Ser Tyr Asn Gln Lys Phe Lys
    530                 535                 540

Gly Lys Ala Thr Leu Thr Ala Asp Lys Ser Ser Ser Thr Ala Tyr Met
545                 550                 555                 560

Gln Leu Ser Ser Leu Thr Ser Glu Asp Ser Ala Val Tyr Tyr Cys Ala
                565                 570                 575

Arg Ser Thr Tyr Tyr Gly Gly Asp Trp Tyr Phe Asn Val Trp Gly Ala
            580                 585                 590

Gly Thr Thr Val Thr Val Ser Ser Gly Gly Gly Gly Ser Gly Gly Gly
        595                 600                 605

Gly Ser Gly Gly Gly Gly Ser Gln Ile Val Leu Ser Gln Ser Pro Ala
    610                 615                 620

Ile Leu Ser Ala Ser Pro Gly Glu Lys Val Thr Met Thr Cys Arg Ala
625                 630                 635                 640

Ser Ser Ser Val Ser Tyr Ile His Trp Phe Gln Gln Lys Pro Gly Ser
                645                 650                 655

Ser Pro Lys Pro Trp Ile Tyr Ala Thr Ser Asn Leu Ala Ser Gly Val
            660                 665                 670

Pro Val Arg Phe Ser Gly Ser Gly Ser Gly Thr Ser Tyr Ser Leu Thr
        675                 680                 685

Ile Ser Arg Val Glu Ala Glu Asp Ala Ala Thr Tyr Tyr Cys Gln Gln
    690                 695                 700

Trp Thr Ser Asn Pro Pro Thr Phe Gly Gly Gly Thr Lys Leu Glu Ile
705                 710                 715                 720

Lys Arg


<210> SEQ ID NO 121
<211> LENGTH: 731
<212> TYPE: PRT
<213> ORGANISM: Artificial Sequence
<220> FEATURE:
<223> OTHER INFORMATION: Protein construct expressed from SEQ ID NO: 112

<400> SEQUENCE: 121

Met Asn Phe Gly Phe Ser Leu Ile Phe Leu Val Leu Val Leu Lys Gly
1               5                   10                  15

Val Gln Cys Glu Val Lys Leu Val Pro Arg Gln Leu Gln Val Gln Leu
            20                  25                  30

Leu Gln Ser Gly Pro Glu Leu Val Lys Pro Gly Ala Ser Val Lys Leu
        35                  40                  45
```

```
Ser Cys Lys Ala Ser Gly Tyr Ser Phe Thr Ser Tyr Asp Ile Asn Trp
    50                  55                  60

Val Lys Gln Arg Pro Gly Gln Gly Leu Glu Trp Val Gly Trp Ile Tyr
65                  70                  75                  80

Pro Arg Asp Gly Asp Thr Lys Tyr Asn Glu Lys Phe Lys Gly Lys Ala
                85                  90                  95

Ile Leu Thr Val Asp Thr Ser Ser Asn Thr Ala Tyr Met Asn Leu His
            100                 105                 110

Ser Leu Thr Ser Glu Asp Ser Ala Val Tyr Phe Cys Ala Arg Leu Thr
        115                 120                 125

Gly Pro Tyr Trp Tyr Phe Asp Val Trp Gly Thr Gly Thr Thr Val Thr
    130                 135                 140

Val Ser Ser Gly Ser Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Ala Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
```

465 470 475 480

Lys Glu Phe Gln Ile Gln Leu Val Gln Ser Gly Pro Glu Val Lys Lys
485 490 495

Pro Gly Glu Thr Val Lys Ile Ser Cys Lys Ala Ser Gly Tyr Thr Phe
500 505 510

Thr Asn Tyr Gly Met Asn Trp Val Lys Gln Ala Pro Gly Lys Gly Leu
515 520 525

Lys Trp Met Gly Trp Ile Asn Thr Tyr Thr Gly Glu Pro Thr Tyr Ala
530 535 540

Asp Ala Phe Lys Gly Arg Phe Ala Phe Ser Leu Glu Thr Ser Ala Ser
545 550 555 560

Thr Ala Tyr Leu Gln Ile Asn Asn Leu Lys Asn Glu Asp Thr Ala Thr
565 570 575

Tyr Phe Cys Ala Arg Asp Tyr Gly Asp Tyr Gly Met Asp Tyr Trp Gly
580 585 590

Gln Gly Thr Ser Val Thr Val Ser Ser Ala Ser Thr Lys Gly Pro Lys
595 600 605

Leu Glu Glu Gly Glu Phe Ser Glu Ala Arg Val Asp Ile Val Leu Thr
610 615 620

Gln Ser Pro Ala Ser Leu Ala Val Ser Leu Gly Gln Arg Ala Thr Ile
625 630 635 640

Ser Cys Arg Ala Ser Lys Ser Val Ser Thr Ser Gly Tyr Ser Phe Met
645 650 655

His Trp Tyr Gln Gln Lys Pro Gly Gln Pro Pro Lys Leu Leu Ile Tyr
660 665 670

Leu Ala Ser Asn Leu Glu Ser Gly Val Pro Ala Arg Phe Ser Gly Ser
675 680 685

Gly Ser Gly Thr Asp Phe Thr Leu Asn Ile His Pro Val Glu Glu Glu
690 695 700

Asp Ala Ala Thr Tyr Tyr Cys Gln His Ser Arg Glu Val Pro Trp Thr
705 710 715 720

Phe Gly Gly Gly Thr Lys Leu Glu Ile Lys Arg
725 730

<210> SEQ ID NO 122
<211> LENGTH: 728
<212> TYPE: PRT
<213> ORGANISM: Artificial Sequence
<220> FEATURE:
<223> OTHER INFORMATION: Protein construct expressed from SEQ ID NO: 113

<400> SEQUENCE: 122

Met Asn Phe Gly Phe Ser Leu Ile Phe Leu Val Leu Val Leu Lys Gly
1 5 10 15

Val Gln Cys Glu Val Lys Leu Val Pro Arg Gln Leu Gln Val Gln Leu
20 25 30

Leu Gln Ser Gly Pro Glu Leu Val Lys Pro Gly Ala Ser Val Lys Leu
35 40 45

Ser Cys Lys Ala Ser Gly Tyr Ser Phe Thr Ser Tyr Asp Ile Asn Trp
50 55 60

Val Lys Gln Arg Pro Gly Gln Gly Leu Glu Trp Val Gly Trp Ile Tyr
65 70 75 80

Pro Arg Asp Gly Asp Thr Lys Tyr Asn Glu Lys Phe Lys Gly Lys Ala
85 90 95

Ile Leu Thr Val Asp Thr Ser Ser Asn Thr Ala Tyr Met Asn Leu His

```
            100                 105                 110

Ser Leu Thr Ser Glu Asp Ser Ala Val Tyr Phe Cys Ala Arg Leu Thr
        115                 120                 125

Gly Pro Tyr Trp Tyr Phe Asp Val Trp Gly Thr Gly Thr Thr Val Thr
    130                 135                 140

Val Ser Ser Gly Ser Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Ala Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

Lys Glu Phe Gln Val Gln Leu Val Glu Ser Gly Gly Gly Val Val Gln
                485                 490                 495

Pro Gly Arg Ser Leu Arg Leu Ser Cys Ala Ala Ser Gly Phe Thr Phe
            500                 505                 510

Ser Ser Tyr Ile Met His Trp Val Arg Gln Ala Pro Gly Lys Gly Leu
        515                 520                 525
```

```
Glu Trp Val Ala Val Ile Ser Tyr Asp Gly Arg Asn Lys Tyr Tyr Ala
    530                 535                 540

Asp Ser Val Lys Gly Arg Phe Thr Ile Ser Arg Asp Asn Ser Lys Asn
545                 550                 555                 560

Thr Leu Tyr Leu Gln Met Asn Ser Leu Arg Ala Glu Asp Thr Ala Val
                565                 570                 575

Tyr Tyr Cys Ala Arg Asp Thr Asp Gly Tyr Asp Phe Asp Tyr Trp Gly
            580                 585                 590

Gln Gly Thr Leu Val Thr Val Ser Ser Gly Gly Gly Gly Ser Gly Gly
        595                 600                 605

Gly Gly Ser Gly Gly Gly Gly Ser Glu Ile Val Leu Thr Gln Ser Pro
    610                 615                 620

Ala Thr Leu Ser Leu Ser Pro Gly Glu Arg Ala Thr Leu Ser Cys Arg
625                 630                 635                 640

Ala Ser Gln Ser Val Ser Ser Tyr Leu Ala Trp Tyr Gln Gln Lys Pro
                645                 650                 655

Gly Gln Ala Pro Arg Leu Leu Ile Tyr Asp Ala Ser Asn Arg Ala Thr
            660                 665                 670

Gly Ile Pro Ala Arg Phe Ser Gly Ser Gly Ser Gly Thr Asp Phe Thr
        675                 680                 685

Leu Thr Ile Ser Ser Leu Glu Pro Glu Asp Phe Ala Val Tyr Tyr Cys
    690                 695                 700

Gln Gln Arg Thr Asn Trp Pro Leu Thr Phe Gly Gly Gly Thr Lys Val
705                 710                 715                 720

Glu Ile Lys Ala Ser Thr Lys Gly
                725


<210> SEQ ID NO 123
<211> LENGTH: 736
<212> TYPE: PRT
<213> ORGANISM: Artificial Sequence
<220> FEATURE:
<223> OTHER INFORMATION: Protein construct expressed from SEQ ID NO: 114

<400> SEQUENCE: 123

Met Asn Phe Gly Phe Ser Leu Ile Phe Leu Val Leu Val Leu Lys Gly
1               5                   10                  15

Val Gln Cys Glu Val Lys Leu Val Pro Arg Gln Leu Asp Tyr Lys Asp
            20                  25                  30

Asp Asp Asp Lys Glu Phe Gln Val Gln Leu Gln Gln Ser Gly Ala Glu
        35                  40                  45

Val Ile Lys Pro Gly Ala Ser Val Lys Leu Ser Cys Lys Ala Ser Gly
    50                  55                  60

Tyr Thr Phe Ser Ser Tyr Trp Met His Trp Val Arg Gln Ala Pro Gly
65                  70                  75                  80

Gln Gly Leu Glu Trp Ile Gly Glu Ile Asn Pro Gly Asn Gly His Thr
                85                  90                  95

Asn Tyr Asn Glu Lys Phe Lys Ser Arg Ala Thr Leu Thr Gly Asp Thr
            100                 105                 110

Ser Thr Ser Thr Val Tyr Met Glu Leu Ser Ser Leu Arg Ser Glu Asp
        115                 120                 125

Thr Ala Val Tyr Tyr Cys Ala Arg Ser Phe Thr Thr Ala Arg Ala Phe
    130                 135                 140

Ala Tyr Trp Gly Gln Gly Thr Leu Val Thr Val Ser Ser Arg Ser Ser
145                 150                 155                 160
```

```
Ser Ala Ser Thr Lys Gly Pro Ser Val Phe Pro Leu Ala Pro Ser Ser
                165                 170                 175

Lys Ser Thr Ser Gly Gly Thr Ala Ala Leu Gly Cys Leu Val Lys Asp
            180                 185                 190

Tyr Phe Pro Glu Pro Val Thr Val Ser Trp Asn Ser Gly Ala Leu Thr
        195                 200                 205

Ser Gly Val His Thr Phe Pro Ala Val Leu Gln Ser Ser Gly Leu Tyr
    210                 215                 220

Ser Leu Ser Ser Val Val Thr Val Pro Ser Ser Ser Leu Gly Thr Gln
225                 230                 235                 240

Thr Tyr Ile Cys Asn Val Asn His Lys Pro Ser Asn Thr Lys Val Asp
                245                 250                 255

Lys Lys Val Glu Pro Lys Ser Cys Asp Lys Thr His Thr Cys Pro Pro
            260                 265                 270

Cys Pro Ala Pro Glu Leu Leu Gly Gly Pro Ser Val Phe Leu Phe Pro
        275                 280                 285

Pro Lys Pro Lys Asp Thr Leu Met Ile Ser Arg Thr Pro Glu Val Thr
    290                 295                 300

Cys Val Val Val Asp Val Ser His Glu Asp Pro Glu Val Lys Phe Asn
305                 310                 315                 320

Trp Tyr Val Asp Gly Val Glu Val His Asn Ala Lys Thr Lys Pro Arg
                325                 330                 335

Glu Glu Gln Tyr Ala Ser Thr Tyr Arg Val Val Ser Val Leu Thr Val
            340                 345                 350

Leu His Gln Asp Trp Leu Asn Gly Lys Glu Tyr Lys Cys Lys Val Ser
        355                 360                 365

Asn Lys Ala Leu Pro Ala Pro Ile Glu Lys Thr Ile Ser Lys Ala Lys
    370                 375                 380

Gly Gln Pro Arg Glu Pro Gln Val Tyr Thr Leu Pro Pro Ser Arg Asp
385                 390                 395                 400

Glu Leu Thr Lys Asn Gln Val Ser Leu Thr Cys Leu Val Lys Gly Phe
                405                 410                 415

Tyr Pro Ser Asp Ile Ala Val Glu Trp Glu Ser Asn Gly Gln Pro Glu
            420                 425                 430

Asn Asn Tyr Lys Thr Thr Pro Pro Val Leu Asp Ser Asp Gly Ser Phe
        435                 440                 445

Phe Leu Tyr Ser Lys Leu Thr Val Asp Lys Ser Arg Trp Gln Gln Gly
    450                 455                 460

Asn Val Phe Ser Cys Ser Val Met His Glu Ala Leu His Asn His Tyr
465                 470                 475                 480

Thr Gln Lys Ser Leu Ser Leu Ser Pro Gly Lys Leu Glu Gln Val Gln
                485                 490                 495

Leu Gln Gln Pro Gly Ala Glu Leu Val Lys Pro Gly Ala Ser Val Lys
            500                 505                 510

Met Ser Cys Lys Ala Ser Gly Tyr Thr Phe Thr Ser Tyr Asn Met His
        515                 520                 525

Trp Val Lys Gln Thr Pro Gly Arg Gly Leu Glu Trp Ile Gly Ala Ile
    530                 535                 540

Tyr Pro Gly Asn Gly Asp Thr Ser Tyr Asn Gln Lys Phe Lys Gly Lys
545                 550                 555                 560

Ala Thr Leu Thr Ala Asp Lys Ser Ser Ser Thr Ala Tyr Met Gln Leu
                565                 570                 575
```

```
Ser Ser Leu Thr Ser Glu Asp Ser Ala Val Tyr Tyr Cys Ala Arg Ser
            580                 585                 590

Thr Tyr Tyr Gly Gly Asp Trp Tyr Phe Asn Val Trp Gly Ala Gly Thr
        595                 600                 605

Thr Val Thr Val Ser Ser Gly Gly Gly Gly Ser Gly Gly Gly Gly Ser
    610                 615                 620

Gly Gly Gly Gly Ser Gln Ile Val Leu Ser Gln Ser Pro Ala Ile Leu
625                 630                 635                 640

Ser Ala Ser Pro Gly Glu Lys Val Thr Met Thr Cys Arg Ala Ser Ser
                645                 650                 655

Ser Val Ser Tyr Ile His Trp Phe Gln Gln Lys Pro Gly Ser Ser Pro
            660                 665                 670

Lys Pro Trp Ile Tyr Ala Thr Ser Asn Leu Ala Ser Gly Val Pro Val
        675                 680                 685

Arg Phe Ser Gly Ser Gly Ser Gly Thr Ser Tyr Ser Leu Thr Ile Ser
    690                 695                 700

Arg Val Glu Ala Glu Asp Ala Ala Thr Tyr Tyr Cys Gln Gln Trp Thr
705                 710                 715                 720

Ser Asn Pro Pro Thr Phe Gly Gly Gly Thr Lys Leu Glu Ile Lys Arg
                725                 730                 735


<210> SEQ ID NO 124
<211> LENGTH: 257
<212> TYPE: PRT
<213> ORGANISM: Artificial Sequence
<220> FEATURE:
<223> OTHER INFORMATION: Protein construct expressed from SEQ ID NO: 115

<400> SEQUENCE: 124

Met Asn Phe Gly Phe Ser Leu Ile Phe Leu Val Leu Val Leu Lys Gly
1               5                   10                  15

Val Gln Cys Glu Val Lys Leu Val Pro Arg Gln Leu Asp Tyr Lys Asp
            20                  25                  30

Asp Asp Asp Lys Glu Leu Asp Ile Val Met Thr Gln Ser Pro Ala Phe
        35                  40                  45

Leu Ser Val Thr Pro Gly Glu Lys Val Thr Ile Thr Cys Arg Ala Ser
    50                  55                  60

Gln Thr Ile Ser Asp Tyr Leu His Trp Tyr Gln Gln Lys Pro Asp Gln
65                  70                  75                  80

Ala Pro Lys Leu Leu Ile Lys Tyr Ala Ser Gln Ser Ile Ser Gly Ile
                85                  90                  95

Pro Ser Arg Phe Ser Gly Ser Gly Ser Gly Thr Asp Phe Thr Phe Thr
            100                 105                 110

Ile Ser Ser Leu Glu Ala Glu Asp Ala Ala Thr Tyr Tyr Cys Gln Asp
        115                 120                 125

Gly His Ser Phe Pro Pro Thr Phe Gly Gln Gly Thr Lys Leu Glu Ile
    130                 135                 140

Lys Gly Ser Glu Ile Lys Arg Thr Val Ala Ala Pro Ser Val Phe Ile
145                 150                 155                 160

Phe Pro Pro Ser Asp Glu Gln Leu Lys Ser Gly Thr Ala Ser Val Val
                165                 170                 175

Cys Leu Leu Asn Asn Phe Tyr Pro Arg Glu Ala Lys Val Gln Trp Lys
            180                 185                 190

Val Asp Asn Ala Leu Gln Ser Gly Asn Ser Gln Glu Ser Val Thr Glu
        195                 200                 205
```

```
Gln Asp Ser Lys Asp Ser Thr Tyr Ser Leu Ser Ser Thr Leu Thr Leu
    210                 215                 220

Ser Lys Ala Asp Tyr Glu Lys His Lys Val Tyr Ala Cys Glu Val Thr
225                 230                 235                 240

His Gln Gly Leu Ser Ser Pro Val Thr Lys Ser Phe Asn Arg Gly Glu
                245                 250                 255

Cys
```

```
<210> SEQ ID NO 125
<211> LENGTH: 749
<212> TYPE: PRT
<213> ORGANISM: Artificial Sequence
<220> FEATURE:
<223> OTHER INFORMATION: Protein construct expressed from SEQ ID NO: 116

<400> SEQUENCE: 125

Met Asn Phe Gly Phe Ser Leu Ile Phe Leu Val Leu Val Leu Lys Gly
1               5                   10                  15

Val Gln Cys Glu Val Lys Leu Val Pro Arg Gln Leu Asp Tyr Lys Asp
            20                  25                  30

Asp Asp Asp Lys Glu Leu Gln Leu Gln Leu Gln Glu Ser Gly Pro Gly
        35                  40                  45

Leu Val Lys Pro Ser Glu Thr Leu Ser Leu Thr Cys Thr Val Ser Gly
    50                  55                  60

Ala Ser Ile Ser Ala Asn Ser Tyr Tyr Gly Val Trp Val Arg Gln Ser
65                  70                  75                  80

Pro Gly Lys Gly Leu Glu Trp Val Gly Ser Ile Ala Tyr Arg Gly Asn
                85                  90                  95

Ser Asn Ser Gly Ser Thr Tyr Tyr Asn Pro Ser Leu Lys Ser Arg Ala
            100                 105                 110

Thr Val Ser Val Asp Thr Ser Lys Asn Gln Val Ser Leu Arg Leu Thr
        115                 120                 125

Ser Val Thr Ala Ala Asp Thr Ala Leu Tyr Tyr Cys Ala Arg Arg Gln
    130                 135                 140

Leu Leu Asp Asp Gly Thr Gly Tyr Gln Trp Ala Ala Phe Asp Val Trp
145                 150                 155                 160

Gly Gln Gly Thr Met Val Thr Val Ser Ser Gly Ser Ser Ser Ala Ser
                165                 170                 175

Thr Lys Gly Pro Ser Val Phe Pro Leu Ala Pro Ser Ser Lys Ser Thr
            180                 185                 190

Ser Gly Gly Thr Ala Ala Leu Gly Cys Leu Val Lys Asp Tyr Phe Pro
        195                 200                 205

Glu Pro Val Thr Val Ser Trp Asn Ser Gly Ala Leu Thr Ser Gly Val
    210                 215                 220

His Thr Phe Pro Ala Val Leu Gln Ser Ser Gly Leu Tyr Ser Leu Ser
225                 230                 235                 240

Ser Val Val Thr Val Pro Ser Ser Ser Leu Gly Thr Gln Thr Tyr Ile
                245                 250                 255

Cys Asn Val Asn His Lys Pro Ser Asn Thr Lys Val Asp Lys Lys Val
            260                 265                 270

Glu Pro Lys Ser Cys Asp Lys Thr His Thr Cys Pro Pro Cys Pro Ala
        275                 280                 285

Pro Glu Leu Leu Gly Gly Pro Ser Val Phe Leu Phe Pro Pro Lys Pro
    290                 295                 300

Lys Asp Thr Leu Met Ile Ser Arg Thr Pro Glu Val Thr Cys Val Val
```

```
305                 310                 315                 320

Val Asp Val Ser His Glu Asp Pro Glu Val Lys Phe Asn Trp Tyr Val
                325                 330                 335

Asp Gly Val Glu Val His Asn Ala Lys Thr Lys Pro Arg Glu Glu Gln
            340                 345                 350

Tyr Ala Ser Thr Tyr Arg Val Val Ser Val Leu Thr Val Leu His Gln
        355                 360                 365

Asp Trp Leu Asn Gly Lys Glu Tyr Lys Cys Lys Val Ser Asn Lys Ala
    370                 375                 380

Leu Pro Ala Pro Ile Glu Lys Thr Ile Ser Lys Ala Lys Gly Gln Pro
385                 390                 395                 400

Arg Glu Pro Gln Val Tyr Thr Leu Pro Pro Ser Arg Asp Glu Leu Thr
                405                 410                 415

Lys Asn Gln Val Ser Leu Thr Cys Leu Val Lys Gly Phe Tyr Pro Ser
            420                 425                 430

Asp Ile Ala Val Glu Trp Glu Ser Asn Gly Gln Pro Glu Asn Asn Tyr
        435                 440                 445

Lys Thr Thr Pro Pro Val Leu Asp Ser Asp Gly Ser Phe Phe Leu Tyr
    450                 455                 460

Ser Lys Leu Thr Val Asp Lys Ser Arg Trp Gln Gln Gly Asn Val Phe
465                 470                 475                 480

Ser Cys Ser Val Met His Glu Ala Leu His Asn His Tyr Thr Gln Lys
                485                 490                 495

Ser Leu Ser Leu Ser Pro Gly Lys Glu Phe Gln Val Gln Leu Gln Gln
            500                 505                 510

Pro Gly Ala Glu Leu Val Lys Pro Gly Ala Ser Val Lys Met Ser Cys
        515                 520                 525

Lys Ala Ser Gly Tyr Thr Phe Thr Ser Tyr Asn Met His Trp Val Lys
    530                 535                 540

Gln Thr Pro Gly Arg Gly Leu Glu Trp Ile Gly Ala Ile Tyr Pro Gly
545                 550                 555                 560

Asn Gly Asp Thr Ser Tyr Asn Gln Lys Phe Lys Gly Lys Ala Thr Leu
                565                 570                 575

Thr Ala Asp Lys Ser Ser Ser Thr Ala Tyr Met Gln Leu Ser Ser Leu
            580                 585                 590

Thr Ser Glu Asp Ser Ala Val Tyr Tyr Cys Ala Arg Ser Thr Tyr Tyr
        595                 600                 605

Gly Gly Asp Trp Tyr Phe Asn Val Trp Gly Ala Gly Thr Thr Val Thr
    610                 615                 620

Val Ser Ser Gly Gly Gly Gly Ser Gly Gly Gly Gly Ser Gly Gly Gly
625                 630                 635                 640

Gly Ser Gln Ile Val Leu Ser Gln Ser Pro Ala Ile Leu Ser Ala Ser
                645                 650                 655

Pro Gly Glu Lys Val Thr Met Thr Cys Arg Ala Ser Ser Ser Val Ser
            660                 665                 670

Tyr Ile His Trp Phe Gln Gln Lys Pro Gly Ser Ser Pro Lys Pro Trp
        675                 680                 685

Ile Tyr Ala Thr Ser Asn Leu Ala Ser Gly Val Pro Val Arg Phe Ser
    690                 695                 700

Gly Ser Gly Ser Gly Thr Ser Tyr Ser Leu Thr Ile Ser Arg Val Glu
705                 710                 715                 720

Ala Glu Asp Ala Ala Thr Tyr Tyr Cys Gln Gln Trp Thr Ser Asn Pro
                725                 730                 735
```

```
Pro Thr Phe Gly Gly Gly Thr Lys Leu Glu Ile Lys Arg
            740                 745


<210> SEQ ID NO 126
<211> LENGTH: 9
<212> TYPE: PRT
<213> ORGANISM: Artificial Sequence
<220> FEATURE:
<223> OTHER INFORMATION: HBBK4 CDR1-H

<400> SEQUENCE: 126

Tyr Thr Phe Ser Ser Tyr Trp Met His
1               5


<210> SEQ ID NO 127
<211> LENGTH: 17
<212> TYPE: PRT
<213> ORGANISM: Artificial Sequence
<220> FEATURE:
<223> OTHER INFORMATION: HBBK4  CDR2-H

<400> SEQUENCE: 127

Glu Ile Asn Pro Gly Asn Gly His Thr Asn Tyr Asn Glu Lys Phe Lys
1               5                   10                  15

Ser


<210> SEQ ID NO 128
<211> LENGTH: 10
<212> TYPE: PRT
<213> ORGANISM: Artificial Sequence
<220> FEATURE:
<223> OTHER INFORMATION: HBBK4 CDR3-H

<400> SEQUENCE: 128

Ser Phe Thr Thr Ala Arg Ala Phe Ala Tyr
1               5                   10


<210> SEQ ID NO 129
<211> LENGTH: 11
<212> TYPE: PRT
<213> ORGANISM: Artificial Sequence
<220> FEATURE:
<223> OTHER INFORMATION: HBBK4 CDR1-L

<400> SEQUENCE: 129

Arg Ala Ser Gln Thr Ile Ser Asp Tyr Leu His
1               5                   10


<210> SEQ ID NO 130
<211> LENGTH: 7
<212> TYPE: PRT
<213> ORGANISM: Artificial Sequence
<220> FEATURE:
<223> OTHER INFORMATION: HBBK4 CDR2-L

<400> SEQUENCE: 130

Leu Ala Ser Gln Ser Ile Ser
1               5


<210> SEQ ID NO 131
<211> LENGTH: 9
<212> TYPE: PRT
<213> ORGANISM: Artificial Sequence
<220> FEATURE:
<223> OTHER INFORMATION: HBBK4 CDR3-L
```

<400> SEQUENCE: 131

Gln Asp Gly His Ser Phe Pro Pro Thr
1               5

<210> SEQ ID NO 132
<211> LENGTH: 9
<212> TYPE: PRT
<213> ORGANISM: Artificial Sequence
<220> FEATURE:
<223> OTHER INFORMATION: URELUMAB CDR1-H

<400> SEQUENCE: 132

Gly Ser Phe Ser Gly Tyr Tyr Trp Ser
1               5

<210> SEQ ID NO 133
<211> LENGTH: 16
<212> TYPE: PRT
<213> ORGANISM: Artificial Sequence
<220> FEATURE:
<223> OTHER INFORMATION: URELUMAB  CDR2-H

<400> SEQUENCE: 133

Glu Ile Asn His Gly Gly Tyr Val Thr Tyr Asn Pro Ser Leu Glu Ser
1               5                   10                  15

<210> SEQ ID NO 134
<211> LENGTH: 13
<212> TYPE: PRT
<213> ORGANISM: Artificial Sequence
<220> FEATURE:
<223> OTHER INFORMATION: URELUMAB CDR3-H

<400> SEQUENCE: 134

Asp Tyr Gly Pro Gly Asn Tyr Asp Trp Tyr Phe Asp Leu
1               5                   10

<210> SEQ ID NO 135
<211> LENGTH: 11
<212> TYPE: PRT
<213> ORGANISM: Artificial Sequence
<220> FEATURE:
<223> OTHER INFORMATION: URELUMAB CDR1-L

<400> SEQUENCE: 135

Arg Ala Ser Gln Ser Val Ser Ser Tyr Leu Ala
1               5                   10

<210> SEQ ID NO 136
<211> LENGTH: 7
<212> TYPE: PRT
<213> ORGANISM: Artificial Sequence
<220> FEATURE:
<223> OTHER INFORMATION: URELUMAB CDR2-L

<400> SEQUENCE: 136

Asp Ala Ser Asn Arg Ala Thr
1               5

<210> SEQ ID NO 137
<211> LENGTH: 11
<212> TYPE: PRT
<213> ORGANISM: Artificial Sequence
<220> FEATURE:
<223> OTHER INFORMATION: URELUMAB CDR3-L

<400> SEQUENCE: 137

Gln Gln Arg Ser Asn Trp Pro Pro Ala Leu Thr
1 5 10

<210> SEQ ID NO 138
<211> LENGTH: 9
<212> TYPE: PRT
<213> ORGANISM: Artificial Sequence
<220> FEATURE:
<223> OTHER INFORMATION: UTOMILUMAB CDR1-H

<400> SEQUENCE: 138

Tyr Ser Phe Ser Thr Tyr Trp Ile Ser
1 5

<210> SEQ ID NO 139
<211> LENGTH: 17
<212> TYPE: PRT
<213> ORGANISM: Artificial Sequence
<220> FEATURE:
<223> OTHER INFORMATION: UTOMILUMAB CDR2-H

<400> SEQUENCE: 139

Lys Ile Tyr Pro Gly Asp Ser Tyr Thr Asn Tyr Ser Pro Ser Phe Gln
1 5 10 15

Gly

<210> SEQ ID NO 140
<211> LENGTH: 7
<212> TYPE: PRT
<213> ORGANISM: Artificial Sequence
<220> FEATURE:
<223> OTHER INFORMATION: UTOMILUMAB CDR3-H

<400> SEQUENCE: 140

Gly Tyr Gly Ile Phe Asp Tyr
1 5

<210> SEQ ID NO 141
<211> LENGTH: 11
<212> TYPE: PRT
<213> ORGANISM: Artificial Sequence
<220> FEATURE:
<223> OTHER INFORMATION: UTOMILUMAB CDR1-L

<400> SEQUENCE: 141

Ser Gly Asp Asn Ile Gly Asp Gln Tyr Ala His
1 5 10

<210> SEQ ID NO 142
<211> LENGTH: 7
<212> TYPE: PRT
<213> ORGANISM: Artificial Sequence
<220> FEATURE:
<223> OTHER INFORMATION: UTOMILUMAB CDR2-L

<400> SEQUENCE: 142

Gln Asp Lys Asn Arg Pro Ser
1 5

<210> SEQ ID NO 143
<211> LENGTH: 11
<212> TYPE: PRT
<213> ORGANISM: Artificial Sequence
<220> FEATURE:
<223> OTHER INFORMATION: UTOMILUMAB CDR3-L

<400> SEQUENCE: 143

Ala Thr Tyr Thr Gly Phe Gly Ser Leu Ala Val
1 5 10

<210> SEQ ID NO 144
<211> LENGTH: 248
<212> TYPE: PRT
<213> ORGANISM: Artificial Sequence
<220> FEATURE:
<223> OTHER INFORMATION: scFv:CD70(1F6) anchoring domain from protein construct of SEQ ID NO: 121

<400> SEQUENCE: 144

Gln Ile Gln Leu Val Gln Ser Gly Pro Glu Val Lys Lys Pro Gly Glu
1 5 10 15

Thr Val Lys Ile Ser Cys Lys Ala Ser Gly Tyr Thr Phe Thr Asn Tyr
20 25 30

Gly Met Asn Trp Val Lys Gln Ala Pro Gly Lys Gly Leu Lys Trp Met
35 40 45

Gly Trp Ile Asn Thr Tyr Thr Gly Glu Pro Thr Tyr Ala Asp Ala Phe
50 55 60

Lys Gly Arg Phe Ala Phe Ser Leu Glu Thr Ser Ala Ser Thr Ala Tyr
65 70 75 80

Leu Gln Ile Asn Asn Leu Lys Asn Glu Asp Thr Ala Thr Tyr Phe Cys
85 90 95

Ala Arg Asp Tyr Gly Asp Tyr Gly Met Asp Tyr Trp Gly Gln Gly Thr
100 105 110

Ser Val Thr Val Ser Ser Ala Ser Thr Lys Gly Pro Lys Leu Glu Glu
115 120 125

Gly Glu Phe Ser Glu Ala Arg Val Asp Ile Val Leu Thr Gln Ser Pro
130 135 140

Ala Ser Leu Ala Val Ser Leu Gly Gln Arg Ala Thr Ile Ser Cys Arg
145 150 155 160

Ala Ser Lys Ser Val Ser Thr Ser Gly Tyr Ser Phe Met His Trp Tyr
165 170 175

Gln Gln Lys Pro Gly Gln Pro Pro Lys Leu Leu Ile Tyr Leu Ala Ser
180 185 190

Asn Leu Glu Ser Gly Val Pro Ala Arg Phe Ser Gly Ser Gly Ser Gly
195 200 205

Thr Asp Phe Thr Leu Asn Ile His Pro Val Glu Glu Glu Asp Ala Ala
210 215 220

Thr Tyr Tyr Cys Gln His Ser Arg Glu Val Pro Trp Thr Phe Gly Gly
225 230 235 240

Gly Thr Lys Leu Glu Ile Lys Arg
245

<210> SEQ ID NO 145
<211> LENGTH: 245
<212> TYPE: PRT
<213> ORGANISM: Artificial Sequence
<220> FEATURE:
<223> OTHER INFORMATION: scFv:CD70(2H5) anchoring domain from protein construct of SEQ ID NO: 122

<400> SEQUENCE: 145

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr

```
            20                  25                  30

Ile Met His Trp Val Arg Gln Ala Pro Gly Lys Gly Leu Glu Trp Val
        35                  40                  45

Ala Val Ile Ser Tyr Asp Gly Arg Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Asp Gly Tyr Asp Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Glu Ile Val Leu Thr Gln Ser Pro Ala Thr Leu
    130                 135                 140

Ser Leu Ser Pro Gly Glu Arg Ala Thr Leu Ser Cys Arg Ala Ser Gln
145                 150                 155                 160

Ser Val Ser Ser Tyr Leu Ala Trp Tyr Gln Gln Lys Pro Gly Gln Ala
                165                 170                 175

Pro Arg Leu Leu Ile Tyr Asp Ala Ser Asn Arg Ala Thr Gly Ile Pro
            180                 185                 190

Ala Arg Phe Ser Gly Ser Gly Ser Gly Thr Asp Phe Thr Leu Thr Ile
        195                 200                 205

Ser Ser Leu Glu Pro Glu Asp Phe Ala Val Tyr Tyr Cys Gln Gln Arg
    210                 215                 220

Thr Asn Trp Pro Leu Thr Phe Gly Gly Gly Thr Lys Val Glu Ile Lys
225                 230                 235                 240

Ala Ser Thr Lys Gly
                245
```

```
<210> SEQ ID NO 146
<211> LENGTH: 2247
<212> TYPE: DNA
<213> ORGANISM: Artificial Sequence
<220> FEATURE:
<223> OTHER INFORMATION: anti-TRAILR2(Cona)-IgG1(N297A)-VH-
      scFv:CD70(9G2)

<400> SEQUENCE: 146

atgaacttcg gcttcagcct gatcttcctg gtgctggtgc tgaagggcgt gcagtgcgaa     60

gtgaagctgg tgccccggca attggactac aaggacgacg acgacaaaga attccaggtg    120

cagctgcagg aatctggccc tggcctcgtg aagcctagcc agaccctgag cctgacctgt    180

accgtgtctg gcggcagcat cagcagcggc gactacttct ggtcctggat cagacagctg    240

cccggcaagg gcctggaatg gatcggccac atccacaaca gcggcaccac ctactacaac    300

cccagcctga agtccagagt gaccatcagc gtggacacca gcaagaagca gttcagcctg    360

cggctgagca gcgtgacagc cgccgataca gccgtgtact actgcgccag agacagaggc    420

ggcgattact actacggcat ggacgtgtgg ggccagggca ccaccgtgac cgtgtctagc    480

agatccagca gcgcctctac aaagggcccc agcgtgttcc ctctggcccc tagcagcaag    540

agcacatctg gcggaacagc cgccctgggc tgcctcgtga aggactactt tcccgagccc    600

gtgaccgtgt cctggaactc tggcgctctg acaagcggcg tgcacacctt tccagccgtg    660

ctgcagagca gcggcctgta ctctctgagc agcgtcgtga cagtgcccag cagctctctg    720
```

```
ggcacccaga cctacatctg caacgtgaac cacaagccca gcaacaccaa ggtggacaag    780

aaggtggaac ccaagagctg cgacaagacc cacacctgtc cccccttgtcc tgcccccgaa   840

ctgctgggag gcccttccgt gttcctgttc cccccaaagc ccaaggacac cctgatgatc    900

agccggaccc ccgaagtgac ctgcgtggtg gtggatgtgt cccacgagga ccctgaagtg    960

aagtttaatt ggtacgtgga cggcgtggaa gtgcacaacg ccaagaccaa gcctagagag   1020

gaacagtacg ccagcaccta ccgggtggtg tccgtgctga cagtgctgca ccaggactgg   1080

ctgaacggca aagagtacaa gtgcaaggtg tccaacaagg ccctgcctgc ccccatcgag   1140

aaaaccatca gcaaggccaa gggccagccc cgcgaacccc aggtgtacac actgccccca   1200

agcagggacg agctgaccaa gaaccaggtg tccctgacct gtctcgtgaa aggcttctac   1260

cccagcgata tcgccgtgga atgggagagc aacggccagc ccgagaacaa ctacaagacc   1320

acccccccctg tgctggacag cgacggctca ttcttcctgt acagcaagct gaccgtggac  1380

aagtcccggt ggcagcaggg caacgtgttc agctgcagcg tgatgcacga ggccctgcac   1440

aaccactaca cccagaagtc cctgagcccc ggcaagctcg agcaggtgca gctggtggaa   1500

tctggcggcg gactgatgca gcctggcggc tctctgagac tgagctgtgc cgccagcggc   1560

ttcaccttta gcagcagcgc catgagctgg gtgcgccagg ctcctggaaa gggcctggaa   1620

tgggtgtcca gcatctacag cgacagcagc tacacctact acgccgacag cgtgaagtcc   1680

cggttcacca tcagcaccga caacgccaag aacaccctgt acctgcagat gaacagcctg   1740

aagcccgacg acaccgccgt gtactactgt gccggcagca gcgattacga gggcagcttt   1800

gcctcttggg gccagggcac acaagtgacc gtgtcctcca gatctagcac caagggcccc   1860

aagctggaag agggcgagtt cagcgaggcc caattgcaga gcgtcgtgac ccagcctcct   1920

agcctgtctg cctctcctgg aagcagcgtg cggctgacct gtacactgag cagcggcaac   1980

agcgtgggca actacgacat cagctggtat cagcagaagg ccggcagccc ccccagatac   2040

ctgctgtact actacagcga ttccgtgaag caccagggca gcggcgtgcc cagcagattt   2100

tccggaagct ctgacgccag cgccaacgcc ggactgctgc tgatttctgg cctgcagcct   2160

gaggacgagg ccgactacta ctgcagcgcc tacaagagcg gcagccacgt gttcggcgga   2220

ggcaccaaac tgacagtgct gggctaa                                      2247
```

```
<210> SEQ ID NO 147
<211> LENGTH: 768
<212> TYPE: DNA
<213> ORGANISM: Artificial Sequence
<220> FEATURE:
<223> OTHER INFORMATION: anti-TRAILR2(Cona)-VL

<400> SEQUENCE: 147

atgaacttcg gcttcagcct gatcttcctg gtgctggtgc tgaagggcgt gcagtgcgaa     60

gtgaagctgg tgccccggca attggactac aaggacgacg acgacaaaga attggagatc    120

gtgctgaccc agagccctgg caccctgtca ctgtctccag gcgagagagc caccctgagc    180

tgtagagcca gccagggcat cagccggtct tacctggcct ggtatcagca gaagcccggc    240

caggctccta gcctgctgat ctacggcgcc agcagcagag ccaccggcat ccccgataga    300

ttttccggca gcggctccgg caccgacttc accctgacaa tcagcagact ggaacccgag    360

gacttcgccg tgtattattg ccagcagttc ggcagcagcc cctggacctt tggccaggga    420

acaaaagtgg gatccgaaat caagcgtacg gtggccgctc ccagcgtgtt catcttccca    480

cctagcgacg agcagctgaa gtccggcaca gcctctgtcg tgtgcctgct gaacaacttc    540
```

```
taccccgcg aggccaaggt gcagtggaag gtggacaatg ccctgcagag cggcaacagc    600

caggaaagcg tgaccgagca ggacagcaag gactccacct acagcctgag cagcaccctg    660

accctgagca aggccgacta cgagaagcac aaggtgtacg cctgcgaagt gacccaccag    720

ggcctgtcta gccccgtgac caagagcttc aaccggggcg agtgctaa                 768
```

<210> SEQ ID NO 148
<211> LENGTH: 2226
<212> TYPE: DNA
<213> ORGANISM: Artificial Sequence
<220> FEATURE:
<223> OTHER INFORMATION: anti-CD40(C)-IgG1(N297A)-VH-scFv:PD-L1(Ave)

<400> SEQUENCE: 148

```
atgaacttcg gcttcagcct gatcttcctg gtgctggtgc tgaagggcgt gcagtgcgaa     60

gtgaagctgg tgccccggca attggactac aaggacgacg acgacaaaga attccaggtg    120

cagctggttc agtctggcgc cgaagtgaaa aagcctggcg cctctgtgaa ggtgtcctgt    180

acagccagcg gcttcaacat caaggactac tacgtgcact gggtcaagca ggcccctgga    240

caaggactgg aatggatggg cagaatcgac cccgaggacg gcgactctaa gtacgcccct    300

aagttccagg gcaaagccac catgaccgcc gataccagca caagcaccgt gtacatggaa    360

ctgagcagcc tgagaagcga ggacaccgcc gtgtactact gcaccaccag ctactatgtg    420

ggcacctacg gctattgggg ccagggcaca ctggtcaccg tgtccagcag atccagcagc    480

gcctctacaa agggccccag cgtgttccct ctggccccta gcagcaagag cacatctggc    540

ggaacagccg ccctgggctg cctcgtgaag gactactttc ccgagcccgt gaccgtgtcc    600

tggaactctg gcgctctgac aagcggcgtg cacacctttc cagccgtgct gcagagcagc    660

ggcctgtact ctctgagcag cgtcgtgaca gtgcccagca gctctctggg cacccagacc    720

tacatctgca acgtgaacca caagcccagc aacaccaagg tggacaagaa ggtggaaccc    780

aagagctgcg acaagaccca cacctgtccc ccttgtcctg cccccgaact gctgggaggc    840

ccttccgtgt tcctgttccc cccaaagccc aaggacaccc tgatgatcag ccggaccccc    900

gaagtgacct gcgtggtggt ggatgtgtcc cacgaggacc ctgaagtgaa gtttaattgg    960

tacgtggacg gcgtggaagt gcacaacgcc aagaccaagc ctagagagga acagtacgcc   1020

agcacctacc gggtggtgtc cgtgctgaca gtgctgcacc aggactggct gaacggcaaa   1080

gagtacaagt gcaaggtgtc caacaaggcc ctgcctgccc ccatcgagaa aaccatcagc   1140

aaggccaagg gccagccccg cgaaccccag gtgtacacac tgcccccaag cagggacgag   1200

ctgaccaaga accaggtgtc cctgacctgt ctcgtgaaag gcttctaccc cagcgatatc   1260

gccgtggaat gggagagcaa cggccagccc gagaacaact acaagaccac cccccctgtg   1320

ctggacagcg acggctcatt cttcctgtac agcaagctga ccgtggacaa gtcccggtgg   1380

cagcagggca acgtgttcag ctgcagcgtg atgcacgagg ccctgcacaa ccactacacc   1440

cagaagtccc tgagcctgag ccccggcaag ctcgaggagg tgcagctgct ggaatctggc   1500

ggaggacttg ttcagcctgg cggctctctg agactgtctt gtgccgccag cggcttcacc   1560

ttcagcagct atatcatgat gtgggtccga caggcccctg gcaaaggcct tgaatgggtg   1620

tccagcatct atcccagcgg cggcatcacc ttttacgccg acacagtgaa gggcagattc   1680

accatcagcc gggacaacag caagaacacc ctgtacctgc agatgaacag cctgagagcc   1740

gaggacaccg ccgtgtacta ctgcgccaga atcaagctgg gcaccgtgac caccgtggat   1800
```

```
tattggggac agggcaccct ggtcaccgtg tcctccagat cttctacaaa gggccccaag   1860

ctggaagagg gcgagtttag cgaagcccaa ttgcagagcg ccctgacaca gcctgcatcc   1920

gtgtctggat ctccaggcca gagcatcacc atctcttgta ccggcacaag ctccgatgtc   1980

ggcggctaca attacgtgtc ctggtatcag cagcaccccg gcaaggcccc taagctgatg   2040

atctacgacg tgtccaacag accctccggc gtgtccaata gattcagcgg cagcaagagc   2100

ggcaacaccg ccagcctgac aattagcgga ctgcaggccg aggacgaggc cgattactac   2160

tgtagcagct acaccagctc ctccaccaga gtgtttggca ccggcaccaa agtgaccgtg   2220

ctttaa                                                              2226
```

<210> SEQ ID NO 149
<211> LENGTH: 771
<212> TYPE: DNA
<213> ORGANISM: Artificial Sequence
<220> FEATURE:
<223> OTHER INFORMATION: anti-CD40(C)-VL

<400> SEQUENCE: 149

```
atgaacttcg gcttcagcct gatcttcctg gtgctggtgc tgaagggcgt gcagtgcgaa     60

gtgaagctgg tgccccggca attggactac aaggacgacg acgacaaaga attggacatc    120

cagatgacac agagccccag cagcctgtct gccagcgtgg gagatagagt gaccatcacc    180

tgtagcgcca gcagcagcgt gtcctacatg ctgtggttcc agcagaagcc tggcaaggcc    240

cctaagctgc tgatctacag cacctccaat ctggccagcg gcgtgccaag cagattttct    300

ggctctggca gcggcaccga cttcaccctg accatatcta gcctgcagcc agaggacttc    360

gccacctact actgccagca gcggacattc taccccctaca cctttggcgg aggcaccaag    420

gtggaaatca agggatccga aatcaagcgt acggtggccg ctcccagcgt gttcatcttc    480

ccacctagcg acgagcagct gaagtccggc acagcctctg tcgtgtgcct gctgaacaac    540

ttctaccccc gcgaggccaa ggtgcagtgg aaggtggaca atgccctgca gagcggcaac    600

agccaggaaa gcgtgaccga gcaggacagc aaggactcca cctacagcct gagcagcacc    660

ctgaccctga gcaaggccga ctacgagaag cacaaggtgt acgcctgcga agtgacccac    720

cagggcctgt ctagccccgt gaccaagagc ttcaaccggg gcgagtgcta a            771
```

<210> SEQ ID NO 150
<211> LENGTH: 1578
<212> TYPE: DNA
<213> ORGANISM: Artificial Sequence
<220> FEATURE:
<223> OTHER INFORMATION: anti-CD40(C)-Fab2-scFv:PD-L1(Ave)

<400> SEQUENCE: 150

```
atgaacttcg gcttcagcct gatcttcctg gtgctggtgc tgaagggcgt gcagtgcgaa     60

gtgaagctgg tgccccggca attggactac aaggacgacg acgacaaaga attccaggtg    120

cagctggttc agtctggcgc cgaagtgaaa aagcctggcg cctctgtgaa ggtgtcctgt    180

acagccagcg gcttcaacat caaggactac tacgtgcact gggtcaagca ggcccctgga    240

caaggactgg aatggatggg cagaatcgac cccgaggacg gcgactctaa gtacgcccct    300

aagttccagg gcaaagccac catgaccgcc gataccagca caagcaccgt gtacatggaa    360

ctgagcagcc tgagaagcga ggacaccgcc gtgtactact gcaccaccag ctactatgtg    420

ggcacctacg gctattgggg ccagggcaca ctggtcaccg tgtccagcag atcctctagc    480

gccagcacaa agggccccag cgtgttccct ctggccccta gcagcaagag cacatctggc    540
```

```
ggaacagccg ccctgggctg cctcgtgaag gactactttc ccgagcccgt gacagtgtcc    600

tggaactctg gcgccctgac aagcggcgtg cacacctttc cagccgtgct gcagagcagc    660

ggcctgtact ctctgagcag cgtcgtgact gtgcccagca gcagcctggg cacccagacc    720

tacatctgca acgtgaacca caagcccagc aacaccaagg tggacaagaa ggtggaaccc    780

aagagctgcg acaagaccca cacctgtccc ccttgtcctg ccctcgagga ggtgcagctg    840

ctggaatctg gcggaggact tgttcagcct ggcggctctc tgagactgtc ttgtgccgcc    900

agcggcttca ccttcagcag ctatatcatg atgtgggtcc gacaggcccc tggcaaaggc    960

cttgaatggg tgtccagcat ctatcccagc ggcggcatca ccttttacgc cgacacagtg   1020

aagggcagat tcaccatcag ccgggacaac agcaagaaca ccctgtacct gcagatgaac   1080

agcctgagag ccgaggacac cgccgtgtac tactgcgcca gaatcaagct gggcaccgtg   1140

accaccgtgg attattgggg acagggcacc ctggtcaccg tgtcctccag atcttctaca   1200

aagggcccca agctggaaga gggcgagttt agcgaagccc aattgcagag cgccctgaca   1260

cagcctgcat ccgtgtctgg atctccaggc cagagcatca ccatctcttg taccggcaca   1320

agctccgatg tcggcggcta caattacgtg tcctggtatc agcagcaccc cggcaaggcc   1380

cctaagctga tgatctacga cgtgtccaac agaccctccg gcgtgtccaa tagattcagc   1440

ggcagcaaga gcggcaacac cgccagcctg acaattagcg gactgcaggc cgaggacgag   1500

gccgattact actgtagcag ctacaccagc tcctccacca gagtgtttgg caccggcacc   1560

aaagtgaccg tgctttaa                                                 1578
```

<210> SEQ ID NO 151
<211> LENGTH: 2229
<212> TYPE: DNA
<213> ORGANISM: Artificial Sequence
<220> FEATURE:
<223> OTHER INFORMATION: anti-41BB(HBBK)-IgG1(N297A)-VH-scFv:PD-L1(Ave)

<400> SEQUENCE: 151

```
atgaacttcg gcttcagcct gatcttcctg gtgctggtgc tgaagggcgt gcagtgcgaa     60

gtgaagctgg tgccccggca attggactac aaggacgacg acgacaaaga attccaggtc    120

cagctgcagc agtctggcgc cgaagttatt aagcctggcg cctccgtgaa gctgagctgt    180

aaagccagcg gctacacctt cagcagctac tggatgcact gggtccgaca ggctccagga    240

caaggcctgg aatggatcgg cgagatcaac cctggcaacg gccacaccaa ctacaacgag    300

aagttcaaga gccgggccac actgaccggc gataccagca caagcaccgt gtacatggaa    360

ctgagcagcc tgagaagcga ggacaccgcc gtgtactact gcgccagatc ctttaccacc    420

gccagagcct ttgcctattg gggccaggga acactggtca ccgtgtccag cagatccagc    480

agcgcctcta caaagggccc cagcgtgttc cctctggccc ctagcagcaa gagcacatct    540

ggcggaacag ccgccctggg ctgcctcgtg aaggactact ttcccgagcc cgtgaccgtg    600

tcctggaact ctggcgctct gacaagcggc gtgcacacct ttccagccgt gctgcagagc    660

agcggcctgt actctctgag cagcgtcgtg acagtgccca gcagctctct gggcacccag    720

acctacatct gcaacgtgaa ccacaagccc agcaacacca aggtggacaa gaaggtggaa    780

cccaagagct gcgacaagac ccacacctgt ccccccttgtc ctgcccccga actgctggga    840

ggcccttccg tgttcctgtt ccccccaaag cccaaggaca ccctgatgat cagccggacc    900

cccgaagtga cctgcgtggt ggtggatgtg tcccacgagg accctgaagt gaagtttaat    960
```

```
tggtacgtgg acggcgtgga agtgcacaac gccaagacca agcctagaga ggaacagtac   1020

gccagcacct accgggtggt gtccgtgctg acagtgctgc accaggactg gctgaacggc   1080

aaagagtaca agtgcaaggt gtccaacaag gccctgcctg cccccatcga gaaaaccatc   1140

agcaaggcca agggccagcc ccgcgaaccc caggtgtaca cactgccccc aagcagggac   1200

gagctgacca agaaccaggt gtccctgacc tgtctcgtga aaggcttcta ccccagcgat   1260

atcgccgtgg aatgggagag caacggccag cccgagaaca actacaagac caccccccct   1320

gtgctggaca gcgacggctc attcttcctg tacagcaagc tgaccgtgga caagtcccgg   1380

tggcagcagg gcaacgtgtt cagctgcagc gtgatgcacg aggccctgca caaccactac   1440

acccagaagt ccctgagcct gagccccggc aagctcgagg aggtgcagct gctggaatct   1500

ggcggaggac ttgttcagcc tggcggctct ctgagactgt cttgtgccgc cagcggcttc   1560

accttcagca gctatatcat gatgtgggtc cgacaggccc ctggcaaagg ccttgaatgg   1620

gtgtccagca tctatcccag cggcggcatc accttttacg ccgacacagt gaagggcaga   1680

ttcaccatca gccgggacaa cagcaagaac accctgtacc tgcagatgaa cagcctgaga   1740

gccgaggaca ccgccgtgta ctactgcgcc agaatcaagc tgggcaccgt gaccaccgtg   1800

gattattggg gacagggcac cctggtcacc gtgtcctcca gatcttctac aaagggcccc   1860

aagctggaag agggcgagtt tagcgaagcc caattgcaga gcgccctgac acagcctgca   1920

tccgtgtctg gatctccagg ccagagcatc accatctctt gtaccggcac aagctccgat   1980

gtcggcggct acaattacgt gtcctggtat cagcagcacc ccggcaaggc ccctaagctg   2040

atgatctacg acgtgtccaa cagaccctcc ggcgtgtcca atagattcag cggcagcaag   2100

agcggcaaca ccgccagcct gacaattagc ggactgcagg ccgaggacga ggccgattac   2160

tactgtagca gctacaccag ctcctccacc agagtgtttg gcaccggcac caaagtgacc   2220

gtgctttaa                                                           2229
```

```
<210> SEQ ID NO 152
<211> LENGTH: 1581
<212> TYPE: DNA
<213> ORGANISM: Artificial Sequence
<220> FEATURE:
<223> OTHER INFORMATION: anti-41BB(HBBK)-Fab2-scFv:PD-L1(Ave)

<400> SEQUENCE: 152
```

```
atgaacttcg gcttcagcct gatcttcctg gtgctggtgc tgaagggcgt gcagtgcgaa     60

gtgaagctgg tgccccggca attggactac aaggacgacg acgacaaaga attccaggtc    120

cagctgcagc agtctggcgc cgaagttatt aagcctggcg cctccgtgaa gctgagctgt    180

aaagccagcg gctacacctt cagcagctac tggatgcact gggtccgaca ggctccagga    240

caaggcctgg aatggatcgg cgagatcaac cctggcaacg gccacaccaa ctacaacgag    300

aagttcaaga gccgggccac actgaccggc gataccagca caagcaccgt gtacatggaa    360

ctgagcagcc tgagaagcga ggacaccgcc gtgtactact gcgccagatc ctttaccacc    420

gccagagcct ttgcctattg gggccaggga acactggtca ccgtgtccag cagatcctct    480

agcgccagca caaagggccc cagcgtgttc cctctggccc ctagcagcaa gagcacatct    540

ggcggaacag ccgccctggg ctgcctcgtg aaggactact ttcccgagcc cgtgacagtg    600

tcctggaact ctggcgccct gacaagcggc gtgcacacct ttccagccgt gctgcagagc    660

agcggcctgt actctctgag cagcgtcgtg actgtgccca gcagcagcct gggcacccag    720

acctacatct gcaacgtgaa ccacaagccc agcaacacca aggtggacaa gaaggtggaa    780
```

```
cccaagagct gcgacaagac ccacacctgt ccccttgtc ctgccctcga ggaggtgcag     840

ctgctggaat ctggcggagg acttgttcag cctggcggct ctctgagact gtcttgtgcc     900

gccagcggct tcaccttcag cagctatatc atgatgtggg tccgacaggc ccctggcaaa     960

ggccttgaat gggtgtccag catctatccc agcggcggca tcacctttta cgccgacaca    1020

gtgaagggca gattcaccat cagccgggac aacagcaaga acaccctgta cctgcagatg    1080

aacagcctga gagccgagga caccgccgtg tactactgcg ccagaatcaa gctgggcacc    1140

gtgaccaccg tggattattg gggacagggc accctggtca ccgtgtcctc cagatcttct    1200

acaaagggcc ccaagctgga agagggcgag tttagcgaag cccaattgca gagcgccctg    1260

acacagcctg catccgtgtc tggatctcca ggccagagca tcaccatctc ttgtaccggc    1320

acaagctccg atgtcggcgg ctacaattac gtgtcctggt atcagcagca ccccggcaag    1380

gcccctaagc tgatgatcta cgacgtgtcc aacagaccct ccggcgtgtc caatagattc    1440

agcggcagca agagcggcaa caccgccagc ctgacaatta gcggactgca ggccgaggac    1500

gaggccgatt actactgtag cagctacacc agctcctcca ccagagtgtt tggcaccggc    1560

accaaagtga ccgtgcttta a                                              1581
```

<210> SEQ ID NO 153
<211> LENGTH: 2208
<212> TYPE: DNA
<213> ORGANISM: Artificial Sequence
<220> FEATURE:
<223> OTHER INFORMATION: anti-PD-L1(Ave)-IgG2-VH-scFv:41BB(HBBK)

<400> SEQUENCE: 153

```
atgaacttcg gcttcagcct gatcttcctg gtgctggtgc tgaagggcgt gcagtgcgaa      60

gtgaagctgg tgccccggca attggactac aaggacgacg acgacaaaga attcgaggtg     120

cagctgctgg aatctggcgg aggacttgtt cagcctggcg gctctctgag actgtcttgt     180

gccgccagcg gcttcacctt cagcagctat atcatgatgt gggtccgaca ggcccctggc     240

aaaggccttg aatgggtgtc cagcatctat cccagcggcg gcatcacctt ttacgccgac     300

acagtgaagg gcagattcac catcagccgg gacaacagca agaacaccct gtacctgcag     360

atgaacagcc tgagagccga ggacaccgcc gtgtactact gcgccagaat caagctgggc     420

accgtgacca ccgtggatta ttggggacag ggcaccctgg tcaccgtgtc ctccagatcc     480

tcgagtgcta gcaccaaggg cccatcggtc ttccccctgg cgccctgctc caggagcacc     540

tccgagagca cagcggccct gggctgcctg gtcaaggact acttccccga accggtgacg     600

gtgtcgtgga actcaggcgc tctgaccagc ggcgtgcaca ccttcccagc tgtcctacag     660

tcctcaggac tctactccct cagcagcgtg gtgaccgtgc cctccagcaa cttcggcacc     720

cagacctaca cctgcaacgt agatcacaag cccagcaaca ccaaggtgga caagacagtt     780

gagcgcaaat gttgtgtcga gtgcccaccg tgcccagcac cacctgtggc aggaccgtca     840

gtcttcctct tcccccaaa acccaaggac accctcatga tctcccggac ccctgaggtc     900

acgtgcgtgg tggtggacgt gagccacgaa gaccccgagg tccagttcaa ctggtacgtg     960

gacggcgtgg aggtgcataa tgccaagaca aagccacggg aggagcagtt caacagcacg    1020

ttccgtgtgg tcagcgtcct caccgttgtg caccaggact ggctgaacgg caaggagtac    1080

aagtgcaagg tctccaacaa aggcctccca gcccccatcg agaaaaccat ctccaaaacc    1140

aaagggcagc cccgagaacc acaggtgtac accctgcccc catcccggga ggagatgacc    1200
```

```
aagaaccagg tcagcctgac ctgcctggtc aaaggcttct accccagcga catcgccgtg   1260

gagtgggaga gcaatgggca gccggagaac aactacaaga ccacgcctcc catgctggac   1320

tccgacggct ccttcttcct ctacagcaag ctcaccgtgg acaagagcag gtggcagcag   1380

gggaacgtct tctcatgctc cgtgatgcat gaggctctgc acaaccacta cacgcagaag   1440

agcctctccc tgtctccggg taaagaattc caggtccagc tgcagcagtc tggcgccgaa   1500

gttattaagc ctggcgcctc cgtgaagctg agctgtaaag ccagcggcta caccttcagc   1560

agctactgga tgcactgggt ccgacaggct ccaggacaag gcctggaatg gatcggcgag   1620

atcaaccctg gcaacggcca caccaactac aacgagaagt tcaagagccg ggccacactg   1680

accggcgata ccagcacaag caccgtgtac atggaactga gcagcctgag aagcgaggac   1740

accgccgtgt actactgcgc cagatccttt accaccgcca gagcctttgc ctattggggc   1800

cagggaacac tggtcaccgt gtccagcaga tctagcacaa agggccccaa gctggaagag   1860

ggcgagttta gcgaggccca attggacatc gtgatgactc agagccccgc cttcctgtct   1920

gtgacccctg gcgagaaagt gaccatcacc tgtagagcca gccagaccat cagcgactac   1980

ctgcactggt atcagcagaa gcccgatcag gcccctaagc tgctgattaa gtacgcctct   2040

cagagcatca gcggcatccc cagcagattt tctggcagcg gctctggcac cgacttcacc   2100

tttaccatca gctccctgga agccgaggat gccgccacct actattgtca ggacggccac   2160

agcttccctc caacctttgg acagggcaca aagctggaaa tcaagtaa                2208
```

<210> SEQ ID NO 154
<211> LENGTH: 783
<212> TYPE: DNA
<213> ORGANISM: Artificial Sequence
<220> FEATURE:
<223> OTHER INFORMATION: anti-PD-L1(Ave)-VL

<400> SEQUENCE: 154

```
atgaacttcg gcttcagcct gatcttcctg gtgctggtgc tgaagggcgt gcagtgcgaa     60

gtgaagctgg tgccccggca attggactac aaggacgacg acgacaaaga attgcagagc    120

gccctgacac agcctgcatc cgtgtctgga tctccaggcc agagcatcac catctcttgt    180

accggcacaa gctccgatgt cggcggctac aattacgtgt cctggtatca gcagcacccc    240

ggcaaggccc ctaagctgat gatctacgac gtgtccaaca gaccctccgg cgtgtccaat    300

agattcagcg gcagcaagag cggcaacacc gccagcctga caattagcgg actgcaggcc    360

gaggacgagg ccgattacta ctgtagcagc tacaccagct cctccaccag agtgtttggc    420

accggcacca aagtgaccgt gcttggatcc gaaatcaagc gtacggtggc cgctcccagc    480

gtgttcatct tcccacctag cgacgagcag ctgaagtccg gcacagcctc tgtcgtgtgc    540

ctgctgaaca acttctaccc ccgcgaggcc aaggtgcagt ggaaggtgga caatgccctg    600

cagagcggca acagccagga aagcgtgacc gagcaggaca gcaaggactc cacctacagc    660

ctgagcagca ccctgaccct gagcaaggcc gactacgaga agcacaaggt gtacgcctgc    720

gaagtgaccc accagggcct gtctagcccc gtgaccaaga gcttcaaccg gggcgagtgc    780

taa                                                                  783
```

<210> SEQ ID NO 155
<211> LENGTH: 2223
<212> TYPE: DNA
<213> ORGANISM: Artificial Sequence
<220> FEATURE:
<223> OTHER INFORMATION: anti-muCD27-IgG1(N297A)-VH-scFv:Fn14(18D1)

<400> SEQUENCE: 155

```
atgaacttcg gcttcagcct gatcttcctg gtgctggtgc tgaagggcgt gcagtgcgaa      60
gtgaagctgg tgccccggca attggactac aaggacgacg acgacaaaga attccaggtc     120
cagctgcagc agtctggcgc cgaacttgtg aagcctggca gcagcgtgaa gatcagctgt     180
aaagccagcg gctacacctt caccagctac gacatgcact ggatcaagca gcagcccggc     240
aaaggcctgg aatggatcgg ctggatctac cccggcaacg gcaacaccaa gtacaaccag     300
aagttcaacg gcaaggccac actgaccgcc gacatctcta gcagcacagc ctacatgcag     360
ctgagcagcc tgaccagcga agatagcgcc gtgtacttct gcgccaaatg gggctacaac     420
aacttcgact actggggcca gggcgtgatg gtcaccgtgt ctagcagatc cagcagcgcc     480
tctacaaagg gccccagcgt gttccctctg gcccctagca gcaagagcac atctggcgga     540
acagccgccc tgggctgcct cgtgaaggac tactttcccg agcccgtgac cgtgtcctgg     600
aactctggcg ctctgacaag cggcgtgcac acctttccag ccgtgctgca gagcagcggc     660
ctgtactctc tgagcagcgt cgtgacagtg cccagcagct ctctgggcac ccagacctac     720
atctgcaacg tgaaccacaa gcccagcaac accaaggtgg acaagaaggt ggaacccaag     780
agctgcgaca agacccacac ctgtccccct tgtcctgccc ccgaactgct gggaggccct     840
tccgtgttcc tgttcccccc aaagcccaag gacaccctga tgatcagccg gacccccgaa     900
gtgacctgcg tggtggtgga tgtgtcccac gaggaccctg aagtgaagtt taattggtac     960
gtggacggcg tggaagtgca caacgccaag accaagccta gagaggaaca gtacgccagc    1020
acctaccggg tggtgtccgt gctgacagtg ctgcaccagg actggctgaa cggcaaagag    1080
tacaagtgca aggtgtccaa caaggccctg cctgccccca tcgagaaaac catcagcaag    1140
gccaagggcc agccccgcga accccaggtg tacacactgc ccccaagcag ggacgagctg    1200
accaagaacc aggtgtccct gacctgtctc gtgaaaggct tctaccccag cgatatcgcc    1260
gtggaatggg agagcaacgg ccagcccgag aacaactaca agaccacccc ccctgtgctg    1320
gacagcgacg gctcattctt cctgtacagc aagctgaccg tggacaagtc ccggtggcag    1380
cagggcaacg tgttcagctg cagcgtgatg cacgaggccc tgcacaacca ctacacccag    1440
aagtccctga gcctgagccc cggcaagctc gaggaggtgc agctggtgga atctggcggc    1500
ggactggtgc agcctggcgg atctctgaga ctgagctgtg ccgccagcgg cttcaccttc    1560
agcaactact ggatgagctg ggtgcgccag gcccctggca aaggactgga atgggtgtcc    1620
ggcatcaacc caggcggcac ctctacctac tacgccgaca gcgtgaaggg ccggttcacc    1680
atcagccggg acaacgccaa gaacaccctg tacctgcaga tgaacagcct gaagtccgag    1740
gacaccgccg tgtactactg cgccaagcac ctgggcaact ggggcgagta caattactgg    1800
ggccagggca cacaagtgac cgtgtccagt agatctagca ccaagggccc caagctggaa    1860
gagggcgagt tcagcgaggc ccaattgcag agcgccctga cccagcctcc aagcgtgtca    1920
ggctctcctg gcaagaccgt gaccatcagc tgtgctggca ccggcggaga tgtgggctac    1980
agaaacagcg tgtcctggta tcagcagctg cccggcatgg cccccaaact gctgatctac    2040
gacgtggaca agcgggcctc tggcatcacc gacagattca gcggcagcaa gagcggcgat    2100
accgccagcc tgacaatcag cggagtgcag agcgaggacg aggccgacta ctactgtgcc    2160
agccagagaa gcggaatcgc cgccgtgttt ggcggaggca cacacctgac agtgctgggc    2220
taa                                                                  2223
```

<210> SEQ ID NO 156
<211> LENGTH: 774
<212> TYPE: DNA
<213> ORGANISM: Artificial Sequence
<220> FEATURE:
<223> OTHER INFORMATION: anti-muCD27-VL

<400> SEQUENCE: 156

```
atgaacttcg gcttcagcct gatcttcctg gtgctggtgc tgaagggcgt gcagtgcgaa     60

gtgaagctgg tgccccggca attggactac aaggacgacg acgacaaaga attggacatc    120

cagatgacac agagccctgc cagcctgtct gcctctctgg gagagacagt gtccatcgat    180

tgtctggcca gcgagggcat cagcaacgac ctggcttggt atcagcagaa gtccggcaag    240

agccctcagc tgctgatcaa cagcgccagc agactggaag atggcgtgcc cagcagattt    300

tctggctctg gcagcggcac ccggtacagc ctgaagattt ctggcatgca gcccgaggac    360

gaggccgaat acttctgcct gcaaagctac agaagcccct ggacctttgg cggaggcaca    420

aagctggaac tgaagggatc cgaaatcaag cgtacggtgg ccgctcccag cgtgttcatc    480

ttcccaccta gcgacgagca gctgaagtcc ggcacagcct ctgtcgtgtg cctgctgaac    540

aacttctacc cccgcgaggc caaggtgcag tggaaggtgg acaatgccct gcagagcggc    600

aacagccagg aaagcgtgac cgagcaggac agcaaggact ccacctacag cctgagcagc    660

accctgaccc tgagcaaggc cgactacgag aagcacaagg tgtacgcctg cgaagtgacc    720

caccagggcc tgtctagccc cgtgaccaag agcttcaacc ggggcgagtg ctaa          774
```

<210> SEQ ID NO 157
<211> LENGTH: 750
<212> TYPE: PRT
<213> ORGANISM: Artificial Sequence
<220> FEATURE:
<223> OTHER INFORMATION: Protein construct expressed from SEQ ID NO: 146

<400> SEQUENCE: 157

```
Met Asn Phe Gly Phe Ser Leu Ile Phe Leu Val Leu Val Leu Lys Gly
1               5                   10                  15

Val Gln Cys Glu Val Lys Leu Val Pro Arg Gln Leu Asp Tyr Lys Asp
            20                  25                  30

Asp Asp Asp Lys Glu Phe Gln Val Gln Leu Gln Glu Ser Gly Pro Gly
        35                  40                  45

Leu Val Lys Pro Ser Gln Thr Leu Ser Leu Thr Cys Thr Val Ser Gly
    50                  55                  60

Gly Ser Ile Ser Ser Gly Asp Tyr Phe Trp Ser Trp Ile Arg Gln Leu
65                  70                  75                  80

Pro Gly Lys Gly Leu Glu Trp Ile Gly His Ile His Asn Ser Gly Thr
                85                  90                  95

Thr Tyr Tyr Asn Pro Ser Leu Lys Ser Arg Val Thr Ile Ser Val Asp
            100                 105                 110

Thr Ser Lys Lys Gln Phe Ser Leu Arg Leu Ser Ser Val Thr Ala Ala
        115                 120                 125

Asp Thr Ala Val Tyr Tyr Cys Ala Arg Asp Arg Gly Gly Asp Tyr Tyr
    130                 135                 140

Tyr Gly Met Asp Val Trp Gly Gln Gly Thr Thr Val Thr Val Ser Ser
145                 150                 155                 160

Arg Ser Ser Ser Ala Ser Thr Lys Gly Pro Ser Val Phe Pro Leu Ala
                165                 170                 175
```

```
Pro Ser Ser Lys Ser Thr Ser Gly Gly Thr Ala Ala Leu Gly Cys Leu
            180                 185                 190

Val Lys Asp Tyr Phe Pro Glu Pro Val Thr Val Ser Trp Asn Ser Gly
        195                 200                 205

Ala Leu Thr Ser Gly Val His Thr Phe Pro Ala Val Leu Gln Ser Ser
    210                 215                 220

Gly Leu Tyr Ser Leu Ser Ser Val Val Thr Val Pro Ser Ser Ser Leu
225                 230                 235                 240

Gly Thr Gln Thr Tyr Ile Cys Asn Val Asn His Lys Pro Ser Asn Thr
                245                 250                 255

Lys Val Asp Lys Lys Val Glu Pro Lys Ser Cys Asp Lys Thr His Thr
            260                 265                 270

Cys Pro Pro Cys Pro Ala Pro Glu Leu Leu Gly Gly Pro Ser Val Phe
        275                 280                 285

Leu Phe Pro Pro Lys Pro Lys Asp Thr Leu Met Ile Ser Arg Thr Pro
    290                 295                 300

Glu Val Thr Cys Val Val Val Asp Val Ser His Glu Asp Pro Glu Val
305                 310                 315                 320

Lys Phe Asn Trp Tyr Val Asp Gly Val Glu Val His Asn Ala Lys Thr
                325                 330                 335

Lys Pro Arg Glu Glu Gln Tyr Ala Ser Thr Tyr Arg Val Val Ser Val
            340                 345                 350

Leu Thr Val Leu His Gln Asp Trp Leu Asn Gly Lys Glu Tyr Lys Cys
        355                 360                 365

Lys Val Ser Asn Lys Ala Leu Pro Ala Pro Ile Glu Lys Thr Ile Ser
    370                 375                 380

Lys Ala Lys Gly Gln Pro Arg Glu Pro Gln Val Tyr Thr Leu Pro Pro
385                 390                 395                 400

Ser Arg Asp Glu Leu Thr Lys Asn Gln Val Ser Leu Thr Cys Leu Val
                405                 410                 415

Lys Gly Phe Tyr Pro Ser Asp Ile Ala Val Glu Trp Glu Ser Asn Gly
            420                 425                 430

Gln Pro Glu Asn Asn Tyr Lys Thr Thr Pro Pro Val Leu Asp Ser Asp
        435                 440                 445

Gly Ser Phe Phe Leu Tyr Ser Lys Leu Thr Val Asp Lys Ser Arg Trp
    450                 455                 460

Gln Gln Gly Asn Val Phe Ser Cys Ser Val Met His Glu Ala Leu His
465                 470                 475                 480

Asn His Tyr Thr Gln Lys Ser Leu Ser Leu Ser Pro Gly Lys Leu Glu
                485                 490                 495

Gln Val Gln Leu Val Glu Ser Gly Gly Gly Leu Met Gln Pro Gly Gly
            500                 505                 510

Ser Leu Arg Leu Ser Cys Ala Ala Ser Gly Phe Thr Phe Ser Ser Ser
        515                 520                 525

Ala Met Ser Trp Val Arg Gln Ala Pro Gly Lys Gly Leu Glu Trp Val
    530                 535                 540

Ser Ser Ile Tyr Ser Asp Ser Ser Tyr Thr Tyr Tyr Ala Asp Ser Val
545                 550                 555                 560

Lys Ser Arg Phe Thr Ile Ser Thr Asp Asn Ala Lys Asn Thr Leu Tyr
                565                 570                 575

Leu Gln Met Asn Ser Leu Lys Pro Asp Asp Thr Ala Val Tyr Tyr Cys
            580                 585                 590

Ala Gly Ser Ser Asp Tyr Glu Gly Ser Phe Ala Ser Trp Gly Gln Gly
```

```
        595                 600                 605

Thr Gln Val Thr Val Ser Ser Arg Ser Ser Thr Lys Gly Pro Lys Leu
    610                 615                 620

Glu Glu Gly Glu Phe Ser Glu Ala Gln Leu Gln Ser Val Val Thr Gln
625                 630                 635                 640

Pro Pro Ser Leu Ser Ala Ser Pro Gly Ser Ser Val Arg Leu Thr Cys
                645                 650                 655

Thr Leu Ser Ser Gly Asn Ser Val Gly Asn Tyr Asp Ile Ser Trp Tyr
            660                 665                 670

Gln Gln Lys Ala Gly Ser Pro Pro Arg Tyr Leu Leu Tyr Tyr Tyr Ser
        675                 680                 685

Asp Ser Val Lys His Gln Gly Ser Gly Val Pro Ser Arg Phe Ser Gly
    690                 695                 700

Ser Ser Asp Ala Ser Ala Asn Ala Gly Leu Leu Leu Ile Ser Gly Leu
705                 710                 715                 720

Gln Pro Glu Asp Glu Ala Asp Tyr Tyr Cys Ser Ala Tyr Lys Ser Gly
                725                 730                 735

Ser His Val Phe Gly Gly Gly Thr Lys Leu Thr Val Leu Gly
            740                 745                 750


<210> SEQ ID NO 158
<211> LENGTH: 255
<212> TYPE: PRT
<213> ORGANISM: Artificial Sequence
<220> FEATURE:
<223> OTHER INFORMATION: Protein construct expressed from SEQ ID NO: 147

<400> SEQUENCE: 158

Met Asn Phe Gly Phe Ser Leu Ile Phe Leu Val Leu Val Leu Lys Gly
1               5                   10                  15

Val Gln Cys Glu Val Lys Leu Val Pro Arg Gln Leu Asp Tyr Lys Asp
            20                  25                  30

Asp Asp Asp Lys Glu Leu Glu Ile Val Leu Thr Gln Ser Pro Gly Thr
        35                  40                  45

Leu Ser Leu Ser Pro Gly Glu Arg Ala Thr Leu Ser Cys Arg Ala Ser
    50                  55                  60

Gln Gly Ile Ser Arg Ser Tyr Leu Ala Trp Tyr Gln Gln Lys Pro Gly
65                  70                  75                  80

Gln Ala Pro Ser Leu Leu Ile Tyr Gly Ala Ser Ser Arg Ala Thr Gly
                85                  90                  95

Ile Pro Asp Arg Phe Ser Gly Ser Gly Ser Gly Thr Asp Phe Thr Leu
            100                 105                 110

Thr Ile Ser Arg Leu Glu Pro Glu Asp Phe Ala Val Tyr Tyr Cys Gln
        115                 120                 125

Gln Phe Gly Ser Ser Pro Trp Thr Phe Gly Gln Gly Thr Lys Val Gly
    130                 135                 140

Ser Glu Ile Lys Arg Thr Val Ala Ala Pro Ser Val Phe Ile Phe Pro
145                 150                 155                 160

Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205

Ser Lys Asp Ser Thr Tyr Ser Leu Ser Ser Thr Leu Thr Leu Ser Lys
```

```
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255


<210> SEQ ID NO 159
<211> LENGTH: 741
<212> TYPE: PRT
<213> ORGANISM: Artificial Sequence
<220> FEATURE:
<223> OTHER INFORMATION: Protein construct expressed from SEQ ID NO: 148

<400> SEQUENCE: 159

Met Asn Phe Gly Phe Ser Leu Ile Phe Leu Val Leu Val Leu Lys Gly
1               5                   10                  15

Val Gln Cys Glu Val Lys Leu Val Pro Arg Gln Leu Asp Tyr Lys Asp
            20                  25                  30

Asp Asp Asp Lys Glu Phe Gln Val Gln Leu Val Gln Ser Gly Ala Glu
        35                  40                  45

Val Lys Lys Pro Gly Ala Ser Val Lys Val Ser Cys Thr Ala Ser Gly
    50                  55                  60

Phe Asn Ile Lys Asp Tyr Tyr Val His Trp Val Lys Gln Ala Pro Gly
65                  70                  75                  80

Gln Gly Leu Glu Trp Met Gly Arg Ile Asp Pro Glu Asp Gly Asp Ser
                85                  90                  95

Lys Tyr Ala Pro Lys Phe Gln Gly Lys Ala Thr Met Thr Ala Asp Thr
            100                 105                 110

Ser Thr Ser Thr Val Tyr Met Glu Leu Ser Ser Leu Arg Ser Glu Asp
        115                 120                 125

Thr Ala Val Tyr Tyr Cys Thr Thr Ser Tyr Tyr Val Gly Thr Tyr Gly
    130                 135                 140

Tyr Trp Gly Gln Gly Thr Leu Val Thr Val Ser Ser Arg Ser Ser Ser
145                 150                 155                 160

Ala Ser Thr Lys Gly Pro Ser Val Phe Pro Leu Ala Pro Ser Ser Lys
                165                 170                 175

Ser Thr Ser Gly Gly Thr Ala Ala Leu Gly Cys Leu Val Lys Asp Tyr
            180                 185                 190

Phe Pro Glu Pro Val Thr Val Ser Trp Asn Ser Gly Ala Leu Thr Ser
        195                 200                 205

Gly Val His Thr Phe Pro Ala Val Leu Gln Ser Ser Gly Leu Tyr Ser
    210                 215                 220

Leu Ser Ser Val Val Thr Val Pro Ser Ser Ser Leu Gly Thr Gln Thr
225                 230                 235                 240

Tyr Ile Cys Asn Val Asn His Lys Pro Ser Asn Thr Lys Val Asp Lys
                245                 250                 255

Lys Val Glu Pro Lys Ser Cys Asp Lys Thr His Thr Cys Pro Pro Cys
            260                 265                 270

Pro Ala Pro Glu Leu Leu Gly Gly Pro Ser Val Phe Leu Phe Pro Pro
        275                 280                 285

Lys Pro Lys Asp Thr Leu Met Ile Ser Arg Thr Pro Glu Val Thr Cys
    290                 295                 300

Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
```

```
                325                 330                 335

Glu Gln Tyr Ala Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
        355                 360                 365

Lys Ala Leu Pro Ala Pro Ile Glu Lys Thr Ile Ser Lys Ala Lys Gly
    370                 375                 380

Gln Pro Arg Glu Pro Gln Val Tyr Thr Leu Pro Pro Ser Arg Asp Glu
385                 390                 395                 400

Leu Thr Lys Asn Gln Val Ser Leu Thr Cys Leu Val Lys Gly Phe Tyr
                405                 410                 415

Pro Ser Asp Ile Ala Val Glu Trp Glu Ser Asn Gly Gln Pro Glu Asn
            420                 425                 430

Asn Tyr Lys Thr Thr Pro Pro Val Leu Asp Ser Asp Gly Ser Phe Phe
        435                 440                 445

Leu Tyr Ser Lys Leu Thr Val Asp Lys Ser Arg Trp Gln Gln Gly Asn
    450                 455                 460

Val Phe Ser Cys Ser Val Met His Glu Ala Leu His Asn His Tyr Thr
465                 470                 475                 480

Gln Lys Ser Leu Ser Leu Ser Pro Gly Lys Leu Glu Glu Val Gln Leu
                485                 490                 495

Leu Glu Ser Gly Gly Gly Leu Val Gln Pro Gly Gly Ser Leu Arg Leu
            500                 505                 510

Ser Cys Ala Ala Ser Gly Phe Thr Phe Ser Ser Tyr Ile Met Met Trp
        515                 520                 525

Val Arg Gln Ala Pro Gly Lys Gly Leu Glu Trp Val Ser Ser Ile Tyr
    530                 535                 540

Pro Ser Gly Gly Ile Thr Phe Tyr Ala Asp Thr Val Lys Gly Arg Phe
545                 550                 555                 560

Thr Ile Ser Arg Asp Asn Ser Lys Asn Thr Leu Tyr Leu Gln Met Asn
                565                 570                 575

Ser Leu Arg Ala Glu Asp Thr Ala Val Tyr Tyr Cys Ala Arg Ile Lys
            580                 585                 590

Leu Gly Thr Val Thr Thr Val Asp Tyr Trp Gly Gln Gly Thr Leu Val
        595                 600                 605

Thr Val Ser Ser Arg Ser Ser Thr Lys Gly Pro Lys Leu Glu Glu Gly
    610                 615                 620

Glu Phe Ser Glu Ala Gln Leu Gln Ser Ala Leu Thr Gln Pro Ala Ser
625                 630                 635                 640

Val Ser Gly Ser Pro Gly Gln Ser Ile Thr Ile Ser Cys Thr Gly Thr
                645                 650                 655

Ser Ser Asp Val Gly Gly Tyr Asn Tyr Val Ser Trp Tyr Gln Gln His
            660                 665                 670

Pro Gly Lys Ala Pro Lys Leu Met Ile Tyr Asp Val Ser Asn Arg Pro
        675                 680                 685

Ser Gly Val Ser Asn Arg Phe Ser Gly Ser Lys Ser Gly Asn Thr Ala
    690                 695                 700

Ser Leu Thr Ile Ser Gly Leu Gln Ala Glu Asp Glu Ala Asp Tyr Tyr
705                 710                 715                 720

Cys Ser Ser Tyr Thr Ser Ser Ser Thr Arg Val Phe Gly Thr Gly Thr
                725                 730                 735

Lys Val Thr Val Leu
            740
```

<210> SEQ ID NO 160
<211> LENGTH: 256
<212> TYPE: PRT
<213> ORGANISM: Artificial Sequence
<220> FEATURE:
<223> OTHER INFORMATION: Protein construct expressed from SEQ ID NO: 149

<400> SEQUENCE: 160

```
Met Asn Phe Gly Phe Ser Leu Ile Phe Leu Val Leu Val Leu Lys Gly
1               5                   10                  15

Val Gln Cys Glu Val Lys Leu Val Pro Arg Gln Leu Asp Tyr Lys Asp
            20                  25                  30

Asp Asp Asp Lys Glu Leu Asp Ile Gln Met Thr Gln Ser Pro Ser Ser
        35                  40                  45

Leu Ser Ala Ser Val Gly Asp Arg Val Thr Ile Thr Cys Ser Ala Ser
    50                  55                  60

Ser Ser Val Ser Tyr Met Leu Trp Phe Gln Gln Lys Pro Gly Lys Ala
65                  70                  75                  80

Pro Lys Leu Leu Ile Tyr Ser Thr Ser Asn Leu Ala Ser Gly Val Pro
                85                  90                  95

Ser Arg Phe Ser Gly Ser Gly Ser Gly Thr Asp Phe Thr Leu Thr Ile
            100                 105                 110

Ser Ser Leu Gln Pro Glu Asp Phe Ala Thr Tyr Tyr Cys Gln Gln Arg
        115                 120                 125

Thr Phe Tyr Pro Tyr Thr Phe Gly Gly Gly Thr Lys Val Glu Ile Lys
    130                 135                 140

Gly Ser Glu Ile Lys Arg Thr Val Ala Ala Pro Ser Val Phe Ile Phe
145                 150                 155                 160

Pro Pro Ser Asp Glu Gln Leu Lys Ser Gly Thr Ala Ser Val Val Cys
                165                 170                 175

Leu Leu Asn Asn Phe Tyr Pro Arg Glu Ala Lys Val Gln Trp Lys Val
            180                 185                 190

Asp Asn Ala Leu Gln Ser Gly Asn Ser Gln Glu Ser Val Thr Glu Gln
        195                 200                 205

Asp Ser Lys Asp Ser Thr Tyr Ser Leu Ser Ser Thr Leu Thr Leu Ser
    210                 215                 220

Lys Ala Asp Tyr Glu Lys His Lys Val Tyr Ala Cys Glu Val Thr His
225                 230                 235                 240

Gln Gly Leu Ser Ser Pro Val Thr Lys Ser Phe Asn Arg Gly Glu Cys
                245                 250                 255
```

<210> SEQ ID NO 161
<211> LENGTH: 525
<212> TYPE: PRT
<213> ORGANISM: Artificial Sequence
<220> FEATURE:
<223> OTHER INFORMATION: Protein construct expressed from SEQ ID NO: 150

<400> SEQUENCE: 161

```
Met Asn Phe Gly Phe Ser Leu Ile Phe Leu Val Leu Val Leu Lys Gly
1               5                   10                  15

Val Gln Cys Glu Val Lys Leu Val Pro Arg Gln Leu Asp Tyr Lys Asp
            20                  25                  30

Asp Asp Asp Lys Glu Phe Gln Val Gln Leu Val Gln Ser Gly Ala Glu
        35                  40                  45

Val Lys Lys Pro Gly Ala Ser Val Lys Val Ser Cys Thr Ala Ser Gly
```

-continued

```
    50                  55                  60

Phe Asn Ile Lys Asp Tyr Tyr Val His Trp Val Lys Gln Ala Pro Gly
65                  70                  75                  80

Gln Gly Leu Glu Trp Met Gly Arg Ile Asp Pro Glu Asp Gly Asp Ser
                85                  90                  95

Lys Tyr Ala Pro Lys Phe Gln Gly Lys Ala Thr Met Thr Ala Asp Thr
            100                 105                 110

Ser Thr Ser Thr Val Tyr Met Glu Leu Ser Ser Leu Arg Ser Glu Asp
        115                 120                 125

Thr Ala Val Tyr Tyr Cys Thr Thr Ser Tyr Tyr Val Gly Thr Tyr Gly
    130                 135                 140

Tyr Trp Gly Gln Gly Thr Leu Val Thr Val Ser Ser Arg Ser Ser Ser
145                 150                 155                 160

Ala Ser Thr Lys Gly Pro Ser Val Phe Pro Leu Ala Pro Ser Ser Lys
                165                 170                 175

Ser Thr Ser Gly Gly Thr Ala Ala Leu Gly Cys Leu Val Lys Asp Tyr
            180                 185                 190

Phe Pro Glu Pro Val Thr Val Ser Trp Asn Ser Gly Ala Leu Thr Ser
        195                 200                 205

Gly Val His Thr Phe Pro Ala Val Leu Gln Ser Ser Gly Leu Tyr Ser
    210                 215                 220

Leu Ser Ser Val Val Thr Val Pro Ser Ser Ser Leu Gly Thr Gln Thr
225                 230                 235                 240

Tyr Ile Cys Asn Val Asn His Lys Pro Ser Asn Thr Lys Val Asp Lys
                245                 250                 255

Lys Val Glu Pro Lys Ser Cys Asp Lys Thr His Thr Cys Pro Pro Cys
            260                 265                 270

Pro Ala Leu Glu Glu Val Gln Leu Leu Glu Ser Gly Gly Gly Leu Val
        275                 280                 285

Gln Pro Gly Gly Ser Leu Arg Leu Ser Cys Ala Ala Ser Gly Phe Thr
    290                 295                 300

Phe Ser Ser Tyr Ile Met Met Trp Val Arg Gln Ala Pro Gly Lys Gly
305                 310                 315                 320

Leu Glu Trp Val Ser Ser Ile Tyr Pro Ser Gly Gly Ile Thr Phe Tyr
                325                 330                 335

Ala Asp Thr Val Lys Gly Arg Phe Thr Ile Ser Arg Asp Asn Ser Lys
            340                 345                 350

Asn Thr Leu Tyr Leu Gln Met Asn Ser Leu Arg Ala Glu Asp Thr Ala
        355                 360                 365

Val Tyr Tyr Cys Ala Arg Ile Lys Leu Gly Thr Val Thr Thr Val Asp
    370                 375                 380

Tyr Trp Gly Gln Gly Thr Leu Val Thr Val Ser Ser Arg Ser Ser Thr
385                 390                 395                 400

Lys Gly Pro Lys Leu Glu Glu Gly Glu Phe Ser Glu Ala Gln Leu Gln
                405                 410                 415

Ser Ala Leu Thr Gln Pro Ala Ser Val Ser Gly Ser Pro Gly Gln Ser
            420                 425                 430

Ile Thr Ile Ser Cys Thr Gly Thr Ser Ser Asp Val Gly Gly Tyr Asn
        435                 440                 445

Tyr Val Ser Trp Tyr Gln Gln His Pro Gly Lys Ala Pro Lys Leu Met
    450                 455                 460

Ile Tyr Asp Val Ser Asn Arg Pro Ser Gly Val Ser Asn Arg Phe Ser
465                 470                 475                 480
```

```
Gly Ser Lys Ser Gly Asn Thr Ala Ser Leu Thr Ile Ser Gly Leu Gln
                485                 490                 495

Ala Glu Asp Glu Ala Asp Tyr Tyr Cys Ser Ser Tyr Thr Ser Ser Ser
            500                 505                 510

Thr Arg Val Phe Gly Thr Gly Thr Lys Val Thr Val Leu
        515                 520                 525


<210> SEQ ID NO 162
<211> LENGTH: 742
<212> TYPE: PRT
<213> ORGANISM: Artificial Sequence
<220> FEATURE:
<223> OTHER INFORMATION: Protein construct expressed from SEQ ID NO: 151

<400> SEQUENCE: 162

Met Asn Phe Gly Phe Ser Leu Ile Phe Leu Val Leu Val Leu Lys Gly
1               5                   10                  15

Val Gln Cys Glu Val Lys Leu Val Pro Arg Gln Leu Asp Tyr Lys Asp
            20                  25                  30

Asp Asp Asp Lys Glu Phe Gln Val Gln Leu Gln Gln Ser Gly Ala Glu
        35                  40                  45

Val Ile Lys Pro Gly Ala Ser Val Lys Leu Ser Cys Lys Ala Ser Gly
    50                  55                  60

Tyr Thr Phe Ser Ser Tyr Trp Met His Trp Val Arg Gln Ala Pro Gly
65                  70                  75                  80

Gln Gly Leu Glu Trp Ile Gly Glu Ile Asn Pro Gly Asn Gly His Thr
                85                  90                  95

Asn Tyr Asn Glu Lys Phe Lys Ser Arg Ala Thr Leu Thr Gly Asp Thr
            100                 105                 110

Ser Thr Ser Thr Val Tyr Met Glu Leu Ser Ser Leu Arg Ser Glu Asp
        115                 120                 125

Thr Ala Val Tyr Tyr Cys Ala Arg Ser Phe Thr Thr Ala Arg Ala Phe
    130                 135                 140

Ala Tyr Trp Gly Gln Gly Thr Leu Val Thr Val Ser Ser Arg Ser Ser
145                 150                 155                 160

Ser Ala Ser Thr Lys Gly Pro Ser Val Phe Pro Leu Ala Pro Ser Ser
                165                 170                 175

Lys Ser Thr Ser Gly Gly Thr Ala Ala Leu Gly Cys Leu Val Lys Asp
            180                 185                 190

Tyr Phe Pro Glu Pro Val Thr Val Ser Trp Asn Ser Gly Ala Leu Thr
        195                 200                 205

Ser Gly Val His Thr Phe Pro Ala Val Leu Gln Ser Ser Gly Leu Tyr
    210                 215                 220

Ser Leu Ser Ser Val Val Thr Val Pro Ser Ser Ser Leu Gly Thr Gln
225                 230                 235                 240

Thr Tyr Ile Cys Asn Val Asn His Lys Pro Ser Asn Thr Lys Val Asp
                245                 250                 255

Lys Lys Val Glu Pro Lys Ser Cys Asp Lys Thr His Thr Cys Pro Pro
            260                 265                 270

Cys Pro Ala Pro Glu Leu Leu Gly Gly Pro Ser Val Phe Leu Phe Pro
        275                 280                 285

Pro Lys Pro Lys Asp Thr Leu Met Ile Ser Arg Thr Pro Glu Val Thr
    290                 295                 300

Cys Val Val Val Asp Val Ser His Glu Asp Pro Glu Val Lys Phe Asn
305                 310                 315                 320
```

```
Trp Tyr Val Asp Gly Val Glu Val His Asn Ala Lys Thr Lys Pro Arg
                325                 330                 335

Glu Glu Gln Tyr Ala Ser Thr Tyr Arg Val Val Ser Val Leu Thr Val
            340                 345                 350

Leu His Gln Asp Trp Leu Asn Gly Lys Glu Tyr Lys Cys Lys Val Ser
        355                 360                 365

Asn Lys Ala Leu Pro Ala Pro Ile Glu Lys Thr Ile Ser Lys Ala Lys
    370                 375                 380

Gly Gln Pro Arg Glu Pro Gln Val Tyr Thr Leu Pro Pro Ser Arg Asp
385                 390                 395                 400

Glu Leu Thr Lys Asn Gln Val Ser Leu Thr Cys Leu Val Lys Gly Phe
                405                 410                 415

Tyr Pro Ser Asp Ile Ala Val Glu Trp Glu Ser Asn Gly Gln Pro Glu
            420                 425                 430

Asn Asn Tyr Lys Thr Thr Pro Pro Val Leu Asp Ser Asp Gly Ser Phe
        435                 440                 445

Phe Leu Tyr Ser Lys Leu Thr Val Asp Lys Ser Arg Trp Gln Gln Gly
    450                 455                 460

Asn Val Phe Ser Cys Ser Val Met His Glu Ala Leu His Asn His Tyr
465                 470                 475                 480

Thr Gln Lys Ser Leu Ser Leu Ser Pro Gly Lys Leu Glu Glu Val Gln
                485                 490                 495

Leu Leu Glu Ser Gly Gly Gly Leu Val Gln Pro Gly Gly Ser Leu Arg
            500                 505                 510

Leu Ser Cys Ala Ala Ser Gly Phe Thr Phe Ser Ser Tyr Ile Met Met
        515                 520                 525

Trp Val Arg Gln Ala Pro Gly Lys Gly Leu Glu Trp Val Ser Ser Ile
    530                 535                 540

Tyr Pro Ser Gly Gly Ile Thr Phe Tyr Ala Asp Thr Val Lys Gly Arg
545                 550                 555                 560

Phe Thr Ile Ser Arg Asp Asn Ser Lys Asn Thr Leu Tyr Leu Gln Met
                565                 570                 575

Asn Ser Leu Arg Ala Glu Asp Thr Ala Val Tyr Tyr Cys Ala Arg Ile
            580                 585                 590

Lys Leu Gly Thr Val Thr Thr Val Asp Tyr Trp Gly Gln Gly Thr Leu
        595                 600                 605

Val Thr Val Ser Ser Arg Ser Ser Thr Lys Gly Pro Lys Leu Glu Glu
    610                 615                 620

Gly Glu Phe Ser Glu Ala Gln Leu Gln Ser Ala Leu Thr Gln Pro Ala
625                 630                 635                 640

Ser Val Ser Gly Ser Pro Gly Gln Ser Ile Thr Ile Ser Cys Thr Gly
                645                 650                 655

Thr Ser Ser Asp Val Gly Gly Tyr Asn Tyr Val Ser Trp Tyr Gln Gln
            660                 665                 670

His Pro Gly Lys Ala Pro Lys Leu Met Ile Tyr Asp Val Ser Asn Arg
        675                 680                 685

Pro Ser Gly Val Ser Asn Arg Phe Ser Gly Ser Lys Ser Gly Asn Thr
    690                 695                 700

Ala Ser Leu Thr Ile Ser Gly Leu Gln Ala Glu Asp Glu Ala Asp Tyr
705                 710                 715                 720

Tyr Cys Ser Ser Tyr Thr Ser Ser Ser Thr Arg Val Phe Gly Thr Gly
                725                 730                 735
```

```
Thr Lys Val Thr Val Leu
            740


<210> SEQ ID NO 163
<211> LENGTH: 526
<212> TYPE: PRT
<213> ORGANISM: Artificial Sequence
<220> FEATURE:
<223> OTHER INFORMATION: Protein construct expressed from SEQ ID NO: 152

<400> SEQUENCE: 163

Met Asn Phe Gly Phe Ser Leu Ile Phe Leu Val Leu Val Leu Lys Gly
1               5                   10                  15

Val Gln Cys Glu Val Lys Leu Val Pro Arg Gln Leu Asp Tyr Lys Asp
            20                  25                  30

Asp Asp Asp Lys Glu Phe Gln Val Gln Leu Gln Gln Ser Gly Ala Glu
        35                  40                  45

Val Ile Lys Pro Gly Ala Ser Val Lys Leu Ser Cys Lys Ala Ser Gly
    50                  55                  60

Tyr Thr Phe Ser Ser Tyr Trp Met His Trp Val Arg Gln Ala Pro Gly
65                  70                  75                  80

Gln Gly Leu Glu Trp Ile Gly Glu Ile Asn Pro Gly Asn Gly His Thr
                85                  90                  95

Asn Tyr Asn Glu Lys Phe Lys Ser Arg Ala Thr Leu Thr Gly Asp Thr
            100                 105                 110

Ser Thr Ser Thr Val Tyr Met Glu Leu Ser Ser Leu Arg Ser Glu Asp
        115                 120                 125

Thr Ala Val Tyr Tyr Cys Ala Arg Ser Phe Thr Thr Ala Arg Ala Phe
    130                 135                 140

Ala Tyr Trp Gly Gln Gly Thr Leu Val Thr Val Ser Ser Arg Ser Ser
145                 150                 155                 160

Ser Ala Ser Thr Lys Gly Pro Ser Val Phe Pro Leu Ala Pro Ser Ser
                165                 170                 175

Lys Ser Thr Ser Gly Gly Thr Ala Ala Leu Gly Cys Leu Val Lys Asp
            180                 185                 190

Tyr Phe Pro Glu Pro Val Thr Val Ser Trp Asn Ser Gly Ala Leu Thr
        195                 200                 205

Ser Gly Val His Thr Phe Pro Ala Val Leu Gln Ser Ser Gly Leu Tyr
    210                 215                 220

Ser Leu Ser Ser Val Val Thr Val Pro Ser Ser Ser Leu Gly Thr Gln
225                 230                 235                 240

Thr Tyr Ile Cys Asn Val Asn His Lys Pro Ser Asn Thr Lys Val Asp
                245                 250                 255

Lys Lys Val Glu Pro Lys Ser Cys Asp Lys Thr His Thr Cys Pro Pro
            260                 265                 270

Cys Pro Ala Leu Glu Glu Val Gln Leu Leu Glu Ser Gly Gly Gly Leu
        275                 280                 285

Val Gln Pro Gly Gly Ser Leu Arg Leu Ser Cys Ala Ala Ser Gly Phe
    290                 295                 300

Thr Phe Ser Ser Tyr Ile Met Met Trp Val Arg Gln Ala Pro Gly Lys
305                 310                 315                 320

Gly Leu Glu Trp Val Ser Ser Ile Tyr Pro Ser Gly Gly Ile Thr Phe
                325                 330                 335

Tyr Ala Asp Thr Val Lys Gly Arg Phe Thr Ile Ser Arg Asp Asn Ser
            340                 345                 350
```

```
Lys Asn Thr Leu Tyr Leu Gln Met Asn Ser Leu Arg Ala Glu Asp Thr
        355                 360                 365

Ala Val Tyr Tyr Cys Ala Arg Ile Lys Leu Gly Thr Val Thr Thr Val
    370                 375                 380

Asp Tyr Trp Gly Gln Gly Thr Leu Val Thr Val Ser Ser Arg Ser Ser
385                 390                 395                 400

Thr Lys Gly Pro Lys Leu Glu Glu Gly Glu Phe Ser Glu Ala Gln Leu
                405                 410                 415

Gln Ser Ala Leu Thr Gln Pro Ala Ser Val Ser Gly Ser Pro Gly Gln
            420                 425                 430

Ser Ile Thr Ile Ser Cys Thr Gly Thr Ser Ser Asp Val Gly Gly Tyr
        435                 440                 445

Asn Tyr Val Ser Trp Tyr Gln Gln His Pro Gly Lys Ala Pro Lys Leu
    450                 455                 460

Met Ile Tyr Asp Val Ser Asn Arg Pro Ser Gly Val Ser Asn Arg Phe
465                 470                 475                 480

Ser Gly Ser Lys Ser Gly Asn Thr Ala Ser Leu Thr Ile Ser Gly Leu
                485                 490                 495

Gln Ala Glu Asp Glu Ala Asp Tyr Tyr Cys Ser Ser Tyr Thr Ser Ser
            500                 505                 510

Ser Thr Arg Val Phe Gly Thr Gly Thr Lys Val Thr Val Leu
        515                 520                 525


<210> SEQ ID NO 164
<211> LENGTH: 735
<212> TYPE: PRT
<213> ORGANISM: Artificial Sequence
<220> FEATURE:
<223> OTHER INFORMATION: Protein construct expressed from SEQ ID NO: 153

<400> SEQUENCE: 164

Met Asn Phe Gly Phe Ser Leu Ile Phe Leu Val Leu Val Leu Lys Gly
1               5                   10                  15

Val Gln Cys Glu Val Lys Leu Val Pro Arg Gln Leu Asp Tyr Lys Asp
            20                  25                  30

Asp Asp Asp Lys Glu Phe Glu Val Gln Leu Leu Glu Ser Gly Gly Gly
        35                  40                  45

Leu Val Gln Pro Gly Gly Ser Leu Arg Leu Ser Cys Ala Ala Ser Gly
    50                  55                  60

Phe Thr Phe Ser Ser Tyr Ile Met Met Trp Val Arg Gln Ala Pro Gly
65                  70                  75                  80

Lys Gly Leu Glu Trp Val Ser Ser Ile Tyr Pro Ser Gly Gly Ile Thr
                85                  90                  95

Phe Tyr Ala Asp Thr Val Lys Gly Arg Phe Thr Ile Ser Arg Asp Asn
            100                 105                 110

Ser Lys Asn Thr Leu Tyr Leu Gln Met Asn Ser Leu Arg Ala Glu Asp
        115                 120                 125

Thr Ala Val Tyr Tyr Cys Ala Arg Ile Lys Leu Gly Thr Val Thr Thr
    130                 135                 140

Val Asp Tyr Trp Gly Gln Gly Thr Leu Val Thr Val Ser Ser Arg Ser
145                 150                 155                 160

Ser Ser Ala Ser Thr Lys Gly Pro Ser Val Phe Pro Leu Ala Pro Cys
                165                 170                 175

Ser Arg Ser Thr Ser Glu Ser Thr Ala Ala Leu Gly Cys Leu Val Lys
            180                 185                 190
```

```
Asp Tyr Phe Pro Glu Pro Val Thr Val Ser Trp Asn Ser Gly Ala Leu
        195                 200                 205

Thr Ser Gly Val His Thr Phe Pro Ala Val Leu Gln Ser Ser Gly Leu
    210                 215                 220

Tyr Ser Leu Ser Ser Val Val Thr Val Pro Ser Ser Asn Phe Gly Thr
225                 230                 235                 240

Gln Thr Tyr Thr Cys Asn Val Asp His Lys Pro Ser Asn Thr Lys Val
                245                 250                 255

Asp Lys Thr Val Glu Arg Lys Cys Cys Val Glu Cys Pro Pro Cys Pro
            260                 265                 270

Ala Pro Pro Val Ala Gly Pro Ser Val Phe Leu Phe Pro Pro Lys Pro
        275                 280                 285

Lys Asp Thr Leu Met Ile Ser Arg Thr Pro Glu Val Thr Cys Val Val
    290                 295                 300

Val Asp Val Ser His Glu Asp Pro Glu Val Gln Phe Asn Trp Tyr Val
305                 310                 315                 320

Asp Gly Val Glu Val His Asn Ala Lys Thr Lys Pro Arg Glu Glu Gln
                325                 330                 335

Phe Asn Ser Thr Phe Arg Val Val Ser Val Leu Thr Val Val His Gln
            340                 345                 350

Asp Trp Leu Asn Gly Lys Glu Tyr Lys Cys Lys Val Ser Asn Lys Gly
        355                 360                 365

Leu Pro Ala Pro Ile Glu Lys Thr Ile Ser Lys Thr Lys Gly Gln Pro
    370                 375                 380

Arg Glu Pro Gln Val Tyr Thr Leu Pro Pro Ser Arg Glu Glu Met Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Met Leu Asp Ser Asp Gly Ser Phe Phe Leu Tyr
        435                 440                 445

Ser Lys Leu Thr Val Asp Lys Ser Arg Trp Gln Gln Gly Asn Val Phe
    450                 455                 460

Ser Cys Ser Val Met His Glu Ala Leu His Asn His Tyr Thr Gln Lys
465                 470                 475                 480

Ser Leu Ser Leu Ser Pro Gly Lys Glu Phe Gln Val Gln Leu Gln Gln
                485                 490                 495

Ser Gly Ala Glu Val Ile Lys Pro Gly Ala Ser Val Lys Leu Ser Cys
            500                 505                 510

Lys Ala Ser Gly Tyr Thr Phe Ser Ser Tyr Trp Met His Trp Val Arg
        515                 520                 525

Gln Ala Pro Gly Gln Gly Leu Glu Trp Ile Gly Glu Ile Asn Pro Gly
    530                 535                 540

Asn Gly His Thr Asn Tyr Asn Glu Lys Phe Lys Ser Arg Ala Thr Leu
545                 550                 555                 560

Thr Gly Asp Thr Ser Thr Ser Thr Val Tyr Met Glu Leu Ser Ser Leu
                565                 570                 575

Arg Ser Glu Asp Thr Ala Val Tyr Tyr Cys Ala Arg Ser Phe Thr Thr
            580                 585                 590

Ala Arg Ala Phe Ala Tyr Trp Gly Gln Gly Thr Leu Val Thr Val Ser
        595                 600                 605

Ser Arg Ser Ser Thr Lys Gly Pro Lys Leu Glu Glu Gly Glu Phe Ser
```

```
    610                 615                 620

Glu Ala Gln Leu Asp Ile Val Met Thr Gln Ser Pro Ala Phe Leu Ser
625                 630                 635                 640

Val Thr Pro Gly Glu Lys Val Thr Ile Thr Cys Arg Ala Ser Gln Thr
                645                 650                 655

Ile Ser Asp Tyr Leu His Trp Tyr Gln Gln Lys Pro Asp Gln Ala Pro
            660                 665                 670

Lys Leu Leu Ile Lys Tyr Ala Ser Gln Ser Ile Ser Gly Ile Pro Ser
        675                 680                 685

Arg Phe Ser Gly Ser Gly Ser Gly Thr Asp Phe Thr Phe Thr Ile Ser
    690                 695                 700

Ser Leu Glu Ala Glu Asp Ala Ala Thr Tyr Tyr Cys Gln Asp Gly His
705                 710                 715                 720

Ser Phe Pro Pro Thr Phe Gly Gln Gly Thr Lys Leu Glu Ile Lys
                725                 730                 735


<210> SEQ ID NO 165
<211> LENGTH: 260
<212> TYPE: PRT
<213> ORGANISM: Artificial Sequence
<220> FEATURE:
<223> OTHER INFORMATION: Protein construct expressed from SEQ ID NO: 154

<400> SEQUENCE: 165

Met Asn Phe Gly Phe Ser Leu Ile Phe Leu Val Leu Val Leu Lys Gly
1               5                   10                  15

Val Gln Cys Glu Val Lys Leu Val Pro Arg Gln Leu Asp Tyr Lys Asp
            20                  25                  30

Asp Asp Asp Lys Glu Leu Gln Ser Ala Leu Thr Gln Pro Ala Ser Val
        35                  40                  45

Ser Gly Ser Pro Gly Gln Ser Ile Thr Ile Ser Cys Thr Gly Thr Ser
    50                  55                  60

Ser Asp Val Gly Gly Tyr Asn Tyr Val Ser Trp Tyr Gln Gln His Pro
65                  70                  75                  80

Gly Lys Ala Pro Lys Leu Met Ile Tyr Asp Val Ser Asn Arg Pro Ser
                85                  90                  95

Gly Val Ser Asn Arg Phe Ser Gly Ser Lys Ser Gly Asn Thr Ala Ser
            100                 105                 110

Leu Thr Ile Ser Gly Leu Gln Ala Glu Asp Glu Ala Asp Tyr Tyr Cys
        115                 120                 125

Ser Ser Tyr Thr Ser Ser Ser Thr Arg Val Phe Gly Thr Gly Thr Lys
    130                 135                 140

Val Thr Val Leu Gly Ser Glu Ile Lys Arg Thr Val Ala Ala Pro Ser
145                 150                 155                 160

Val Phe Ile Phe Pro Pro Ser Asp Glu Gln Leu Lys Ser Gly Thr Ala
                165                 170                 175

Ser Val Val Cys Leu Leu Asn Asn Phe Tyr Pro Arg Glu Ala Lys Val
            180                 185                 190

Gln Trp Lys Val Asp Asn Ala Leu Gln Ser Gly Asn Ser Gln Glu Ser
        195                 200                 205

Val Thr Glu Gln Asp Ser Lys Asp Ser Thr Tyr Ser Leu Ser Ser Thr
    210                 215                 220

Leu Thr Leu Ser Lys Ala Asp Tyr Glu Lys His Lys Val Tyr Ala Cys
225                 230                 235                 240

Glu Val Thr His Gln Gly Leu Ser Ser Pro Val Thr Lys Ser Phe Asn
```

```
                245                 250                 255

Arg Gly Glu Cys
            260


<210> SEQ ID NO 166
<211> LENGTH: 740
<212> TYPE: PRT
<213> ORGANISM: Artificial Sequence
<220> FEATURE:
<223> OTHER INFORMATION: Protein construct expressed from SEQ ID NO: 155

<400> SEQUENCE: 166

Met Asn Phe Gly Phe Ser Leu Ile Phe Leu Val Leu Val Leu Lys Gly
1               5                   10                  15

Val Gln Cys Glu Val Lys Leu Val Pro Arg Gln Leu Asp Tyr Lys Asp
            20                  25                  30

Asp Asp Asp Lys Glu Phe Gln Val Gln Leu Gln Gln Ser Gly Ala Glu
        35                  40                  45

Leu Val Lys Pro Gly Ser Ser Val Lys Ile Ser Cys Lys Ala Ser Gly
    50                  55                  60

Tyr Thr Phe Thr Ser Tyr Asp Met His Trp Ile Lys Gln Gln Pro Gly
65                  70                  75                  80

Lys Gly Leu Glu Trp Ile Gly Trp Ile Tyr Pro Gly Asn Gly Asn Thr
                85                  90                  95

Lys Tyr Asn Gln Lys Phe Asn Gly Lys Ala Thr Leu Thr Ala Asp Ile
            100                 105                 110

Ser Ser Ser Thr Ala Tyr Met Gln Leu Ser Ser Leu Thr Ser Glu Asp
        115                 120                 125

Ser Ala Val Tyr Phe Cys Ala Lys Trp Gly Tyr Asn Asn Phe Asp Tyr
    130                 135                 140

Trp Gly Gln Gly Val Met Val Thr Val Ser Ser Arg Ser Ser Ser Ala
145                 150                 155                 160

Ser Thr Lys Gly Pro Ser Val Phe Pro Leu Ala Pro Ser Ser Lys Ser
                165                 170                 175

Thr Ser Gly Gly Thr Ala Ala Leu Gly Cys Leu Val Lys Asp Tyr Phe
            180                 185                 190

Pro Glu Pro Val Thr Val Ser Trp Asn Ser Gly Ala Leu Thr Ser Gly
        195                 200                 205

Val His Thr Phe Pro Ala Val Leu Gln Ser Ser Gly Leu Tyr Ser Leu
    210                 215                 220

Ser Ser Val Val Thr Val Pro Ser Ser Ser Leu Gly Thr Gln Thr Tyr
225                 230                 235                 240

Ile Cys Asn Val Asn His Lys Pro Ser Asn Thr Lys Val Asp Lys Lys
                245                 250                 255

Val Glu Pro Lys Ser Cys Asp Lys Thr His Thr Cys Pro Pro Cys Pro
            260                 265                 270

Ala Pro Glu Leu Leu Gly Gly Pro Ser Val Phe Leu Phe Pro Pro Lys
        275                 280                 285

Pro Lys Asp Thr Leu Met Ile Ser Arg Thr Pro Glu Val Thr Cys Val
    290                 295                 300

Val Val Asp Val Ser His Glu Asp Pro Glu Val Lys Phe Asn Trp Tyr
305                 310                 315                 320

Val Asp Gly Val Glu Val His Asn Ala Lys Thr Lys Pro Arg Glu Glu
                325                 330                 335

Gln Tyr Ala Ser Thr Tyr Arg Val Val Ser Val Leu Thr Val Leu His
```

```
            340                 345                 350

Gln Asp Trp Leu Asn Gly Lys Glu Tyr Lys Cys Lys Val Ser Asn Lys
        355                 360                 365

Ala Leu Pro Ala Pro Ile Glu Lys Thr Ile Ser Lys Ala Lys Gly Gln
    370                 375                 380

Pro Arg Glu Pro Gln Val Tyr Thr Leu Pro Pro Ser Arg Asp Glu Leu
385                 390                 395                 400

Thr Lys Asn Gln Val Ser Leu Thr Cys Leu Val Lys Gly Phe Tyr Pro
                405                 410                 415

Ser Asp Ile Ala Val Glu Trp Glu Ser Asn Gly Gln Pro Glu Asn Asn
            420                 425                 430

Tyr Lys Thr Thr Pro Pro Val Leu Asp Ser Asp Gly Ser Phe Phe Leu
        435                 440                 445

Tyr Ser Lys Leu Thr Val Asp Lys Ser Arg Trp Gln Gln Gly Asn Val
    450                 455                 460

Phe Ser Cys Ser Val Met His Glu Ala Leu His Asn His Tyr Thr Gln
465                 470                 475                 480

Lys Ser Leu Ser Leu Ser Pro Gly Lys Leu Glu Glu Val Gln Leu Val
                485                 490                 495

Glu Ser Gly Gly Gly Leu Val Gln Pro Gly Gly Ser Leu Arg Leu Ser
            500                 505                 510

Cys Ala Ala Ser Gly Phe Thr Phe Ser Asn Tyr Trp Met Ser Trp Val
        515                 520                 525

Arg Gln Ala Pro Gly Lys Gly Leu Glu Trp Val Ser Gly Ile Asn Pro
    530                 535                 540

Gly Gly Thr Ser Thr Tyr Tyr Ala Asp Ser Val Lys Gly Arg Phe Thr
545                 550                 555                 560

Ile Ser Arg Asp Asn Ala Lys Asn Thr Leu Tyr Leu Gln Met Asn Ser
                565                 570                 575

Leu Lys Ser Glu Asp Thr Ala Val Tyr Tyr Cys Ala Lys His Leu Gly
            580                 585                 590

Asn Trp Gly Glu Tyr Asn Tyr Trp Gly Gln Gly Thr Gln Val Thr Val
        595                 600                 605

Ser Ser Arg Ser Ser Thr Lys Gly Pro Lys Leu Glu Glu Gly Glu Phe
    610                 615                 620

Ser Glu Ala Gln Leu Gln Ser Ala Leu Thr Gln Pro Pro Ser Val Ser
625                 630                 635                 640

Gly Ser Pro Gly Lys Thr Val Thr Ile Ser Cys Ala Gly Thr Gly Gly
                645                 650                 655

Asp Val Gly Tyr Arg Asn Ser Val Ser Trp Tyr Gln Gln Leu Pro Gly
            660                 665                 670

Met Ala Pro Lys Leu Leu Ile Tyr Asp Val Asp Lys Arg Ala Ser Gly
        675                 680                 685

Ile Thr Asp Arg Phe Ser Gly Ser Lys Ser Gly Asp Thr Ala Ser Leu
    690                 695                 700

Thr Ile Ser Gly Val Gln Ser Glu Asp Glu Ala Asp Tyr Tyr Cys Ala
705                 710                 715                 720
```

-continued

```
Ser Gln Arg Ser Gly Ile Ala Ala Val Phe Gly Gly Gly Thr His Leu
                725                 730                 735

Thr Val Leu Gly
            740


<210> SEQ ID NO 167
<211> LENGTH: 257
<212> TYPE: PRT
<213> ORGANISM: Artificial Sequence
<220> FEATURE:
<223> OTHER INFORMATION: Protein construct expressed from SEQ ID NO: 156

<400> SEQUENCE: 167

Met Asn Phe Gly Phe Ser Leu Ile Phe Leu Val Leu Val Leu Lys Gly
1               5                   10                  15

Val Gln Cys Glu Val Lys Leu Val Pro Arg Gln Leu Asp Tyr Lys Asp
            20                  25                  30

Asp Asp Asp Lys Glu Leu Asp Ile Gln Met Thr Gln Ser Pro Ala Ser
        35                  40                  45

Leu Ser Ala Ser Leu Gly Glu Thr Val Ser Ile Asp Cys Leu Ala Ser
    50                  55                  60

Glu Gly Ile Ser Asn Asp Leu Ala Trp Tyr Gln Gln Lys Ser Gly Lys
65                  70                  75                  80

Ser Pro Gln Leu Leu Ile Asn Ser Ala Ser Arg Leu Glu Asp Gly Val
                85                  90                  95

Pro Ser Arg Phe Ser Gly Ser Gly Ser Gly Thr Arg Tyr Ser Leu Lys
            100                 105                 110

Ile Ser Gly Met Gln Pro Glu Asp Glu Ala Glu Tyr Phe Cys Leu Gln
        115                 120                 125

Ser Tyr Arg Ser Pro Trp Thr Phe Gly Gly Gly Thr Lys Leu Glu Leu
    130                 135                 140

Lys Gly Ser Glu Ile Lys Arg Thr Val Ala Ala Pro Ser Val Phe Ile
145                 150                 155                 160

Phe Pro Pro Ser Asp Glu Gln Leu Lys Ser Gly Thr Ala Ser Val Val
                165                 170                 175

Cys Leu Leu Asn Asn Phe Tyr Pro Arg Glu Ala Lys Val Gln Trp Lys
            180                 185                 190

Val Asp Asn Ala Leu Gln Ser Gly Asn Ser Gln Glu Ser Val Thr Glu
        195                 200                 205

Gln Asp Ser Lys Asp Ser Thr Tyr Ser Leu Ser Ser Thr Leu Thr Leu
    210                 215                 220

Ser Lys Ala Asp Tyr Glu Lys His Lys Val Tyr Ala Cys Glu Val Thr
225                 230                 235                 240

His Gln Gly Leu Ser Ser Pro Val Thr Lys Ser Phe Asn Arg Gly Glu
                245                 250                 255

Cys
```